United States Patent
Angell et al.

(10) Patent No.: US 11,427,615 B2
(45) Date of Patent: Aug. 30, 2022

(54) PEPTIDE COMPOUND AND APPLICATION THEREOF, AND COMPOSITION CONTAINING PEPTIDE COMPOUND

(71) Applicant: XDCEXPLORER (SHANGHAI) CO., LTD., Shanghai (CN)

(72) Inventors: Yvonne Angell, Shanghai (CN); Yun Wu, Shanghai (CN); Yan Wang, Shanghai (CN); Weimin Liu, Shanghai (CN); Kin Chiu Fong, Shanghai (CN); Jie Wen, Shanghai (CN); Yonghan Hu, Shanghai (CN)

(73) Assignee: XDCEXPLORER (SHANGHAI) CO., LTD., Shanghai (CN)

( * ) Notice: Subject to any disclaimer, the term of this patent is extended or adjusted under 35 U.S.C. 154(b) by 0 days.

(21) Appl. No.: 16/628,586

(22) PCT Filed: Jul. 5, 2018

(86) PCT No.: PCT/CN2018/094618
§ 371 (c)(1),
(2) Date: Jan. 3, 2020

(87) PCT Pub. No.: WO2019/007383
PCT Pub. Date: Jan. 10, 2019

(65) Prior Publication Data
US 2020/0172575 A1    Jun. 4, 2020

(30) Foreign Application Priority Data

Jul. 5, 2017 (CN) .......................... 201710543383.0
Jul. 4, 2018 (CN) .......................... 201810725881.1

(51) Int. Cl.
C07K 7/06 (2006.01)
A61K 47/60 (2017.01)
A61P 35/04 (2006.01)
A61K 38/00 (2006.01)

(52) U.S. Cl.
CPC .............. *C07K 7/06* (2013.01); *A61K 47/60* (2017.08); *A61P 35/04* (2018.01); *A61K 38/00* (2013.01)

(58) Field of Classification Search
CPC . C07K 7/06; C07K 7/08; C07K 14/47; A61K 47/60; A61K 38/00; A61K 38/08; A61K 38/10; A61K 38/16; A61P 35/04; A61P 5/00; A61P 15/00; A61P 15/08; A61P 25/24; A61P 35/00
See application file for complete search history.

(56) References Cited

U.S. PATENT DOCUMENTS

| 6,800,611 | B2 | 10/2004 | Fujii et al. |
| 7,625,869 | B2 | 12/2009 | Kitada et al. |
| 7,754,220 | B2 | 7/2010 | Ohtaki et al. |
| 7,960,348 | B2* | 6/2011 | Asami ............... A61P 15/08 514/19.8 |
| 8,361,986 | B2 | 1/2013 | Kandimalla et al. |
| 8,592,379 | B2 | 11/2013 | Fujii et al. |
| 8,765,909 | B2 | 7/2014 | Asami et al. |
| 8,878,871 | B2 | 11/2014 | Clark et al. |
| 2004/0180407 | A1 | 9/2004 | Watanabe et al. |
| 2005/0240008 | A1 | 10/2005 | Ohtaki et al. |
| 2009/0093615 | A1 | 4/2009 | Asami et al. |
| 2011/0171160 | A1* | 7/2011 | Minamitani ............ A61K 47/60 424/78.17 |
| 2015/0361138 | A1* | 12/2015 | Beltramo ................ C07K 7/00 514/19.3 |

FOREIGN PATENT DOCUMENTS

| CN | 101341168 A | 1/2009 | |
| CN | 101341168 B | 1/2013 | |
| CN | 106544322 A | 3/2017 | |
| JP | 2003002841 A | 1/2003 | |
| JP | 2009520682 A | 5/2009 | |
| JP | 2010507565 A | 3/2010 | |
| JP | 2012502990 A | 2/2012 | |
| TW | 201906856 A | 12/2019 | |
| WO | 0024890 A1 | 5/2000 | |
| WO | 0175104 A1 | 10/2001 | |
| WO | 02085399 A1 | 10/2002 | |
| WO | 2007072997 A1 | 6/2007 | |
| WO | WO-2009131191 A1 * | 10/2009 | ............ A61P 15/00 |
| WO | 2010033224 A1 | 3/2010 | |
| WO | WO-2014118318 A1 * | 8/2014 | ............ C07K 7/00 |

OTHER PUBLICATIONS

First Office Action dated Jun. 15, 2021 issued in Taiwan Application No. 107123335, with English translation, 9 pages.
Notice of Rejection dated Nov. 29, 2021 issued in corresponding Taiwan Application No. 107123335, with English translation, 14 pages.
International Search Report dated Sep. 27, 2018 issued in International Patent Application No. PCT/CN2018/094618 with English translation, 9 pages.
Written Opinion of the International Searching Authority dated Sep. 27, 2018 issued in International Patent Application No. PCT/CN2018/094618 with English translation, 10 pages.
Partial Supplementary European Search Report dated Jul. 17, 2020 issued in corresponding EP Application No. 18828694.2, 13 pages.
Jiang, Fusheng, et al., "Research progress of polyethylene glycol prodrugs," Chin Pharm J, vol. 42, Issue 12, 2007, 13 pages.

(Continued)

*Primary Examiner* — Sudhakar Katakam
(74) *Attorney, Agent, or Firm* — Foley & Lardner LLP

(57) ABSTRACT

Disclosed are a peptide compound and an application thereof, and a composition containing the peptide compound. The present invention provides a peptide compound represented by formula (1), and a pharmaceutically acceptable salt, a tautomer, a solvate, a crystal form or a prodrug thereof. The compound has good stability and good activity for Kiss1R.

Cap-AA1-AA2-XX3-Asn-AA5-AA6-AA7-Leu-AA9-AA10-P    (1)

2 Claims, No Drawings

(56) References Cited

OTHER PUBLICATIONS

Lee, Jeong-Hyung, et al., "KiSS-1, a novel human malignant melanoma metastasis-suppressor gene," Journal of the National Cancer Institute, vol. 88, No. 23, 1996, pp. 1731-1737.
Ohtaki, T., et al., "Metastasis suppressor gene KiSS-1 encodes peptide ligand of a G-protein-coupled receptor," Letters to Nature, vol. 411, Issue 6837, 2001, pp. 613-617.
Kotani, Masato, et al., "The Metastasis Suppressor Gene KiSS-1 Encodes Kisspeptins, the Natural Ligands of the Orphan G Protein-coupled Receptor GPR54," J. Biol. Chem., vol. 276, 2001, pp. 34631-34636.
Nash, Kevin T., et al., "The KISS 1 metastasis suppressor: mechanistic insights and clinical utility," Frontiers in Bioscience, vol. 11, 2006, pp. 647-659.
Lee, Jeong-Hyung, et al., "Identification of highly expressed genes in metastasis-suppressed chromosome 6/human malignant melanoma hybrid cells using subtractive hybridization and differential display," Int. J Cancer, vol. 71, Issue 6, 1997, pp. 1035-1044.
Roa, J., et al., "Hypothalamic expression of KiSS-1 system and gonadotropin-releasing effects of kisspeptin in different reproductive states of the female Rat," Endocrinology, vol. 147, Issue 6, 2006, pp. 2864-2878.
Stahl, P. Heinrich, et al., "Handbook of Pharmaceutical Salts for a review of pharmaceutically acceptable salts: Properties, Selection, and Use," Chapter 4, Wiley-VCH, 2002, 34 pages.
Rautio, J., "Prodrugs: design and clinical applications," Nature Reviews | Drug Discovery, vol. 7, Issue 3, 2008, pp. 255-270.
Stella, Valentino J., et al., "Prodrugs: Challenges and rewards," Springer, 2007.
Lu, Gui-shen, et al., "Improved Synthesis of 4-Alkoxybenzyl Alcohol Resin," J. Org. Chem, vol. 46, Issue 17, 1981, pp. 3433-3436.
Asami, Taiji, et al., "Design, Synthesis, and Biological Evaluation of Novel Investigational Nonapeptide KISS1R Agonists with Testosterone-Suppressive Activity," Journal of Medicinal Chemistry, vol. 56, Issue 21, 2013, pp. 8298-8307.
Decourt, C., et al., "A synthetic kisspeptin analog that triggers ovulation and advances puberty," Scientific Reports, vol. 6, Issue 1, 2016, pp. 1-10.
Beltramo, Massimiliano, et al., Rational Design of Triazololipopeptides Analogs of Kisspeptin Inducing a Long-Lasting Increase of Gonadotropins, Journal of Medicinal Chemistry, vol. 58, Issue 8, 2015, pp. 3459-3470.
Asami, Taiji, et al., "Serum stability of selected decapeptide agonists of KISS1R using pseudopeptides," Bioorganic & Medicinal Chemistry Letters, vol. 22, Issue 20, 2012, pp. 6391-6396.
Extended European Search Report dated Dec. 10, 2020 issued in EP Application No. 18828694.2, 12 pages.
Notice of Reasons for Refusal dated Jun. 28, 2022 issued in corresponding JP Application No. 2020-500192, with English translation, 8 pages.

* cited by examiner

PEPTIDE COMPOUND AND APPLICATION THEREOF, AND COMPOSITION CONTAINING PEPTIDE COMPOUND

This application is a 371 of PCT/CN2018/094618 filed Jul. 5, 2018, which claims the priority of Chinese patent application CN201710543383.0 filed on Jul. 5, 2017 and Chinese patent application CN201810725881.1 filed on Jul. 4, 2018. The content of all of the above applications are hereby incorporated by reference in its entirety.

FIELD OF INVENTION

The disclosure relates to a peptide compound and an application thereof, and a composition containing the peptide compound.

PRIOR ARTS

Kiss-1 gene is a novel type of gene that inhibit the metastasis of human melanoma discovered by Jeong-Hyung Lee et al. (Lee J H, et al. Journal of the national cancer institute, vol. 88 (23): 1731-1737 (1996)). Kiss-1 gene is located on human chromosome 1q32 and consists of four exons, two untranslated and two partially translated exons, which encodes a precursor polypeptide containing 145 amino acids. The precursor peptide is cleaved into 54 amino acid length Kisspeptin-54 (also known as metastin or transfer inhibitor), and can be further truncated to 14 [kisspeptin-14/metastin (40-54)], 13 [kisspeptin-13/metastin (41-54)], or 10 [kisspeptin-10/metastin (45-54)] amino acids. These truncations and precursors are collectively referred to as Kisspeptin (Kp) and are highly conserved in mammals (Kotanim, et. al. Journal of biological chemistry, vol. 276 (27): 34631-34636; Ohtaki T. et al., Nature Vol, 411(6837): 613-671 (2001)). The four kisspeptins all contain the same 10 amino acid residues, the C-terminal of which has arginine and amidated phenylalanine (RF-amide), but the N-terminal polypeptides differ in length. The C-terminal part of the kisspeptins is related to the efficient binding and activation of the receptors, and the activity of truncated peptides, for example Kisspeptin-10 and Kisspeptin-14 is 3-10 times higher than that of Kisspeptin-54. mRNA of the Kiss-1 is mainly expressed in human placenta and is also widely expressed in the whole central nervous system: the highest expression is in the shell, the higher expression is in caudate nucleus, globus pallidus, hypothalamus, nucleus accumbens and cerebellum, and the lower expression is in superior frontal gyrus, amygdala, cingulate gyrus, hippocampus, para hippocampal gyrus, thalamus, substantia nigra, locus coeruleus and medulla oblongata, and the very low expression is in spinal cord.

At present, it is known that the receptor for these kisspeptins (Kiss1R) is a member of retinoic acid-inducible orphan G protein-coupled receptor family (namely GPR54 in rats and AXOR12 in humans). Kiss1R contains 398 amino acid residues and is related to the galanin receptor family, but it does not bind to galanin. Rat GPR54 is highly conserved in mammals and has 81% homology with human receptors and 85% homology with mice. The mRNA of human Kiss R is expressed abundantly in placenta, pituitary, spinal cord and pancreas, and is expressed at a low level in other tissues including different parts of brain (thalamus, caudate nucleus, substantia nigra, hippocampus, amygdala, and cerebellum), stomach, small intestine, thymus, spleen, lung, testis, kidney and fetal liver. Kisspeptin and its receptors are distributed in brain and in various peripheral tissues and organs, including hypothalamus, aorta, ovary, prostate and placenta, and the receptors are also expressed in pituitary gland. Their functions include regulating reproductive function, affecting endocrine, and affecting the growth and metastasis of tumor cells.

The signal transmission between kisspeptin and Kiss1R (GPR54) is to activate phospholipase C (PLC) in the cell after the polypeptide binds with its receptor, and then hydrolyze phosphatidylinositol diphosphate (PIP2) to produce inositol triphosphate (IP3) and diacylglyceride (DAG), which promote the increasement of intracellular calcium ion, the realsing of arachidonic acid, the activation of protein kinase C(PKC), and the phosphorylation of the extracellular signal regulatory kinases (ERK1 and ERK2) and p38 mitotic activated protein kinase (MAPK), thus producing the biological effects. An important role of the signalling between Kisspeptin and Kiss R is to start secreting gonadotropin-releasing hormone (GnRH) during puberty. The release of gonadotropin-releasing hormone is the behavior of the anterior pituitary gland, which also includes the release of luteinizing hormone, LH) and follicle stimulating hormone, FSH). Disruption of this signaling pathway will lead to insufficient GnRH release, resulting in hypogonadism in humans and rodents. Abnormal release or absence is the main cause of abnormal sexual reproduction for men and women. Studies have proved that GnRH analogue kisspeptin plays a role at hypothalamic level to stimulate GnRH release (U.S. Pat. No. 7,754,220). The input of kisspeptin can stimulate GnRH to release at all stages. The use of Kiss1R agonist is a method for preventing or treating hormone-related diseases for example prostate cancer, breast cancer, endometriosis, hysteromyoma, breast cancer before amenorrhea, central precocious puberty, sexual functional diseases, etc. It is also used in in vitro fertilization to induce ovulation and as a new generation of contraceptives.

The binding of the kisspeptin and Kiss1R (GPR54) has many functions, among which the inhibition of cell proliferation is an important one (Kotanim, et al., *J. Biol. Chem.* vol. 276: 34631-34636). Kiss1R agonist can inhibit cell proliferative diseases selected from the following disease groups: benign prostatic hyperplasia, prostate cancer, breast cancer, ovarian cancer, uterine cancer, cervical cancer, endometrial cancer, melanoma, pancreatic cancer, gastric cancer, renal cell cancer, esophageal cancer, bladder cancer, brain cancer, etc.

Kiss1 gene is initially named as Kiss1 metastasis inhibitory gene, which can manage tumor cell metastasis and has clinical value. The expression level of primary melanoma cell line expressing Kiss1 gene is negatively related to the metastatic potential of melanoma cell line. C8161 cells expressed Kiss1 gene, and lung metastasis was inhibited by more than 95% (Nash et al., The KISS1 metastasis suppressor: mechanistic insights and clinical utility, *Front. Biosci.* vol. 11, pp. 647-659 (2006)). Kisspeptin can reduce cell mobility and inhibit tumor cell metastasis by inducing excessive cell adhesion phenotype (Lee J H and Welch D R, *Int. J. Cancer*, vol. 71 (6): 1035-1044 (1997)). Metastin derivatives also have excellent biological activities (e.g., cancer cell metastasis inhibitory activity, cancer cell growth inhibitory activity, etc.) (US 68061B2, U.S. Pat. No. 7,625, 869B2, U.S. Pat. No. 8,361,986B2, U.S. Pat. No. 8,592, 379B2). Kiss1R agonist inhibits tumor metastasis and migration, and affects the invasion of trophoblast cells, wherein said disease or disease state is selected from melanoma, pancreatic cancer, breast cancer, ovarian cancer, uterine cancer, cervical cancer, endometrial cancer, thyroid cancer, bladder cancer, esophageal squamous cell cancer, gastric cancer, liver cancer and other cancers.

Kiss1R (GPR54) is also highly expressed in the central nervous system (CNS) and the hippocampus region. It has been proved that, Kiss1R can reversibly enhance the synaptic transmission in hippocampal dentate gyrus cells through mechanisms involving MAP kinases, which appears to be regulated by calcium-activated kinases and tyrosine kinases (Roa J, Hypothalamic expression of KiSS-1 system and gonadotropin-releasing effects of kisspeptin in different reproductive states of the female Rat. et. al. Endocrinology 147(6): 1624-1632, 2006). Studies have proved that injection of kisspeptin can enhance limbic brain activity and produce sexual stimulation. Therefore, kisspeptin can stimulate sexual desire in essence and is related to the feeling of sex appeal, romance and sexual excitement. Kiss1R agonist can enhance the erotic signals from brain and emotion, thus treating sexual dysfunction caused by psychological reasons.

Kisspeptin also has the function of affecting placental function, therefore, Kiss1R agonist is effective in treating the disease or disease state selected from: choriocarcinoma, invasive nevus, abortion, fetal hypoplasia, abnormal glucose metabolism, abnormal lipid metabolism, etc. (WO00/24890; WO01/75104 2; WO 02/85399).

Takeda company has disclosed kisspeptin analog TAK448 in patents CN101341168B, U.S. Pat. No. 8,592,379B2, U.S. Pat. No. 8,765,909B2 and U.S. Pat. No. 9,778,871B2:

wherein Cap is

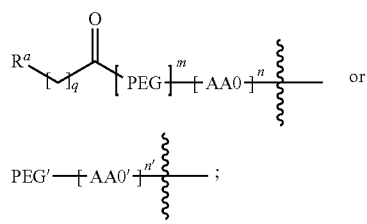

or

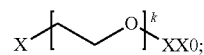

$R^a$ is $CH_3$—, and q is 0-18 (for example, any two of the following values can be selected as two endpoints of a range: 0, 1, 2, 3, 4, 5, 6, 7, 8, 9, 10, 11, 12, 13, 14, 15, 16, 17 and 18); for another example, 0 to 14; for another example, 4-14); alternatively, $R^a$ is HOOC—, and q is 1-18 (for example, any two of the following values can be selected as two endpoints of a range: 1, 2, 3, 4, 5, 6, 7, 8, 9, 10, 11, 12, 13, 14, 15, 16, 17, and 18; for another example, 1 to 16);

m is 0 to 2 (e.g. 0, 1 or 2);

PEG is independently

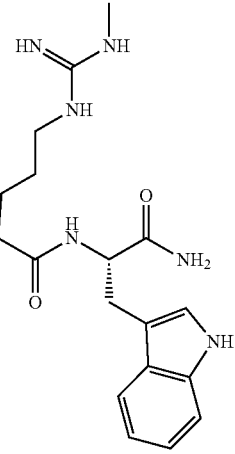

X is independently —$NHR^b$ or —OH, $R^b$ is independently hydrogen or $C_{1-3}$ alkyl (e.g., methyl, ethyl, isopropyl or

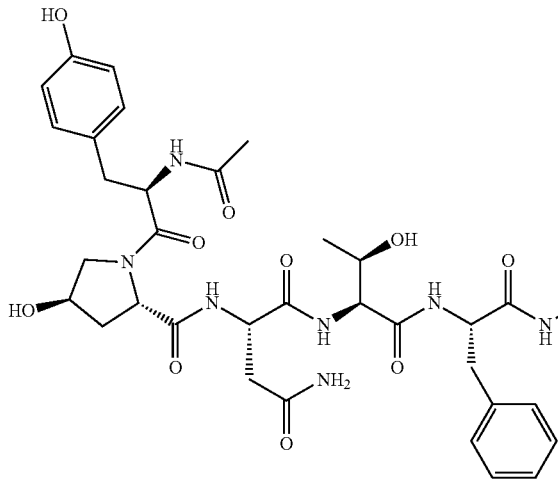

TAK448

Contents of the Present Disclosure

The technical problem to be solved by the present disclosure is that the existing peptide compound has low stability and low activity to Kiss1R. Therefore, the present disclosure provides a peptide compound, an application thereof and a composition containing the peptide compound, which has better stability and activity to Kiss1R.

The present disclosure provides a peptide compound represented by formula 1, a pharmaceutically acceptable salt thereof, a tautomer thereof, a solvate thereof, a crystal form thereof or a prodrug thereof:

Cap-AA1-AA2-XX3-Asn-AA5-AA6-AA7-Leu-AA9-AA10-P     1;

n-propyl); k is independently 2-24 (for example, any two of the following values can be selected as two endpoints of a range: 2, 3, 4, 5, 6, 8, 12, 16, 20 or 24; for another example 2-8, also for example 4-8); and XX0 is independently,

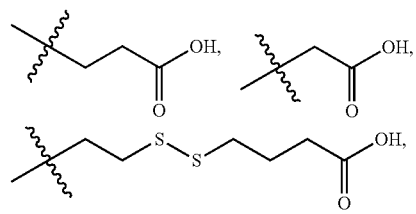

-continued

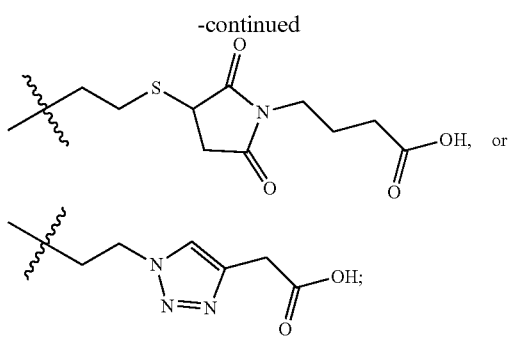

the X end of PEG is linked with the carbonyl group, and the XX0 end is linked with AA0 or AA1;
said X can be —NH$_2$; said K can be independently 2 to 8 (e.g., 4-8); and said

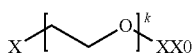

can be independently OEG, PEG4, PEG5, PEG8,

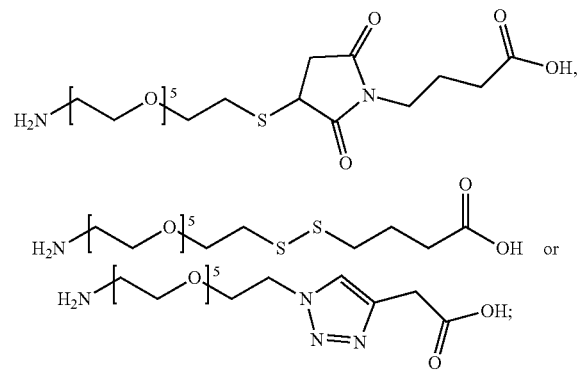

when m is 2, in the PEG that linked to AA0 or AA1, said X can be —NH$_2$; when m is 2, in the PEG that linked to AA0 or AA1, said k can be 2-4 (e.g., 2, 3 or 4); when m is 2, in PEG linked to AA0 or AA1, said XX0 can be

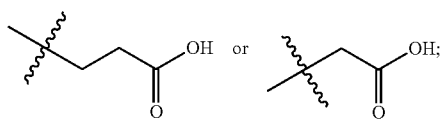 [SMILES: *CCC(=O)O ; *CC(=O)O]

when m is 2, in the PEG that linked with AA0 or AA1, said

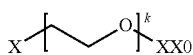

can be OEG or PEG4;
said

can be a chemical bond, "OEG", "PEG4", "PEG8", "OEG-OEG", "PEG4-PEG4",

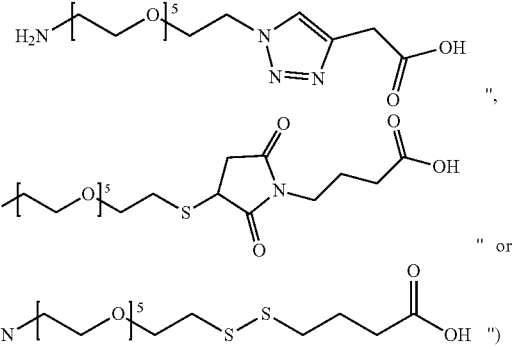

n is 0 to 3 (e.g., 0, 1, 2 or 3);
all of AA0s are independently Gly, Beta-Ala, Ahx or Ac-Lys; (for example, when n is 2 or 3, at least 2 of AA0s are Gly; for another example,

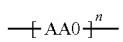

can be a chemical bond, "Gly-Gly" or "Ac-Lys-Gly-Gly" {the left side of which is linked to XX0});
however, when q is 0, then m and n are not 0 at the same time; (i.e.

is not acetyl; for example, when m is 0 and n is 0, q is 1 to 18; for another example, any two of the following values can be selected as two endpoints of a range: 1, 2, 3, 4, 5, 6, 7, 8, 9, 10, 11, 12, 13, 14, 15, 16, 17, and 18; for another example, 4-14); PEG' is

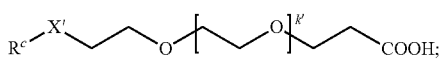

R$^c$ is C$_{14}$-C$_{18}$ linear alkyl (e.g., C$_{16}$ linear alkyl), X' is "five- or six-membered heteroaryl, wherein the heteroatom is one or more of N, O and S, and the number of the heteroatom is 1-3" (e.g., "five- or six-membered heteroaryl, wherein the heteroatom is N, the number of the heteroatom is 1-3 five-membered or six-membered heteroaryl", for another example,

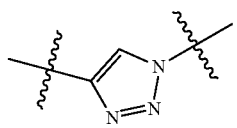 [SMILES: *c1cn(*)nn1]

{the left end of which is linked to R$^c$}) or

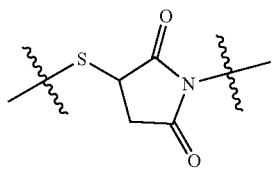 [SMILES: *SC1CC(=O)N(*)C1=O]

(the left end of which is linked to R$^c$), and k' is 5-9 (e.g., 5-7);

(said PEG' can be

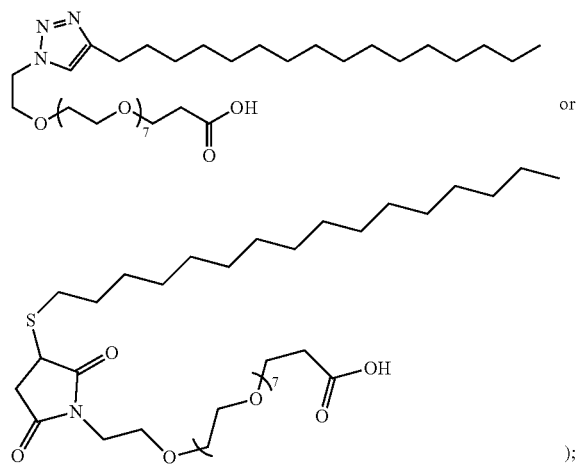

n' is 0 to 3 (e.g., 0, 1, 2 or 3, and e.g., 2);

All of AA0' are independently Gly, Beta-Ala, Ahx or Ac-Lys; (For example, when n' is 2 or 3, at least 2 of AA0' are Gly; For example,

can be a chemical bond, "Gly-Gly" or "AC-Lys-Gly-Gly" {the left side of which is linked to PEG'});

AA1 is an amino acid whose the amino group is unsubstituted or substituted (when the amino acid has a plurality of amino groups, the amino group can be located on a chiral carbon atom, or can also be a primary amino group) by a C$_{1-3}$ alkyl group (e.g., methyl, ethyl, n-propyl or isopropyl) (said "substituted amino acids" is, for example, N-Me-Ala, N-Me-D-Ala, N-Me-Leu, N-Me-D-Leu, N-Me-Phe or N-Me-D-Phe), wherein the amino acid is selected from: D-Ala, Leu, D-Leu, Tyr, D-Tyr, Thi, (S)-Pip, Ala, αMeTyr, 1Nal, 2Nal, 4Pal, Dap(Dnp), D-2Fua, Pro(5Ph), 2Pal, 3Pal, Tyr(Me), Ala(dip), A6c, ACPA, D-Tic, 3-[(1-methylpyridinium)-3-yl] alanine, and

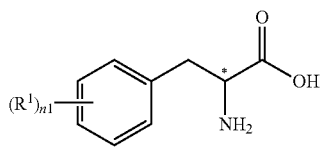

{e.g., Phe, D-Phe, Phe(4-F), D-Phe(4-F), Phe(3-Cl), D-Phe (3-Cl), Phe(4-Cl), D-Phe(4-Cl), Phe(4-I), D-Phe(4-I), Phe (4-Me), Phe(4-tBu), or, D-Phe(2,4-diCl)}; n1 is 0 to 2 (e.g., 0, 1 or 2), all of R$^1$ are independently C$_1$-C$_4$ alkyl (e.g., methyl, ethyl, n-propyl, isopropyl, n-butyl, sec-butyl or isobutyl), C$_1$-C$_4$ alkoxy (e.g., methoxy, ethoxy, n-propoxy, isopropoxy, n-butoxy, sec-butoxy or isobutoxy) or halogen (e.g., fluorine, chlorine or iodine), and carbon atoms labeled with * are the chiral carbon atoms, which are in R configuration or S configuration (all of R$^1$ can be independently located at the ortho-, para- and meta-positions of amino acid side chain, e.g., when n1 is 2, R$^1$ can be located at the ortho and para positions of the amino acid side chain; for another example, it is

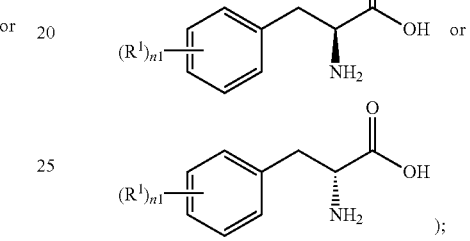

AA2 is Asn, Hyp, Pro, Ala, Thz, Pro(diF), Pro(4-NH$_2$), Thi, NAsn, ACPA, D-2Fua, A6c, azaPro, Ind, (S)-Pip, (R)-Pip, Oic, azaTic, AlphaMeLeu, Cba, A6c, Aze, CPA or D-TIC;

XX3 is Trp, Ala, Phe(4-I) or a chemical bond;

AA5 is 2Fua, Thr or Ser;

AA6 is an amino acid whose the amino group is unsubstituted or substituted (when the amino acid has a plurality of amino groups, the amino group can be located on a chiral carbon atom, or can also be a primary amino group) by a C$_{1-3}$ alkyl group (e.g., methyl, ethyl, n-propyl or isopropyl) (said "substituted amino acids" is, for example, N-Me-Phe), wherein the amino acid is selected from: Ala, 1Nal, 2Nal, Trp, αMePhe, Bta, 4Pal, HoPhe, BetaPhe, BetaHomoPhe, Bpa, Ala(dip), Bip, D-2Fua, A6c, Tic, azaTic, azaPhe, and,

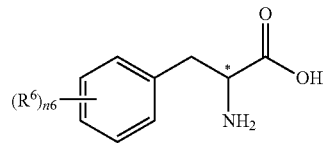

{(e.g., Phe, D-Phe, Phe(4-F), Phe(pentaF), Phe(3-Cl), Phe (2-Br), Phe(4-I), Phe(4-tBu), or phe (4-CF3)); n6 is 0-5 (e.g., 0, 1, 2, 3, 4 or 5), and all of R$^6$ are independently halogenated C$_1$-C$_4$ alkyl (said "halogen" is for example, fluorine, chlorine, bromine or iodine; said "C$_1$-C$_4$ alkyl" is, for example, methyl, ethyl, n-propyl, isopropyl, n-butyl, sec-butyl or isobutyl; said "halogenated C1-C4 alkyl" is, for example, trifluoromethyl), C$_1$-C$_4$ alkyl (e.g. methyl, ethyl, isopropyl or isobutyl) or halogen (e.g. fluorine, chlorine, bromine or iodine), the carbon atom marked with * is a chiral carbon atom, which is in R configuration or S configuration (all of R$^6$ can be independently located at the ortho, meta or para position of the amino acid side chain, for example, when n6 is 1, $R^6$ can be located at the ortho, meta or para position of the amino acid side chain; for example, it can be

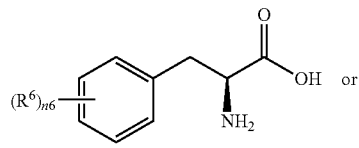 or

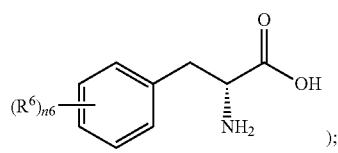);

AA7 is an amino acid whose the amino group is unsubstituted or substituted (when the amino acid has a plurality of amino groups, it can be the amino group on the chiral carbon atom, or can also be a primary amino group) by a $C_{1-3}$ alkyl group (e.g., methyl, ethyl, n-propyl or isopropyl) (the "substituted amino acids" is, for example, N-Me-A6c or aza-N-Me-Gly), and the amino group is selected from: Gly, azaGly, Ala, Alg, Ava, Aib, Sar, Chg, BetaAla, ACPO, Aze, D-2Fua, A6c, azaPro, Ind, (S)-Pip, (R)-Pip, azaTic, Oic, Hyp, cycloLeu, BetaHomoAla, Cba, ACPA, Alg, morpholino cyclic amino acid, beta-(thiazoly-4-yl)-L-Ala,

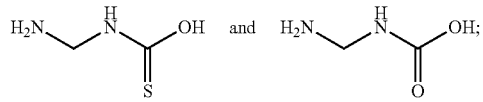 [SMILES: NCNC(O)=S ; NCNC(=O)O]

When AA6 is

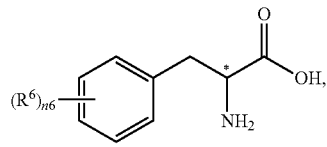

"AA6-AA7" refers to a group containing

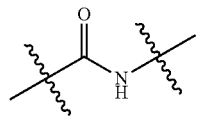 [SMILES: *NC(*)=O]

that formed by joining the carboxyl group of AA6 (when the amino acid has multiple carboxyls, the carbonyl can be located on a chiral carbon atom) to the amino group of AA7 (when the amino acid has a plurality of amino groups, the amino group can be located on a chiral carbon atom, or can also be a primary amino group), or, the group formed after the

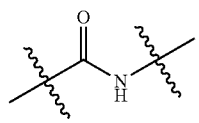 [SMILES: *NC(*)=O]

of "the group containing

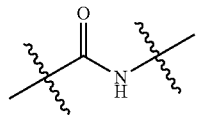 [SMILES: *NC(*)=O]

that formed by joining the carbonyl group of AA6 to the amino group of AA7" is substituted by any one of the groups shown below:

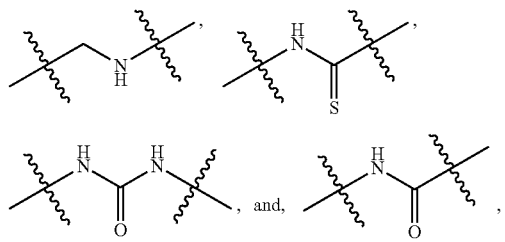

the left end of said group is linked with AA6 (for example, when AA6 is Phe and AA7 is Gly, "AA6-AA7" refers to

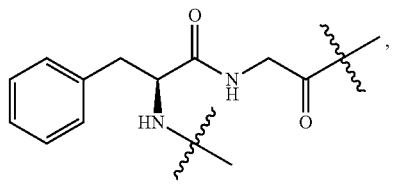

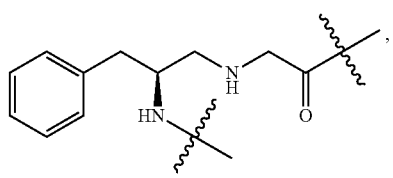

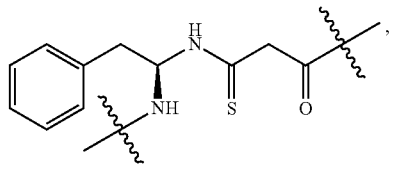

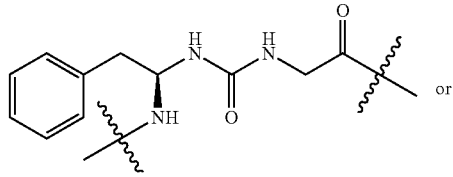 or

-continued

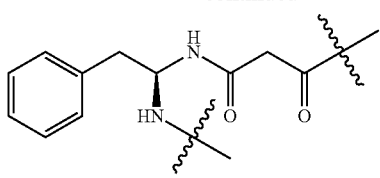
);

Alternatively, AA6 and AA7 together form

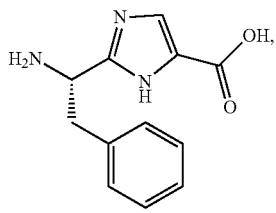

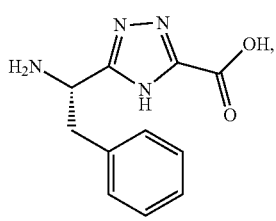

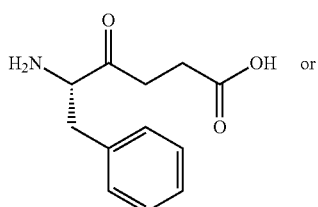 or

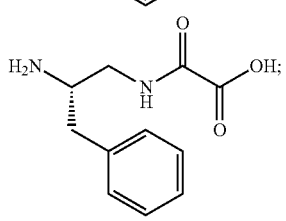

"AA7-Leu" refers to the

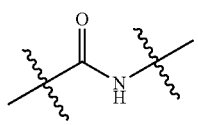 [SMILES: *NC(*)=O]

group formed by joining the carboxyl group of AA7 (when the amino acid has a plurality of carboxyls, the carbonyl can be located on a chiral carbon atom) to the amino group of Leu (when the amino acid has a plurality of amino groups, the amino group can be located on a chiral carbon atom, or can also be a primary amino group), or the group formed after the

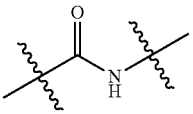 [SMILES: *NC(*)=O]

of "the group containing

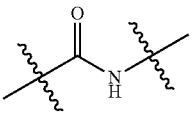 [SMILES: *NC(*)=O]

formed by joining the carboxyl group of AA7 to the amino group of Leu" is substituted by any one of the group shown below:

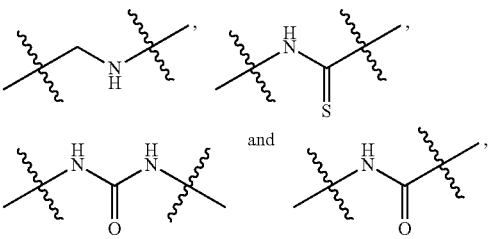

the left end of the group is linked with AA7 (for example, when AA7 is Gly and AA7 is Leu, and "AA7-Leu" refers to

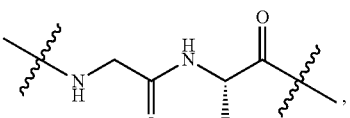

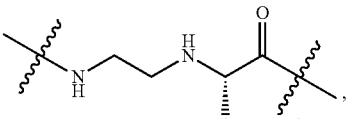

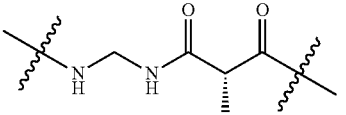 or

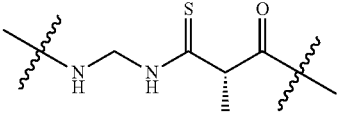

)

AA9 is an amino acid whose amino group is unsubstituted or substituted (when the amino acid has a plurality of amino groups, the amino group can be located on a chiral carbon atom, or can also be a primary amino group) by a $C_{1-3}$ alkyl group (e.g., methyl, ethyl, n-propyl or isopropyl) (the "substituted amino acids" is, for example, N-Me-Arg, N-Me-HoLeu or N-ME-D-HoLeu), wherein the amino acid is selected from: ARG, Arg(Me), Ala, His, HOLEU, D-HoLeu, 4Pal, Phe(4-amidino),

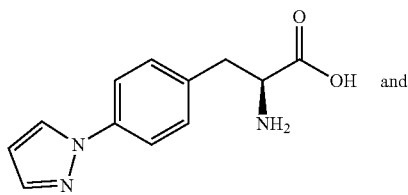
and

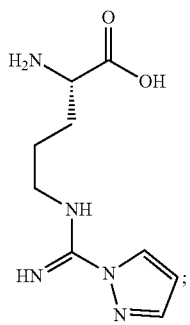
;

AA10 is an amino acid whose amino group is unsubstituted or substituted (when the amino acid has a plurality of amino groups, the amino group can be located on a chiral carbon atom, or can also be a primary amino group) by a $C_{1-3}$ alkyl group (e.g., methyl, ethyl, n-propyl or isopropyl) (the "substituted amino acids" is, for example, N-Me-Phe), wherein the amino acid is selected from: Trp, Ala, αMePhe, 1Nal, 2Nal, 4Pal, BetaPhe, BetahoPhe, Bpa, Ala(dip), NPhe, Bip, D-2Fua, A6c, Tic, and

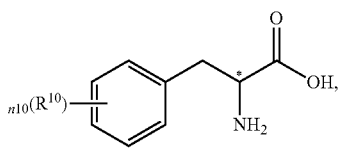

{e.g., Phe, D-Phe, Phe(4-F), Phe(pentaF), Phe(2-Br), Phe (4-I), or, Phe (4-CF3)}; N10 is 0-5 (e.g., 0, 1, 2, 3, 4 or 5), and all of $R^{10}$ are independently halogenated $C_1$-$C_4$ alkyl (said "halogen" is, for example, fluorine, chlorine, bromine or iodine; said "$C_1$-$C_4$ alkyl" is, for example, methyl, ethyl, n-propyl, isopropyl, n-butyl, sec-butyl or isobutyl; said "halogenated C1-C4 alkyl" is, for example, trifluoromethyl) or halogen (for example fluorine, chlorine, bromine or iodine), the carbon atom marked with * is a chiral carbon atom, which is in R configuration or an S configuration (all $R^{10}$ can be independently located at the ortho, meta or para position of the amino acid side chain, for example, when n10 is 1, $R^{10}$ can be located at the ortho or para position of the amino acid side chain; for example, it can be

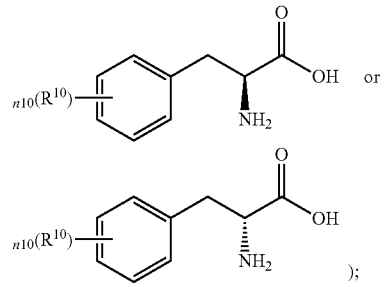

P is —$NH_2$, —OH, —NH-tBu, —NH-Et, —NH-Me, 1H-1,2,3-triazol-4-yl or 2H-tetrazole-5-yl.

In a certain technical solution, the definition of each group in the compound 1 can be as follows (the uncommented definition is as described above):

Cap is

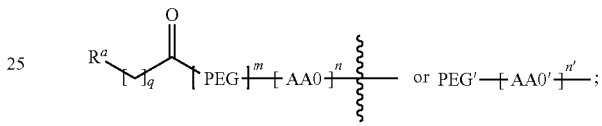

$R^a$ is $CH_3$—, q is 0-16 (for example, any two of the following values can be selected as the two endpoints of a range: 0, 1, 2, 3, 4, 5, 6, 7, 8, 9, 10, 11, 12, 13, 14, 15 and 16; for another example, 0-14; for another example: 4-14); alternatively, $R^a$ is HOOC—, q is 2 to 18 (for example, any two of the following values can be selected as two endpoints of a range: 2, 3, 4, 5, 6, 7, 8, 9, 10, 11, 12, 13, 14, 15, and 16; for another example 2 to 16);

m is 0 to 2 (e.g., 0, 1 or 2);

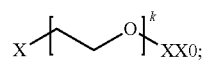

PEG is independently X is independently —$NHR_b$ or —OH, Rb is independently hydrogen or $C_{1-3}$ alkyl (e.g., methyl, ethyl, isopropyl or n-propyl); k is independently 2-12 (for example, any two of the following values can be selected as two endpoints of a range: 2, 3, 4, 5, 6, 8 or 12); XX0 is independently

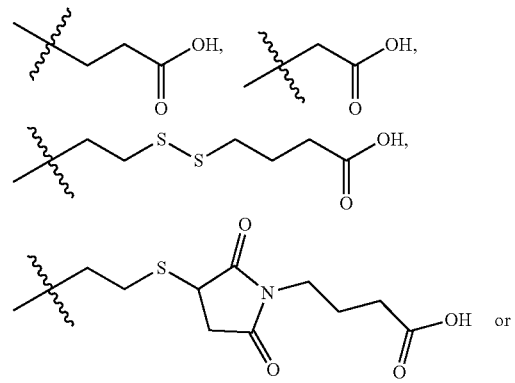

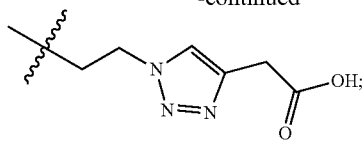

(said X can be —NH$_2$; said k can be independently 2-8 (e.g., 4-8); said

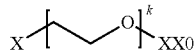

can independently be OEG, PEG4, PEG5, PEG8,

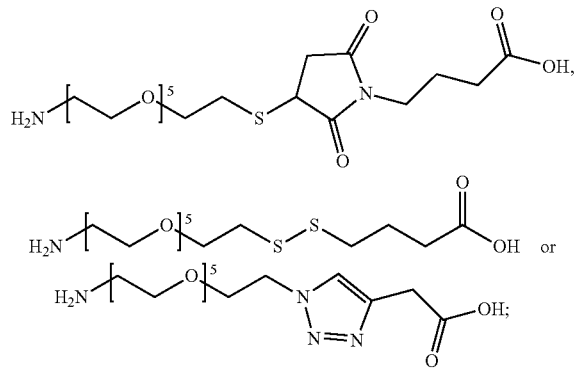

when m is 2, said X can be —NH$_2$ in the PEG that linked to AA0 or AA1; when m is 2, said k can be 2-4 (e.g., 2, 3 or 4) in the PEG that linked to AA0 or AA1; when

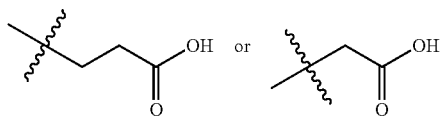 [SMILES: *CCC(=O)O ; *CC(=O)O]

m is 2, said XX0 can be in PEG linked to AA0 or AA1;

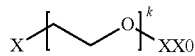

when m is 2, said can be OEG or PEG4 in the PEG that linked with AA0 or AA1;

said can be a chemical bond, "OEG", "PEG4", "PEG8", "OEG-OEG", "PEG4-PEG4",

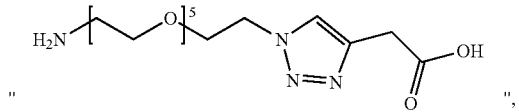

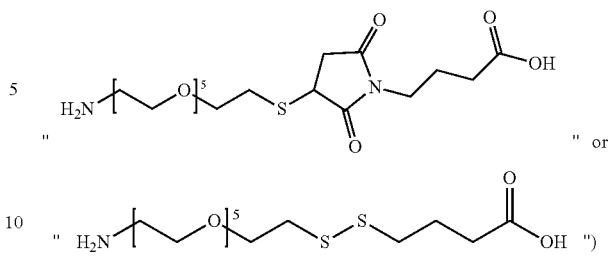

n is 0 to 3 (e.g., 0, 1, 2 or 3);

All of AA0s are independently Gly, Beta-Ala, Ahx or Ac-Lys; (for example,

when n is 2 or 3, at least 2 of AA0s are Gly; for another example, can be a chemical bond, "Gly-Gly" or "Ac-Lys-Gly-Gly" {the left side of which is linked to XX0})

however, when q is 0, then m and n are not 0 at the same time; (i.e.

is not acetyl; for example, when m is 0 and n is 0, q is 1 to 18;

for another example, any two of the following values can be selected as of two endpoints of a range: 1, 2, 3, 4, 5, 6, 7, 8, 9, 10, 11, 12, 13, 14, 15, 16, 17, and 18; for another example, 4-14);

PEG' is

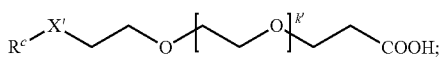

R$^c$ is C$_{14}$-C$_{18}$ linear alkyl (e.g., C$_{16}$ linear alkyl), X' is "five- or six-membered heteroaryl, wherein the heteroatom is one or more of N, O and S, and the number of the heteroatom is 1-3" (e.g., "five- or six-membered heteroaryl, wherein the heteroatom is N, the number of the heteroatom is 1-3 five-membered or six-membered heteroaryl", for another example,

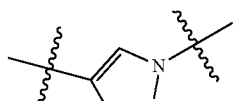

{the left end of which is linked to $R^c$}) or

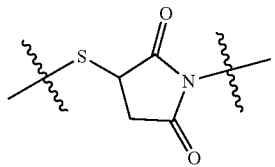 [SMILES: *SC1CC(=O)N(*)C1=O]

(the left end of which is linked to $R^c$), and k' is 5-9 (e.g., 5-7);

(said PEG' can be

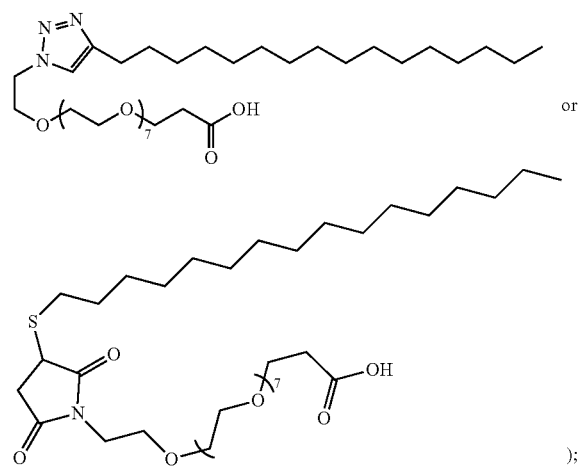

n' is 0-3 (e.g., 0, 1, 2 or 3, or e.g., 2);

All of AA0' are independently Gly, Beta-Ala, Ahx or Ac-Lys; (for example, when n' is 2 or 3, at least 2 of AA0' are Gly; for another example,

can be a chemical bond, "Gly-Gly" or "Ac-Lys-Gly-Gly" {the left side of which is linked to PEG'})

AA1 is an amino acid which is unsubstituted or the amino group is substituted (when the amino acid has a plurality of amino groups, the amino group can be located on a chiral carbon atom, or can also be a primary amino group) by a $C_{1-3}$ alkyl group (e.g., methyl, ethyl, n-propyl or isopropyl) (the "substituted amino acids" is for example N-Me-Phe or N-Me-D-Phe), wherein the amino acid is selected from: Tyr, D-Tyr, Thi, (S)-Pip, αMeTyr, 1Nal, 2Nal, 4Pal, Dap(Dnp), D-2Fua, Pro(5Ph), 2Pal, 3Pal, Tyr(Me), Ala(dip), A6c, ACPA, D-Tic, 3-[(1-methylpyridinium)-3-yl] alanine, and

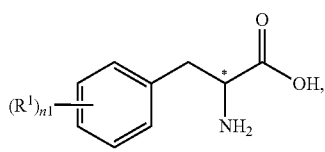

{e.g., Phe, D-Phe, Phe(4-F), D-Phe(4-F), Phe(3-Cl), D-Phe (3-Cl), Phe(4-Cl), D-Phe(4-Cl), Phe(4-I), D-Phe(4-I), Phe (4-Me), Phe(4-tBu), or, D-Phe (2,4-diCl)}; N1 is 0 to 2 (e.g., 0, 1 or 2), all of R1 are independently methyl, methoxy, $C_4$ alkoxy (e.g., isobutoxy) or halogen (e.g., fluorine, chlorine or iodine), the carbon atom marked with * is a chiral carbon atom, which is in R configuration or S configuration (all $R^1$ can be independently located at the ortho, meta or para position of the amino acid side chain, for example, when n1 is 1, $R^1$ can be located at the meta or para position of the amino acid side chain; when n1 is 2, $R^1$ can be located at the ortho and para positions of the amino acid side chain; for another example, it can be

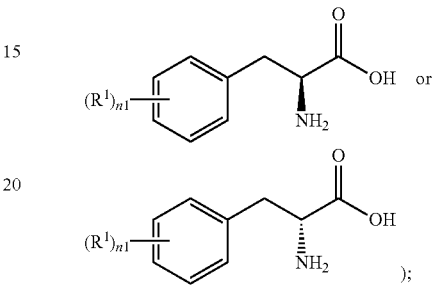

AA2 is Asn, Hyp, Pro, Ala, Thz, Pro(diF), Pro(4-NH$_2$), Thi, ACPA, D-2Fua, A6c, azaPro, Ind, (S)-Pip, (R)-Pip, Oic, AlphaMeLeu, Cba, A6c, Aze, CPA or D-Tic;

XX3 is Trp, Ala, Phe(4-I) or a chemical bond;

AA5 is 2Fua, Thr or Ser;

AA6 is an amino acid whose the amino group is unsubstituted or substituted (when the amino acid has a plurality of amino groups, the amino group can be located on a chiral carbon atom, and can also be a primary amino group) by a $C_{1-3}$ alkyl group (e.g., methyl, ethyl, n-propyl or isopropyl) (the "substituted amino acids" is for example N-Me-Phe), wherein the amino acid is selected from: 1Nal, 2Nal, αMePhe, 4Pal, HoPhe, BetaPhe, BetaHomoPhe, Bpa, D-2Fua, A6c, Tic, azaPhe, and

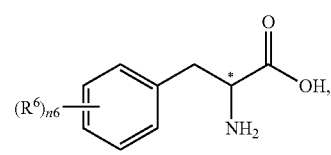

{e.g. Phe, D-Phe, Phe(4-F), Phe(pentaF), Phe(3-Cl), Phe(2-Br), Phe(4-I), Phe(4-tBu), or, Phe (4-CF3)}; n6 is 0, 1 or 2, all of $R^6$ are independently $C_1$-$C_4$ alkyl (e.g., methyl, ethyl, isopropyl or isobutyl) or halogen (e.g., fluorine, chlorine, bromine or iodine), and the carbon atom marked with * is a chiral carbon atom, which is in R configuration or S configuration (all of $R^6$ can be independently located at the ortho, meta or para position of the amino acid side chain, for example, when n6 is 1, $R^6$ can be located at the ortho, meta or para position of the amino acid side chain; for another example, it can be

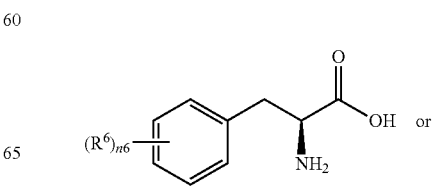

-continued

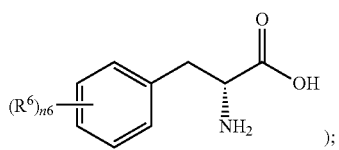

AA7 is an amino acid whose the amino group is unsubstituted or substituted (when the amino acid has a plurality of amino groups, the amino group can be located on a chiral carbon atom, or can also be a primary amino group) by a $C_{1-3}$ alkyl group (e.g., methyl, ethyl, n-propyl or isopropyl) (the "substituted amino acids" is for example N-Me-A6c or aza-N-Me-Gly) wherein the amino group is selected form: Gly, azaGly, Ala, Alg, Ava, Aib, Sar, Chg, BetaAla, ACPO, Aze, D-2Fua, A6c, azaPro, Ind, (S)-Pip, (R)-Pip, Oic, Hyp, cycloLeu, BetaHomoAla, Cba, ACPA, Alg, morpholino cyclic amino acid, beta-(thiazoly-4-yl)-L-Ala,

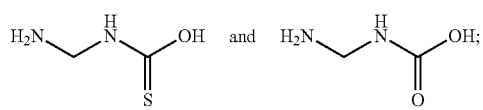 [SMILES: NCNC(O)=S ; NCNC(=O)O]

When AA6 is

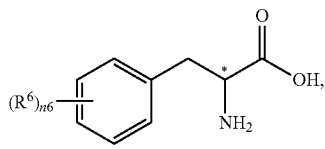

the term "AA6-AA7" refers to a group containing

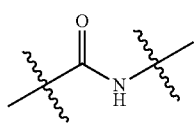 [SMILES: *NC(*)=O]

that formed by joining the carboxyl group of AA6 (when the amino acid has a plurality of carbonyls, the carbonyl groups can be located on a chiral carbon atom) to the amino group of AA7 (when the amino acid has a plurality of amino groups, the amino group can be located on a chiral carbon atom, or can also be a primary amino group), or the group formed after the

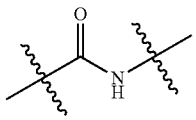 [SMILES: *NC(*)=O]

in "the group containing

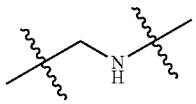 [SMILES: *CN*]

that formed by joining the carboxyl group of AA6 to the amino group of AA7" is substituted with the groups shown below:

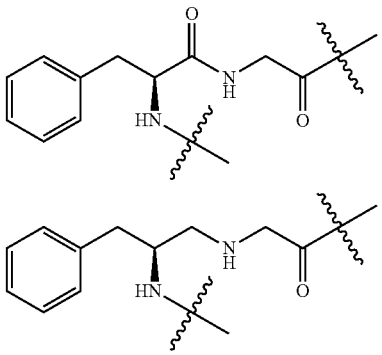

and the left end of the group is linked to AA6 (for example, when AA6 is Phe and AA7 is Gly, "AA6-AA7" refers to

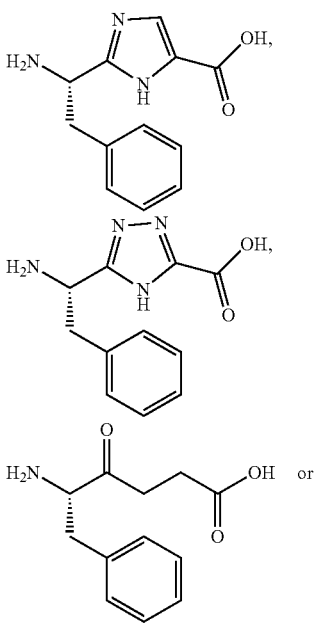

Alternatively, AA6 and AA7 together form

-continued

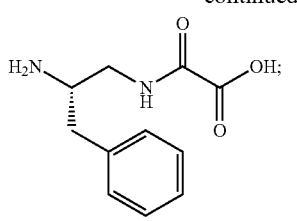

"AA7-Leu" refers to a group containing

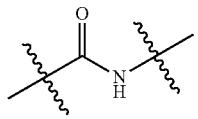 [SMILES: *NC(*)=O]

that formed by joining the carboxyl group of AA7 (which can be a carboxyl group on a chiral carbon atom when the amino acid has a plurality of carboxyl groups) to the amino group of Leu (which can be an amino group on a chiral carbon atom or a primary amino group when the amino acid has a plurality of amino groups), or the group formed after the

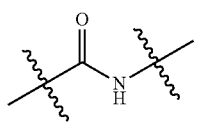 [SMILES: *NC(*)=O]

in "the group containing

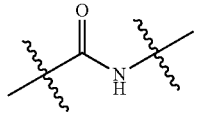 [SMILES: *NC(*)=O]

formed by joining the carboxyl group of AA7 to the amino group of Leu" is substituted by

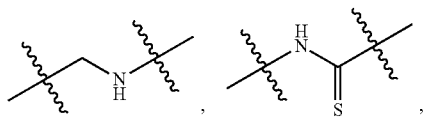

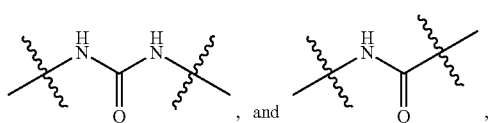

and the left end of the group is linked with AA7 (for example, when AA7 is Gly and AA7 is Leu, "AA7-Leu refers to

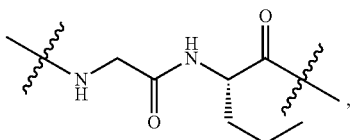

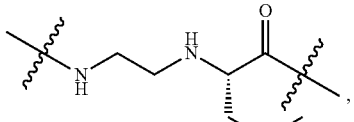

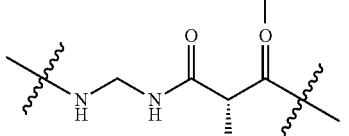

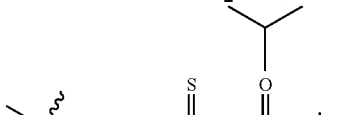

or

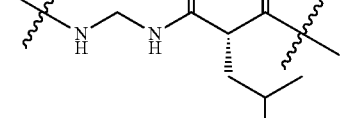

)

AA9 is an amino acid whose the amino group is unsubstituted or substituted (when the amino acid has a plurality of amino groups, the amino group can be located on a chiral carbon atom, or can also be a primary amino group) by a $C_{1-3}$ alkyl group (e.g., methyl, ethyl, n-propyl or isopropyl) (the "substituted amino acids" is, for example, N-Me-Arg, N-Me-HoLeu or N-ME-D-HoLeu), wherein the amino acid is selected from: ARG, Arg(Me), Ala, His, HOLEU, D-Ho-Leu, 4Pal, Phe(4-amidino), and

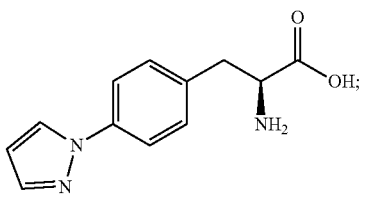 [SMILES: N[C@@H](Cc1ccc(-n2cccn2)cc1)C(=O)O]

AA10 is an amino acid whose the amino group is unsubstituted or substituted (when the amino acid has a plurality of amino groups, the amino group can be located on a chiral carbon atom, or can also be a primary amino group) by a $C_{1-3}$ alkyl group (e.g., methyl, ethyl, n-propyl or isopropyl) (the "substituted amino acids" is, for example, n-me-phe), wherein the amino acid is selected from: Trp, αMePhe, 1Nal, 2Nal, 4Pal, BetaPhe, BetaHoPhe, Bpa, NPhe, D-2Fua, A6c, Tic, and

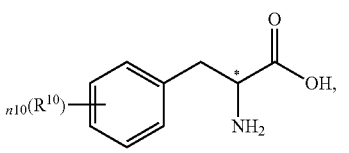

{e.g. Phe, D-Phe, Phe(4-F), Phe(pentaF), Phe(3-Cl), Phe(2-Br), Phe(4-I), Phe(4-tBu), or, Phe (4-CF3)}; n10 is 0, the carbon atom marked with * is a chiral carbon atom, which is in R configuration or S configuration (all of $R^{10}$ can be independently located at the ortho, meta or para position of the amino acid side chain, for example, when n6 is 1, $R^{10}$ can be located at the ortho, meta or para position of the amino acid side chain; for another example, it can be

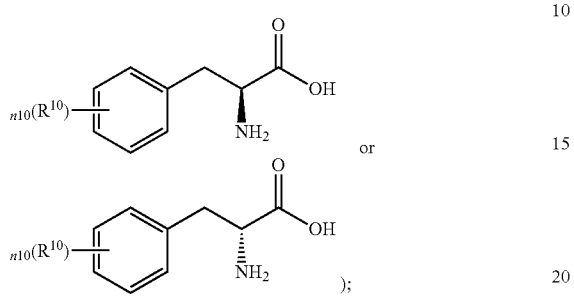

P is —NH$_2$, —OH, —NH-tBu, —NH-Et, —NH-Me, 1H-1,2,3-triazol-4-yl or 2H-tetrazole-5-yl.

In a certain technical solution, the definition of each group in the compound 1 can be as follows (the uncommented definition is as described above):

Where Cap is

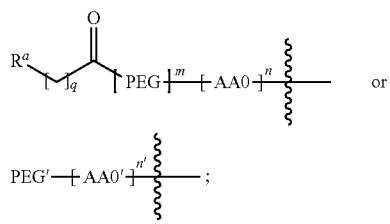

$R^a$ is CH$_3$—, q is 0-14 (for example, any two of the following values can be selected as two endpoints of a range: 0, 1, 2, 3, 4, 5, 6, 7, 8, 9, 10, 11, 12, 13 and 14; for another example, 4-14); alternatively, $R^a$ is HOOC—, q is 14 to 18 (for example, any two of the following values can be selected as two endpoints of a range: 14, 15, 16, 17 and 18; for another example, 14-16);

m is 0 to 2 (e.g. 0, 1 or 2);

PEG is independently

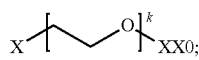

X is independently —NHR$^b$, R$^b$ is independently hydrogen; k is independently 2-8 (for example, any two of the following values can be selected as two endpoints of a range any two of the following values can be selected as two endpoints of a range: 2, 3, 4, 5, 6, 8, for another example 4-8); XX0 is independently,

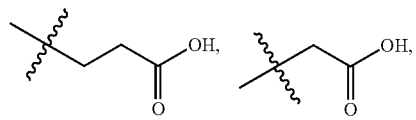

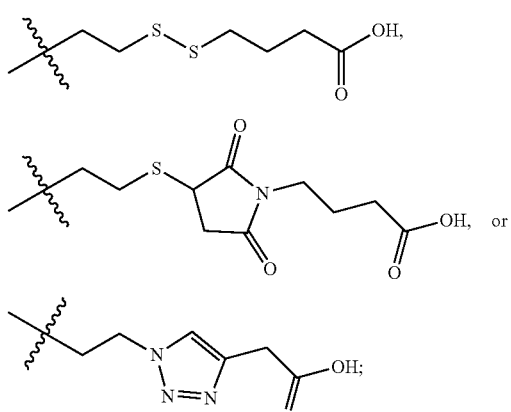

(said

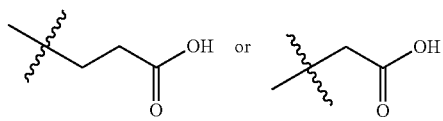 [SMILES: *CCC(=O)O ; *CC(=O)O]

is independently OEG, PEG4, PEG5, PEG8,

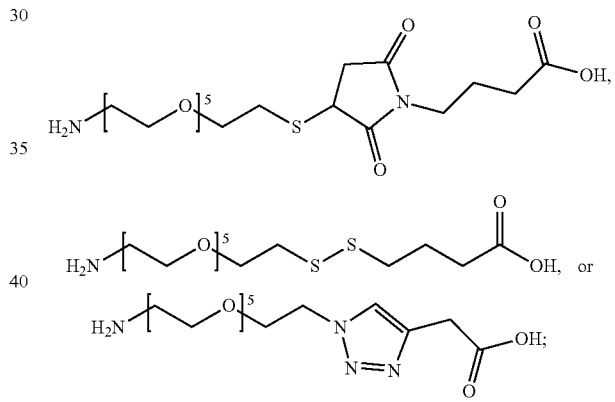

when m is 2, said X can be —NH$_2$ in the PEG that linked to AA0 or AA1; when m is 2, said k can be 2-4 (e.g., 2, 3 or 4) in the PEG that linked to AA0 or AA1; when m is 2, said XX0 can be in PEG linked to AA0 or AA1; when m is 2, said

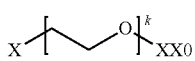

can be OEG or PEG4 in the PEG that linked with AA0 or AA1;
said

can be a chemical bond, "OEG", "PEG4", "PEG8", "OEG-OEG", "PEG4-PEG4",

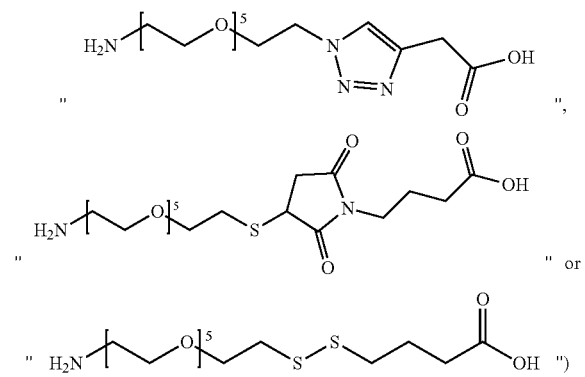

n is 0 to 3 (e.g., 0, 1, 2 or 3);
All of AA0s are independently Gly, Beta-Ala, Ahx or Ac-Lys; (for example, when n is 2 or 3, at least 2 of AA0s are Gly; for another example,

can be a chemical bond, "Gly-Gly" or "Ac-Lys-Gly-Gly" {the left side of which is linked to XX0});
however, when q is 0, m and n are not 0 at the same time;
PEG' is

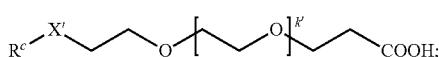

$R^c$ is $C_{14}$-$C_{18}$ linear alkyl (e.g., $C_{16}$ linear alkyl), X' is "five- or six-membered heteroaryl, wherein the heteroatom is one or more of N, O and S, and the number of the heteroatom is 1-3" (e.g., "five- or six-membered heteroaryl, wherein the heteroatom is N, the number of the heteroatom is 1-3", for another example,

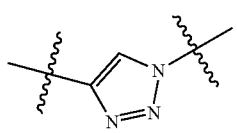 [SMILES: *c1cn(*)nn1]

{the left end of which is linked to $R^c$}) or

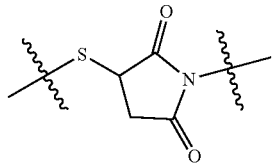 [SMILES: *SC1CC(=O)N(*)C1=O]

(the left end of which is linked to $R^c$), and k' is 5-9 (e.g., 5-7);
(said PEG' can be

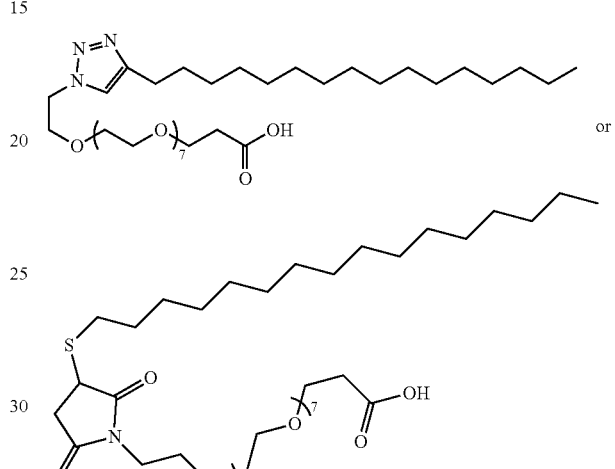

n' is 0-3 (e.g., 0, 1, 2 or 3, and e.g., 2);
All of AA0' are independently Gly, Beta-Ala, Ahx or Ac-Lys; (for example, when n' is 2 or 3, at least 2 of AA0' are Gly; for another example,

can be a chemical bond, "Gly-Gly" or "Ac-Lys-Gly-Gly" {the left side of which is linked to PEG'})
AA1 is any of the following amino acids: Tyr, D-Tyr, D-2Fua, and

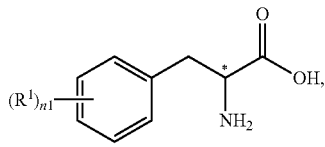

{e.g., Phe, D-Phe, Phe(4-F), D-Phe(4-F), Phe(3-Cl), D-Phe(3-Cl), Phe(4-Cl), D-Phe(4-Cl), Phe(4-I), D-Phe(4-I), Phe(4-Me), Phe(4-tBu), or D-Phe (2,4-diCl); n1 is 0 to 2 (e.g., 0, 1 or 2), all of $R^1$ are independently $C_1$-$C_4$ alkyl (e.g., methyl, ethyl, n-propyl, isopropyl, n-butyl, sec-butyl or isobutyl), $C_1$-$C_4$ alkoxy (e.g., methoxy, ethoxy, n-propoxy, isopropoxy, n-butoxy, sec-butoxy or isobutoxy) or halogen (e.g., fluorine, chlorine or iodine), and carbon atoms labeled with * are the chiral carbon atoms, which are in R configuration or S configuration (all $R^1$ can be independently located at meta, ortho and para positions of the amino acid side chains) when n1 is 2, R¹ can be located at the ortho and para positions of the amino acid side chain; for another example, it is

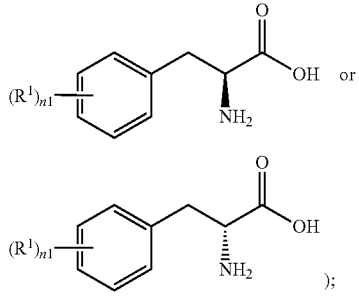

AA2 is Asn, Hyp, Thz, Pro(diF), Pro(4-NH₂), Thi, AlphaMeLeu, Cba, A6c, Aze, Cpa or A6c;

XX3 is Trp or a chemical bond;

AA5 is Thr or Ser;

AA6 is

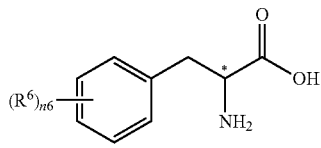

{e.g. Phe, D-Phe, Phe(4-F), Phe(pentaF), Phe(3-Cl), Phe(2-Br), Phe(4-I), Phe(4-tBu), or Phe(4-CF3)}; n6 is 0-5 (e.g., 0, 1, 2, 3, 4 or 5), and all of R⁶ are independently halogenated C1-C4 alkyl (the "halogen" is e.g., fluorine, chlorine, bromine or iodine; the "C₁-C₄ alkyl" is, for example, methyl, ethyl, n-propyl, isopropyl, n-butyl, sec-butyl or isobutyl; the "halogenated C₁-C₄ alkyl" is, for example trifluoromethyl), C₁-C₄ alkyl (e.g. methyl, ethyl, isopropyl or isobutyl) or halogen (e.g. fluorine, chlorine, bromine or iodine), the carbon atom marked with * is a chiral carbon atom, which is in R configuration or S configuration (all R⁶ can be independently located at the ortho, meta or para position of the amino acid side chain, for example, when n6 is 1, R⁶ can be located at the ortho, meta or para position of the amino acid side chain; For example, it can be

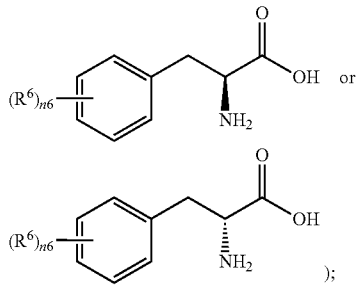

AA7 is any of the following amino acids: Gly, azaGly, Alg, Aze, D-2Fua, Alg, morpholino cyclic amino acid, beta-(thiazoly-4-yl)-L-Ala,

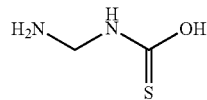

and A6c;

When AA6 is

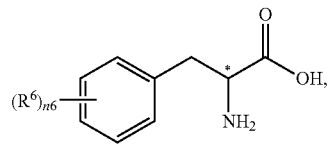

the term "AA6-AA7" refers to a group containing

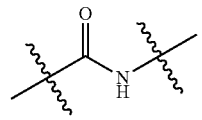 [SMILES: *NC(*)=O]

that formed by joining the carboxyl group of AA6 (when the amino acid has a plurality of amino groups, the amino group can be located on a chiral carbon atom, or can also be a primary amino group) to the amino group of AA7 (when the amino acid has a plurality of amino groups, the amino group can be located on a chiral carbon atom, or can also be a primary amino group);

When AA7 is Gly, "AA7-Leu" refers to the group containing

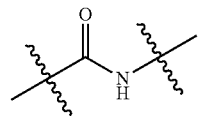 [SMILES: *NC(*)=O]

that formed by joining the carboxyl of AA7 (which can be a carboxyl group on a chiral carbon atom when the amino acid has a plurality of carboxyl groups) to the amino of Leu (when the amino acid has a plurality of amino groups, the amino group can be located on a chiral carbon atom, or can also be a primary amino group) or a group formed after the

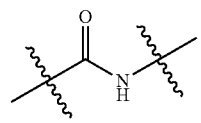 [SMILES: *NC(*)=O]

in "the group containing

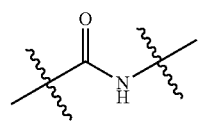 [SMILES: *NC(*)=O]

formed by joining the carboxyl group of AA7 to the amino group of Leu" is substituted by any of the following groups:

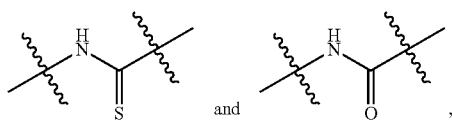 [SMILES: *NC(*)=S ; *NC(*)=O]

the left end of said group is linked with AA7 (for example, when AA7 is Gly and AA7 is Leu, "AA7-Leu" refers to

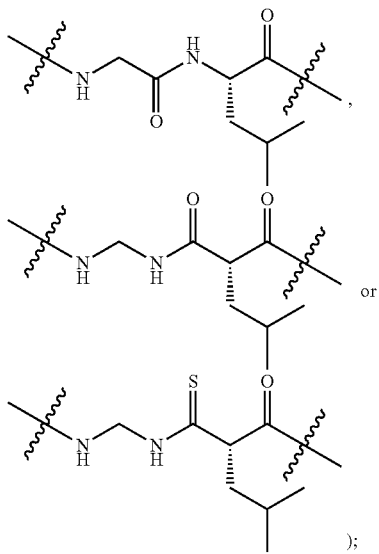

AA9 is any of the following amino acids: Arg and Arg(Me);

AA10 is Trp, or

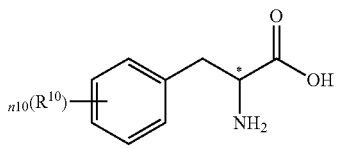

{e.g., Phe, D-Phe, Phe(4-F), Phe(pentaF), Phe(2-Br), Phe (4-I), or, Phe(4-CF3)}; n10 is 0-5 (e.g., 0, 1, 2, 3, 4 or 5), and all $R^{10}$ are independently halogenated $C_1$-$C_4$ alkyl (the "halogen" is, for example fluorine, chlorine, bromine or iodine; The "$C_1$-$C_4$ alkyl" is, for example methyl, ethyl, n-propyl, isopropyl, n-butyl, sec-butyl or isobutyl; said "halogenated $C_1$-$C_4$ alkyl" is, for example trifluoromethyl) or halogen (e.g. fluorine, chlorine, bromine or iodine), the carbon atom marked with * is a chiral carbon atom, which is in R configuration or an S configuration (all $R^{10}$ can be independently located at the ortho, meta or para position of the amino acid side chain, for example, when n10 is 1, $R^{10}$ can be located at the ortho or para position of the amino acid side chain; for example, it can be

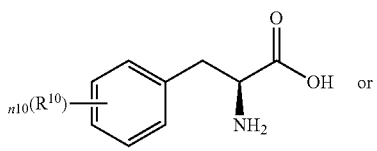

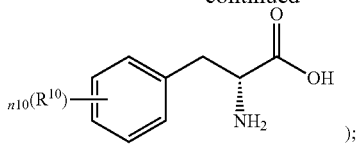

P is —$NH_2$.

In a certain technical solution, the definition of each group in the compound 1 can be as follows (the uncommented definition is as described above):

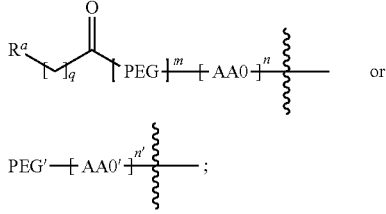

Where Cap is $R^a$ is $CH_3$—, q is 0-14 (for example, any two of the following values can be selected as two endpoints of a range: 0, 1, 2, 3, 4, 5, 6, 7, 8, 9, 10, 11, 12, 13 and 14; for another example, 4-14); alternatively, $R^a$ is HOOC—, q is 14 to 18 (for example, any two of the following values can be selected as two endpoints of a range: 14, 15, 16, 17 and 18; for another example, 14-16);

m is 0 to 2 (e.g. 0, 1 or 2);

PEG is independently

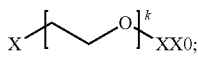

X is independently —$NHR^b$, $R^b$ is independently hydrogen; k is independently 2-8 (for example, any two of the following values can be selected as two endpoints of a range: 2, 3, 4, 5, 6, 8, for another example 4-8); XX0 is independently,

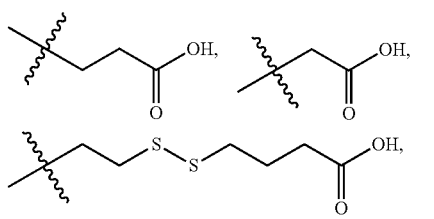

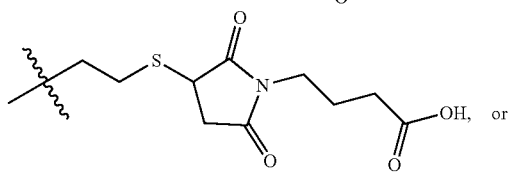

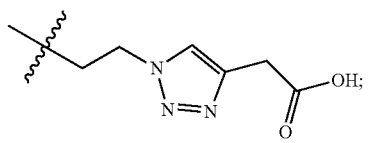

(said

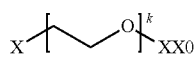

is independently OEG, PEG4, PEG5, PEG8,

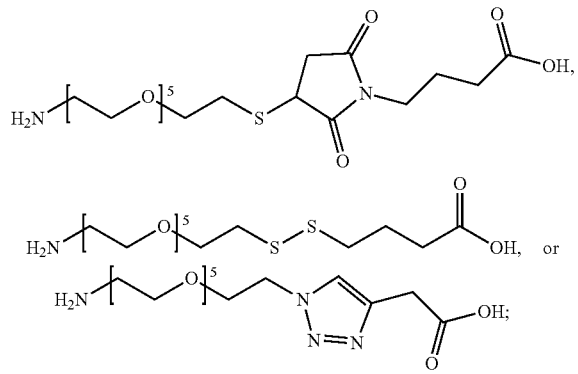

when m is 2, said X can be —NH$_2$ in the PEG that linked to AA0 or AA1; when m is 2, said k can be 2-4 (e.g., 2, 3 or 4) in the PEG that linked to AA0 or AA1; when m is 2, said XX0 can be

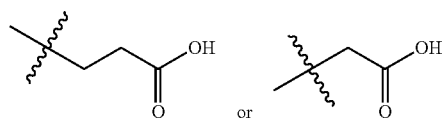 [SMILES: *CCC(=O)O ; *CC(=O)O]

in PEG linked to AA0 or AA1; when m is 2, said

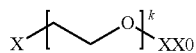

can be OEG or PEG4 in the PEG that linked with AA0 or AA1;

said

can be a chemical bond, "OEG", "PEG4", "PEG8", "OEG-OEG", "PEG4-PEG4",

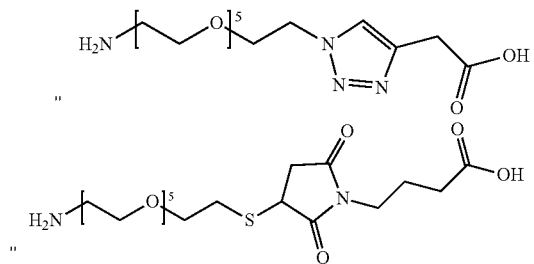

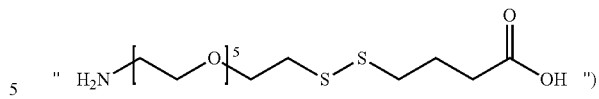

n is 0 to 3 (e.g., 0, 1, 2 or 3);

All of AA0s are independently Gly, Beta-Ala, Ahx or Ac-Lys; (for example, when n is 2 or 3, at least 2 of AA0s are Gly; and for another example,

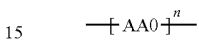

can be a chemical bond, "Gly-Gly" or "Ac-Lys-Gly-Gly" {the left side of which is linked to XX0})

However, when q is 0, m and n are not 0 at the same time;

PEG' is

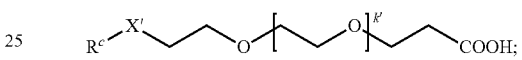

R$^c$ is C$_{14}$-C$_{18}$ linear alkyl (e.g., C$_{16}$ linear alkyl), X' is

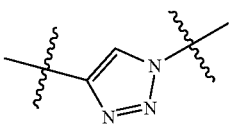 [SMILES: *c1cn(*)nn1]

{the left end of which is linked to R$^c$}) or

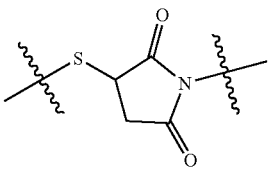 [SMILES: *SC1CC(=O)N(*)C1=O]

(the left end of which is linked to R$^c$), and k' is 5-9 (e.g., 5-7);

(said PEG' can be

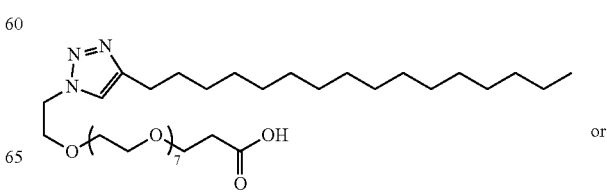

or

-continued

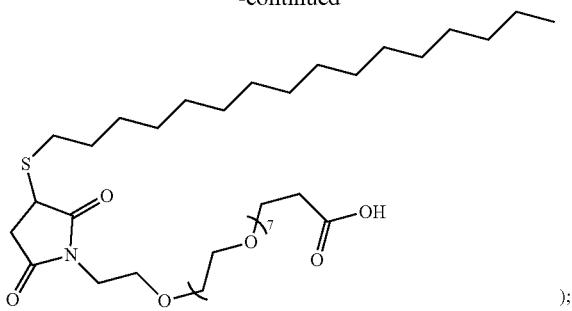

n' is 0-3 (e.g., 0, 1, 2 or 3, and e.g., 2);

All of AA0' are independently Gly, Beta-Ala, Ahx or Ac-Lys; (for example, when n' is 2 or 3, at least 2 of AA0' are Gly; and for another example,

can be a chemical bond, "Gly-Gly" or "Ac-Lys-Gly-Gly" {the left side of which is linked to PEG'})

AA1 is Tyr, D-Tyr, D-2Fua, D-Phe(4-I) or Phe (4-I);

AA2 is Asn, Hyp, Thz, Pro(diF), Pro(4-NH$_2$), Thi, AlphaMeLeu, Cba, A6c, Aze, Cpa or A6C;

XX3 is Trp or a chemical bond;

AA5 is Thr or Ser;

AA6 is Phe;

AA7 is any of the following amino acids: Gly, azaGly, Alg, Aze, D-2Fua, Alg, morpholino cyclic amino acid, beta-(thiazoly-4-yl)-L-Ala, and A6c;

When AA6 is

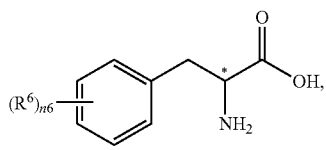

the term "AA6-AA7" refers to a group containing

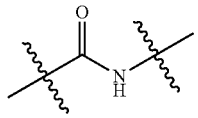 [SMILES: *NC(*)=O]

that formed by joining the carboxyl group of AA6 (when the amino acid has a plurality of amino groups, the amino group can be located on a chiral carbon atom, or can also be a primary amino group) to the amino group of AA7 (when the amino acid has a plurality of amino groups, the amino group can be located on a chiral carbon atom, or can also be a primary amino group);

When AA7 is Gly, "AA7-Leu" refers to the group containing

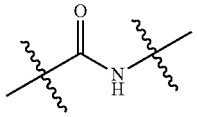 [SMILES: *NC(*)=O]

that formed by joining carboxyl of AA7 (which can be a carboxyl group on a chiral carbon atom when the amino acid has a plurality of carboxyl groups) to amino of Leu (when the amino acid has a plurality of amino groups, the amino group can be located on a chiral carbon atom, or can also be a primary amino group) or a group formed after the

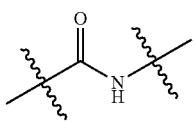 [SMILES: *NC(*)=O]

in "the group containing

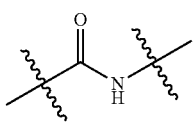 [SMILES: *NC(*)=O]

formed by joining the carboxyl group of AA7 to the amino group of Leu" is substituted by any of the following groups:

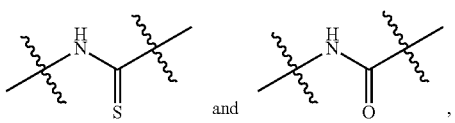 [SMILES: *NC(*)=S ; *NC(*)=O]

the left end of said group is linked with AA7 (for example, when AA7 is Gly and AA7 is Leu, "AA7-Leu" refers to

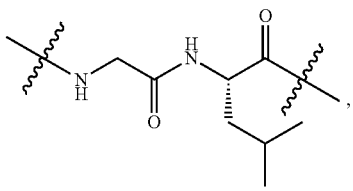

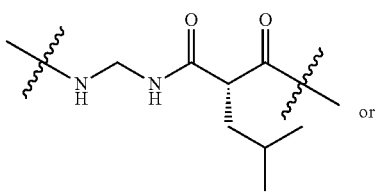 or

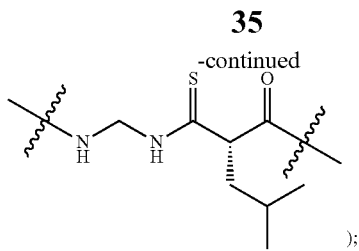

AA9 is any of the following amino acids: Arg and Arg(Me);
AA10 is Trp or Phe;
P is —NH₂.

In a certain technical solution, the definition of each group in the compound 1 can be as follows (the uncommented definition is as described above):
Where Cap is

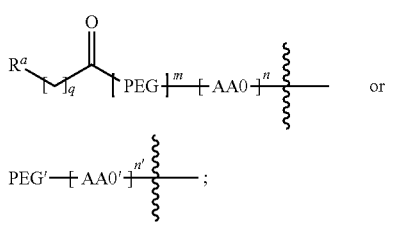

$R^a$ is CH₃—, q is 0-14 (for example, any two of the following values can be selected as two endpoints of a range: 0, 1, 2, 3, 4, 5, 6, 7, 8, 9, 10, 11, 12, 13 and 14; for another example, 4-14); alternatively, $R^a$ is HOOC—, q is 14 to 18 (for example, any two of the following values can be selected as two endpoints of a range: 14, 15, 16, 17 and 18; for another example, 14-16);
m is 0 to 2 (e.g. 0, 1 or 2);
PEG is independently

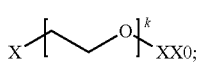

X is independently —NHR$^b$, R$^b$ is independently hydrogen; k is independently 2-8 (for example, any two of the following values can be selected as two endpoints of a range any two of the following values can be selected as two endpoints of a range: 2, 3, 4, 5, 6, 8, for another example 4-8); XX0 is independently,

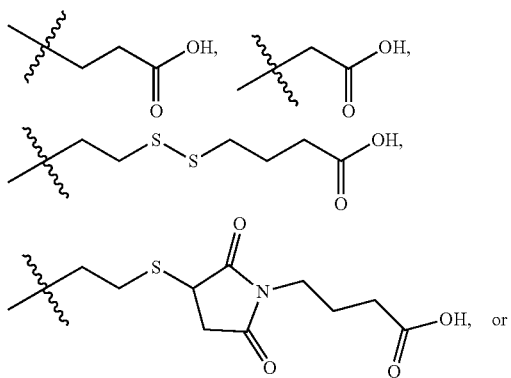

(said

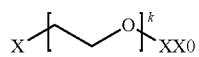

is independently OEG, PEG4, PEG5, PEG8,

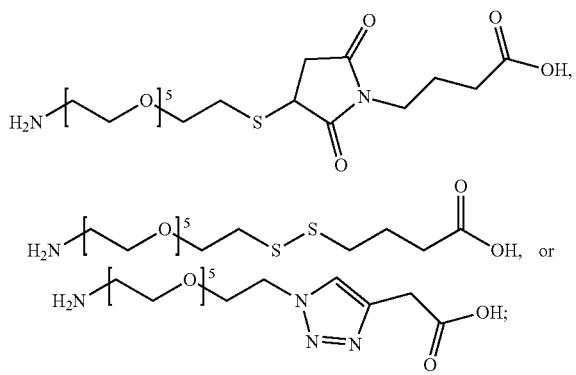

when m is 2, said X can be —NH₂ in the PEG that linked to AA0 or AA1; when m is 2, said k can be 2-4 (e.g., 2, 3 or 4) in the PEG that linked to AA0 or AA1; when m is 2, said XX0 can be

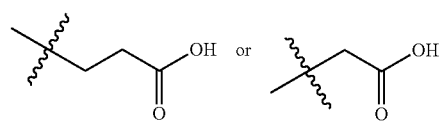 [SMILES: *CCC(=O)O ; *CC(=O)O]

in PEG linked to AA0 or AA1; when m is 2, said

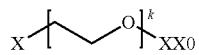

can be OEG or PEG4 in the PEG that linked with AA0 or AA1;

said can be a chemical bond, "OEG", "PEG4", "PEG8", "OEG-OEG", "PEG4-PEG4",

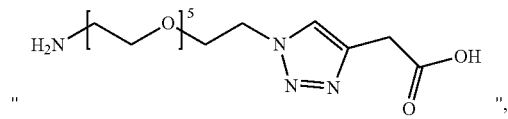

-continued

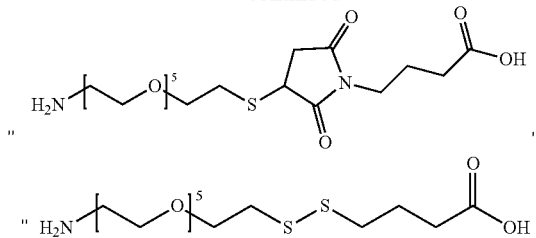
" or

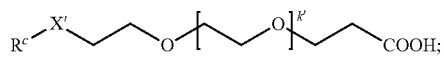
")

n is 0 to 3 (e.g., 0, 1, 2 or 3);
All of AA0s are independently Gly, Beta-Ala, Ahx or Ac-Lys; (for example, when n is 2 or 3, at least 2 of AA0s are Gly; for another example,

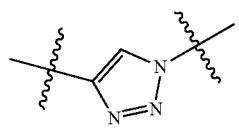 [SMILES: *c1cn(*)nn1]

can be a chemical bond, "Gly-Gly" or "Ac-Lys-Gly-Gly" {the left side of which is linked to XX0});
However, when q is 0, m and n are not 0 at the same time;
PEG' is

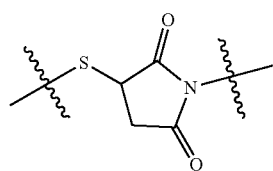 [SMILES: *SC1CC(=O)N(*)C1=O]

$R^c$ is $C_{14}$-$C_{18}$ linear alkyl (e.g., $C_{16}$ linear alkyl), X' is "five- or six-membered heteroaryl, wherein the heteroatom is one or more of n, o and s, and the number of the heteroatom is 1-3" (e.g., "five- or six-membered heteroaryl, wherein the heteroatom is n, the number of the heteroatom is 1-3", and for another example,

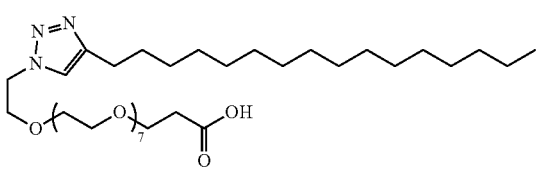

{the left end of which is linked to $R^c$}) or

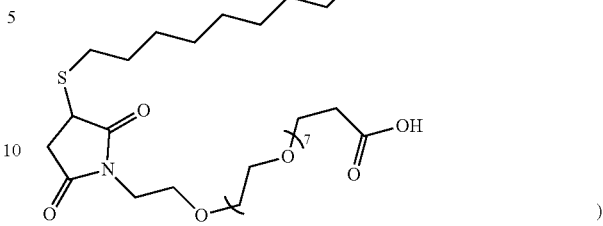

(the left end of which is linked to $R^c$), and k' is 5-9 (e.g., 5-7);
(said PEG' can be

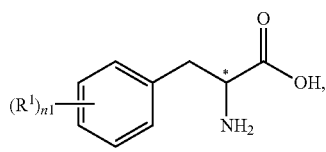
or

-continued

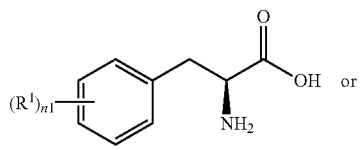
)

n' is 0-3 (e.g., 0, 1, 2 or 3, and e.g., 2);
All of AA0' are independently Gly, Beta-Ala, Ahx or Ac-Lys; (for example, when n' is 2 or 3, at least 2 of AA0' are Gly; for another example,

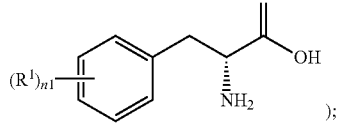

can be a chemical bond, "Gly-Gly" or "Ac-Lys-Gly-Gly" {the left side of which is linked to PEG'})
AA1 is any of the following amino acids: Tyr, D-Tyr, D-2Fua, and

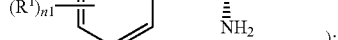

{e.g., Phe, D-Phe, Phe(4-F), D-Phe(4-F), Phe(3-Cl), D-Phe (3-Cl), Phe(4-Cl), D-Phe(4-Cl), Phe(4-I), D-Phe(4-I), Phe (4-Me), Phe(4-tBu), or D-Phe (2,4-diDl); n1 is 0 to 2 (e.g., 0, 1 or 2), all of $R^1$ are independently $C_1$-$C_4$ alkyl (e.g., methyl, ethyl, n-propyl, isopropyl, n-butyl, sec-butyl or isobutyl), $C_1$-$C_4$ alkoxy (e.g., methoxy, ethoxy, n-propoxy, isopropoxy, n-butoxy, sec-butoxy or isobutoxy) or halogen (e.g., fluorine, chlorine or iodine), and carbon atoms labeled with * are the chiral carbon atoms, which are in R configuration or S configuration (all of $R^1$ can be independently located at meta, ortho and para positions of the amino acid side chains) when n1 is 2, $R^1$ can be located at the ortho and para positions of the amino acid side chain; and for another example, it can be

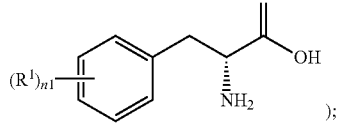 or

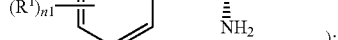
);

AA2 is Asn, Hyp, Pro(diF), Pro(4-NH$_2$) or A6c;
XX3 is Trp or a chemical bond;
AA5 is Thr or Ser;
AA6 is

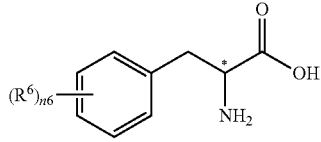

{e.g. Phe, D-Phe, Phe(4-F), Phe(pentaF), Phe(3-Cl), Phe(2-Br), Phe(4-I), Phe(4-tBu), or Phe(4-CF3)}; n6 is 0-5 (e.g., 0, 1, 2, 3, 4 or 5), and all of R$^6$ are independently halogenated C$_1$-C$_4$ alkyl (the "halogen" is e.g., fluorine, chlorine, bromine or iodine; The "C$_1$-C$_4$ alkyl" is, for example methyl, ethyl, n-propyl, isopropyl, n-butyl, sec-butyl or isobutyl; the "halogenated C$_1$-C$_4$ alkyl" is, for example trifluoromethyl), C$_1$-C$_4$ alkyl (e.g. methyl, ethyl, isopropyl or isobutyl) or halogen (e.g. fluorine, chlorine, bromine or iodine), the carbon atom marked with * is a chiral carbon atom, which is in R configuration or S configuration (all of R$^6$ can be independently located at the ortho, meta or para position of the amino acid side chain, for example, when n6 is 1, R$^6$ can be located at the ortho, meta or para position of the amino acid side chain; For example, it can be

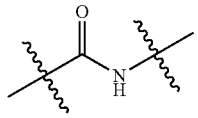 [SMILES: *NC(*)=O]

AA7 is any of the following amino acids: Gly, azaGly, Alg, Aze, D-2Fua and A6c;
When AA6 is the term "AA6-AA7" refers to a group containing

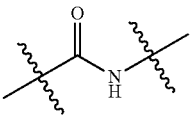

that formed by joining the carboxyl group of AA6 (when the amino acid has a plurality of amino groups, the amino group can be located on a chiral carbon atom) to the amino group of AA7 (when the amino acid has a plurality of amino groups, the amino group can be located on a chiral carbon atom, or can also be a primary amino group);

When AA7 is Gly, "AA7-Leu" refers to the group containing

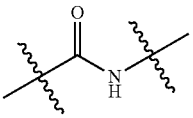 [SMILES: *NC(*)=O]

that formed by joining the carboxyl of AA7 (which can be a carboxyl group on a chiral carbon atom when the amino acid has a plurality of carboxyl groups) to the amino group of Leu (when the amino acid has a plurality of amino groups, the amino group can be located on a chiral carbon atom, or can also be a primary amino group) or a group formed after the

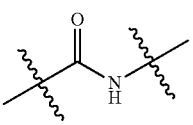

in "the group containing

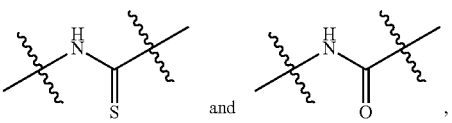 [SMILES: *NC(*)=S ; *NC(*)=O]

formed by joining the carboxyl group of AA7 to the amino group of Leu" is substituted by any of the following groups:

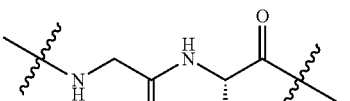

the left end of said group is linked with AA7 (for example, when AA7 is Gly and AA7 is Leu, "AA7-Leu" refers to

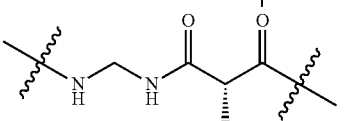

 or

-continued

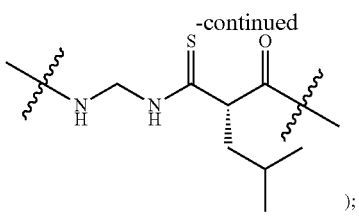
);

AA9 is any of the following amino acids: Arg and Arg(Me);
AA10 is Trp, or

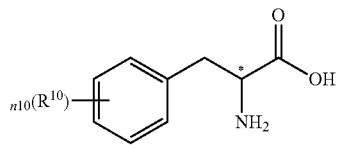

{e.g., Phe, D-Phe, Phe(4-F), Phe(pentaF), Phe(2-Br), Phe (4-I), or, Phe(4-CF3)}; n10 is 0-5 (e.g., 0, 1, 2, 3, 4 or 5), and all of $R^{10}$ are independently halogenated $C_1$-$C_4$ alkyl (the "halogen" is, for example fluorine, chlorine, bromine or iodine; The "$C_1$-$C_4$ alkyl" is, for example methyl, ethyl, n-propyl, isopropyl, n-butyl, sec-butyl or isobutyl; said "halogenated $C_1$-$C_4$ alkyl" is, for example trifluoromethyl) or halogen (e.g. fluorine, chlorine, bromine or iodine), the carbon atom marked with * is a chiral carbon atom, which is in R configuration or an S configuration (all of $R^{10}$ can be independently located at the ortho, meta or para position of the amino acid side chain, for example, when n10 is 1, $R^{10}$ can be located at the ortho or para position of the amino acid side chain; For example, it can be

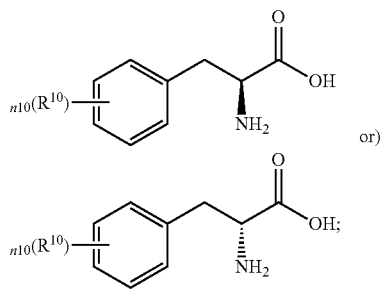

P is —$NH_2$.
In a certain technical solution, the definition of each group in the compound 1 can be as follows (the uncommented definition is as described above):

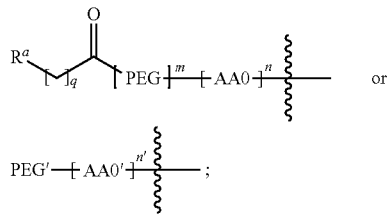

Where Cap is
$R^a$ is $CH_3$—, q is 0-14 (for example, any two of the following values can be selected as two endpoints of a range: 0, 1, 2, 3, 4, 5, 6, 7, 8, 9, 10, 11, 12, 13 and 14; for another example, 4-14); alternatively, $R^a$ is HOOC—, q is 14 to 18 (for example, any two of the following values can be selected as two endpoints of a range: 14, 15, 16, 17 and 18; for another example, 14-16);
m is 0 to 2 (e.g. 0, 1 or 2);
PEG is independently

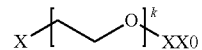

X is independently —$NHR^b$, $R^b$ is independently hydrogen; k is independently 2-8 (for example, any two of the following values can be selected as two endpoints of a range any two of the following values can be selected as two endpoints of a range: 2, 3, 4, 5, 6, 8, for another example 4-8); XX0 is independently,

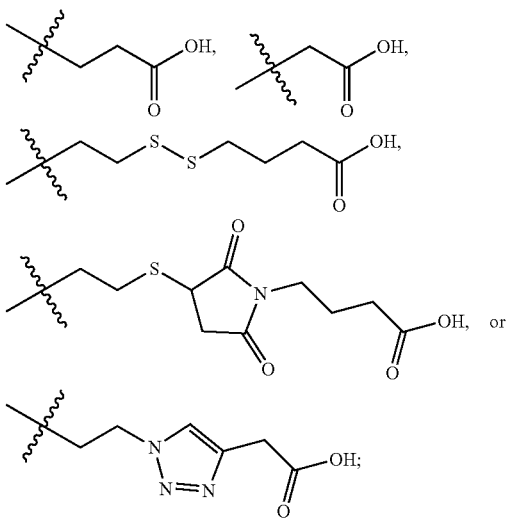

(said

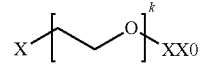

is independently OEG, PEG4, PEG5, PEG8,

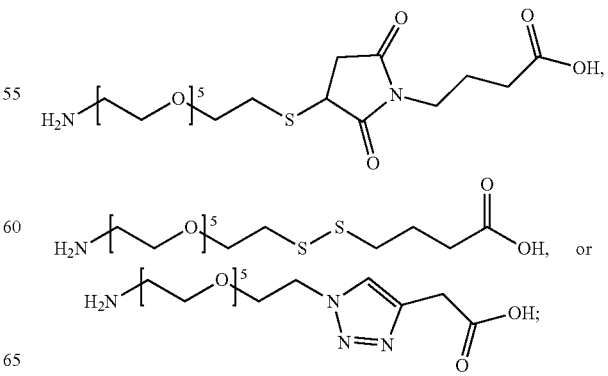

when m is 2, said X can be —NH$_2$ in the PEG that linked to AA0 or AA1; when m is 2, said k can be 2-4 (e.g., 2, 3 or 4) in the PEG that linked to AA0 or AA1; when m is 2, said XX0 can be

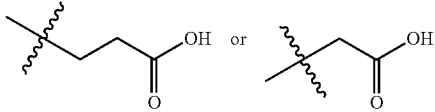 [SMILES: *CCC(=O)O ; *CC(=O)O]

in PEG linked to AA0 or AA1; when m is 2, said

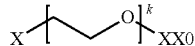

can be OEG or PEG4 in the PEG that linked with AA0 or AA1;

said

can be a chemical bond, "OEG", "PEG4", "PEG8", "OEG-OEG", "PEG4-PEG4",

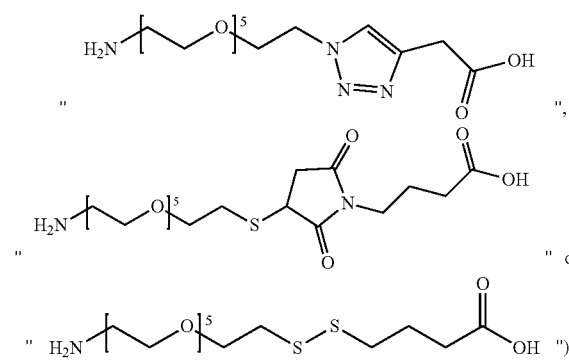

n is 0 to 3 (e.g., 0, 1, 2 or 3);

All of AA0s are independently Gly, Beta-Ala, Ahx or Ac-Lys; (for example, when n is 2 or 3, at least 2 of AA0s are Gly; and for another example,

can be a chemical bond, "Gly-Gly" or "Ac-Lys-Gly-Gly" {the left side of which is linked to XX0});

however, when q is 0, m and n are not 0 at the same time;

PEG' is

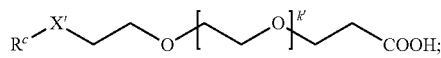

R$^c$ is C$_{14}$-C$_{18}$ linear alkyl (e.g., C$_{16}$ linear alkyl), X' is

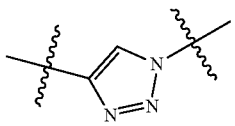 [SMILES: *c1cn(*)nn1]

{the left end of which is linked to R$^c$}) or

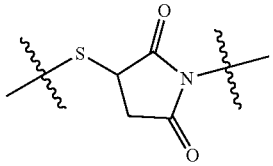 [SMILES: *SC1CC(=O)N(*)C1=O]

(the left end of which is linked to R$^c$), and k' is 5-9 (e.g., 5-7);

(said PEG' can be

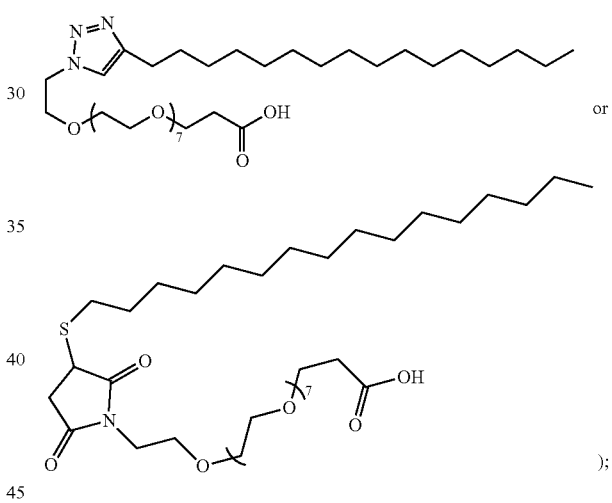

n' is 0-3 (e.g., 0, 1, 2 or 3, or e.g., 2);

All of AA0' are independently Gly, Beta-Ala, Ahx or Ac-Lys; (for example, when n' is 2 or 3, at least 2 of AA0' are Gly; and for another example,

can be a chemical bond, "Gly-Gly" or "Ac-Lys-Gly-Gly" {the left side of which is linked to PEG'});

AA1 is Tyr, D-Tyr, D-2Fua or D-Phe(4-I);

AA2 is Asn, Hyp, Pro(diF), Pro(4-NH$_2$) or A6c;

XX3 is Trp or a chemical bond;

AA5 is Thr or Ser;

AA6 is Phe;

AA7 is any of the following amino acids: Gly, azaGly, Alg, Aze, D-2Fua and A6c;

When AA6 is

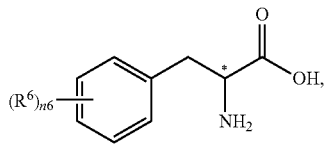

the term "AA6-AA7" refers to a group containing

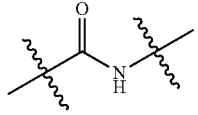 [SMILES: *NC(*)=O]

that formed by joining the carboxyl group of AA6 (when the amino acid has a plurality of amino groups, the amino group can be located on a chiral carbon atom) to the amino group of AA7 (when the amino acid has a plurality of amino groups, the amino group can be located on a chiral carbon atom, or can also be a primary amino group);

When AA7 is Gly, "AA7-Leu" refers to the group containing

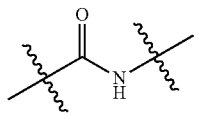 [SMILES: *NC(*)=O]

that formed by joining the carboxyl of AA7 (which can be a carboxyl group on a chiral carbon atom when the amino acid has a plurality of carboxyl groups) to the amino of Leu (when the amino acid has a plurality of amino groups, the amino group can be located on a chiral carbon atom, or can also be a primary amino group) or a group formed after the

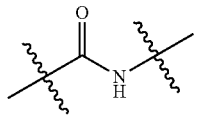

in "the group containing

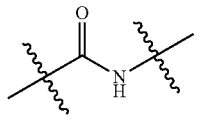 [SMILES: *NC(*)=O]

formed by joining the carboxyl group of AA7 to the amino group of Leu" is substituted by any of the following groups:

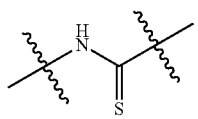 and 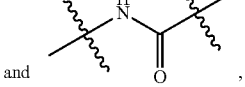, the left end of said group is linked with AA7 (for example, when AA7 is Gly and AA7 is Leu, and "AA7-Leu" refers to

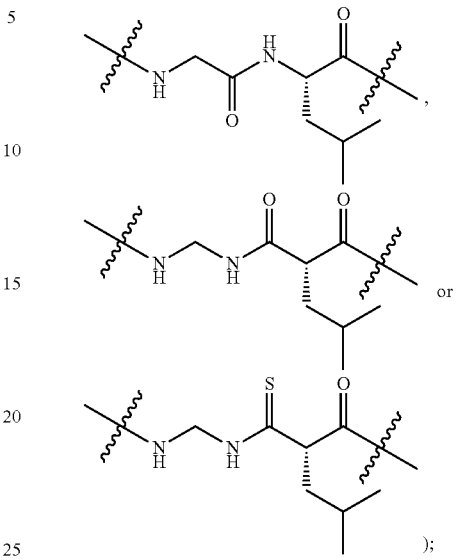);

AA9 is any of the following amino acids: Arg and Arg(Me);

AA10 is Trp or Phe;

P is —NH$_2$.

In a certain technical solution, the definition of each group in the compound 1 can be as follows (the uncommented definition is as described above):

Where Cap is

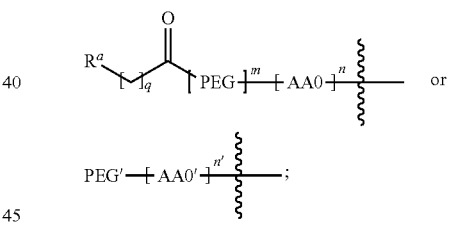

$R^a$ is CH$_3$—, q is 0-14 (for example, any two of the following values can be selected as two endpoints of a range: 0, 1, 2, 3, 4, 5, 6, 7, 8, 9, 10, 11, 12, 13 and 14; for another example, 4-14); alternatively, $R^a$ is HOOC—, q is 14 to 18 (for example, any two of the following values can be selected as two endpoints of a range: 14, 15, 16, 17 and 18; for another example, 14-16);

m is 0 to 2 (e.g. 0, 1 or 2);

PEG is independently

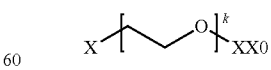

X is independently —NHR$^b$, R$^b$ is independently hydrogen; k is independently 2-8 (for example, any two of the following values can be selected as two endpoints of a range any two of the following values can be selected as two endpoints of a range: 2, 3, 4, 5, 6, 8, for another example 4-8); XX0 is independently,

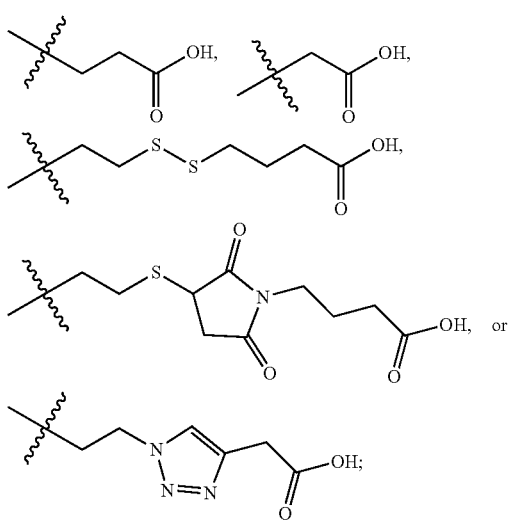

(said

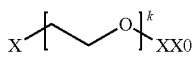

is independently OEG, PEG4, PEG5, PEG8,

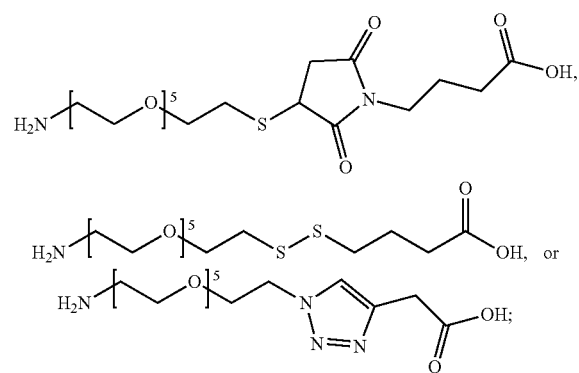

when m is 2, said X can be —NH$_2$ in the PEG that linked to AA0 or AA1; when m is 2, said k can be 2-4 (e.g., 2, 3 or 4) in the PEG that linked to AA0 or AA1; when m is 2, said XX0 can be

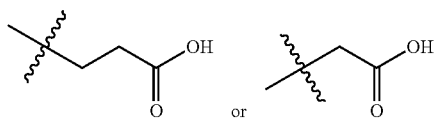 [SMILES: *CCC(=O)O ; *CC(=O)O]

in PEG linked to AA0 or AA1; when m is 2, said

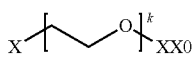

can be OEG or PEG4 in the PEG that linked with AA0 or AA1;
said

can be a chemical bond, "OEG", "PEG4", "PEG8", "OEG-OEG", "PEG4-PEG4",

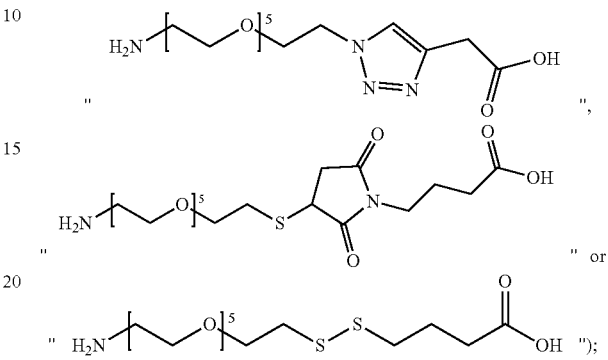

n is 0 to 3 (e.g., 0, 1, 2 or 3);
All of AA0s are independently Gly, Beta-Ala, Ahx or Ac-Lys; (for example, when n is 2 or 3, at least 2 of AA0s are Gly; and for another example,

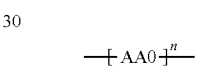

can be a chemical bond, "Gly-Gly" or "Ac-Lys-Gly-Gly" {the left side of which is linked to XX0});
however, when q is 0, m and n are not 0 at the same time;
PEG' is

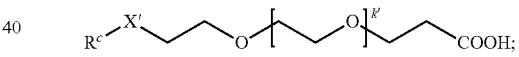

R$^c$ is C$_{14}$-C$_{18}$ linear alkyl (e.g., C$_{16}$ linear alkyl), X' is "five- or six-membered heteroaryl, wherein the heteroatom is one or more of N, O and S, and the number of the heteroatom is 1-3" (e.g., "five- or six-membered heteroaryl, wherein the heteroatom is N, the number of the heteroatom is 1-3", for another example,

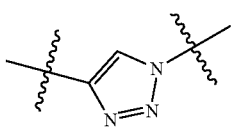 [SMILES: *c1cn(*)nn1]

{the left end of which is linked to R$^c$}) or

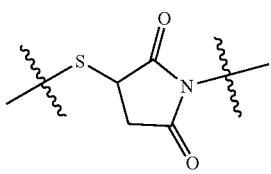 [SMILES: *SC1CC(=O)N(*)C1=O]

(the left end of which is linked to R^c), and k' is 5-9 (e.g., 5-7);

(said PEG' can be

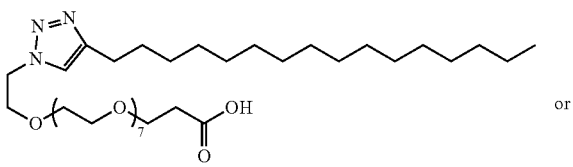

or

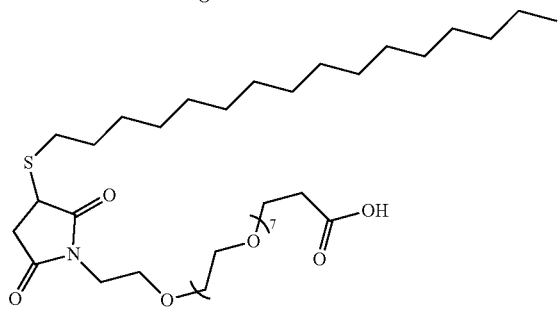

)

n' is 0-3 (e.g., 0, 1, 2 or 3, and e.g., 2);

All of AA0' are independently Gly, Beta-Ala, Ahx or Ac-Lys; (for example, when n' is 2 or 3, at least 2 of AA0' are Gly; for another example,

can be a chemical bond, "Gly-Gly" or "Ac-Lys-Gly-Gly" {the left side of which is linked to PEG'});

AA1 is any of the following amino acids: Tyr, D-Tyr, D-2Fua, and

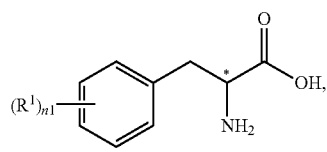

{e.g., Phe, D-Phe, Phe(4-F), D-Phe(4-F), Phe(3-Cl), D-Phe (3-Cl), Phe(4-Cl), D-Phe(4-Cl), Phe(4-I), D-Phe(4-I), Phe (4-Me), Phe(4-tBu), or D-Phe (2,4-diCl)}; n1 is 0 to 2 (e.g., 0, 1 or 2), all of $R^1$ are independently C1 to C4 alkyl (e.g., methyl, ethyl, n-propyl, isopropyl, n-butyl, sec-butyl or isobutyl), C1 to C4 alkoxy (e.g., methoxy, ethoxy, n-propoxy, isopropoxy, n-butoxy, sec-butoxy or isobutoxy) or halogen (e.g., fluorine, chlorine or iodine), and carbon atoms labeled with * are the chiral carbon atoms, which are in R configuration or S configuration (all $R^1$ can be independently located at meta, ortho and para positions of the amino acid side chains, when n1 is 2, $R^1$ can be located at the ortho and para positions of the amino acid side chain; and for another example, it can be

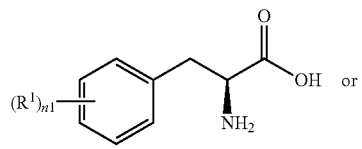

or

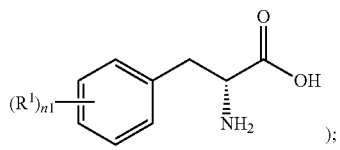

);

AA2 is Asn, Hyp, Pro(diF) or A6c;
XX3 is Trp or a chemical bond;
AA5 is Thr or Ser;
AA6 is

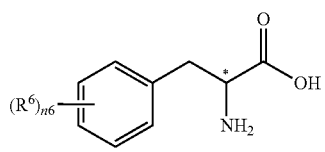

{e.g. Phe, D-Phe, Phe(4-F), Phe(pentaF), Phe(3-Cl), Phe(2-Br), Phe(4-I), Phe(4-tBu), or phe (4-CF3)}; n6 is 0-5 (e.g., 0, 1, 2, 3, 4 or 5), and all of $R^6$ are independently halogenated C1-C4 alkyl (the "halogen" is e.g., fluorine, chlorine, bromine or iodine; The "$C_1$-$C_4$ alkyl" is, for example methyl, ethyl, n-propyl, isopropyl, n-butyl, sec-butyl or isobutyl; the "halogenated $C_1$-$C_4$ alkyl" is, for example, trifluoromethyl), $C_1$-$C_4$ alkyl (e.g. methyl, ethyl, isopropyl or isobutyl) or halogen (e.g. fluorine, chlorine, bromine or iodine), the carbon atom marked with * is a chiral carbon atom, which is in R configuration or S configuration (all of $R^6$ can be independently located at the ortho, meta or para position of the of amino acid side chain, for example, when n6 is 1, $R^6$ can be located at the ortho, meta or para position of the amino acid side chain; For example, it can be

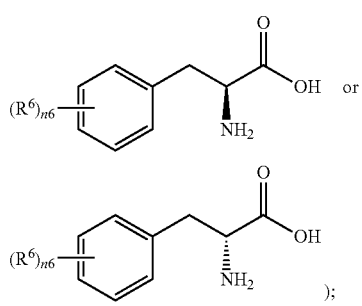

AA7 is any of the following amino acids: Gly, azaGly, Alg, Aze, D-2Fua and A6c;

When AA6 is

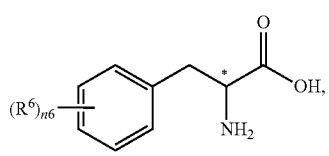

the term "AA6-AA7" refers to a group containing

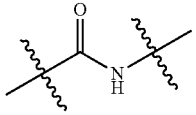 [SMILES: *NC(*)=O]

that formed by joining the carboxyl group of AA6 (when the amino acid has a plurality of amino groups, the amino group can be located on a chiral carbon atom) to the amino group of AA7 (when the amino acid has a plurality of amino groups, the amino group can be located on a chiral carbon atom, or can also be a primary amino group);

When AA7 is Gly, "AA7-Leu" refers to the group containing

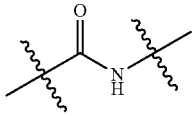 [SMILES: *NC(*)=O]

that formed by joining the carboxyl of AA7 (which can be a carboxyl group on a chiral carbon atom when the amino acid has a plurality of carboxyl groups) to the amino group of Leu (when the amino acid has a plurality of amino groups, the amino group can be located on a chiral carbon atom, or can also be a primary amino group) or a group formed after the

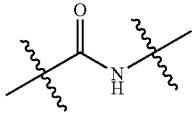 [SMILES: *NC(*)=O]

in "the group containing

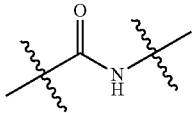 [SMILES: *NC(*)=O]

formed by joining the carboxyl group of AA7 to the amino group of Leu" is substituted by any of the following groups:

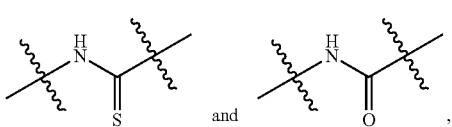 [SMILES: *NC(*)=S ; *NC(*)=O]

and the left end of said group is linked with AA7 (for example, when AA7 is Gly and AA7 is Leu, "AA7-Leu" refers to

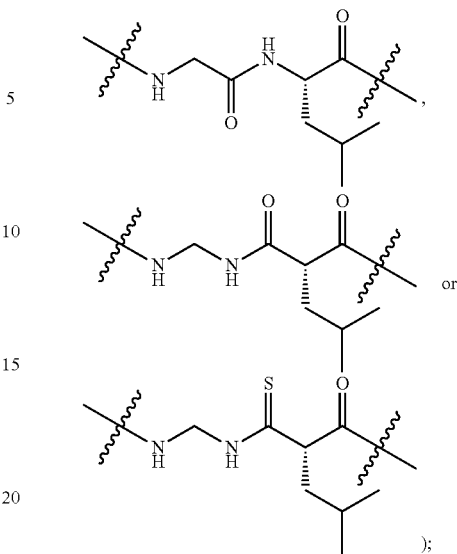

AA9 is any of the following amino acids: Arg and Arg(Me);

AA10 is Trp, or

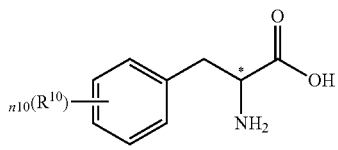

{e.g., Phe, D-Phe, Phe(4-F), Phe(pentaF), Phe(2-Br), Phe(4-I), or, Phe(4-CF3)}; n10 is 0-5 (e.g., 0, 1, 2, 3, 4 or 5), and all of $R^{10}$ are independently halogenated $C_1$-$C_4$ alkyl (the "halogen" is, for example, fluorine, chlorine, bromine or iodine; The "$C_1$-$C_4$ alkyl" is, for example, methyl, ethyl, n-propyl, isopropyl, n-butyl, sec-butyl or isobutyl; said "halogenated $C_1$-$C_4$ alkyl" is, for example, trifluoromethyl) or halogen (e.g. fluorine, chlorine, bromine or iodine), the carbon atom marked with * is a chiral carbon atom, which is in R configuration or an S configuration (all of $R^{10}$ can be independently located at the ortho, meta or para position of the amino acid side chain, for example, when n10 is 1, $R^{10}$ can be located at the ortho or para position of the amino acid side chain; For example, it can be or);

P is —$NH_2$.

In a certain technical solution, the definition of each group in the compound 1 can be as follows (the uncommented definition is as described above):

Where Cap is

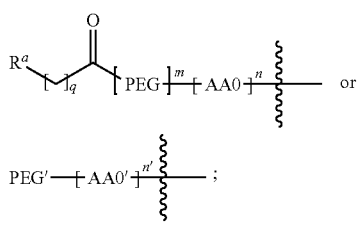

$R^a$ is $CH_3$—, q is 0-14 (for example, any two of the following values can be selected as two endpoints of a range: 0, 1, 2, 3, 4, 5, 6, 7, 8, 9, 10, 11, 12, 13 and 14; for another example, 4-14); alternatively, $R^a$ is HOOC—, q is 14 to 18 (for example, any two of the following values can be selected as two endpoints of a range: 14, 15, 16, 17 and 18; for another example, 14-16);

m is 0 to 2 (e.g. 0, 1 or 2);

PEG is independently

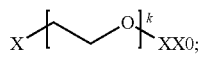

X is independently —$NHR^b$, $R^b$ is independently hydrogen; k is independently 2-8 (for example, any two of the following values can be selected as two endpoints of a range: 2, 3, 4, 5, 6, 8, for another example 4-8); XX0 is independently

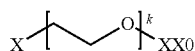

(said

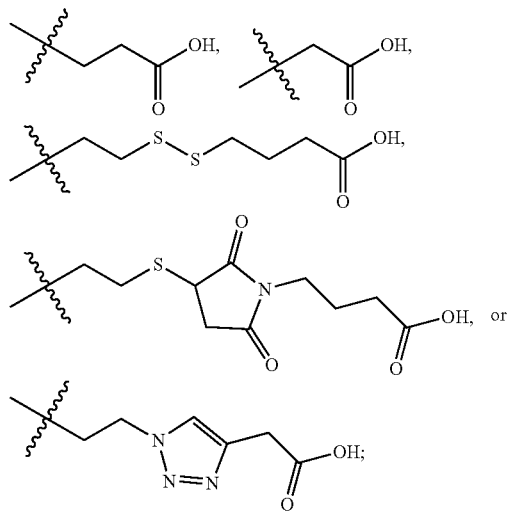

is independently OEG, PEG4, PEG5, PEG8,

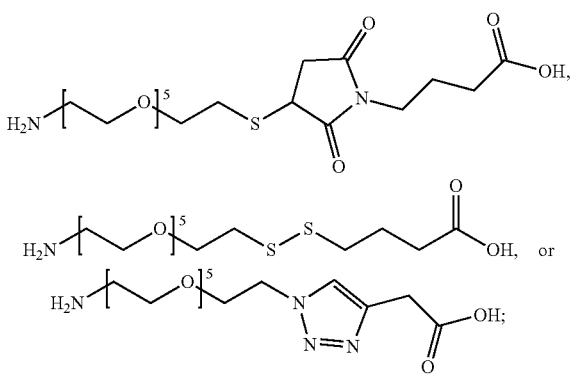

when m is 2, said X can be —$NH_2$ in the PEG that linked to AA0 or AA1; when m is 2, said k can be 2-4 (e.g., 2, 3 or 4) in the PEG that linked to AA0 or AA1; when m is 2, said XX0 can be

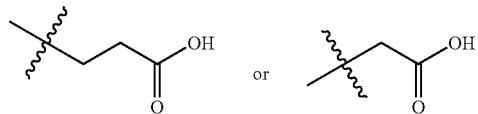 [SMILES: *CCC(=O)O ; *CC(=O)O]

in PEG linked to AA0 or AA1; when m is 2, said

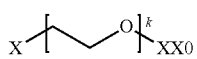

can be OEG or PEG4 in the PEG that linked with AA0 or AA1;

said

can be a chemical bond, "OEG", "PEG4", "PEG8", "OEG-OEG", "PEG4-PEG4",

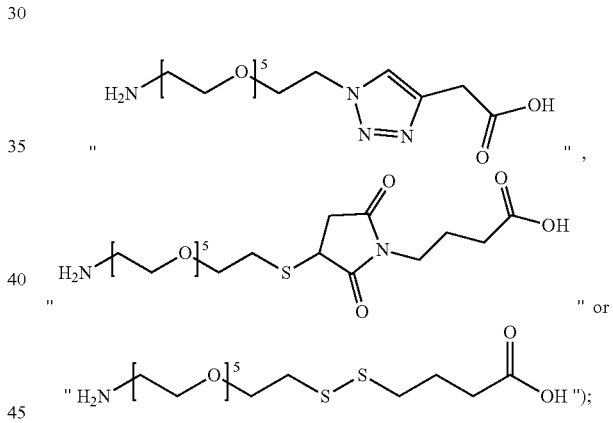

n is 0 to 3 (e.g., 0, 1, 2 or 3);

All of AA0s are independently Gly, Beta-Ala, Ahx or Ac-Lys; (for example, when n is 2 or 3, at least 2 of AA0s are Gly; for another example,

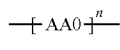

can be a chemical bond, "Gly-Gly" or "Ac-Lys-Gly-Gly" {the left side of which is linked to XX0});

however, when q is 0, m and n are not 0 at the same time;

PEG' is

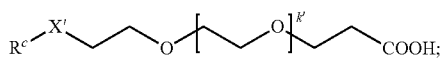

$R^c$ is $C_{14}$-$C_{18}$ linear alkyl (e.g., $C_{16}$ linear alkyl), X' is

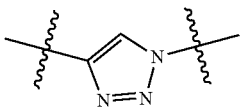 [SMILES: *c1cn(*)nn1]

{the left end of which is linked to $R^c$}) or

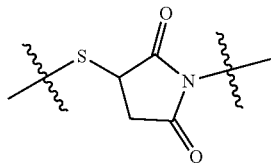 [SMILES: *SC1CC(=O)N(*)C1=O]

(the left end of which is linked to $R^c$), and k' is 5-9 (e.g., 5-7);

(said PEG' can be

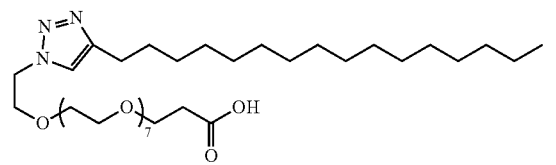

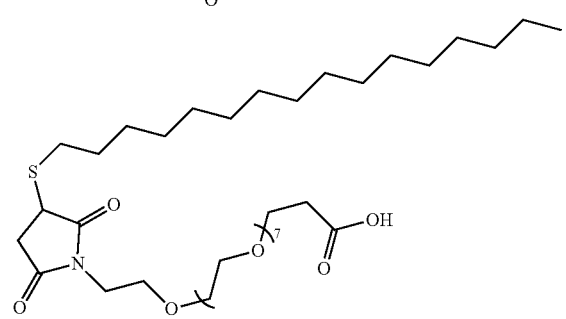
);

n' is 0-3 (e.g., 0, 1, 2 or 3, and e.g., 2);

All of AA0' are independently Gly, Beta-Ala, Ahx or Ac-Lys; (for example, when n' is 2 or 3, at least 2 of AA0' are Gly; and for another example,

can be a chemical bond, "Gly-Gly" or "Ac-Lys-Gly-Gly" {the left side of which is linked to PEG'})

AA1 is Tyr, D-Tyr, D-2Fua or Phe(4-I);

AA2 is Asn, Hyp, Pro(diF) or A6c;

XX3 is Trp or a chemical bond;

AA5 is Thr or Ser;

AA6 is Phe;

AA7 is any of the following amino acids: Gly, azaGly, Alg, Aze, D-2Fua and A6c;

When AA6 is

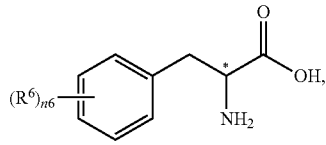

the term "AA6-AA7" refers to a group containing

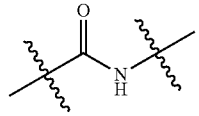 [SMILES: *NC(*)=O]

that formed by joining the carboxyl group of AA6 (when the amino acid has a plurality of amino groups, the amino group can be located on a chiral carbon atom) to the amino group of AA7 (when the amino acid has a plurality of amino groups, the amino group can be located on a chiral carbon atom, or can also be a primary amino group);

When AA7 is Gly, "AA7-Leu" refers to the group containing

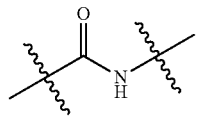 [SMILES: *NC(*)=O]

that formed by joining the carboxyl of AA7 (which can be a carboxyl group on a chiral carbon atom when the amino acid has a plurality of carboxyl groups) to the amino group of Leu (when the amino acid has a plurality of amino groups, the amino group can be located on a chiral carbon atom, or can also be a primary amino group) or a group formed after the

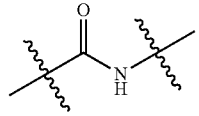 [SMILES: *NC(*)=O]

in "the group containing

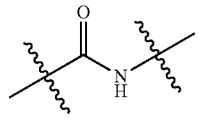 [SMILES: *NC(*)=O]

formed by joining the carboxyl group of AA7 to the amino group of Leu" is substituted by any of the following groups:

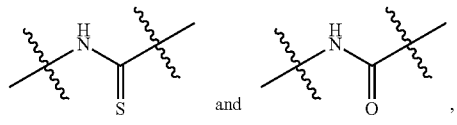 [SMILES: *NC(*)=S ; *NC(*)=O]

the left end of said group is linked with AA7 (for example, when AA7 is Gly and AA7 is Leu, "AA7-Leu" refers to

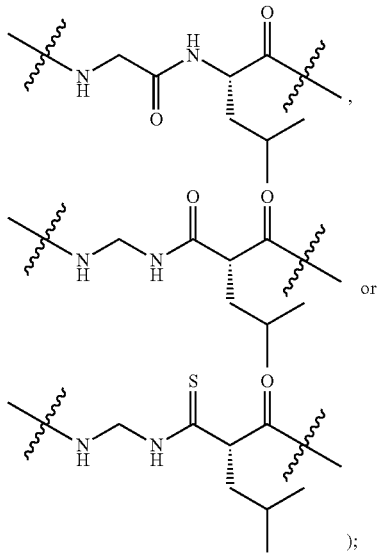

AA9 is any of the following amino acids: Arg and Arg(Me);
AA10 is Trp or Phe;
P is —NH$_2$.

In a certain technical solution, the definition of each group in the compound 1 can be as follows (the uncommented definition is as described above):
$R^a$ is CH$_3$—, q is 0-16 (for example, any two of the following values can be selected as two endpoints of a range: 0, 1, 2, 3, 4, 5, 6, 7, 8, 9, 10, 11, 12, 13, 14, 15 and 16; for another example, 0-14; for another example: 4-14);

In a certain technical solution, the definition of each group in the compound 1 can be as follows (the uncommented definition is as described above):
$R^a$ is CH$_3$—, q is 0-16 (for example, any two of the following values can be selected as two endpoints of a range: 0, 1, 2, 3, 4, 5, 6, 7, 8, 9, 10, 11, 12, 13 and 14; for another example: 4-14);

In a certain technical solution, the definition of each group in the compound 1 can be as follows (the uncommented definition is as described above):
$R^a$ is HOOC—, q is 2-18 (for example, any two of the following values can be selected as two endpoints of a range: 0, 3, 4, 5, 6, 7, 8, 9, 10, 11, 12, 13, 14, 15 and 16; for another example: 2-16);

In a certain technical solution, the definition of each group in the compound 1 can be as follows (the uncommented definition is as described above):
$R^a$ is HOOC—, q is 14-18 (for example, any two of the following values can be selected as two endpoints of a range: 14, 15, 16, and 18; for another example: 14-16).

In a certain technical solution, the definition of each group in the compound 1 can be as follows (the uncommented definition is as described above):
k is independently 2-8 (for example, any two of the following values can be selected as two endpoints of a range: 2, 3, 4, 5, 6 and 8; for another example: 4-8).

In a certain technical solution, the definition of each group in the compound 1 can be as follows (the uncommented definition is as described above):

AA1 is an amino acid whose the amino group is unsubstituted or substituted (when the amino acid has a plurality of amino groups, the amino group can be located on a chiral carbon atom, and can also be a primary amino group) by a C$_{1-3}$ alkyl group (e.g., methyl, ethyl, n-propyl or isopropyl) (the "substituted amino acids" is for example N-Me-Phe or N-Me-D-Phe), wherein the amino acid is selected from: Tyr, D-Tyr, Thi, (S)-Pip, αMeTyr, 1Nal, 2Nal, 4Pal, Dap(Dnp), D-2Fua, Pro(5Ph), 2Pal, 3Pal, Tyr(Me), Ala(dip), A6c, ACPA, D-Tic, 3-[(1-methylpyridinium)-3-yl] alanine, and

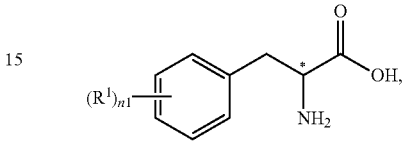

{e.g., Phe, D-Phe, Phe(4-F), D-Phe(4-F), Phe(3-Cl), D-Phe (3-Cl), Phe(4-Cl), D-Phe(4-Cl), Phe(4-I), D-Phe(4-I), Phe (4-Me), Phe(4-tBu), or, D-Phe (2,4-diCl)}; N1 is 0 to 2 (e.g., 0, 1 or 2), all of R1 are independently methyl, methoxy, C$_4$ alkoxy (e.g., isobutoxy) or halogen (e.g., fluorine, chlorine or iodine), the carbon atom marked with * is a chiral carbon atom, which is in R configuration or S configuration (all $R^1$ can be independently located at the ortho, meta or para position of the amino acid side chain, for example, when n1 is 1, $R^1$ can be located at the meta or para position of the amino acid side chain; When n1 is 2, $R^1$ can be located at the ortho and para positions of the amino acid side chain; for another example, it can be

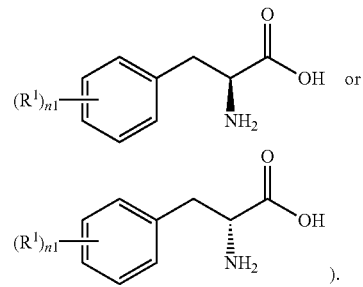

In a certain technical solution, the definition of each group in the compound 1 can be as follows (the uncommented definition is as described above):
AA1 is any of the following amino acids: Tyr, D-Tyr, D-2Fua, and

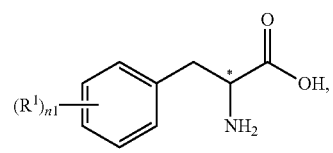

{e.g., Phe, D-Phe, Phe(4-F), D-Phe(4-F), Phe(3-Cl), D-Phe(3-Cl), Phe(4-Cl), D-Phe(4-Cl), Phe(4-I), D-Phe(4-I), Phe(4-Me), Phe(4-tBu), or D-Phe (2,4-diCl); n1 is 0 to 2 (e.g., 0, 1 or 2), all of R1 are independently C1 to C4 alkyl (e.g., methyl, ethyl, n-propyl, isopropyl, n-butyl, sec-butyl or isobutyl), C1 to C4 alkoxy (e.g., methoxy, ethoxy, n-propoxy, isopropoxy, n-butoxy, sec-butoxy or isobutoxy)

or halogen (e.g., fluorine, chlorine or iodine), and carbon atoms labeled with * are the chiral carbon atoms, which are in R configuration or S configuration (all of $R^1$ can be independently located at meta, ortho and para positions of the amino acid side chains) when n1 is 2, $R^1$ can be located at the ortho and para positions of the amino acid side chain; for another example, it can be

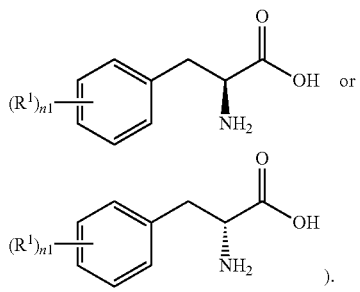

In a certain technical solution, the definition of each group in the compound 1 can be as follows (the uncommented definition is as described above):

AA1 is Tyr, D-Tyr, D-2Fua, D-Phe(4-I) or Phe(4-I);

In a certain technical solution, the definition of each group in the compound 1 can be as follows (the uncommented definition is as described above):

AA1 is Tyr, D-Tyr, D-2Fua or D-Phe (4-I).

In a certain technical solution, the definition of each group in the compound 1 can be as follows (the uncommented definition is as described above):

AA1 is Tyr, D-Tyr, D-2Fua or Phe (4-I).

In a certain technical solution, the definition of each group in the compound 1 can be as follows (the uncommented definition is as described above):

AA2 is Asn, Hyp, Pro, Ala, Thz, Pro(diF), Pro(4-NH₂), Thi, ACPA, D-2Fua, A6c, azaPro, Ind, (S)-Pip, (R)-Pip, Oic, AlphaMeLeu, Cba, A6c, Aze, CPA or D-Tic.

In a certain technical solution, the definition of each group in the compound 1 can be as follows (the uncommented definition is as described above):

AA2 is Asn, Hyp, Thz, Pro (diF), Pro(4-NH₂), Thi, AlphaMeLeu, Cba, A6c, Aze, Cpa or A6c.

In a certain technical solution, the definition of each group in the compound 1 can be as follows (the uncommented definition is as described above):

AA2 is Asn, Hyp, Pro (4-NH₂), AlphaMeLeu, Cba, A6c, Aze, Cpa or A6c.

In a certain technical solution, the definition of each group in the compound 1 can be as follows (the uncommented definition is as described above):

AA2 is Asn, Hyp, AlphaMeLeu, Cba, A6c, Aze, Cpa or A6c.

In a certain technical solution, the definition of each group in the compound 1 can be as follows (the uncommented definition is as described above):

AA2 is Asn, Hyp, Pro (4-NH₂), Pro (diF) or A6c.

In a certain technical solution, the definition of each group in the compound 1 can be as follows (the uncommented definition is as described above):

AA2 is Asn, Hyp, Pro (diF) or A6c.

In a certain technical solution, the definition of each group in the compound 1 can be as follows (the uncommented definition is as described above):

XX3 is Trp or a chemical bond.

In a certain technical solution, the definition of each group in the compound 1 can be as follows (the uncommented definition is as described above):

AA5 is Thr or Ser.

In a certain technical solution, the definition of each group in the compound 1 can be as follows (the uncommented definition is as described above):

AA6 is an amino acid whose the amino group is unsubstituted or substituted (when the amino acid has a plurality of amino groups, the amino group can be located on a chiral carbon atom, or can also be a primary amino group) by a $C_{1-3}$ alkyl group (e.g., methyl, ethyl, n-propyl or isopropyl) (the "substituted amino acids" is e.g. N-Me-Phe), wherein the amino acid is selected from: 1Nal, 2Nal, αMePhe, 4Pal, HoPhe, BetaPhe, BetaHomoPhe, Bpa, D-2Fua, A6c, Tic, azaPhe, and

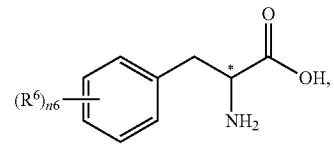

{e.g. Phe, D-Phe, Phe(4-F), Phe(pentaF), Phe(3-Cl), Phe(2-Br), Phe(4-I), Phe(4-tBu), or, phe (4-CF3)}; n6 is 0, 1 or 2, all of $R^6$ are independently $C_1$-$C_4$ alkyl (e.g., methyl, ethyl, isopropyl or isobutyl) or halogen (e.g., fluorine, chlorine, bromine or iodine), the carbon atom marked with * is a chiral carbon atom, which is in R configuration or S configuration (all of $R^6$ can be independently located at the ortho, meta or para position of the amino acid side chain, for example, when n6 is 1, $R^6$ can be located at the ortho, meta or para position of the amino acid side chain; for another example, it can be

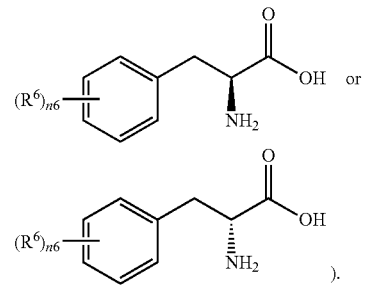

In a certain technical solution, the definition of each group in the compound 1 can be as follows (the uncommented definition is as described above):

AA6 is

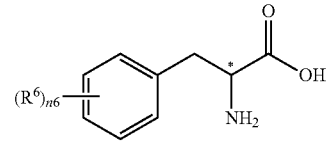

{e.g. Phe, D-Phe, Phe(4-F), Phe(pentaF), Phe(3-Cl), Phe(2-Br), Phe(4-I), Phe(4-tBu), or phe}; n6 is 0-5 (e.g., 0, 1, 2, 3, 4 or 5), and all of $R^6$ are independently halogenated $C_1$-$C_4$ alkyl (the "halogen" is e.g., fluorine, chlorine, bromine or iodine; the "$C_1$-$C_4$ alkyl" is, for example methyl, ethyl, n-propyl, isopropyl, n-butyl, sec-butyl or isobutyl; the "halogenated $C_1$-$C_4$ alkyl" is, for example trifluoromethyl), $C_1$-$C_4$ alkyl (e.g. methyl, ethyl, isopropyl or isobutyl) or halogen (e.g. fluorine, chlorine, bromine or iodine), the carbon atom marked with * is a chiral carbon atom, which is in R configuration or S configuration (all of $R^6$ can be independently located at the ortho, meta or para position of the amino acid side chain, for example, when n6 is 1, $R^6$ can be located at the ortho, meta or para position of the amino acid side chain; For example, it can be

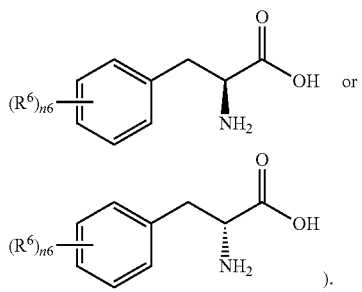

In a certain technical solution, the definition of each group in the compound 1 can be as follows (the uncommented definition is as described above):

AA6 is Phe;

In a certain technical solution, the definition of each group in the compound 1 can be as follows (the uncommented definition is as described above):

AA7 is an amino acid whose the amino group is unsubstituted or substituted (when the amino acid has a plurality of amino groups, the amino group can be located on a chiral carbon atom, or can also be a primary amino group) by a $C_{1-3}$ alkyl group (e.g., methyl, ethyl, n-propyl or isopropyl) (the "substituted amino acids" if for example N-Me-A6c or aza-N-Me-Gly), wherein the amino group is selected form: Gly, azaGly, Ala, Alg, Ava, Aib, Sar, Chg, BetaAla, ACPO, Aze, D-2Fua, A6c, azaPro, Ind, (S)-Pip, (R)-Pip, Oic, Hyp, cycloLeu, BetaHomoAla. Cba. ACPA. Ala. morpholino cyclic amino acid, beta-(thiazoly-4-yl)-L-Ala,

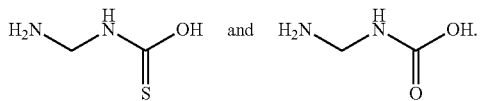

In a certain technical solution, the definition of each group in the compound 1 can be as follows (the uncommented definition is as described above):

AA7 is an amino acid whose amino group is unsubstituted or substituted by a $C_{1-3}$ alkyl, wherein the amino acid is selected from: Gly, azaGly, Ala, Ava, Aib, Sar, Chg, BetaAla, ACPO, Aze, Alg, D-2Fua, A6c, azaPro, Ind, (S)-Pip, (R)-Pip, azaTic, Oic, Hyp, cycloLeu, BetaHomoAla, Cba, ACPA and

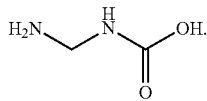

In a certain technical solution, the definition of each group in the compound 1 can be as follows (the uncommented definition is as described above):

AA7 is any of the following amino acids: Gly, azaGly, Alg, Aze, D-2Fua, Alg, morpholino cyclic amino acid, beta-(thiazoly-4-yl)-L-Ala,

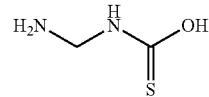

and A6c.

In a certain technical solution, the definition of each group in the compound 1 can be as follows (the uncommented definition is as described above):

AA7 is any of the following amino acids: Gly, azaGly, Alg, Aze, D-2Fua, Alg, morpholino cyclic amino acid, beta-(thiazoly-4-yl)-L-Ala,

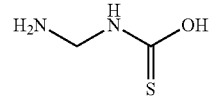

and A6c.

In a certain technical solution, the definition of each group in the compound 1 can be as follows (the uncommented definition is as described above):

AA7 is azaGly, Aib, A6c, Alg, cycloLeu, Ind, Cba, Aze, Gly or D-2Fua.

In a certain technical solution, the definition of each group in the compound 1 can be as follows (the uncommented definition is as described above):

AA7 is azaGly, Aib, A6c, Alg, cycloLeu, Ind, Cba, Aze or Gly.

In a certain technical solution, the definition of each group in the compound 1 can be as follows (the uncommented definition is as described above):

AA7 is any of the following amino acids: Gly, azaGly, Alg, Aze, D-2Fua and A6c.

In a certain technical solution, the definition of each group in the compound 1 can be as follows (the uncommented definition is as described above):

AA7 is AzaGly, A6c, Alg, D-2Fua or Aze.

In a certain technical solution, the definition of each group in the compound 1 can be as follows (the uncommented definition is as described above):

When AA6 is

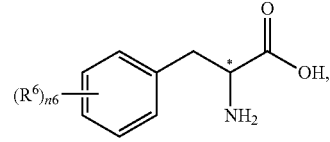

the term "AA6-AA7" refers to a group containing

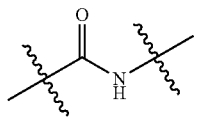 [SMILES: *NC(*)=O]

that formed by joining the carboxyl group of AA6 (when the amino acid has a plurality of carbonyls, the carbonyl groups can be located on a chiral carbon atom) to the amino group of AA7 (when the amino acid has a plurality of amino groups, the amino group can be located on a chiral carbon atom, or can also be a primary amino group), or the group formed after the

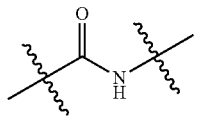 [SMILES: *NC(*)=O]

in "the group containing

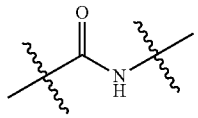 [SMILES: *NC(*)=O]

that formed by joining the carboxyl group of AA6 to the amino group of AA7" is substituted with the groups shown below:

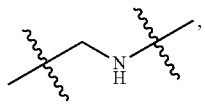 [SMILES: *CN*]

and the left end of the group is linked to AA6 (for example, when AA6 is Phe and AA7 is Gly, "AA6-AA7" refers to

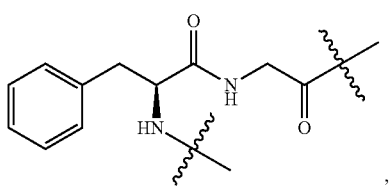

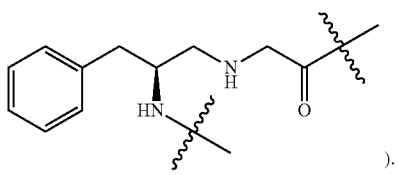

).

In a certain technical solution, the definition of each group in the compound 1 can be as follows (the uncommented definition is as described above):

When AA6 is

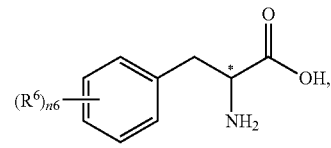

the term "AA6-AA7" refers to a group containing

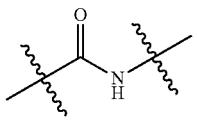 [SMILES: *NC(*)=O]

that formed by joining the carboxyl group of AA6 (when the amino acid has a plurality of amino groups, the amino group can be located on a chiral carbon atom) to the amino group of AA7 (when the amino acid has a plurality of amino groups, the amino group can be located on a chiral carbon atom, or can also be a primary amino group).

In a certain technical solution, the definition of each group in the compound 1 can be as follows (the uncommented definition is as described above):

When AA7 is Gly, "AA7-Leu" refers to the group containing

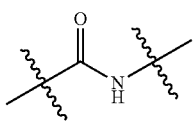 [SMILES: *NC(*)=O]

that formed by joining the carboxyl group (which can be the carboxyl group on a chiral carbon atom when the amino acid has a plurality of carboxyl groups) of AA7 to the amino group (when the amino acid has a plurality of amino groups, the amino group can be located on a chiral carbon atom, or can also be a primary amino group) of Leu or a group formed after the

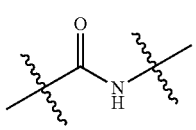 [SMILES: *NC(*)=O]

in "the group containing

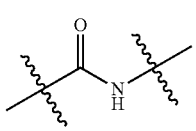 [SMILES: *NC(*)=O]

formed by joining the carboxyl group of AA7 to the amino group of Leu" is substituted by any of the following groups:

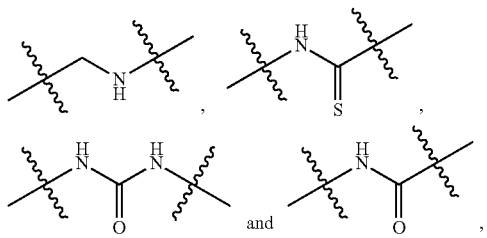

and the left end of said group is linked with AA7 (for example, when AA7 is Gly and AA7 is Leu, "AA7-Leu" refers to

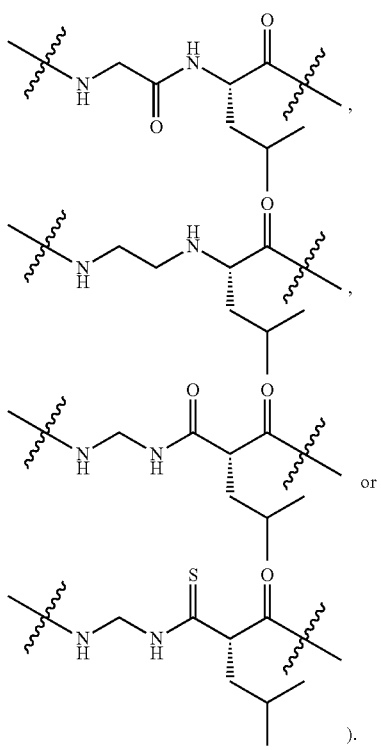

).

In a certain technical solution, the definition of each group in the compound 1 can be as follows (the uncommented definition is as described above):

When AA7 is Gly, "AA7-Leu" refers to the group containing

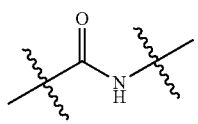 [SMILES: *NC(*)=O]

that formed by joining the carboxyl group (which can be the carboxyl group on a chiral carbon atom when the amino acid has a plurality of carboxyl groups) of AA7 to the amino group (when the amino acid has a plurality of amino groups, the amino group can be located on a chiral carbon atom, and can also be a primary amino group) of Leu or a group formed after the

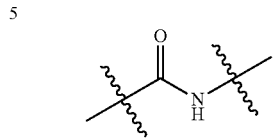

in "the group containing

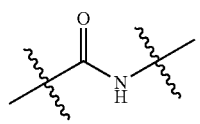 [SMILES: *NC(*)=O]

formed by joining the carboxyl group of AA7 to the amino group of Leu" is substituted by any of the following groups:

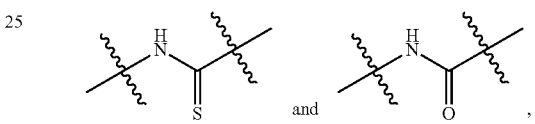

and the left end of said group is linked with AA7 (for example, when AA7 is Gly and AA7 is Leu, "AA7-Leu" refers to

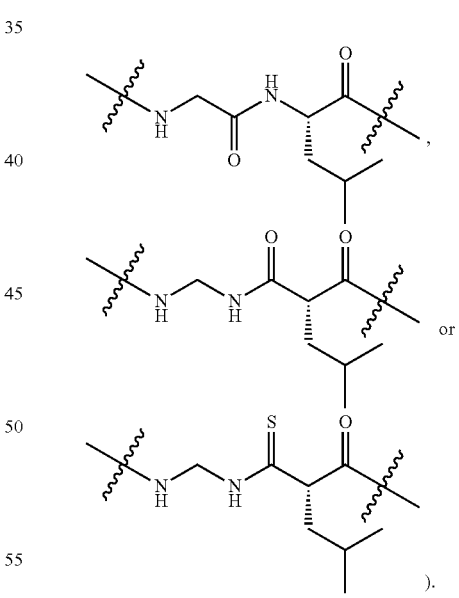

).

In a certain technical solution, the definition of each group in the compound 1 can be as follows (the uncommented definition is as described above):

AA9 is an amino acid whose the amino group (when the amino acid has a plurality of amino groups, the amino group can be located on a chiral carbon atom, or can also be a primary amino group) is unsubstituted or substituted by a $C_{1-3}$ alkyl group (e.g., methyl, ethyl, n-propyl or isopropyl) (the "substituted amino acids" is, for example N-Me-Arg, N-Me-HoLeu or N-ME-D-HoLeu), wherein the amino acid is selected from: Arg, Arg(Me), Ala, His, HoLeu, D-HoLeu, 4Pal, Phe(4-amidino), and

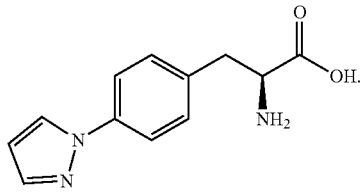 [SMILES: N[C@@H](Cc1ccc(-n2cccn2)cc1)C(=O)O]

In a certain technical solution, the definition of each group in the compound 1 can be as follows (the uncommented definition is as described above):

AA9 is any of the following amino acids: Arg and Arg(Me).

In a certain technical solution, the definition of each group in the compound 1 can be as follows (the uncommented definition is as described above):

AA10 is an amino acid whose the amino group (when the amino acid has a plurality of amino groups, the amino group can be located on a chiral carbon atom, and can also be a primary amino group) is unsubstituted or substituted by a C1-3 alkyl group (e.g., methyl, ethyl, n-propyl or isopropyl) (the "substituted amino acids" is for example N-Me-Phe), wherein the amino acid is selected from: Trp, αMePhe, 1Nal, 2Nal, 4Pal, BetaPhe, BetaHoPhe, Bpa, NPhe, D-2Fua, A6c, Tic, and

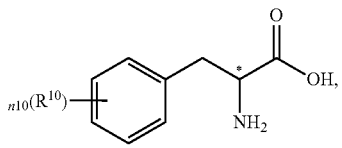

{e.g. Phe, D-Phe, Phe(4-F), Phe(pentaF), Phe(3-Cl), Phe(2-Br), Phe(4-I), Phe(4-tBu), or, phe (4-CF3)}; n10 is 0, the carbon atom marked with * is a chiral carbon atom, which is in R configuration or S configuration (all of $R^{10}$ can be independently located at the ortho, meta or para position of the amino acid side chain, for example, when n6 is 1, $R^{10}$ can be located at the ortho, meta or para position of the amino acid side chain; and for another example, it can be

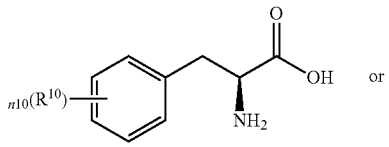

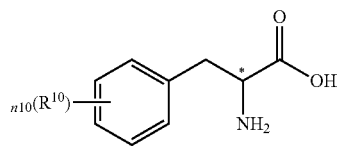

In a certain technical solution, the definition of each group in the compound 1 can be as follows (the uncommented definition is as described above):

AA10 is Trp, or

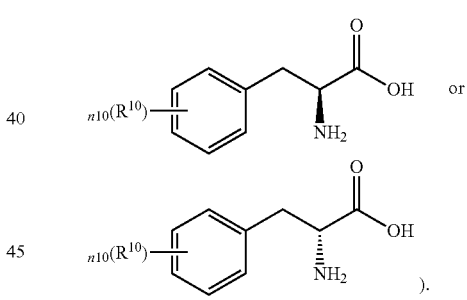

{e.g., Phe, D-Phe, Phe(4-F), Phe(pentaF), Phe(2-Br), Phe(4-I), or, Phe(4-CF3)}; n10 is 0-5 (e.g., 0, 1, 2, 3, 4 or 5), and all of $R^{10}$ are independently halogenated $C_1$-$C_4$ alkyl (the "halogen" is, for example fluorine, chlorine, bromine or iodine; the "$C_1$-$C_4$ alkyl" is, for example methyl, ethyl, n-propyl, isopropyl, n-butyl, sec-butyl or isobutyl; said "halogenated $C_1$-$C_4$ alkyl" is, for example trifluoromethyl) or halogen (e.g. fluorine, chlorine, bromine or iodine), and the carbon atom marked with * is a chiral carbon atom, which is in R configuration or an S configuration (all $R^{10}$ can be independently located at the ortho, meta or para position of the amino acid side chain, for example, when n10 is 1, $R^{10}$ can be located at the ortho or para position of the amino acid side chain; for example, it can be In a certain technical solution, the definition of each group in the compound 1 can be as follows (the uncommented definition is as described above):

AA10 is Trp or Phe.

In a certain technical solution, the definition of each group in the compound 1 can be as follows (the uncommented definition is as described above):

P is —$NH_2$.

In a certain technical solution, the definition of each group in the compound 1 can be as follows (the uncommented definition is as described above):

Cap is

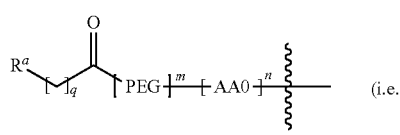

(i.e.

-continued 1-1

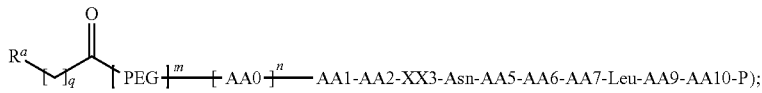

wherein, $R^a$ is $CH_3-$, q is 0-18 (for example, any two of the following values can be selected as the two endpoints of a range: 0, 1, 2, 3, 4, 5, 6, 7, 8, 9, 10, 11, 12, 13, 14, 15, 16, 17 and 18); for another example, 0 to 14; for another example, 4-14); alternatively, $R^a$ is HOOC—, q is 1-18 (for example, any two of the following values can be selected as two endpoints of a range: 1, 2, 3, 4, 5, 6, 7, 8, 9, 10, 11, 12, 13, 14, 15, 16, 17, and 18; for another example, 1 to 16).

m is 0 to 2 (e.g. 0, 1 or 2);

PEG is independently

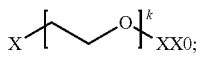

X is independently —$NHR_b$ or —OH, $R^b$ is independently hydrogen or $C_{1-3}$ alkyl (e.g., methyl, ethyl, isopropyl or n-propyl); k is independently 2-12 (for example, any two of the following values can be selected as two endpoints of a range: 2, 3, 4, 5, 6, 8 12, 16, 20 or 24); XX0 is independently

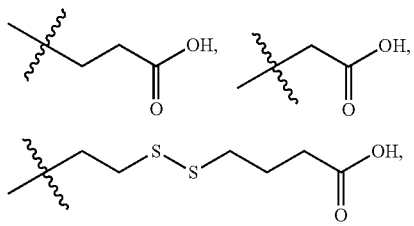

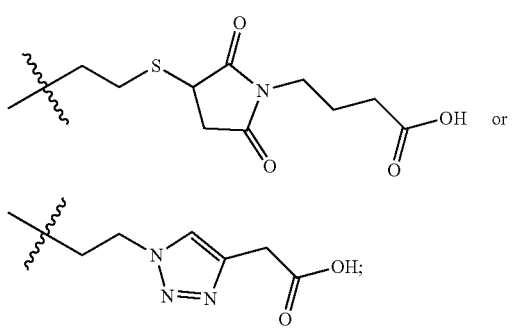

(said X can be —$NH_2$; said k can be independently 2 to 12 (e.g., 4 to 8); said

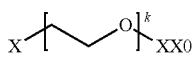

can be independently OEG, PEG4, PEG5, PEG8,

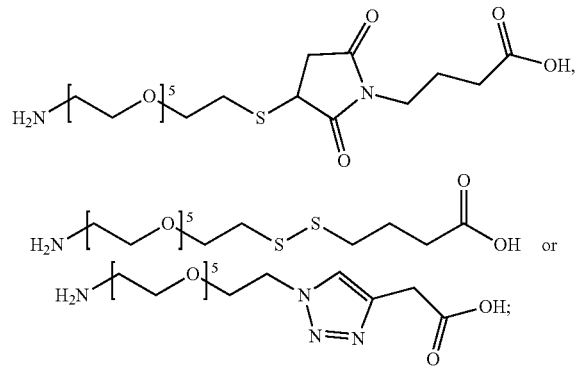

when m is 2, said X can be —$NH_2$ in the PEG that linked to AA0 or AA1; when m is 2, said k can be 2-4 (e.g., 2, 3 or 4) in the PEG that linked to AA0 or AA1; when m is 2, said XX0 can be

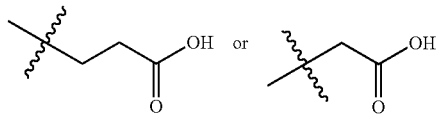 [SMILES: *CCC(=O)O ; *CC(=O)O]

in PEG linked to AA0 or AA1; when m is 2, said

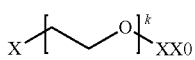

can be OEG or PEG4 in the PEG that linked with AA0 or AA1;

said

can be a chemical bond, "OEG", "PEG4", "PEG8", "OEG-OEG", "PEG4-PEG4" or

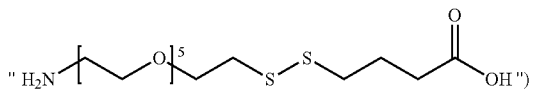

n is 0 to 3 (e.g., 0, 1, 2 or 3);

All of AA0s are independently Gly, Beta-Ala, Ahx or Ac-Lys; (for example, when n is 2 or 3, at least 2 of AA0s are Gly; for another example,

can be a chemical bond, "Gly-Gly" or "Ac-Lys-Gly-Gly" {the left side of which is linked to XX0})

however, when q is 0, m and n are not 0 at the same time; (i.e.

is not acetyl; for example, when m is 0 and n is 0, q is 1 to 18;

for another example, any two of the following values can be selected as two endpoints of a range: 1, 2, 3, 4, 5, 6, 7, 8, 9, 10, 11, 12, 13, 14, 15, 16, 17, and 18; for another example, 4-14);

AA1 is an amino acid in which the amino group (when the amino acid has a plurality of amino groups, the amino group can be located on a chiral carbon atom, or can also be a primary amino group) is unsubstituted or substituted by a $C_{1-3}$ alkyl group (e.g., methyl, ethyl, n-propyl or isopropyl) (said "substituted amino acids" is, for example, N-Me-Ala, N-Me-D-Ala, N-Me-Leu, N-Me-D-Leu, N-Me-Phe or N-Me-D-Phe), wherein the amino acid is selected from: D-Ala, Leu, D-Leu, Tyr, D-Tyr, Thi, (S)-Pip, Ala, αMeTyr, 1Nal, 2Nal, 4Pal, Dap(Dnp), D-2Fua, Pro(5Ph), 2Pal, 3Pal, Tyr(Me), Ala(dip), A6c, ACPA, D-Tic, 3-[(1-methylpyridinium)-3-yl] alanine, and

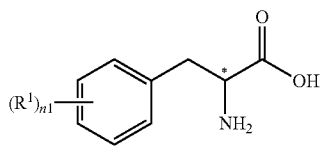

{e.g., Phe, D-Phe, Phe(4-F), D-Phe(4-F), Phe(3-Cl), D-Phe (3-Cl), Phe(4-Cl), D-Phe(4-Cl), Phe(4-I), Phe(4-Me), Phe (4-tBu), or, d-phe (2,4-diCl)}; n1 is 0 to 2 (e.g., 0, 1 or 2), all of $R^1$ are independently $C_1$ to $C_4$ alkyl (e.g., methyl, ethyl, n-propyl, isopropyl, n-butyl, sec-butyl or isobutyl), $C_1$-$C_4$ alkoxy (e.g., methoxy, ethoxy, n-propoxy, isopropoxy, n-butoxy, sec-butoxy or isobutoxy) or halogen (e.g., fluorine, chlorine), and carbon atoms labeled with * are chiral carbon atoms, which are in R configuration or S configuration (all of $R^1$ can be independently located at the ortho-, para- and meta-positions of amino acid side chain, for example, when n1 is 2, $R^1$ can be located at the ortho and para positions of the amino acid side chain; and for another example, it is

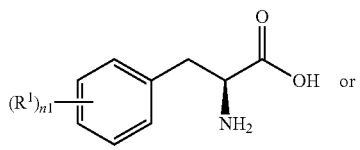

-continued

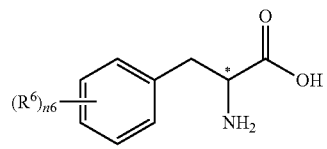

AA2 is Asn, Hyp, Pro, Ala, Thz, Pro(diF), Pro(4-NH$_2$), Thi, NAsn, ACPA, D-2Fua, A6c, azaPro, Ind, (S)-Pip, (R)-Pip, Oic, azaTic, or D-Tic;

XX3 is Trp, Ala, Phe(4-I) or a chemical bond;

AA5 is 2Fua, Thr or Ser;

AA6 is an amino acid in which the amino group (when the amino acid has a plurality of amino groups, the amino group can be located on a chiral carbon atom, and can also be a primary amino group) is unsubstituted or substituted by a $C_{1-3}$ alkyl group (e.g., methyl, ethyl, n-propyl or isopropyl) (said "substituted amino acids" is, for example, N-Me-Phe), wherein the amino acid is selected from: Ala, 1Nal, 2Nal, Trp, αMePhe, Bta, 4Pal, HoPhe, BetaPhe, BetaHomoPhe, Bpa, Ala(dip), Bip, D-2Fua, A6c, Tic, azaTic, azaPhe, and,

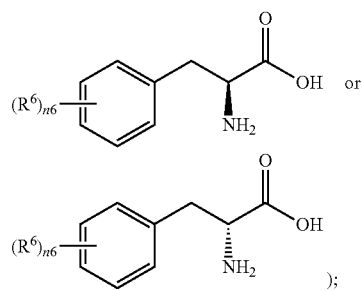

{(e.g., Phe, D-Phe, Phe(4-F), Phe(pentaF), Phe(3-Cl), Phe (2-Br), Phe(4-I), Phe(4-tBu), or Phe (4-CF3)); n6 is 0-5 (e.g., 0, 1, 2, 3, 4 or 5), and all of $R^6$ are independently halogenated $C_1$-$C_4$ alkyl (said "halogen" is for example, fluorine, chlorine, bromine or iodine; said "$C_1$-$C_4$ alkyl" is, for example, methyl, ethyl, n-propyl, isopropyl, n-butyl, sec-butyl or isobutyl; said "halogenated $C_1$-$C_4$ alkyl" is, for example, trifluoromethyl), $C_1$-$C_4$ alkyl (e.g. methyl, ethyl, n-propyl, isopropyl, n-butyl, sec-butyl or isobutyl) or halogen (e.g. fluorine, chlorine, bromine or iodine), the carbon atom marked with * is a chiral carbon atom, which is in R configuration or S configuration (all of $R^6$ can be independently located at the ortho, meta or para position of the amino acid side chain, for example, when n6 is 1, $R^6$ can be located at the ortho, meta or para position of the amino acid side chain; for example, it can be AA7 is an amino acid in which the amino group (when the amino acid has a plurality of amino groups, it can be amino group on chiral carbon atom, or can also be a primary amino group) is unsubstituted or substituted by a $C_{1-3}$ alkyl group (e.g., methyl, ethyl, n-propyl or isopropyl) (the "substituted amino acids" is for example N-Me-A6c or aza-N-Me-Gly), and the amino group is selected from: Gly, azaGly, Ala, Alg, Ava, Aib, Sar, Chg, BetaAla, ACPO, Aze, D-2Fua, A6c, azaPro, Ind, (S)-Pip, (R)-Pip, azaTic, Oic, Hyp, cycloLeu, BetaHomoAla, Cba, ACPA and

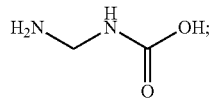

When AA6 is

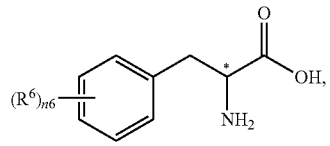

"AA6-AA7" refers to a group containing

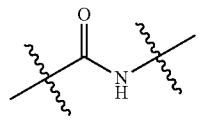 [SMILES: *NC(*)=O]

that formed by joining the carboxyl group (when the amino acid has a plurality of carboxyls, the carbonyl can be located on a chiral carbon atom) of AA6 to amino group (when the amino acid has a plurality of amino groups, the amino group can be located on a chiral carbon atom, and can also be a primary amino group) of AA7, or, the group formed after the

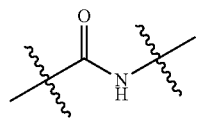 [SMILES: *NC(*)=O]

of "the group containing

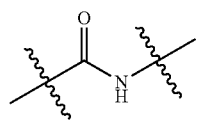 [SMILES: *NC(*)=O]

that formed by joining the carbonyl group of AA6 to the amino group of AA7" is substituted by any one of the groups shown below:

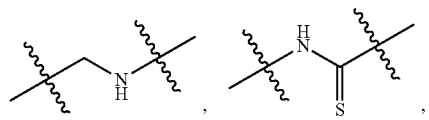

-continued

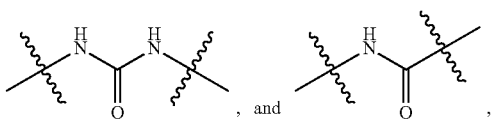

and the left end of said group is linked with AA6 (for example, when AA6 is Phe and AA7 is Gly, "AA6-AA7" refers to

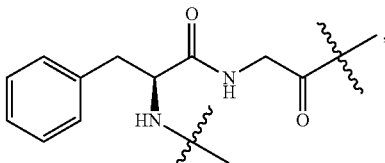

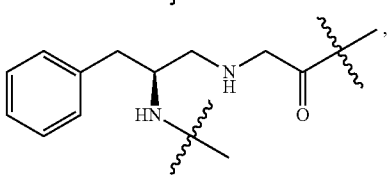

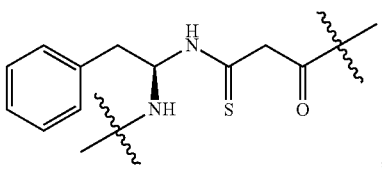

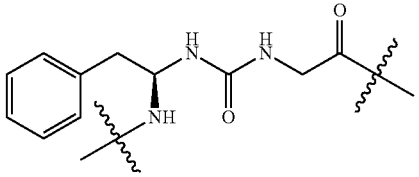

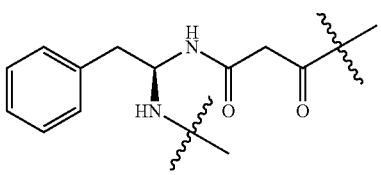

);

Alternatively, AA6 and AA7 together form

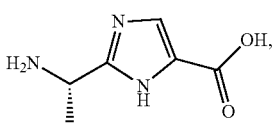

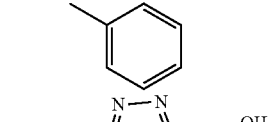

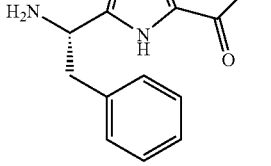

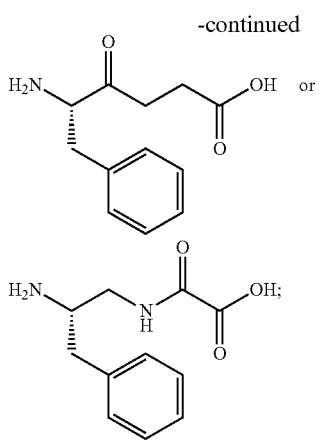

AA9 is an amino acid whose the amino group (when the amino acid has a plurality of amino groups, the amino group can be located on a chiral carbon atom, and can also be a primary amino group) is unsubstituted or substituted by a $C_{1-3}$ alkyl group (e.g., methyl, ethyl, n-propyl or isopropyl) (the "substituted amino acids" is, for example N-Me-Arg, N-Me-HoLeu or N-ME-D-HoLeu), wherein the amino acid is selected from: Arg, Arg(Me), Ala, His, HoLeu, D-HoLeu, 4Pal, Phe(4-amidino),

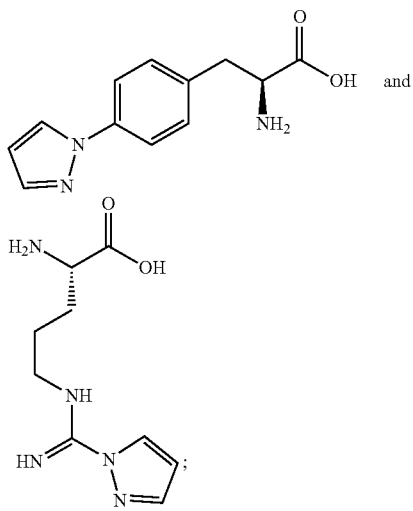

AA10 is an amino acid whose the amino group (when the amino acid has a plurality of amino groups, the amino group can be located on a chiral carbon atom, or can also be a primary amino group) is unsubstituted or substituted by a $C_{1-3}$ alkyl group (e.g., methyl, ethyl, n-propyl or isopropyl) (the "substituted amino acids" is, for example n-me-phe), wherein the amino acid is selected from: Trp, Ala, αMePhe, 1Nal, 2Nal, 4Pal, BetaPhe, BetahoPhe, Bpa, Ala(dip), NPhe, Bip, D-2Fua, A6c, Tic, and

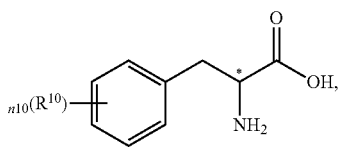

{e.g., Phe, D-Phe, Phe(4-F), Phe(pentaF), Phe(2-Br), Phe (4-I), or, Phe(4-CF3)}; N10 is 0-5 (e.g., 0, 1, 2, 3, 4 or 5), and all of $R^{10}$ are independently halogenated $C_1$-$C_4$ alkyl (said "halogen" is, for example, fluorine, chlorine, bromine or iodine; said "$C_1$-$C_4$ alkyl" is, for example, methyl, ethyl, n-propyl, isopropyl, n-butyl, sec-butyl or isobutyl; said "halogenated C1-C4 alkyl" is, for example, trifluoromethyl) or halogen (for example fluorine, chlorine, bromine or iodine), and the carbon atom marked with * is a chiral carbon atom, which is in R configuration or an S configuration (all of $R^{10}$ can be independently located at the ortho, meta or para position of the amino acid side chain, for example, when n10 is 1, $R^{10}$ can be located at the ortho or para position of the amino acid side chain; for example, it can be P is —NH$_2$, —OH, —NH-tBu, —NH-Et, —NH-Me, 1H-1,2,3-triazol-4-yl or 2H-tetrazole-5-yl.

In a certain technical solution, the definition of each group in the compound 1 can be as follows (the uncommented definition is as described above):

m is 1 or 2.

In a certain technical solution, the definition of each group in the compound 1 can be as follows (the uncommented definition is as described above):

m is 0, n is 0, $R^a$ is CH$_3$— or HOOC—, q is 1-18 (for example, any two of the following values can be selected as two endpoints of a range: 0, 3, 4, 5, 6, 7, 8, 9, 10, 11, 12, 13, 14, 15 and 18; for another example: 4-14);

In a certain technical solution, the definition of each group in the compound 1 can be as follows (the uncommented definition is as described above):

M is 0, n is 1-3.

In a certain technical solution, the definition of each group in the compound 1 can be as follows (the uncommented definition is as described above):

wherein, $R^a$ is CH$_3$—, q is 0-18 (for example, any two of the following values can be selected as two endpoints of a range: 0, 1, 2, 3, 4, 5, 6, 7, 8, 9, 10, 11, 12, 13, 14, 15 and 16); alternatively, $R^a$ is HOOC—, q is 1-16 (for example, any two of the following values can be selected as two endpoints of a range: 1, 2, 3, 4, 5, 6, 7, 8, 9, 10, 11, 12, 13, 14, 15 and 16).

In a certain technical solution, the definition of each group in the compound 1 can be as follows (the uncommented definition is as described above):

m is 0 to 2 (e.g., 1);

In a certain technical solution, the definition of each group in the compound 1 can be as follows (the uncommented definition is as described above):

X is —NH$_2$.

In a certain technical solution, the definition of each group in the compound 1 can be as follows (the uncommented definition is as described above):

k is independently 2-8 (for example, any two of the following values can be selected as two endpoints of a range: 2, 3, 4, 5, 6, l and 8; for another example: 4-8).

In a certain technical solution, the definition of each group in the compound 1 can be as follows (the uncommented definition is as described above):

XX0 is independently

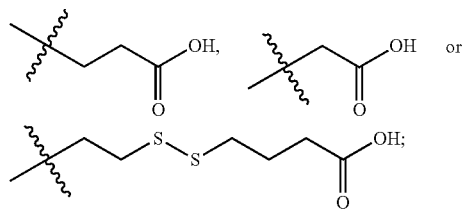

(for example, said

can be a chemical bond, "OEG", "PEG4", "PEG8", "OEG-OEG", "PEG4-PEG4" or

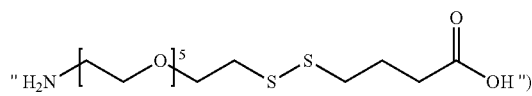

In a certain technical solution, the definition of each group in the compound 1 can be as follows (the uncommented definition is as described above):

n is 0 to 3 (e.g., 0, 1, 2 or 3).

In a certain technical solution, the definition of each group in the compound 1 can be as follows (the uncommented definition is as described above):

All of AA0 is independently Gly or Ac-Lys. (for example, when n is 2 or 3, at least 2 of AA0s are Gly; and for another example,

can be a chemical bond, "Gly-Gly" or "Ac-Lys-Gly-Gly" {the left side of which is linked to XX0});

In a certain technical solution, the definition of each group in the compound 1 can be as follows (the uncommented definition is as described above):

AA1 is Tyr, D-Tyr, or D-2Fua.

In a certain technical solution, the definition of each group in the compound 1 can be as follows (the uncommented definition is as described above):

AA2 is Asn, Hyp, or Pro (diF).

In a certain technical solution, the definition of each group in the compound 1 can be as follows (the uncommented definition is as described above):

XX3 is Trp or a chemical bond.

In a certain technical solution, the definition of each group in the compound 1 can be as follows (the uncommented definition is as described above):

AA5 is Thr or Ser.

In a certain technical solution, the definition of each group in the compound 1 can be as follows (the uncommented definition is as described above):

AA6 is Phe;

In a certain technical solution, the definition of each group in the compound 1 can be as follows (the uncommented definition is as described above):

AA7 is Gly, azaGly, Aze, D-2Fua or A6c.

In a certain technical solution, the definition of each group in the compound 1 can be as follows (the uncommented definition is as described above):

AA9 is Arg or Arg(Me).

In a certain technical solution, the definition of each group in the compound 1 can be as follows (the uncommented definition is as described above):

AA10 is Trp or Phe.

In a certain technical solution, the definition of each group in the compound 1 can be as follows (the uncommented definition is as described above):

P is —$NH_2$.

In a certain technical solution, the definition of each group in the compound 1 can be as follows (the uncommented definition is as described above):

AA1 is Dap (Dnp), D-Phe(2,4-diCl), D-Tic, 2Pal, 3Pal, D-Tyr, Ala (dip), or D-2Fua.

In a certain technical solution, the definition of each group in the compound 1 can be as follows (the uncommented definition is as described above):

AA2 is Thz, Oic, A6c, Thi, D-2Fua, ACPA or Pro.

In a certain technical solution, the definition of each group in the compound 1 can be as follows (the uncommented definition is as described above):

AA5 is 2Fua.

In a certain technical solution, the definition of each group in the compound 1 can be as follows (the uncommented definition is as described above):

AA6 is Phe.

In a certain technical solution, the definition of each group in the compound 1 can be as follows (the uncommented definition is as described above):

AA7 is azaGly, Aib, A6c, cycloLeu, Ind, Cba, Aze or Gly (e.g "AA6-AA7" refers to

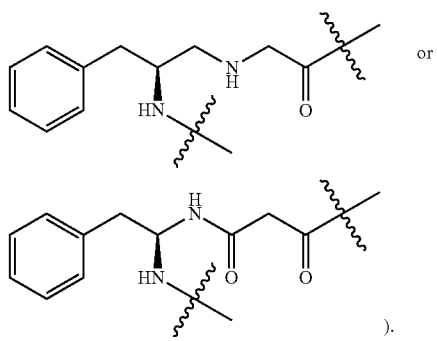

).

In a certain technical solution, the definition of each group in the compound 1 can be as follows (the uncommented definition is as described above):

Alternatively, AA6 and AA7 together form

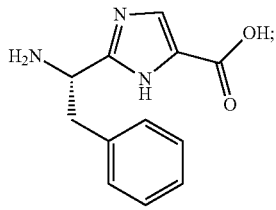 [SMILES: N[C@@H](Cc1ccccc1)c1ncc(C(=O)O)[nH]1]

In a certain technical solution, the definition of each group in the compound 1 can be as follows (the uncommented definition is as described above):

AA10 is 2-Nal.

In a certain technical solution, the definition of each group in the compound 1 can be as follows (the uncommented definition is as described above):

P is —NH$_2$.

In a certain technical solution, the definition of each group in the compound 1 can be as follows (the uncommented definition is as described above):

AA1 is Dap (Dnp), D-Phe(2,4-diCl), D-Tic, 2Pal, 3Pal,

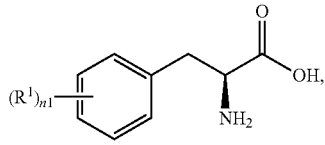

Tyr, D-Tyr, Ala(dip), or D-2Fua; n1 is 1 or 2, and all of R$^1$ are independently C$_1$-C$_3$ alkyl (e.g. methyl, ethyl, n-propyl or isopropyl), C$_1$-C$_3$ alkoxy (e.g. methoxy, ethoxy, n-propoxy or isopropyl) or halogen (e.g. fluorine or chlorine).

In a certain technical solution, the definition of each group in the compound 1 can be as follows (the uncommented definition is as described above):

AA2 is Thz, Oic, A6c, Thi, D-2Fua, ACPA, Pro, Asn, Hyp, or Pro(diF).

In a certain technical solution, the definition of each group in the compound 1 can be as follows (the uncommented definition is as described above):

XX3 is Trp or a chemical bond.

In a certain technical solution, the definition of each group in the compound 1 can be as follows (the uncommented definition is as described above):

AA5 is 2Fua, Thr or Ser.

In a certain technical solution, the definition of each group in the compound 1 can be as follows (the uncommented definition is as described above):

AA6 is Phe;

AA7 is Aib, cycloLeu, Ind, Cba, Gly, azaGly, Aze, D-2Fua or A6c (e.g "AA6-AA7" refers to

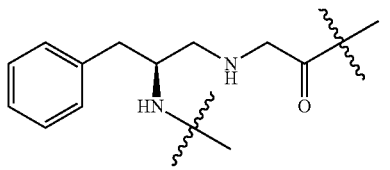

or

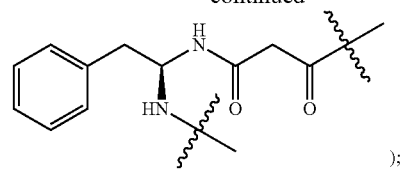

);

alternatively, AA6 and AA7 together form

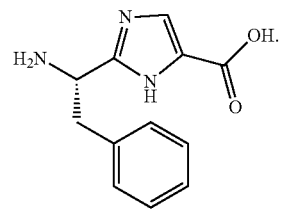 [SMILES: N[C@@H](Cc1ccccc1)c1ncc(C(=O)O)[nH]1]

In a certain technical solution, the definition of each group in the compound 1 can be as follows (the uncommented definition is as described above):

AA9 is Arg or Arg(Me).

In a certain technical solution, the definition of each group in the compound 1 can be as follows (the uncommented definition is as described above):

AA10 is 2-Nal, Trp or Phe.

In a certain technical solution, the definition of each group in the compound 1 can be as follows (the uncommented definition is as described above):

P is —NH$_2$.

In a certain technical solution, the definition of each group in the compound 1 can be as follows (the uncommented definition is as described above):

All of AA0 is independently Gly BetaAla, Ac-Lys or Ahx.

In a certain technical solution, the definition of each group in the compound 1 can be as follows (the uncommented definition is as described above):

AA1 is D-Tyr, D-Phe (2,4-DiCl), D-2Fua, L-Phe(4-F), D-Phe(4-F), Thi, (S)-Pip, D-Tic, Dap(Dnp), D-Phe(4-Cl), D-Phe(3-Cl), 2-Pal, 3Pal, Ala(dip), or ACPA.

In a certain technical solution, the definition of each group in the compound 1 can be as follows (the uncommented definition is as described above):

AA2 is Hyp, Thi, A6c, Thz, Pro (diF), Pro, Pro(4-NH$_2$), D-2Fua, (S)-Pip, ACPA, (R)-Pip or Oic.

In a certain technical solution, the definition of each group in the compound 1 can be as follows (the uncommented definition is as described above):

XX3 is Trp or a chemical bond.

In a certain technical solution, the definition of each group in the compound 1 can be as follows (the uncommented definition is as described above):

AA5 is 2Fua or Thr.

In a certain technical solution, the definition of each group in the compound 1 can be as follows (the uncommented definition is as described above):

AA6 is Phe.

In a certain technical solution, the definition of each group in the compound 1 can be as follows (the uncommented definition is as described above):

AA7 is azaGly, Aib, A6c, Alg, cycloLeu, Ind, Cba, Aze, Gly or D-2Fua or Aze. (e.g. "AA6-AA7" is

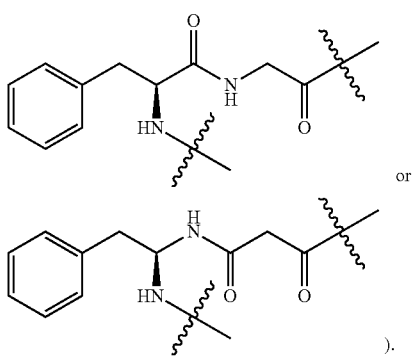

or

).

In a certain technical solution, the definition of each group in the compound 1 can be as follows (the uncommented definition is as described above):
alternatively, AA6 and AA7 together form

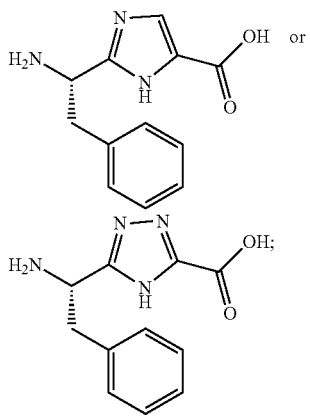

In a certain technical solution, the definition of each group in the compound 1 can be as follows (the uncommented definition is as described above):
AA9 is Arg(Me).

In a certain technical solution, the definition of each group in the compound 1 can be as follows (the uncommented definition is as described above):
AA10 is Trp or 2-Nal.

In a certain technical solution, the definition of each group in the compound 1 can be as follows (the uncommented definition is as described above):
P is OH or NH$_2$.

In a certain technical solution, the definition of each group in the compound 1 can be as follows (the uncommented definition is as described above):
AA1 is D-Tyr, D-Phe (2, 4-DiCl), D-2Fua, Thi, (S)-Pip or D-Phe (4-F).

In a certain technical solution, the definition of each group in the compound 1 can be as follows (the uncommented definition is as described above):
AA2 is Hyp, Thi, A6c, Thz, Pro (diF), Pro(4-NH$_2$), D-2Fua, (S)-Pip, (R)-Pip or Oic.

In a certain technical solution, the definition of each group in the compound 1 can be as follows (the uncommented definition is as described above):
XX3 is a chemical bond.

In a certain technical solution, the definition of each group in the compound 1 can be as follows (the uncommented definition is as described above):
AA6 is Phe.

In a certain technical solution, the definition of each group in the compound 1 can be as follows (the uncommented definition is as described above):
AA7 is AzaGly, A6c, D-2Fua or Aze. (e.g. "AA6-AA7" is

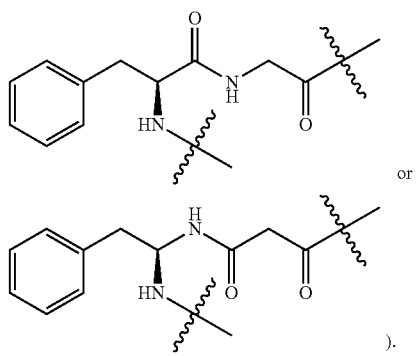

or

).

In a certain technical solution, the definition of each group in the compound 1 can be as follows (the uncommented definition is as described above):
alternatively, AA6 and AA7 together form

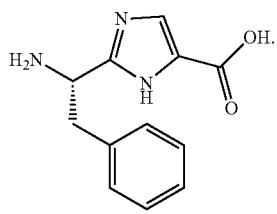 [SMILES: N[C@@H](Cc1ccccc1)c1ncc(C(=O)O)[nH]1]

In a certain technical solution, the definition of each group in the compound 1 can be as follows (the uncommented definition is as described above):
AA9 is Arg(Me).

In a certain technical solution, the definition of each group in the compound 1 can be as follows (the uncommented definition is as described above):
AA10 is Trp or 2-Nal.

In a certain technical solution, the definition of each group in the compound 1 can be as follows (the uncommented definition is as described above):
P is OH or NH$_2$.

In a certain technical solution, said compound 1 can be any one of the compounds shown as follows:

| Compound number | | Sequence |
|---|---|---|
| YA-150 | M10 [Ac, PEG4, D-Y45, Hyp46, des47, T49, azaGly51, R(Me)53, W54] | Ac-PEG4-(D-Tyr)-Hyp-Asn-Thr-Phe-azaGly-Leu-Arg(Me)-Trp-NH$_2$ |

-continued

| Compound number | | Sequence |
|---|---|---|
| YA-151 | M10 [Ac, PEG8, D-Y45, Hyp46, des47, T49, azaGly51, R(Me)53, W54] | Ac-PEG8-(D-Tyr)-Hyp-Asn-Thr-Phe-azaGly-Leu-Arg(Me)-Trp-NH$_2$ |
| YA-156 | M10 [Palm-PEG8, G43, G44, D-Y45, Hyp46, des47, T49, azaGly51, R(Me)53, W54] | Palm-PEG8-Gly-Gly-(D-Tyr)-Hyp-Asn-Thr-Phe-azaGly-Leu-Arg(Me)-Trp-NH$_2$ |
| YA-157 | M10 [Ac, K(Palm-PEG8)42, G43, G44, D-Y45, Hyp46, des47, T49, azaGly51, R(Me)53, W54] | Ac-Lys(Palm-PEG8)-Gly-Gly-(D-Tyr)-Hyp-Asn-Thr-Phe-azaGly-Leu-Arg(Me)-Trp-NH$_2$ |
| YA-158 | M10 (Palm-PEG8, G43, G44) | Palm-PEG8-Gly-Gly-Tyr-Asn-Trp-Asn-Ser-Phe-Gly-Leu-Arg-Phe-NH$_2$ |
| YA-220 | M10 [Palm-PEG8, G43, G44, D-2Fua45, Pro(diF)46, des47, T49, A6c51, R(Me)53, W54] | Palm-PEG8-Gly-Gly-[3-(2-furyl)-D-Ala]-DifluorPro-Asn-Thr-Phe-A6c-Leu-Arg(Me)-Trp-NH$_2$ |
| YA-264 | M10 [Palm-PEG8-Gly-Gly, D-Tyr45, Hyp46, des47, Thr49, A6c51, Arg(Me)53, Trp54] | Palm-PEG8-Gly-Gly-DTyr-Hyp-Asn-Thr-Phe-A6c-Leu-Arg(Me)-Trp-NH$_2$ |
| YA-267 | M10 [Palm-PEG8, D-2Fua45, Pro(diF)46, des47, Thr49, A6c51, Arg(Me)53, Trp54] | Palm-PEG8-(D-2Fua)-Pro(diF)-Asn-Thr-Phe-A6c-Leu-Arg(Me)-Trp-NH$_2$ |
| YA-268 | M10 [Palm-PEG8-Gly-Gly, D-Tyr45, A6c46, des47, Thr49, azaGly51, Arg(Me)53, Trp54] | Palm-PEG8-G-G-DY-A6c-Asn-Thr-Phe-azaG-Leu-Arg(Me)-Trp-NH$_2$ |
| YA-273 | M10 [C18 diacid-OEG-OEG, D-Tyr45, Hyp46, des47, Thr49, azaGly51, Arg(Me)53, Trp54] | C18 diacid-OEG-OEG-DY-Hyp-Asn-Thr-Phe-azaG-Leu-Arg(Me)-Trp-NH$_2$ |
| YA-287 | M10 [Palm-PEG8-Gly-Gly, D-Tyr45, Hyp46, des47, Thr49, Aze51, Arg(Me)53, Trp54] | Palm-PEG8-Gly-Gly-(D-Tyr)-Hyp-Asn-Thr-Phe-Aze-Leu-Arg(Me)-Trp-NH$_2$ |
| YA-288 | M10 [Palm-PEG8-Gly-Gly, D-Tyr45, Hyp46, des47, Thr49, D-2Fua51, Arg(Me)53, Trp54] | Palm-PEG8-Gly-Gly-(D-Tyr)-Hyp-Asn-Thr-Phe-(D-2Fua)-Leu-Arg(Me)-Trp-NH$_2$ |
| YA-294 | M10 [hexanoyl, D-Tyr45, Hyp46, des47, Thr49, azaGly51, Arg(Me)53, Trp54] | Hexanoyl-(D-Tyr)-Hyp-Asn-Thr-Phe-azaGly-Leu-Arg(Me)-Trp-NH$_2$ |
| YA-295 | M10 [nonanoyl-OEG, D-Tyr45, Hyp46, des47, Thr49, azaGly51, Arg(Me)53, Trp54] | Nonanoyl-OEG-(D-Tyr)-Hyp-Asn-Thr-Phe-azaGly-Leu-Arg(Me)-Trp-NH$_2$ |
| YA-296 | M10 [dodecanoyl-PEG4-PEG4, D-Tyr45, Hyp46, des47, Thr49, azaGly51, Arg(Me)53, Trp54] | Dodecanoyl-PEG4-PEG4-(D-Tyr)-Hyp-Asn-Thr-Phe-azaGly-Leu-Arg(Me)-Trp-NH$_2$ |
| YA-297 | M10 [Palm, D-Tyr45, Hyp46, des47, Thr49, azaGly51, Arg(Me)53, Trp54] | Palm-DY-Hyp-N-T-F-azaG-L-R(Me)-W-NH$_2$ |
| YA-298 | M10 [Palm-PEG8, D-Tyr45, Hyp46, des47, Thr49, azaGly51, Arg(Me)53, Trp54] | Palm-PEG8-(D-Tyr)-Hyp-Asn-Thr-Phe-azaGly-Leu-Arg(Me)-Trp-NH$_2$ |
| YA-324 | M10 [dodecanoyl-PEG5-S-S-butanoyl, D-Tyr45, Hyp46, des47, Thr49, azaGly51, Arg(Me)53, Trp54] | Dodecanoyl- 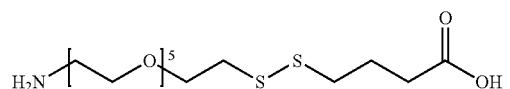 {                                        }- (D-Tyr)-Hyp-Asn-Thr-Phe-azaGly-Leu-Arg(Me)-Trp-NH$_2$ |
| YA-325 | M10 [dodecanoyl-PEG5-S-maleimide-butanoyl, D-Tyr45, Hyp46, des47, Thr49, azaGly51, Arg(Me)53, Trp54] | Dodecanoyl- 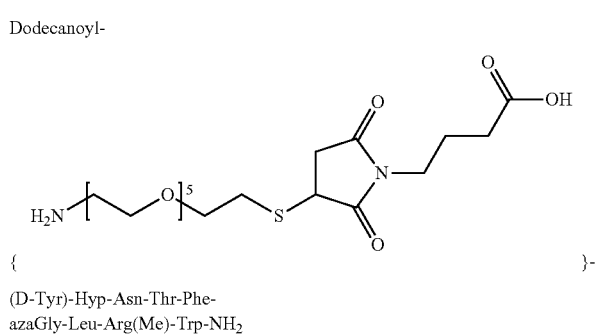 {                                        }- (D-Tyr)-Hyp-Asn-Thr-Phe-azaGly-Leu-Arg(Me)-Trp-NH$_2$ |

-continued

| Compound number | | Sequence | |
|---|---|---|---|
| YA-326 | M10 [Nonanoyl-PEG5-1,2,3-Triazole cyclic-butanoyl, D-Tyr45, Hyp46, des47, Thr49, azaGly51, Arg(Me)53, Trp54] | Nonanoyl- <br> {(D-Tyr)-Hyp-Asn-Thr-Phe-azaGly-Leu-Arg(Me)-Trp-NH₂ | |
| YA-338 | M10 [Nonanoyl-PEG4, D-Tyr45, Hyp46, des47, Thr49, Aze51, Arg(Me)53, Trp54] | Nonanoyl-PEG4-(D-Tyr)-Hyp-Asn-Thr-Phe-Aze-Leu-Arg(Me)-Trp-NH₂ | |
| YA-339 | M10 [Dodecanoyl-PEG8, D-Tyr45, Hyp46, des47, Thr49, D-2Fua51, Arg(Me)53, Trp54] | Dodecanoyl-PEG4-(D-Tyr)-Hyp-Asn-Thr-Phe-(D-2Fua)-Leu-Arg(Me)-Trp-NH₂ | |
| YA-348 | M10 [Dodecanoyl-PEG5-1,2,3-Triazole cyclic-Acetyl, D-Tyr45, Hyp46, des47, Thr49, Gψ(NHCS)51, Arg(Me)53, Trp54] | Dodecanoyl- <br> {(D-Tyr-Hyp-Asn-Thr-Phe-ψ(NHCS)-Leu-Arg(Me)-Trp-NH₂ | |
| YA-360 | M10 [Palm-PEG8, G43, G44, D-Y45, Hyp46, des47, T49, Alg51, R(Me)53, W54] | Palm-PEG8-Gly-Gly-(D-Tyr)-Hyp-Asn-Thr-Phe-Alg-Leu-Arg(Me)-Trp-NH₂ | |
| YA-366 | M10 [Palm-PEG8, G43, G44, D-Phe(4-I)45, Hyp46, des47, T49, azaGly51, R(Me)53, W54] | Palm-PEG8-Gly-Gly-(D-Phe(4-I))-Hyp-Asn-Thr-Phe-AzaGly-Leu-Arg(Me)-Trp-NH₂ | |
| YA-367 | M10 [Hexadecyl-1,2,3-Triazole-PEG8, G43, G44, D-Tyr45, Hyp46, des47, T49, AzaGly51, R(Me)53, W54] | Gly-Gly-(D-Tyr)-Hyp-Asn-Thr-Phe-azaGly-Leu-Arg(Me)-Trp-NH₂ | |
| YA-368 | M10 [Hexadecyl-S-maleimide-PEG8, G43, G44, D-Tyr45, Hyp46, des47, T49, AzaGly51, R(Me)53, W54] | Gly-Gly-(D-Tyr)-Hyp-Asn-Thr-Phe-azaGly-Leu-Arg(Me)-Trp-NH₂ | |

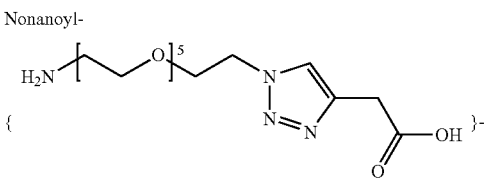

The present disclosure also provides a use of the compound 1, the pharmaceutically acceptable salts, tautomers, crystal forms, solvates or prodrugs thereof in manufacturing a medicament for treating and/or preventing diseases related to kisspeptin receptors.

Said diseases related to kisspeptin receptor such as hormone-related diseases, cell proliferative diseases, or diseases related to placental function.

Said hormone-related disease is, for example, prostate cancer, breast cancer (e.g., breast cancer before amenorrhea), endometriosis, hysteromyoma, central precocious puberty, estrogen receptor positive, sexual functional diseases (e.g., sexual dysfunction, sexual apathy), infertility, depression, or pregnancy.

Said cell proliferative disease is, for example, benign prostatic hyperplasia or cancer. Said cancer is, for example, prostate cancer, breast cancer, ovarian cancer, uterine cancer, cervical cancer, endometrial cancer, thyroid cancer, bladder cancer, liver cancer, melanoma, pancreatic cancer, gastric cancer, renal cell cancer, esophageal cancer (such as esophageal squamous cell cancer), bladder cancer or brain cancer.

Said diseases related to placental function is, for example, choriocarcinoma, invasive nevus, abortion, fetal hypoplasia, abnormal glucose metabolism or abnormal lipid metabolism.

The present disclosure also provides a pharmaceutical composition comprising the compound 1, the pharmaceutically acceptable salts thereof, the tautomers thereof, the crystal forms thereof, the solvates thereof or the prodrugs thereof, and one or more pharmaceutical excipients.

The pharmaceutical excipients can be those widely used in the field of pharmaceutical production. Said excipients are mainly used to provide a safe, stable and functional pharmaceutical composition, and can also provide methods to enable the active ingredient to dissolve out at a desired rate after the subject receives administration, or to promote effective absorption of the active ingredient after the subject receives administration of the composition. Said pharmaceutical excipients can be inert fillers or provide certain functions, such as stabilizing the overall pH value of the composition or preventing degradation of the active ingredients of the composition. The pharmaceutical excipients may include one or more of the following adjuvants: binder, suspending agents, emulsifier, diluent, filler, granulating agent, adhesive, disintegrating agent, lubricant, anti-adhesion agent, glidant, wetting agent, gelling agent, absorption delaying agent, dissolution inhibitor, reinforcing agent, adsorbent, buffer, chelating agent, preservative, colorant, flavoring agent and sweetener.

The pharmaceutical composition of the present disclosure can be prepared according to the disclosure using any method known to those skilled in the art, for example, conventional mixing, dissolving, granulating, emulsifying, grinding, encapsulating, embedding or lyophilizing processes.

The pharmaceutical composition of the present disclosure can be formulated for administration in any form, including injection (intravenous), mucosal, oral (solid and liquid preparations), inhalation, ocular, rectal, local or parenteral (infusion, injection, implantation, subcutaneous, intravenous, intra-arterial, intramuscular) administration. The pharmaceutical composition of the present disclosure may also be a controlled release or delayed release dosage form (e.g., liposome or microsphere). Examples of solid oral preparations include, but are not limited to, powders, capsules, caplets, soft capsules and tablets. Examples of liquid preparations for oral or mucosal administration include, but are not limited to, suspensions, emulsions, elixirs and solutions. Examples of topical preparations include, but are not limited to, emulsions, gels, ointments, creams, patches, pastes, foams, lotions, drops or serum preparations. Examples of preparations for parenteral administration include, but are not limited to, injectable solutions, dry preparations that can be dissolved or suspended in pharmaceutically acceptable carriers, injectable suspensions, and injectable emulsions. Examples of other suitable preparations of the pharmaceutical composition include, but are not limited to, eye drops and other ophthalmic preparations; aerosol: such as nasal spray or inhalant; liquid dosage forms suitable for parenteral administration; suppositories and lozenges.

The present disclosure also provides a peptide compound 3, pharmaceutically acceptable salts thereof, tautomers thereof, solvates thereof, crystal forms thereof or prodrugs thereof, wherein the peptide compound 3 has any of the following structures:

| Compound number | | Sequence |
| --- | --- | --- |
| YA-41 | M10 [Ac, Dap(Dnp)45, Hyp46, des47, T49, azaGly51, R(Me)53, W54] | Ac-Dap(Dnp)-Hyp-Asn-Thr-Phe-azaGly-Leu-Arg(Me)-Trp-NH$_2$ |
| YA-42 | M10 [Ac, D-Phe(2,4-diCl)45, Hyp46, des47, T49, azaGly51, R(Me)53, W54] | Ac-[D-Phe(2,4-DiCl)]-Hyp-Asn-Thr-Phe-azaGly-Leu-Arg(Me)-Trp-NH$_2$ |
| YA-43 | M10 [Ac, D-2Fua45, Hyp46, des47, T49, azaGly51, R(Me)53, W54] | Ac-(D-2Fua)-Hyp-Asn-Thr-Phe-azaGly-Leu-Arg(Me)-Trp-NH$_2$ |
| YA-44 | M10 [Ac, Pro(5Ph)45, Hyp46, des47, T49, azaGly51, R(Me)53, W54] | Ac-Pro(5Ph)-Hyp-Asn-Thr-Phe-azaGly-Leu-Arg(Me)-Trp-NH$_2$ |
| YA-45 | M10 [Ac, D-Y45, Thz46, des47, T49, azaGly51, R(Me)53, W54] | Ac-(D-Tyr)-Thz-Asn-Thr-Phe-azaGly-Leu-Arg(Me)-Trp-NH$_2$ |
| YA-68 | M10 [Ac, 2Pal45, Hyp46, des47, T49, azaGly51, R(Me)53, W54] | Ac-2Pal-Hyp-Asn-Thr-Phe-azaGly-Leu-Arg(Me)-Trp-NH$_2$ |
| YA-69 | M10 [Ac, 3Pal45, Hyp46, des47, T49, azaGly51, R(Me)53, W54] | Ac-3Pal-Hyp-Asn-Thr-Phe-azaGly-Leu-Arg(Me)-Trp-NH$_2$ |

-continued

| Compound number | | Sequence |
|---|---|---|
| YA-70 | M10 [Ac, Phe(3-Cl)45, Hyp46, des47, T49, azaGly51, R(Me)53, W54] | Ac-Phe(3-Cl)-Hyp-Asn-Thr-Phe-azaGly-Leu-Arg(Me)-Trp-NH$_2$ |
| YA-71 | M10 [Ac, Phe(4-F)45, Hyp46, des47, T49, azaGly51, R(Me)53, W54] | Ac-Phe(4-F)-Hyp-Asn-Thr-Phe-azaGly-Leu-Arg(Me)-Trp-NH$_2$ |
| YA-74 | M10 [Ac, Phe(4-Me)45, Hyp46, des47, T49, azaGly51, R(Me)53, W54] | Ac-Phe(4-Me)-Hyp-Asn-Thr-Phe-azaGly-Leu-Arg(Me)-Trp-NH$_2$ |
| YA-80 | M10 [Ac, D-Y45, Pro(di-F)46, des47, T49, azaGly51, R(Me)53, W54] | Ac-(D-Tyr)-diFluorPro-Asn-Thr-Phe-azaGly-Leu-Arg(Me)-Trp-NH$_2$ |
| YA-81 | M10 [Ac, D-Y45, Hyp46, des47, T49, azaGly51, R(Me)53, 2Nal54] | Ac-(D-Tyr)-Hyp-Asn-Thr-Phe-azaGly-Leu-Arg(Me)-2Nal-NH$_2$ |
| YA-83 | M10 [Ac, D-Y45, Pro(4-NH$_2$)46, des47, T49, azaGly51, R(Me)53, W54] | Ac-(D-Tyr)-Pro(4-NH$_2$)-Asn-Thr-Phe-azaGly-Leu-Arg(Me)-Trp-NH$_2$ |
| YA-84 | M10 [Ac, D-Y45, Thi46, des47, T49, azaGly51, R(Me)53, W54] | Ac-(D-Tyr)-Thi-Asn-Thr-Phe-azaGly-Leu-Arg(Me)-Trp-NH$_2$ |
| YA-85 | M10 [Ac, D-Y45, S-Pip46, des47, T49, azaGly51, R(Me)53, W54] | Ac-(D-Tyr)-(S-Pip)-Asn-Thr-Phe-azaGly-Leu-Arg(Me)-Trp-NH$_2$ |
| YA-132 | M10 [Ac, Ala(dip)45, Hyp46, des47, T49, azaGly51, R(Me)53, W54] | Ac-Ala(dip)-Hyp-Asn-Thr-Phe-azaGly-Leu-Arg(Me)-Trp-NH$_2$ |
| YA-143 | M10 [Ac, D-Y45, Hyp46, des47, 2Fua49, azaGly51, R(Me)53, W54] | Ac-(D-Tyr)-Hyp-Asn-2Fua-Phe-azaGly-Leu-Arg(Me)-Trp-NH$_2$ |
| YA-144 | M10 [Ac, D-Y45, Hyp46, des47, Thi49, azaGly51, R(Me)53, W54] | Ac-(D-Tyr)-Hyp-Asn-Thi-Phe-azaGly-Leu-Arg(Me)-Trp-NH$_2$ |
| YA-145 | M10 [Ac, D-Y45, ACPA46, des47, T49, azaGly51, R(Me)53, W54] | Ac-(D-Tyr)-ACPA-Asn-Thr-Phe-azaGly-Leu-Arg(Me)-Trp-NH$_2$ |
| YA-153 | M10 (Ac, D-Y45, Hyp46, des47, T49, Aze51, R(Me)53, W54] | Ac-(D-Tyr)-Hyp-Asn-Thr-Phe-Aze-Leu-Arg(Me)-Trp-NH$_2$ |
| YA-165 | M10 [Ac, D-Y45, D-2Fua46, des47, T49, azaGly51, R(Me)53, W54] | Ac-(D-Tyr)-(D-2Fua)-Asn-Thr-Phe-azaGly-Leu-Arg(Me)-Trp-NH$_2$ |
| YA-166 | M10 (Ac, D-Y45, Hyp46, des47, D-2Fua50, azaGly51, R(Me)53, W54] | Ac-(D-Tyr)-Hyp-Asn-[3-(2-furyl)-D-Ala]-Phe-azaGly-L-Arg(Me)-Trp-NH$_2$ |
| YA-167 | M10 (Ac, D-Y45, Hyp46, des47, T49, D-2Fua50, azaGly51, R(Me)53, W54] | Ac-(D-Tyr)-Hyp-Asn-Thr--(D-2Fua)-azaGly-L-Arg(Me)-Trp-NH$_2$ |
| YA-168 | M10 [Ac, D-Y45, Hyp46, des47, T49, D-2Fua51, R(Me)53, W54] | Ac-(D-Tyr)-Hyp-Asn-Thr-Phe-[3-(2-furyl)-D-Ala]-Leu-Arg(Me)-Trp-NH$_2$ |
| YA-170 | M10 [Ac, D-Phe(4-F)45, Hyp46, des47, T49, azaGly51, R(Me)53, W54] | Ac-[D-Phe(4-F)]-Hyp-Asn-Thr-Phe-azaGly-Leu-Arg(Me)-Trp-NH$_2$ |
| YA-172 | M10 [Ac, D-Y45, A6c46, des47, T49, azaGly51, R(Me)53, W54] | Ac-(D-Tyr)-A6c-Asn-Thr-Phe-azaGly-Leu-Arg(Me)-Trp-NH$_2$ |
| YA-175 | M10 [Ac, D-Y45, Hyp46, des47, T49, A6c51, R(Me)53, W54] | Ac-(D-Tyr)-Hyp-Asn-Thr-Phe-A6c-Leu-Arg(Me)-Trp-NH$_2$ |
| YA-178 | M10 [Ac, D-Phe(2,4-diCl)45, Thi46, des47, T49, azaGly51, R(Me)53, W54] | Ac-[D-Phe(2,4-DiCl)]-Thi-Asn-Thr-Phe-azaGly-Leu-Arg(Me)-Trp-NH$_2$ |
| YA-180 | M10 [Ac, D-Phe(2,4-diCl)45, Pro(diF)46, des47, T49, azaGly51, R(Me)53, W54] | Ac-[D-Phe(2,4-DiCl)]-Pro(diF)-Asn-Thr-Phe-azaGly-Leu-Arg(Me)-Trp-NH$_2$ |
| YA-181 | M10 [Ac, D-2Fua45, S-Pip46, des47, T49, azaGly51, R(Me)53, W54] | Ac-(D-2Fua)-(S-Pip)-Asn-Thr-Phe-azaGly-Leu-Arg(Me)-Trp-NH$_2$ |
| YA-182 | M10 [Ac, D-Phe(2,4-diCl)45, S-Pip46, des47, T49, azaGly51, R(Me)53, W54] | Ac-[D-Phe(2,4-DiCl)]-(S-Pip)-Asn-Thr-Phe-azaGly-Leu-Arg(Me)-Trp-NH$_2$ |

| Compound number | | Sequence |
|---|---|---|
| YA-183 | M10 [Ac, D-2Fua45, Pro(diF)46, des47, T49, azaGly51, R(Me)53, W54] | Ac-(D-2Fua)-Pro(diF)-Asn-Thr-Phe-azaGly-Leu-Arg(Me)-Trp-NH$_2$ |
| YA-188 | M10 [Ac, D-Phe(2,4-diCl)45, Hyp46, des47, T49, Aze51, R(Me)53, W54] | Ac-[D-Phe(2,4-DiCl)]-Hyp-Asn-Thr-Phe-Aze-Leu-Arg(Me)-Trp-NH$_2$ |
| YA-191 | M10 [Ac, D-Y45, Thi46, des47, T49, Aze51, R(Me)53, W54] | Ac-(D-Tyr)-Thi-Asn-Thr-Phe-Aze-Leu-Arg(Me)-Trp-NH$_2$ |
| YA-194 | M10 [Ac, D-Y45, S-Pip46, des47, T49, Aze51, R(Me)53, W54] | Ac-(D-Tyr)-(S-Pip)-Asn-Thr-Phe-Aze-Leu-Arg(Me)-Trp-NH$_2$ |
| YA-195 | M10 [Ac, D-Phe(4-F)45, Hyp46, des47, T49, A6c51, R(Me)53, W54] | Ac-[D-Phe(4-F)]-Hyp-Asn-Thr-Phe-A6c-Leu-Arg(Me)-Trp-NH$_2$ |
| YA-196 | M10 [Ac, D-Phe(2,4-diCl)45, Hyp46, des47, T49, A6c51, R(Me)53, W54] | Ac-[D-Phe(2,4-DiCl)]-Hyp-Asn-Thr-Phe-A6c-Leu-Arg(Me)-Trp-NH$_2$ |
| YA-197 | M10 [Ac, D-2Fua45, Hyp46, des47, T49, A6c51, R(Me)53, W54] | Ac-(D-2Fua)-Hyp-Asn-Thr-Phe-A6c-Leu-Arg(Me)-Trp-NH$_2$ |
| YA-201 | M10 [Ac, D-2Fua45, Pro(diF)46, des47, T49, A6c51, R(Me)53, W54] | Ac-[3-(2-furyl)-D-Ala]-DiFluorPro-Asn-Thr-Phe-A6c-Leu-Arg(Me)-Trp-NH$_2$ |
| YA-208 | M10 [Ac, D-Y45, Hyp46, des47, T49, Imc51, R(Me)53, W54] | Ac-(D-Tyr)-Hyp-Asn-Thr-{(S)-2-(1-amino-2-phenylethyl)-1H-imidazole-5-carboxylic acid}-Leu-Arg(Me)-Trp-NH$_2$ |
| YA-209 | M10 [Ac, D-Y45, Hyp46, des47, T49, Tr3c51, R(Me)53, W54] | Ac-(D-Tyr)-Hyp-Asn-Thr-{(S)-5-(1-amino-2-phenylethyl)-4H-1,2,4-triazole-3-carboxylic acid}-Leu-Arg(Me)-Trp-NH$_2$ |
| YA-212 | M10 [Ac, D-Phe(4-F)45, Pro(di-F)46, des47, T49, A6c51, R(Me)53, W54] | Ac-[D-Phe(4-F)]-DiFluorPro-Asn-Thr-Phe-A6c-Leu-Arg(Me)-Trp-NH$_2$ |
| YA-213 | M10 [Ac, D-Phe(4-F)45, Pro(di-F)46, des47, T49, Aze51, R(Me)53, W54] | Ac-[D-Phe(4-F)]-DiFluorPro-Asn-Thr-Phe-Aze-Leu-Arg(Me)-Trp-NH$_2$ |
| YA-214 | M10 [Ac, D-Phe(4-Cl)45, Hyp46, des47, T49, azaGly51, R(Me)53, W54] | Ac-[D-Phe(4-Cl)]-Hyp-Asn-Thr-Phe-azaGly-Leu-Arg(Me)-Trp-NH$_2$ |
| YA-215 | M10 [Ac, D-Phe(3-Cl)45, Hyp46, des47, T49, azaGly51, R(Me)53, W54] | Ac-[D-Phe(3-Cl)]-Hyp-Asn-Thr-Phe-azaGly-Leu-Arg(Me)-Trp-NH$_2$ |
| YA-216 | M10 [Ac, D-Y45, Hyp46, des47, T49, Tic50, azaGly51, R(Me)53, W54] | Ac-(D-Tyr)-Hyp-Asn-Thr-Tic-azaGly-Leu-Arg(Me)-Trp-NH$_2$ |
| YA-221 | M10 [Ac, D-Y45, Hyp46, des47, T49, Ind51, R(Me)53, W54] | Ac-(D-Tyr)-Hyp-Asn-Thr-Phe-Ind-Leu-Arg(Me)-Trp-NH$_2$ |
| YA-228 | M10 [Ac, D-Y45, S-Pip46, des47, T49, A6c51, R(Me)53, W54] | Ac-(D-Tyr)-(S-Pip)-Asn-Thr-Phe-A6c-Leu-Arg(Me)-Trp-NH$_2$ |
| YA-230 | M10 [Ac, D-Y45, Oic46, des47, T49, azaGly51, R(Me)53, W54] | Ac-(D-Tyr)-Oic-Asn-Thr-Phe-azaGly-Leu-Arg(Me)-Trp-NH$_2$ |
| YA-236 | M10 [Ac, D-Tic45, Hyp46, des47, T49, azaGly51, R(Me)53, W54] | Ac-(D-Tic)-Hyp-Asn-Thr-Phe-azaGly-Leu-Arg(Me)-Trp-NH$_2$ |
| YA-241 | M10 [Ac, D-Phe(2,4-diCl)45, S-Pip46, des47, T49, azaPhe50, R(Me)53, W54] | Ac-[D-Phe(2,4-DiCl)]-(S-Pip)-Asn-Thr-azaPhe-Gly-Leu-Arg(Me)-Trp-NH$_2$ |
| YA-243 | M10 [Ac, D-Y45, A6c46, des47, T49, A6c51, R(Me)53, W54] | Ac-(D-Tyr)-A6c-Asn-Thr-Phe-A6c-Leu-Arg(Me)-Trp-NH$_2$ |
| YA-248 | M10 [Ac, D-Phe(2,4-diCl)45, Pro(diF)46, des47, T49, A6c51, R(Me)53, W54] | Ac-D-Phe(2,4-DiCl)-DiFluorPro-Asn-Thr-Phe-A6c-Leu-Arg(Me)-Trp-NH$_2$ |
| YA-251 | M10 [Ac, D-Y45, Pro(diF)46, des47, T49, A6c51, R(Me)53, W54] | Ac-DTyr-DiFluorPro-Asn-Thr-Phe-A6c-Leu-Arg(Me)-Trp-NH$_2$ |
| YA-254 | M10 [Ac, D-Y45, Hyp46, des47, T49, Gψ(NHCS)51, R(Me)53, W54] | Ac-DTyr-Hyp-Asn-Thr-Phe-ψ(NHCS)G-Leu-Arg(Me)-Trp-NH$_2$ |

-continued

| Compound number | | Sequence |
|---|---|---|
| YA-255 | M10 [Ac, D-Phe(2,4-diCl)45, Pro(diF)46, des47, T49, Gψ(NHCS)51, R(Me)53, W54] | Ac-D-Phe(2,4-DiCl)-DiFluorPro-Asn-Thr-Phe-ψ(NHCS)G-Leu-Arg(Me)-Trp-NH$_2$ |
| YA-260 | M10 [Ac, D-Phe(2,4-diCl)45, A6c46, des47, T49, azaGly51, R(Me)53, W54] | Ac-D-Phe(2,4-DiCl)-A6c-Asn-Thr-Phe-azaG-Leu-Arg(Me)-Trp-NH$_2$ |
| YA-266 | M10 [Ac, des45, A6c46, des47, Thr49, azaGly51, Arg(Me)53, Trp54] | Ac-A6c-Asn-Thr-Phe-azaG-Leu-Arg(Me)-Trp-NH$_2$ |
| YA-271 | M10 [Ac, D-2Fua45, A6c46, des47, Thr49, azaGly51, Arg(Me)53, Trp54] | Ac-(D-2Fua)-A6c-Asn-Thr-Phe-azaG-Leu-Arg(Me)-Trp-NH$_2$ |
| YA-274 | M10 [Ac, D-Tyr45, Hyp46, des47, Thr49, (—CH2CH2CO—)51, Arg(Me)53, Trp54] | Ac-(D-Tyr)-Hyp-Asn-Thr-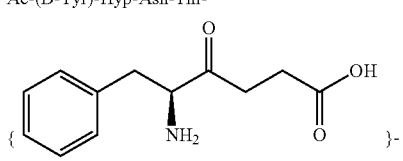-Leu-Arg(Me)-Trp-NH$_2$ |
| YA-282 | M10 [Ac, D-Tyr45, Hyp46, des47, Thr49, cycloLeu51, Arg(Me)53, Trp54] | Ac-(D-Tyr)-Hyp-Asn-Thr-Phe-cycloLeu-Leu-Arg(Me)-Trp-NH$_2$ |
| YA-291 | M10 [Ac-Gly-Arg-Lys-Lys-Arg-Arg-Gln-Arg-Arg-Arg-Pro-Gln-BetaAla-BataAla, D-Tyr45, Hyp46, des47, Thr49, azaGly51, Arg(Me)53, Trp54] | Ac-GRKKRRQRRRPQ-beta-Ala-beta-Ala-DY-Hyp--N-T-F-azaG-L-R(Me)-W-NH$_2$ |
| YA-303 | M10 [Ac, D-Tyr45, Hyp46, des47, Thr49, ψ(NHCO)Gly51, Arg(Me)53, Trp54] | Ac-(D-Tyr)-Hyp-Asn-Thr-Phe-ψ(NHCO)Gly-Leu-Arg(Me)-Trp-NH$_2$ |
| YA-332 | M10 [Ac, D-Phe(2,4-diCl)45, HomoPro46, des47, Thr49, ψ(NHCO)Gly51, Arg(Me)53, Trp54] | Ac-[D-Phe(2,4-diCl)]-HomoPro-Asn-Thr-Phe-ψ(NHCO)Gly-Leu-Arg(Me)-Trp-NH$_2$ |
| YA-333 | M10 [Ac, D-2Fua45, HomoPro46, des47, Thr49, ψ(NHCO)Gly51, Arg(Me)53, Trp54] | Ac-(D-2Fua)-HomoPro-Asn-Thr-Phe-ψ(NHCO)Gly-Leu-Arg(Me)-Trp-NH$_2$ |
| YA-334 | M10 [Ac, D-Phe(2,4-diCl)45, Pro(diF)46, des47, Thr49, ψ(NHCO)Gly51, Arg(Me)53, Trp54] | Ac-[D-Phe(2,4-diCl)]-Pro(diF)-Asn-Thr-Phe-ψ(NHCO)Gly-Leu-Arg(Me)-Trp-NH$_2$ |
| YA-350 | M10 (Ac, D-Y45, Hyp46, des47, T49, Alg51, R(Me)53, W54] | Ac-(D-Tyr)-Hyp-Asn-Thr-Phe-Alg-Leu-Arg(Me)-Trp-NH$_2$ |
| YA-354 | M10 [Ac, D-Tyr45, Hyp46, des47, Thr49, Morpholino cyclic amino acid51, Arg(Me)53, Trp54] | Ac-(D-Tyr)-Hyp-Asn-Thr-Phe-morpholino cyclic amino acid-Leu-Arg(Me)-Trp-NH$_2$ |
| YA-357 | M10 [Ac, D-Phe(4-I)45, Hyp46, des47, T49, Beta-(thiazoly-4-yl)-L-Ala51, R(Me)53, W54] | Ac-(D-Tyr)-Hyp-Asn-Thr-Phe-Beta-(thiazoly-4-yl)-L-Ala-Leu-Arg(Me)-Trp-NH$_2$ |
| YA-358 | M10 [Ac, D-Phe(4-I)45, Hyp46, des47, T49, AzaGly51, R(Me)53, W54] | Ac-(D-Phe(4-I))-Hyp-Asn-Thr-Phe-azaGly-Leu-Arg(Me)-Trp-NH$_2$ |
| YA-379 | M10 [Ac, D-Tyr45, AlphaMeLeu46, des47, T49, azaGly51, R(Me)53, W54] | Ac-(D-Tyr)-AlphaMeLeu-Asn-Thr-Phe-azaGly-Leu-Arg(Me)-Trp-NH$_2$ |

-continued

| Compound number | | Sequence |
|---|---|---|
| YA-380 | M10 [Ac, D-Tyr45, Cba46, des47, T49, azaGly51, R(Me)53, W54] | Ac-(D-Tyr)-Cba-Asn-Thr-Phe-azaGly-Leu-Arg(Me)-Trp-$NH_2$ |
| YA-381 | M10 [Ac, D-Tyr45, A6c46, des47, T49, azaGly51, R(Me)53, W54] | Ac-(D-Tyr)-A6c-Asn-Thr-Phe-azaGly-Leu-Arg(Me)-Trp-$NH_2$ |
| YA-382 | M10 [Ac, D-Tyr45, Aze46, des47, T49, azaGly51, R(Me)53, W54] | Ac-(D-Tyr)-Aze-Asn-Thr-Phe-azaGly-Leu-Arg(Me)-Trp-$NH_2$ |
| YA-383 | M10 [Ac, D-Tyr45, Cpa46, des47, T49, azaGly51, R(Me)53, W54] | Ac-(D-Tyr)-Cpa-Asn-Thr-Phe-azaGly-Leu-Arg(Me)-Trp-$NH_2$ |
| YA-384 | M10 [Ac, D-Tyr45, ACBC 46, des47, T49, azaGly51, R(Me)53, W54] | Ac-(D-Tyr)-ACBC-Asn-Thr-Phe-azaGly-Leu-Arg(Me)-Trp-$NH_2$ |
| YA-387 | M10 [Ac, D-Tyr45, Hyp46, des47, A6c49, azaGly51, R(Me)53, W54] | Ac-(D-Tyr)-Hyp-Asn-A6c-Phe-azaGly-Leu-Arg(Me)-Trp-$NH_2$ |
| YA-388 | M10 [Ac, D-Tyr45, Hyp46, des47, Aze49, azaGly51, R(Me)53, W54] | Ac-(D-Tyr)-Hyp-Asn-Aze-Phe-azaGly-Leu-Arg(Me)-Trp-$NH_2$ |
| YA-403 | M10 [Ac, D-Tyr45, Hyp46, des47, beta, beta- diMe-L-serine49, azaGly51, R(Me)53, W54] | Ac-(D-Tyr)-Hyp-Asn-beta,beta-diMe-L-serine-Phe-azaGly-Leu-Leu-Arg(Me)-Trp-$NH_2$ |

The present disclosure also provides a use of the compound 3, the pharmaceutically acceptable salts, tautomers, crystal forms, solvates or prodrugs thereof in manufacturing a medicament for treating and/or preventing diseases related to kisspeptin receptors.

Said diseases related to kisspeptin receptor are, for example, hormone-related diseases, cell proliferative diseases, or diseases related to placental function.

Said hormone-related diseases are, for example, prostate cancer, breast cancer (e.g., breast cancer before amenorrhea), endometriosis, hysteromyoma, central precocious puberty, estrogen receptor positive, sexual functional diseases (e.g., sexual dysfunction, sexual apathy), infertility, depression, or pregnancy.

Said cell proliferative disease is, for example, benign prostatic hyperplasia or cancer. Said cancers as prostate cancer, breast cancer, ovarian cancer, uterine cancer, cervical cancer, endometrial cancer, thyroid cancer, bladder cancer, liver cancer, melanoma, pancreatic cancer, gastric cancer, renal cell cancer, esophageal cancer (such as esophageal squamous cell cancer), bladder cancer or brain cancer.

Said diseases related to placental function are, for example, choriocarcinoma, invasive nevus, abortion, fetal hypoplasia, abnormal glucose metabolism or abnormal lipid metabolism.

The present disclosure also provides a pharmaceutical composition comprising the compound 3, the pharmaceutically acceptable salts thereof, the tautomers thereof, the crystal forms thereof, the solvates thereof or the prodrugs thereof, and one or more pharmaceutical excipients.

The pharmaceutical excipients can be those widely used in the field of pharmaceutical production. Said excipients are mainly used to provide a safe, stable and functional pharmaceutical composition, and can also provide methods to enable the active ingredient to dissolve out at a desired rate after the subject receives administration, or to promote the effective absorption of the active ingredient after the subject receives administration of the composition. Said pharmaceutical excipients can be inert fillers or provide certain functions, such as stabilizing the overall pH value of the composition or preventing degradation of the active ingredients of the composition. The pharmaceutical excipients may include one or more of the following adjuvants: binder, suspending agents, emulsifier, diluent, filler, granulating agent, adhesive, disintegrating agent, lubricant, anti-adhesion agent, glidant, wetting agent, gelling agent, absorption delaying agent, dissolution inhibitor, reinforcing agent, adsorbent, buffer, chelating agent, preservative, colorant, flavoring agent and sweetener.

The pharmaceutical composition of the present disclosure can be prepared according to the disclosure using any method known to those skilled in the art, for example, conventional mixing, dissolving, granulating, emulsifying, grinding, encapsulating, embedding or lyophilizing processes.

The pharmaceutical composition of the present disclosure can be formulated for administration in any form, including injection (intravenous), mucosal, oral (solid and liquid preparations), inhalation, ocular, rectal, local or parenteral (infusion, injection, implantation, subcutaneous, intravenous, intra-arterial, intramuscular) administration. The pharmaceutical composition of the present disclosure may also be a controlled release or delayed release dosage form (e.g., liposome or microsphere). Examples of solid oral preparations include, but are not limited to, powders, capsules, caplets, soft capsules and tablets. Examples of liquid preparations for oral or mucosal administration include, but are not limited to, suspensions, emulsions, elixirs and solutions. Examples of topical preparations include, but are not limited to, emulsions, gels, ointments, creams, patches, pastes, foams, lotions, drops or serum preparations. Examples of preparations for parenteral administration include, but are not limited to, injectable solutions, dry preparations that can be dissolved or suspended in pharmaceutically acceptable carriers, injectable suspensions, and injectable emulsions. Examples of other suitable preparations of the pharmaceutical composition include, but are not limited to, eye drops and other ophthalmic preparations; aerosol: such as nasal spray or inhalant; liquid dosage forms suitable for parenteral administration; suppositories and lozenges.

On the basis of not violating common knowledge in the art, the above-mentioned preferred conditions can be combined arbitrarily to give various preferred examples of the present invention.

The reagents and raw materials used in the present disclosure are commercially available.

Unless otherwise specified, the terms used in the present invention have the following meanings:

In the structural formula,

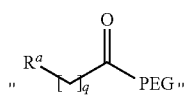

refers to a group formed by substituting a hydrogen atom on an amino group or hydroxyl group in PEG by

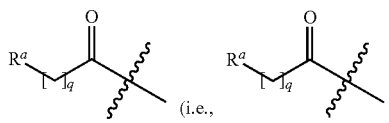 (i.e., is linked to the amino group or hydroxyl group of PEG). For example, when $R^a$ is methyl, Q is 0, and PEG is

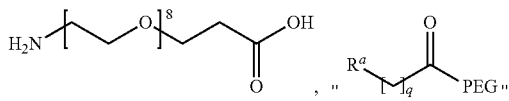

refers to

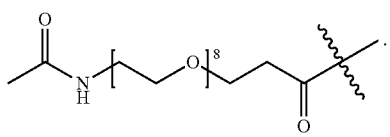

In the structural formula,

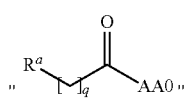

refers to a group formed by substituting a hydrogen atom on the amino group of AA0 with

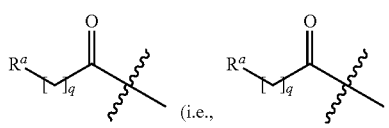 (i.e., is linked to the amino group of AA0).

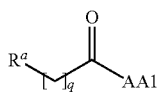

is the same. For example, when $R^a$ is methyl, Q is 0, M is 0, n is 1, and AA0 is Gly,

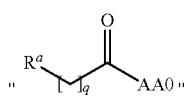

means

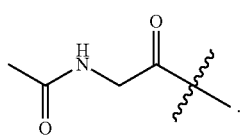 [SMILES: *C(=O)CNC(C)=O]

In the structural formula, the term "AA0-AA1" refers to a group containing

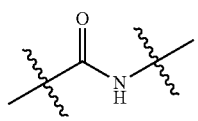 [SMILES: *NC(*)=O]

that formed by joining the carbonyl group (when the amino acid has a plurality of carbonyl groups, the carbonyl groups can be located on a chiral carbon atom) of AA0 to the amino group (when the amino acid has a plurality of amino groups, the amino group can be located on a chiral carbon atom, or can also be a primary amino group) of AA1. "PEG-PEG" (in this case, the carboxyl group of the former PEG is joined to the amino group or hydroxyl group of the latter PEG), "PEG-AA0", "PEG-AA1", "PEG'-AA0", "PEG'-AA1", "AA0-AA0", "AA1-AA2", "AA2-XX3", "AA2-Asn", "XX3-Asn", "Asn-AA5", "AA5-AA6", "AA6-AA7", "AA7-Leu" and "AA9-AA10" are the same. For example, "AA6-AA7" refers to

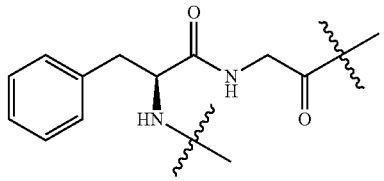 [SMILES: *N[C@@H](Cc1ccccc1)C(=O)NCC(*)=O]

when AA6 is Phe and AA7 is Gly. That is, the left end of formula 1 is the N-terminus and the right end of which is the C-terminus.

In the structural formula, "AA10-P" refers to a group formed by substituting —OH in carboxyl (—COOH) of AA10 with P, for example, "AA10-P" refers to

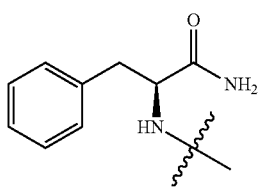 [SMILES: *N[C@@H](Cc1ccccc1)C(N)=O]

when AA10 is Phe and P is —NH$_2$. If the right end of the specific sequence ends with amino acid (AA10), and it is not specified which group —P is, it means that P is —OH by default.

In the structural formula, the "chemical bond" of XX3 means that the former group and the latter group are linked by the chemical bond "—", and the specific chemical bond has the same meaning as described above. The same is true for "m is 0" and "n is 0". For example, when XX3 is a chemical bond, AA2 and Asn are linked by a chemical bond "—" in the case of "AA2-Asn".

The peptide molecules of the present invention are defined herein using conventional single letter codes for representing amino acids. The term "amino acid" includes water-soluble organic compounds having carboxyl (—COOH) and amino (—NH$_2$) groups attached to α-carbon atoms. The amino acid can be represented by the general formula R—CH(NH$_2$)COOH; said R group is a hydrogen or an organic group and determines the properties of any specific amino acid. Tetrahedral arrangement of four different groups around α-carbon atoms makes amino acids optically active. The two mirror image isomers are called L-isomer and D-isomer. Generally, only L-amino acids are components of proteins such as eukaryotic proteins.

Unless otherwise stated, the peptide molecules of the present disclosure comprise L-amino acids. When D-amino acid is present in the peptide molecule of the present disclosure, it is represented by a conventional single-letter amino acid code prefixed with "(D)".

As described, the molecule of the present disclosure may comprise or consist of a peptide sequence having "any D-amino acid" at a specific position. Said "any D-amino acid" includes any natural or unnatural (e.g., chemically modified) D-amino acid at a specific position in the sequence. Examples of natural D-amino acids are as follows: D-alanine; D-aspartic acid D-cysteine; D-glutamic acid; D-phenylalanine; D-glycine; D-histidine; D-isoleucine; D-lysine; D-leucine; D-methionine; D-asparagine; D-proline; D-glutamine; D-arginine; D-serine; D-threonine; D-valine; D-tryptophan; D-tyrosine. Examples of unnatural D-amino acids are as follows: naphthylalanine; D-pyridylalanine; D-tert-butylserine; D-ornithine; D-ε aminolysine; D-hyperarginine; D-α methylleucine and the substitution of halogens (e.g., F) for protons in these and other unnatural amino acids.

By forming peptide bonds, amino acids are combined to form short chains (peptides) or longer chains (polypeptides). It is known that proteins and/or peptides are composed of about 20 common amino acids with different mobile phase ratios, and their sequences determine the shape, properties and biological effects of proteins and/or peptides. Amino acid residues in the chain of such peptides or polypeptides are usually represented by their arrangement positions on the chain, and the first site (i.e., site 1) is designated as the amino acid at the N-terminus of the chain.

TABLE 1

| Explanation of Amino Acid Abbreviations | |
|---|---|
| Abbreviation | Full name |
| Ala | Alanine |
| Cys | Cysteine |
| Asp | Aspartic acid |
| Glu | glutamate |
| Phe | Phenylalanine |
| Gly | glycine |
| His | histidine |
| Ile | Isoleucine |
| Lys | Lysine |
| Leu | leucine |
| Met | met |
| Asn | asparagine |
| Pro | proline |
| Gln | Glutamine |
| Arg | Arginine |
| Ser | Serine |
| Thr | Threonine |
| Val | val |
| Trp | Tryptophan |
| Tyr | tyr |
| D-Ala | D-alanine |
| D-Cys | D-cysteine |
| D-Asp | D-aspartic acid |
| D-Glu | D-glutamic acid |
| D-Phe | D-Phenylalanine |
| D-Gly | D-glycine |
| D-His | D-histidine |
| D-Ile | D-isoleucine |
| D-Lys | D-lysine |
| D-Leu | D-leucine |
| D-Met | D-methionine |
| D-Asn | D-asparagine |
| D-Pro | D-proline |
| D-Gln | D-glutamine |
| D-Arg | D-arginine |

TABLE 1-continued

| Explanation of Amino Acid Abbreviations | |
|---|---|
| Abbreviation | Full name |
| D-Ser | D-serine |
| D-Thr | D-threonine |
| D-Val | D-valine |
| D-Trp | D-tryptophan |
| D-Tyr, DTyr | D-tyrosine |
| Ac | Acetyl |
| cyc | The amino group of the N-terminal amino acid and the carboxyl group of the C-terminal amino acid are condensed to form an amide bond to form a ring. |
| Hyp | Trans-4-hydroxyproline |
| azaGly, azaG | Azoglycine |
| Arg(Me), R(Me) | N omega-methyl arginine, 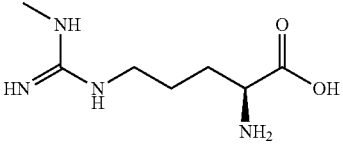 |
| N—Me-Arg, N—MeArg, NMeArg, NMe-Arg | N alpha-methyl arginine, 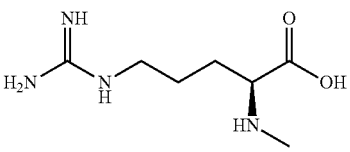 |
| αMePhe, α-Me-Phe, αMe-Phe, α-MePhe | Alpha-methyl phenylalanine, 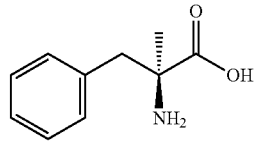 |
| NMePhe, N—Me-Phe, N-MePhe, NMe-Phe | N-methyl phenylalanine |
| N—Me-D-Phe, NMe—D-Phe | N-methyl-D-phenylalanine |
| 1Nal, Nal1, Nal-1,1-Nal | 1-naphthylalanine, 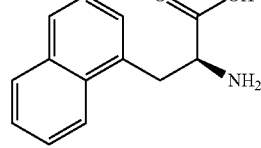 |
| 2Nal, Nal2, Nal-2,2-Nal | 2-naphthylalanine, 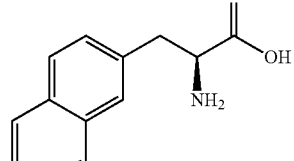 |
| 4Pal, 4-Pal | 4-pyridylalanine, 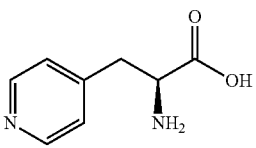 |

TABLE 1-continued

| Explanation of Amino Acid Abbreviations | |
|---|---|
| Abbreviation | Full name |
| Phe(4-F) | 4-fluorophenylalanine |
| αMeTyr, αMe-Tyr | Alpha-methyl tyrosine, 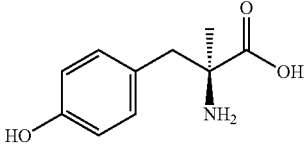 |
| ψ(CH2NH)51 | The —CONH— bond between the 51st amino acid and the 52nd amino acid is replaced by the —CH$_2$NH— bond. |
| Ava | Delta-amyl acid, 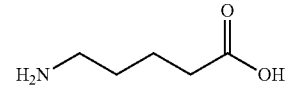 |
| Aib | Alpha-methyl alanine, 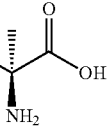 |
| Sar | N-methylglycine, sarcosine |
| Chg | L-α-alpha-cyclohexylglycine, 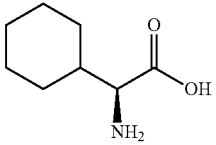 |
| Dap(Dnp) | N'-(2,4-dinitrophenyl)-L-2,3-diaminopropionic acid, 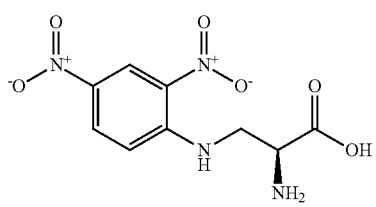 |
| D-Phe(2,4-diCl), D-Phe(2,4-DiCl) | 2,4-dichloro-D-phenylalanine |
| D-2Fua, 3-(2-furyl)-D-Ala, 3-(2-furyl)-D-Alanine | 3-(2-furyl)-D-alanine, 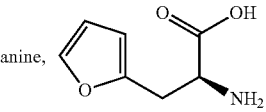 |
| Pro(5Ph), Pro(5-phenyl) | (2S,5R)-5-phenylpyrrolidine-2-carboxylic acid |
| Thz | 4-thioproline |
| Phe(3-Cl) | 3-chlorophenylalanine |
| Bta | 3-(3-benzothiophene)alanine |
| HoPhe, HomoPhe | High phenylalanine (α-amino acid) |
| Phe(4-tBu) | 4-tert-butylphenylalanine |
| HoSer, HomoSer | Homoserine (α-amino acid) |
| 2Pal, 2-Pal | 2-pyridylalanine, 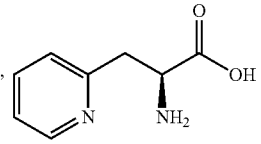 |

TABLE 1-continued

Explanation of Amino Acid Abbreviations

| Abbreviation | Full name |
|---|---|
| 3Pal, 3-Pal | 3-pyridylalanine, 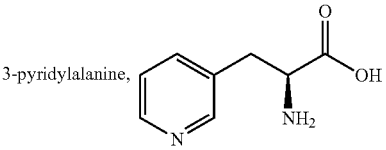 [SMILES: N[C@@H](Cc1cccnc1)C(=O)O] |
| Phe(4-Cl) | 4-chlorophenylalanine |
| Tyr(Me) | O-methyl tyrosine, 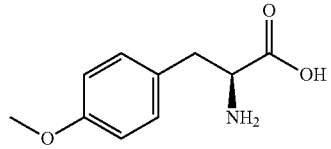 |
| Phe(4-Me) | 4-Methylphenylalanine |
| Cbz | carbobenzoxy- |
| Pro(di-F), Pro(diF), DifluoroPro, DiFluorPro | 4,4-difluoroproline |
| BetaAla, Beta-Ala | Beta-alanine |
| N—Me-Ala, NMe-Ala, NMeAla, N-MeAla | N-methyl alanine |
| N—Me-D-Ala, NMe-D-Ala, NMeD-Ala | N-methyl-D-alanine |
| N—Me-Leu, NMe-Leu, NMeLeu | N-methylleucine |
| N—Me-D-Leu, NMe-D-Leu, NMeD-Leu | N-methyl-D-leucine |
| Pro(4-NH$_2$), (4-aminoPro) | (2S,4R)-4-aminopyrrolidine-2-carboxylic acid |
| Thi | 3-(2-thienyl)-alanine |
| S-Pip | S-high proline, (S)-piperidine-2-formic acid |
| BetaHoLeu, BetaHomoLeu | Beta-homoleucine |
| HoLeu, HomoLeu | Homoleucine (α-amino acid) |
| D-HoLeu D-HomoLeu | D-homoleucine (α-amino acid) |
| N—Me-HoLeu, N—Me-HomoLeu, NMe-HomoLeu | N-methyl homoleucine (α-amino acid) |
| N—Me-D-HoLeu, N—Me-D-HomoLeu, NMe-D-HomoLeu | D-N-methyl homoleucine (α-amino acid) |
| Nle | N-leucine |
| Cha | 3-cyclohexylalanine |
| Sta | (3S,4S)-4-amino-3-hydroxy-6-methylheptanoic acid |
| stapled | Two olefin groups in the same peptide undergo olefin metathesis reaction to form a ring. |
| X | (S)-2-amino-2-methyl-6-heptenoic acid |
| BetaPhe | Beta-phenylalanine |
| BataHoPhe, BetaHomoPhe | Beta-homophenylalanine |
| Phe(2-Br) | 2-bromophenylalanine |
| Phe(pentaF) | Pentafluorophenylalanine |
| Phe(4-CF3) | (4-trifluoromethyl)-phenylalanine |
| Bpa | (4-benzoyl)-phenylalanine |
| Ala(dip) | 3,3-diphenyl alanine |
| NAsn | 2-((2-amino-2-oxoethyl)amino)acetic acid, 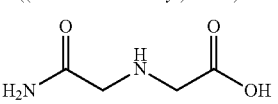 |
| NLeu | N-(2-methylpropyl) glycine |
| NPhe | N-benzyl glycine |
| Phe(4-I) | 4-iodophenylalanine |
| 2Fua | 3-(2-furyl)-alanine |
| ACPA | 1-aminomethyl cyclopropylformic acid |

TABLE 1-continued

Explanation of Amino Acid Abbreviations

| Abbreviation | Full name |
|---|---|
| PEG4 | 1-amino-3,6,9,12-tetraoxa-pentadec-15-acid, 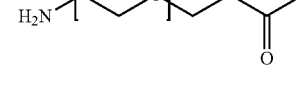 |
| PEG5 | 1-amino-3,6,9,12,15-pentaoxa-octadecyl-18-acid, 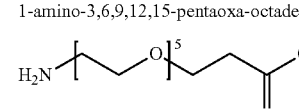 |
| PEG8 | 1-amino-3,6,9,12,15,18,21,24-octaoxa-27C-27-acid, 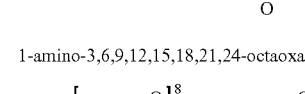 |
| PEG12 | 1-amino-3,6,9,12,15,18,21,24,27,30,33,36-dodecaoxa-39 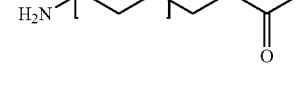 carbon-39-acid, |
| ACPO | 3-Amino-1-Carboxymethyl-Pyridine-2-one |
| Aze | (S)-acridine-2-carboxylic acid |
| Bip | L-4,4'-biphenylalanine |
| Ac-Lys | 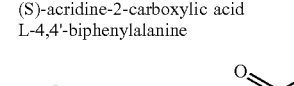 |
| Palm, Palmitoyl | Palmitoyl |
| D-Phe(4-F) | D-4-fluorophenylalanine |
| A6c | 1-aminocyclohexyl formic acid |
| azaPro | Pyrazole alkane-1-formic acid, 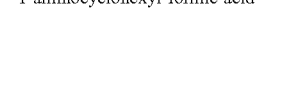 |
| D-Phe(4-Cl) | D-4-chlorophenylalanine |
| D-Phe(3-Cl) | D-3-chlorophenylalanine |
| Tic | L-1,2,3,4-tetrahydroisoquinoline-3-carboxylic acid |
| Ind | L-indoline-2-carboxylic acid |
| R-Pip, (R)-Pip, HoPro, HomoPro | R-homoproline, (R)-piperidine-2-formic acid |
| S-Pip, (S)-Pip | S-homoproline, (S)-piperidine-2-formic acid |
| L-Pip | L-homoproline |
| Oic | L-octahydroindole-2-carboxylic acid |
| azaTic | 3,4-dihydrophthalazine-2(1H)-formic acid |
| N—Me-A6c, NMe-A6c, MeA6c | (1-methylamino)-cyclohexyl formic acid |
| D-Tic | D-1,2,3,4-tetrahydroisoquinoline-3-carboxylic acid |
| Phe(4-amidino), 4-(amidino)phenylalanine | 4-amidinophenylalanine |
| Phe(4-Pyrazol), Phe(4-Pyra), (S)-3-(4-(1H-pyrazol-1-yl)phenyl)-2-aminopropanoic acid | [4-(1H-pyrazol-1-yl)]phenylalanine |
| Aza-N—Me-Gly, azaNMeGly, aza-NMeGly | Aza-(N-methylglycine) |

TABLE 1-continued

Explanation of Amino Acid Abbreviations

| Abbreviation | Full name |
|---|---|
| 1H-1,2,3-triazol-4-yl | Carboxyl-terminated —CONH$_2$ was substituted with 1H-1,2,3-triazol-4-yl |
| 2H-tetrazol-5-yl | Carboxyl-terminated —CONH$_2$ was substituted with 2H-tetrazole-5-yl |
| ψ(NHCO)51 | The —CONH— bond between amino acids 51 and 52 was replaced by —NHCO— bond. |
| ψ(NHCS)51 | The —CONH— bond between amino acids 51 and 52 was replaced by —NHCS— bond. |
| ψ(NH—CO—NH)51 | The —CONH— bond between amino acids 51 and 52 was replaced by —NH—CO—NH— bond. |
| Biotin | D-biotin, vitamin H |
| OEG | 2-(2-(2-aminoethoxy)ethoxy)acetic acid |
| azaPhe | Azaphenylalanine, 1-benzylhydrazine-1-formic acid |
| cycloLeu | 1-aminocyclopentyl formic acid |
| BetaHoAla, BetaHomoAla | Beta-homoalanine |
| Cba | Beta-cyclobutylalanine, |
| Hexanoyl | Hexanoyl |
| Nonanoyl | Nonyl |
| Dodecanoyl | Dodecanoyl |
| C18 diacid | 1,18-octadecanedioic acid |
| Maleimide | Maleimide/Maleimide |
| Ahx | 6-aminocaproic acid |
| 3-[(1-methylpyridinium)-3-yl]alanine, (S)-3-(2-Amino-2-carboxyethyl)-1-methylpyridonium | |
| Alg | |
| Deg | |
| AlphaMeLeu | |

TABLE 1-continued

Explanation of Amino Acid Abbreviations

| Abbreviation | Full name |
|---|---|
| Cpa | [structure: cyclopropyl-CH₂-CH(NH₂)-COOH] |
| ACBC | [structure: 1-aminocyclobutane-carboxylic acid] |
| Cpg | [structure: cyclopropyl-CH(NH₂)-COOH] |
| morpholino cyclic amino acid | [structure: 4-amino-tetrahydropyran-4-carboxylic acid] |
| beta-(thiazoly-4-yl)-L-Ala | [structure: thiazol-4-yl-CH₂-CH(NH₂)-COOH] |

The term "pharmaceutically acceptable salt" refers to a pharmaceutically acceptable organic or inorganic salt. Exemplary acid salts include, but are not limited to, sulfate, citrate, acetate, oxalate, chloride, bromide, iodide, nitrate, bisulfate, phosphate, acid phosphate, isonicotinic acid salt, lactate, salicylate, acid citrate, tartrate, oleate, tannate, pantothenate, hydrogen tartrate, ascorbate, succinate, maleate, fumarate, gluconate, glucuronic acid, gluconate, formate, benzoate, Glutamate, methanesulfonate, ethane sulfonate, benzenesulfonate, p-toluenesulfonate and pamoate (i.e., 1-1-methylene-bis (2-hydroxy-3-naphthalate)). The compound used in the present disclosure can form pharmaceutically acceptable salts with various amino acids. Suitable alkali salts include, but are not limited to, aluminum salts, calcium salts, lithium salts, magnesium salts, potassium salts, sodium salts, zinc salts, bismuth and diethanolamine salts. See Handbook of Pharmaceutical Salts for a review of pharmaceutically acceptable salts: Properties, Selection, and Use (P. Heinrich Stahl and Camille G. Wermuth, ed., Wiley-VCH, 2002).

The term "crystal form" refers to one or more crystal structures formed by different arrangement of molecules in lattice space during crystallization.

The term "solvate" is a crystalline form that contains, in addition to active molecules, one or more solvent molecules incorporated into the crystalline structure. The solvate may include a stoichiometric amount or a non-stoichiometric amount of solvent, and solvent molecules in the solvent may exist in an ordered or non-ordered arrangement. Solvents containing non-stoichiometric amounts of solvent molecules can be obtained by the solvate losing at least some (but not all) of the solvent molecules. In a particular embodiment, a solvate is a hydrate, meaning that the crystalline form of the compound may include water molecules.

The term "prodrug" refers to a derivative of a compound containing a bioreactive functional group such that under biological conditions (in vitro or in vivo), the bioreactive functional group can be cleaved from the compound or otherwise react to provide the compound. In general, prodrugs are inactive, or at least less active than the compound itself, so that their activity cannot be exerted until the compound is cleaved from the bioreaction functional group. The bioreaction functional group can be hydrolyzed or oxidized under biological conditions to provide the compound. For example, the prodrug may contain a biohydrolyzable group, and examples of biohydrolyzable groups include, but are not limited to, biohydrolyzable phosphates, biohydrolyzable esters, biohydrolyzable amides, biohydrolyzable carbonates, biohydrolyzable carbamates, and biohydrolyzable ureides. For the summary of prodrugs, see, for example, J. Rautio et al., nature reviews drug discovery (2008) 7, 255-270 and prodrugs: Challenges and rewards (v.stella et al. ed., springer, 2007).

The term "alkyl" refers to a saturated linear or branched monovalent hydrocarbon group having one to eighteen carbon atoms (e.g., C1-C6 alkyl, also e.g., C1-C4 alkyl). Examples of alkyl include, but are not limited to, methyl, ethyl, 1-propyl, 2-propyl, 1-butyl, 2-methyl-1-butyl, 2-butyl, 2-methyl-2-propyl, 1-pentyl, 2-pentyl, 3-pentyl, 2-methyl-2-butyl, 3-methyl-2-butyl, 3-methyl-1-butyl, 2-methyl-1- butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl, 3,3-dimethyl-2-butyl, 1-heptyl, 1-octyl.

The positive and progressive effect of the present disclosure is that the compound of the present disclosure has better stability and better activity to Kiss1R.

DETAILED DESCRIPTION OF THE PREFERRED EMBODIMENT

The following embodiments further illustrate the present disclosure, but the present disclosure is not limited thereto. The conditions of the experimental methods that didn't specified by the following embodiments were selected according to conventional methods and conditions, or according to the commercial instructions.

The peptide compounds of the present disclosure were all synthesized according to Lu et al (1981) *J. Org. Chem.* 46, 3433 and Fmoc-polyamide solid phase peptide synthesis method disclosed in its references. 9-fluorenylmethoxycarbonyl (Fmoc) group is used to provide a temporary protection for N-amino. Repeated removal of the highly alkali labile protecting group is performed using N,N-dimethylformamide containing 20% piperidine. The side chain functional groups can be protected by their butyl ethers (in the case of serine, threonine and tyrosine), butyl esters (in the case of glutamic acid and aspartic acid), butyl oxycarboxyl derivatives (in the case of lysine and histidine), trityl derivatives (in the case of asparagine and glutamine) and 4-methoxy-2,3,6-trimethylbenzenesulfonyl derivatives (in the case of arginine). When the C-terminal residue is glutamine or asparagine, a 4,4'-dimethoxybenzhydryl group is used to protect the side chain amino functional group. The solid phase carrier is based on a polydimethyl-acrylamide polymer composed of three monomers of dimethylacrylamide (main chain monomer), diallylethylenediamine (cross-linking agent) and acryloyl sarcosinate methyl ester (functionalizing reagent). The peptide-resin cleavable connector used herein is the acid unstable 4-hydroxymethyl-phenoxy-acetic acid derivative. Except for asparagine and glutamine, all amino acid derivatives were added as their prefabricated symmetric anhydride derivatives, while asparagine and glutamine were added using reverse N,N-dicyclohexylcarbodiimide/1-hydroxybenzotriazole mediated coupling method. All coupling and deprotection reactions were monitored using ninhydrin, trinitrobenzenesulfonic acid or isotin detection methods. When the synthesis was completed, the peptide was cleaved from the resin carrier, and at the same time, the protecting group of the side chain was removed by treatment with 95% trifluoroacetic acid containing 50% scavenger mixture. Scavengers that commonly used were ethanedithiol, phenol, anisole and water, and the accurate selection depended on the amino acid composition of the synthesized peptide. Trifluoroacetic acid was removed by vacuum evaporation, followed by grinding with diethyl ether to provide crude peptide. Any scavenger present was removed by a simple extraction step, wherein the crude peptide free of scavenger was provided by lyophilizing the aqueous phase. Reagents for peptide synthesis can be generally purchased from calbiochem-novabiochem (UK) ltd., Nottingham NG7 2QJ, uk. Purification can be achieved by any one or combination of techniques such as volume exclusion chromatography, ion exchange chromatography, and (mainly) reverse phase high performance liquid chromatography. Peptide analysis can be performed using thin layer chromatography, reversed-phase high performance liquid chromatography, amino acid analysis after acid hydrolysis, and rapid atom bombardment (FAB) mass spectrometry.

At the same time, the peptide compounds of the present disclosure can also be synthesized by liquid phase method well known to those skilled in the chemical and biochemical fields.

After synthesis, the peptide sequence of the active agent of the present disclosure can be purified using methods known in the art, such as HPLC and chromatography.

Preparation Embodiment 1 Preparation of Fmoc-Phe-Aza-Leu-OH (Special Compound Included in YA-3)

(2-(((9H-fluorene-9-yl) methoxy) carbonyl-L-phenylalaninyl-2-hydrazino-1-carbonyl-L-leucine)

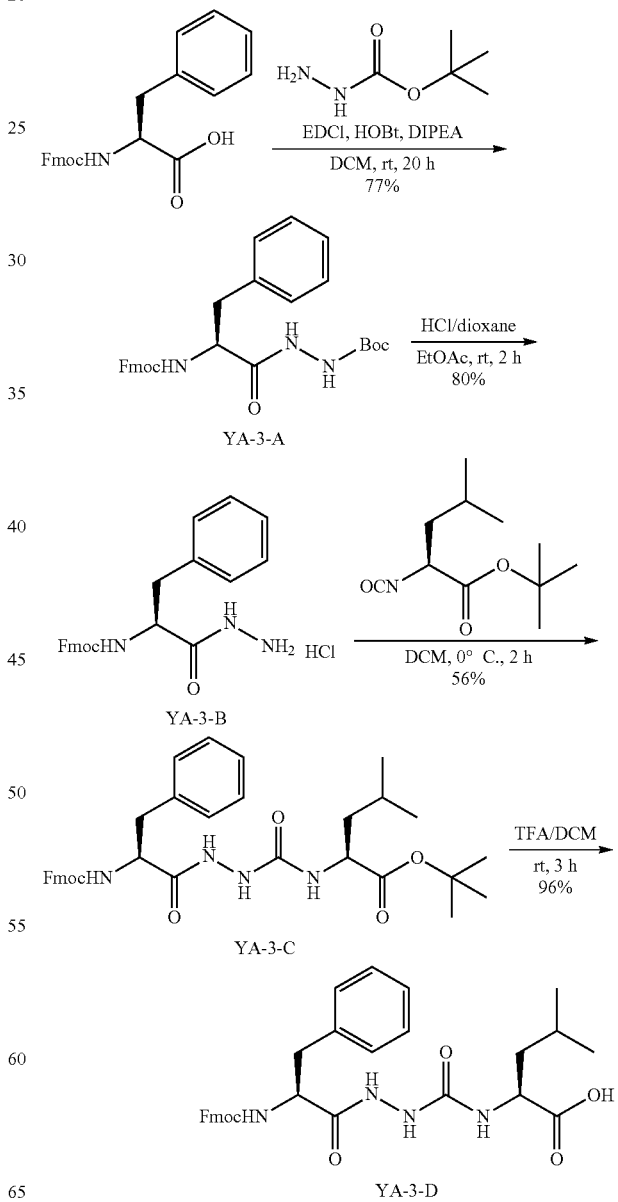

Step 1: (S)-2-(2-((9H-fluorene-9-yl) methoxy) carbonylamino)-3-phenylpropionyl) tert-butyl Hydrazinocarboxylate (Compound YA-3-A)

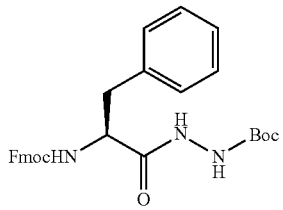

(S)-2-((9 hydrogen-fluorene-9-yl) methoxy) carbonylamino)-3-phenylalanine (10 g, 25.8 mmol), tert-butyl hydrazine formate (3.41 g, 25.8 mmol), HOBt (5.23 g, 38.7 mmol) and 1-(3-dimethylaminopropyl)-3-ethylcarbodiimide hydrochloride (7.42 g, 38.7 mmol) were dissolved in dichloromethane (250 mL), and after stirring at room temperature for 10 minutes, diisopropylethylamine (6.67 g, 51.6 mmol) was added. The mixture was stirred at room temperature for 20 hours and then concentrated. 300 mL of petroleum ether and 30 mL of water were added to the residue, stirred at room temperature for 10 minutes, filtered, the solid was washed with mixed solution EA:PE=1:5 (180 mL), and the filter cake was dried to give the captioned compound (10 g, 77%) as a white solid. LCMS (ESI) [M-99]$^+$=402.0.

Step 2: (S)-2-(2-((9H-fluorene-9-yl) methoxy) carbonylamino)-3-phenylpropionyl) hydrazine hydrochloride (Compound YA-3-B)

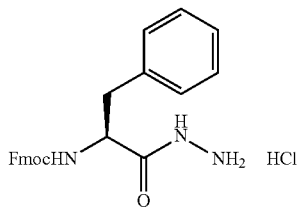

The compound (S)-2-(2-((9H-fluorene-9-yl) methoxy) carbonylamino)-3-phenylpropionyl) hydrazinocarboxylate tert-butyl ester (10 g, 19.94 mmol) was dissolved in ethyl acetate (100 mL), then HCl/dioxane (4M, 100 mL) was added. The reaction mixture was stirred at room temperature for 2 hours. After filtration, the solid was washed twice with the mixed solution EA:PE=2:3 (50 mL), and the filter cake was dried to give the captioned compound (6.4 g, 80%) as a white solid. LCMS (ESI) [M+H]$^+$=402.2.

Step 3: (2-((((9H-fluorene-9-yl) methoxycarbonyl)-L-phenylalaninyl-2-hydrazino-1-carbonyl-L-leucine tert-butyl ester (Compound YA-3-D)

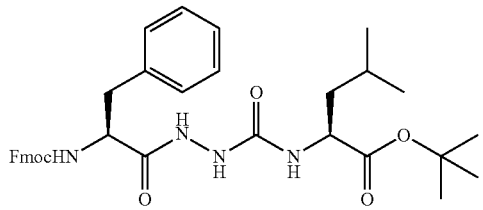

The hydrochloride of compound (S)-2-(2-((9 hydrogen-fluorene-9-yl) methoxy) carbonylamino)-3-phenylpropionyl) hydrazine (6.4 g, 16 mmol) and tert-butyl (S)-2-isocyanate-4-methylpentanoate (4.42 g, 20.7 mmol) were dissolved in methylene chloride (200 mL), and the reaction mixture was stirred at 0° C. for 2 hours. The reaction mixture was concentrated, and the crude product was isolated and purified by high-speed chromatography (petroleum ether/ethyl acetate=1/3) to give the captioned compound (5.5 g, 56%) as a white solid. LCMS (ESI) [M-55]$^+$=559.3.

Step 4: (2-((((9H-fluorene-9-yl) methoxycarbonyl-L-phenylalaninyl-2-hydrazino-1-carbonyl-L-leucine) (Compound YA-3-D)

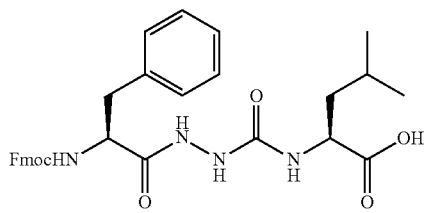

The compound (2-((((9 hydrogen-fluorene-9-yl) methoxy) carbonyl)-L-phenylalaninyl-2-hydrazino-1-carbonyl-L-leucine tert-butyl ester (5.5 g, 8.95 mmol) was dissolved in dichloromethane (20 mL), trifluoroacetic acid (20 mL) was added, and the reaction mixture was stirred at room temperature for 3 hours. The reaction mixture was concentrated, and the resulting residue was isolated and purified by high-speed chromatography (dichloromethane/methanol=4/1) to give the captioned compound (4.8 g, 96%) as a white solid. LCMS (ESI) [M+H]$^+$=559.2. $^1$H NMR (400 MHz, DMSO-d6) δ 8.34 (s, 1H), 8.23 (s, 1H), 7.99 (s, 1H), 7.88 (d, J=7.6 Hz, 2H), 7.75 (d, J=7.6 Hz, 1H), 7.64 (q, J=11.6 Hz, 2H), 7.42-7.25 (m, 9H), 7.20 (d, J=7.2 Hz, 1H), 4.16-4.11 (m, 3H), 3.02 (d, J=10.0 Hz, 1H), 2.84 (d, J=10.8 Hz, 1H), 2.51 (s, 2H), 1.63 (s, 1H), 1.48-1.46 (m, 2H), 0.87-0.82 (m, 6H).

Preparation Embodiment 2: (5R, 11S)-1-(9H-fluoren-9-yl)-5-(furan-2-ylmethyl)-11-isobutyl-3,6,9-trioxo-2-oxa-4,7,8,10-tetraazadodecane-12-acid (Compound YA-167-d)

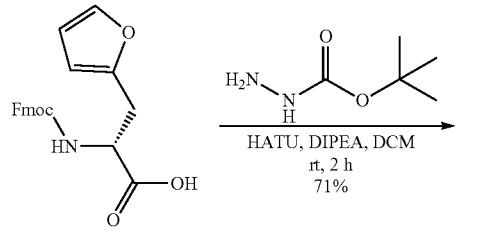

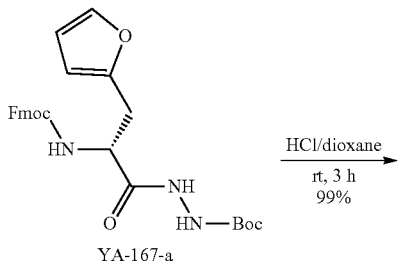

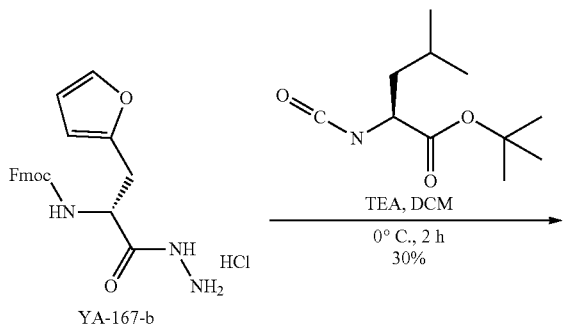

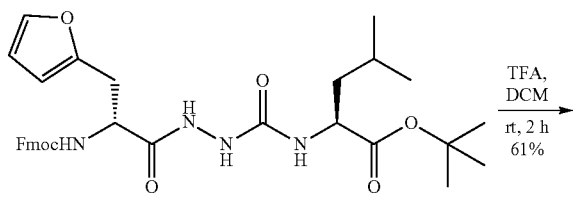

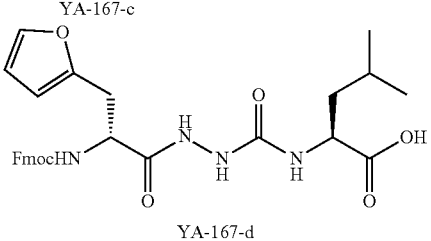

Step 1: (R)-2-(2(((9H-fluoren-9-yl) methoxy) carbonylamino)-3-(furan-2-yl) propanoyl) hydrazinecarboxylic acid tert-butyl ester (Compound YA-167-a)

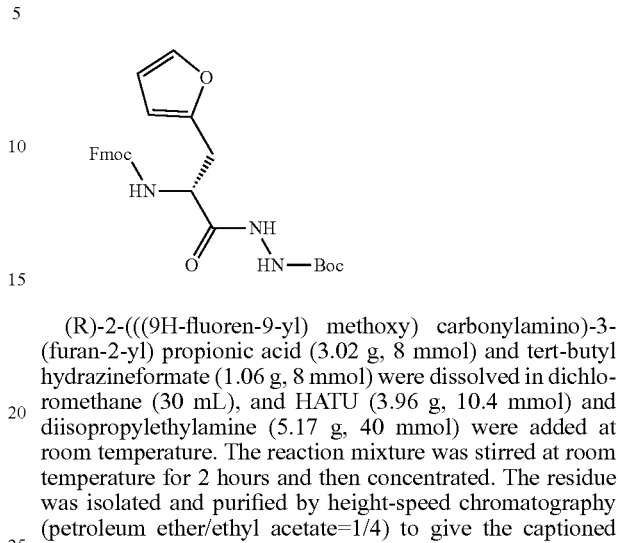

(R)-2-(((9H-fluoren-9-yl) methoxy) carbonylamino)-3-(furan-2-yl) propionic acid (3.02 g, 8 mmol) and tert-butyl hydrazineformate (1.06 g, 8 mmol) were dissolved in dichloromethane (30 mL), and HATU (3.96 g, 10.4 mmol) and diisopropylethylamine (5.17 g, 40 mmol) were added at room temperature. The reaction mixture was stirred at room temperature for 2 hours and then concentrated. The residue was isolated and purified by height-speed chromatography (petroleum ether/ethyl acetate=1/4) to give the captioned compound (2.8 g, 71%) as a white solid. LCMS (ESI) [M-99]$^+$=392.2.

Step 2: (R)-2-(2-(((9Hydroxy-9-yl) methoxy) carbonylamino)-3-(furan-2-yl) propanoyl) hydrazine hydrochloride (Compound YA-167-b)

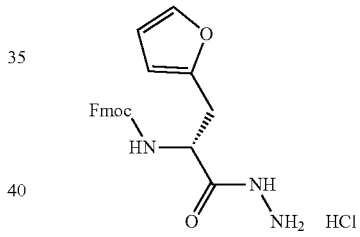

The mixed solution of (R)-2-(2(((9H-fluoren-9-yl) methoxy) carbonylamino)-3-(furan-2-yl) propanoyl) hydrazinecarboxylic acid tert-butyl ester (2.8 g, 5.84 mmol) and a 1,4-dioxane solution of hydrochloric acid (4 M, 20 mL) were stirred at room temperature for 3 hours. The reaction mixture was then concentrated to give the captioned compound (2.2 g, 99%) as a white solid. LCMS (ESI) [M+H]$^+$= 392.1.

Step 3: (5R,11S)-1-(9H-fluoren-9-yl)-5-(furan-2-ylmethyl)-11-isobutyl-3,6,9-trioxo-2-oxo-4,7,8,10-tetraazadodecane-12-acid tert-butyl ester (Compound YA-167-c)

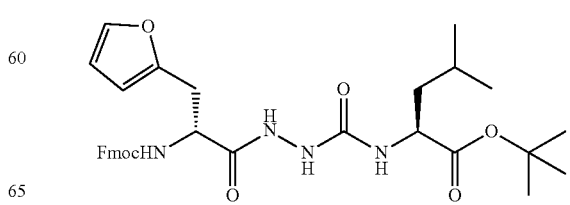

Compound (R)-2-(2-(((9hydro-fluoren-9-yl) methoxy) carbonylamino)-3-(furan-2-yl) propanoyl) hydrazine hydrochloride (2.43 g, 12.96 mmol) was dissolved in dichloromethane (40 mL), and then (S)-2-isocyanato-4-methylvaleric acid tert-butyl ester (2.76 g, 12.96 mmol) was added at 0° C. The reaction mixture was stirred at 0° C. for 2 hours, and then concentrated. The residue was purified by height-speed chromatography (pure ethyl acetate) to give the captioned compound (1.8 g, 30%) as a white solid. LCMS (ESI) [M-55]=549.1.

Step 4: (5R, 11S)-1-(9hydro-fluoren-9-yl)-5-(furan-2-ylmethyl)-11-isobutyl-3,6,9-trioxo-2-oxa-4,7,8,10-tetraazadodecane-12-acid (Compound YA-167-d)

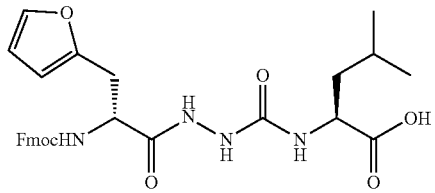

Compound (5R, 11S)-1-(9 hydro-fluoren-9-yl)-5-(furan-2-ylmethyl)-11-isobutyl-3,6,9-trioxo-2-oxa-4,7,8,10-tetraazadodecane-12-acid tert-butyl ester (1.8 g, 2.98 mmol) was dissolved in dichloromethane (20 mL), and then trifluoroacetic acid (20 mL) was added. The reaction mixture was stirred at room temperature for 2 hours and then concentrated. The residue was isolated and purified by height-speed chromatography (dichloromethane/methanol=20/1) to give the captioned compound (1 g, 61%) as a white solid. LCMS (ESI) [M+H]+=549.1; 1H NMR (400 MHz, DMSO-d6) δ 12.55 (s, 1H), 9.87 (s, 1H), 7.97 (s, 1H), 7.89 (d, J=7.6 Hz, 2H), 7.76 (d, J=8.0 Hz, 1H), 7.68 (d, J=6.8 Hz, 2H), 7.52 (s, 1H), 7.42 (t, J=7.2 Hz, 2H), 7.32 (q, J=12.4 Hz, 2H), 6.41 (d, J=8.4 Hz, 1H), 6.34 (s, 1H), 6.18 (s, 1H), 4.33-4.09 (m, 5H), 3.06 (q, J=15.2 Hz, 1H), 2.91 (q, J=15.2 Hz, 1H), 1.68-1.61 (m, 1H), 1.48 (t, J=6.0 Hz, 2H), 0.88-0.84 (m, 6H).

Preparation Embodiment 3: (S)-2-(2((S)-2-((9H-fluorene-9-yl) methoxy) carbonylamino)-3-phenyl-propionyl) pyrazolone-1-carboxamido)-4-methyl-pentanoic acid (Compound YA-184-g)

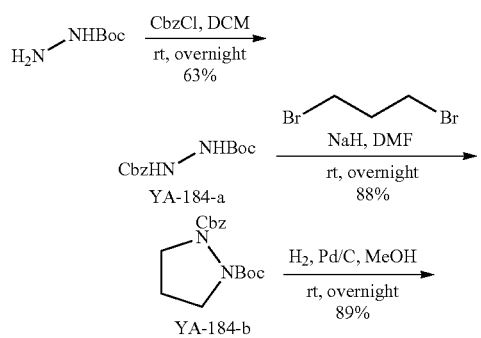

Step 1: Tert-Butyl Hydrazine-1,2-dibenzyl diacid ester (Compound YA-184-a)

CbzHN-NHBoc

Mono-tert-butyl hydrazine diacid (23.7 g, 17.9 mmol) was dissolved in dichloromethane (600 mL), and a dichloromethane (100 mL) solution dissolved with benzyl chloroformate (33.6 g, 19.7 mmol) was added dropwise at room temperature. The reaction mixture was stirred overnight at room temperature, and the reaction mixture was washed with saturated aqueous sodium bicarbonate solution (300 mL×2), saturated saline solution (300 mL×2) and water (300 mL×2), respectively. The organic phase was isolated, dried

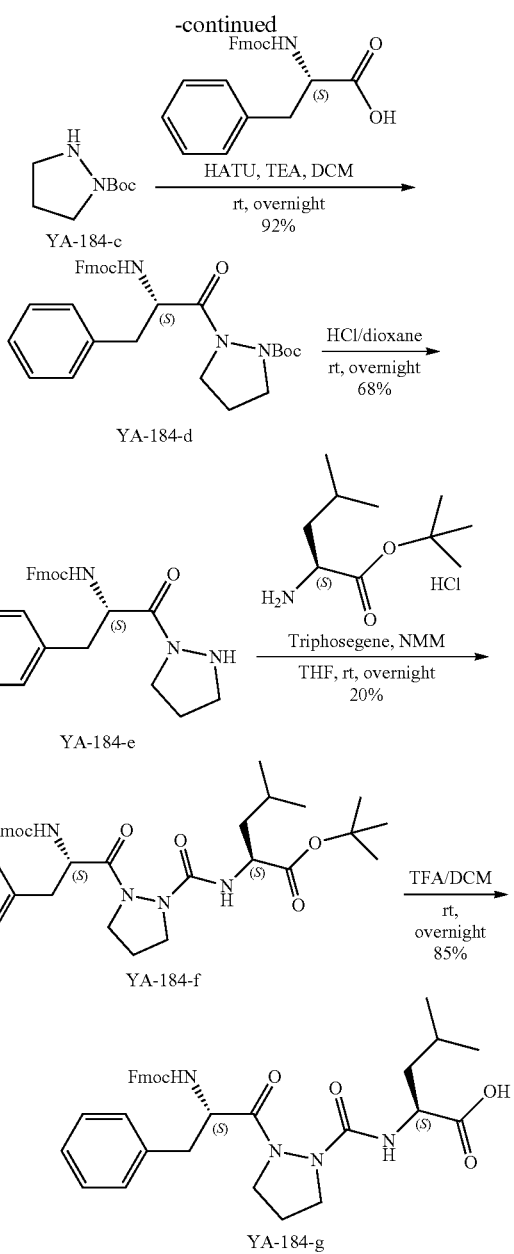

over anhydrous sodium sulfate, filtered and concentrated. The residue was washed twice with petroleum ether (100 mL) to give the captioned compound (30 g, 63%) as a white solid. LCMS (ESI) [M+Na]⁺=289.0.

Step 2: Pyrazolidine-1,2-dibenzyl ester tert-butyl ester (Compound YA-184-b)

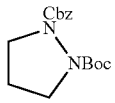

In an ice water bath, sodium hydride (60%, 4.5 g, 112.8 mmol) was suspended in N,N-dimethylformamide (500 mL), and then the solution of N,N-dimethylformamide (100 mL) dissolved with tert-butyl hydrazine-1,2-dibenzoate (15 g, 56.3 mmol) was added dropwise. After the mixed solution was stirred in an ice-water bath for 3 hours, a solution of N,N-dimethylformamide (150 mL) dissolved with 1,3-dibromopropane (11.9 g, 1.05 mmol) was added dropwise. The reaction mixture was stirred overnight at room temperature. Then, the reaction mixture was washed with saturated aqueous sodium bicarbonate solution (150 mL×2), saturated saline solution (150 mL×2) and water (150 mL×2), respectively. The organic phase was isolated, dried over anhydrous sodium sulfate, filtered and concentrated. The residue was isolated and purified by high-speed chromatography (petroleum ether/ethyl acetate=5/1) to give the captioned compound (15 g, 88%) as colorless liquid. LCMS (ESI) [M+Na]⁺=329.1.

Step 3: Pyrazolidine-1,2-dicarboxylic acid mono-tert-butyl ester (Compound YA-184-c)

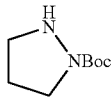

Tert-butyl pyrazole alkyl-1,2-dibasic benzyl ester (5 g, 16.3 mmol) was dissolved in methanol (100 mL) with palladium carbon (0.5 g), the reaction flask is replaced with hydrogen 3 times, and then stirred overnight at room temperature under the protection of hydrogen balloon. The insoluble matter was filtered off and the filter residue was washed 3 times with methanol (15 mL). The filtrate was concentrated and the residue was isolated and purified by high-speed chromatography (petroleum ether/ethyl acetate=2/1) to give the captioned compound (2.5 g, 89%) as a colorless liquid. LCMS (ESI) [M+Na]⁺=195.1.

Step 4: (S)-2-(2-((9H-fluorene-9-yl) methoxy) carbonylamino)-3-phenylpropionyl) pyrazolone-1-carboxylic acid tert-butyl ester (Compound YA-184-d)

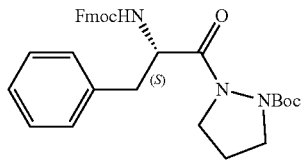

(S)-2-((9 hydrogen-fluorene-9-yl) methoxy) carbonylamino)-3-phenylalanine (2.5 g, 6.4 mmol) were dissolved in methylene chloride (60 mL), and HAT U(3.3 g, 8.7 mmol), HOAt(0.87 g, 6.4 mmol) and triethylamine (2.42 mL, 17.4 mmol) were added sequentially at room temperature. After the mixture were stirred at room temperature for 0.5 hours, pyrazolone-1,2-diacid mono-tert-butyl ester (1 g, 5.8 mmol) were added, and the reaction mixture were stirred overnight at room temperature. Then, the reaction mixture were washed with saturated brine (50 mL×2) and water (50 ml), respectively. The organic phase were isolated, dried over anhydrous sodium sulfate, filtered and concentrated. The residue were isolated and purified by high-speed chromatography (petroleum ether/ethyl acetate=1/1) to give the captioned compound (3.2 g, 92%) as a white solid. LCMS (ESI) [M+Na]⁺=564.2.

Step 5: (S)-2-(2-((9H-fluorene-9-yl) methoxy) carbonylamino)-3-phenylpropionyl) pyrazolone (Compound YA-184-e)

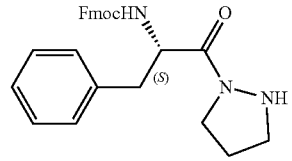

The compound (S)-2-(2-((9 hydrogen-fluorene-9-yl) methoxy) carbonylamino)-3-phenylpropionyl) pyrazolone-1-carboxylic acid tert-butyl ester (2.2 g, 4.06 mmol) were dissolved in methylene chloride (60 mL), followed by adding with HCl/dioxane (4M, 5 mL). The reaction mixture were stirred overnight at room temperature. Then, the reaction mixture were washed with saturated aqueous sodium bicarbonate solution (20 mL×2), saturated saline solution (50 mL×2) and water (50 ml), respectively. The organic phase were isolated, dried over anhydrous sodium sulfate, filtered and concentrated. The residue were isolated and purified by high-speed chromatography (petroleum ether/ethyl acetate=1/0-0/1) to give the captioned compound (1.2 g, 68%) as a white solid. LCMS (ESI) [M+H]⁺=442.1.

Step 6: (S)-2-(2-((2S)-2-((9H-fluorene-9-yl) methoxy) carbonylamino)-3-phenylpropionyl) pyrazolone-1-carboxamido)-4-methyl tert-butyl valerate (Compound YA-184-f)

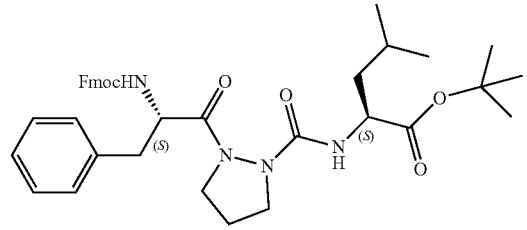

The compound (S)-2-(2-((9 hydrogen-fluorene-9-yl) methoxy) carbonylamino)-3-phenylpropionyl) pyrazolane (1.2 g, 2.7 mmol) was dissolved in tetrahydrofuran (30 mL), subsequently, N-methylmorpholine (273 mg, 2.7 mmol) and triphosgene (267 mg, 0.9 mmol) were added under nitrogen protection, and the reaction mixture was stirred at 0° C. for 1 hour. Then, a solution of L-leucine hydrochloride (602 mg, 2.7 mmol) in tetrahydrofuran (10 mL) was added dropwise, and the reaction mixture was stirred overnight at room temperature. The reaction mixture was concentrated, and the residue was isolated and purified by high-speed chromatography (petroleum ether/ethyl acetate=10/1-0/1) to give the captioned compound (350 mg, 20%) as a white solid. LCMS (ESI) [M+Na]$^+$=677.3.

Step 7: (S)-2-(2-((S)-2-((9H-fluorene-9-yl) methoxy) carbonylamino)-3-phenylpropionyl) pyrazolone-1-carboxamido)-4-methylpentanoic acid (Compound YA-184-g)

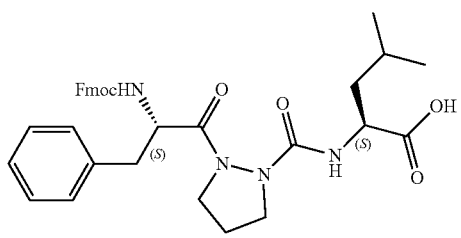

The compound (S)-2-(2-((S)-2-((9H-fluorene-9-yl) methoxy) carbonylamino)-3-phenylpropionyl) pyrazolone-1-carboxamido)-4-methyl tert-butyl valerate (350 mg, 0.54 mmol) was dissolved in methylene chloride (5 mL), subsequently, trifluoroacetic acid (5 mL) was added under ice-water bath, and the reaction mixture was stirred overnight at room temperature. The reaction mixture was concentrated and the residue was isolated and purified by high-speed chromatography (dichloromethane/methanol=1/0-10/1) to give the captioned compound (280 mg, 85%) as a white solid. LCMS (ESI) [M+H]$^+$=599.

Preparation Embodiment 4: (S)-2-(2-((R)-2-((9H-fluorene-9-yl) methoxy) carbonylamino)-3-phenylpropionyl)-3-(2,4-dichlorophenyl) propionyl) pyrazolone-1-carboxamido)-4-oxo-4-(tritylamino) butyric acid (Compound YA-200-d)

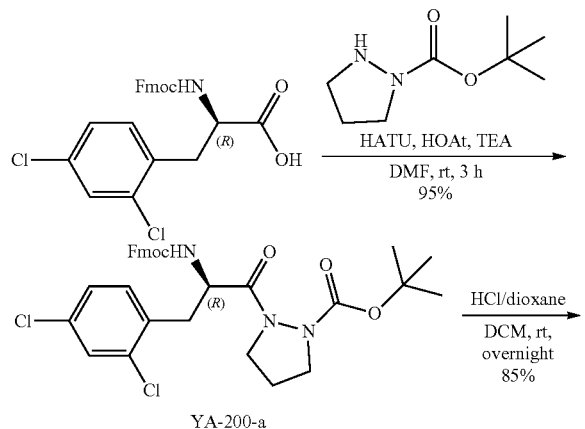

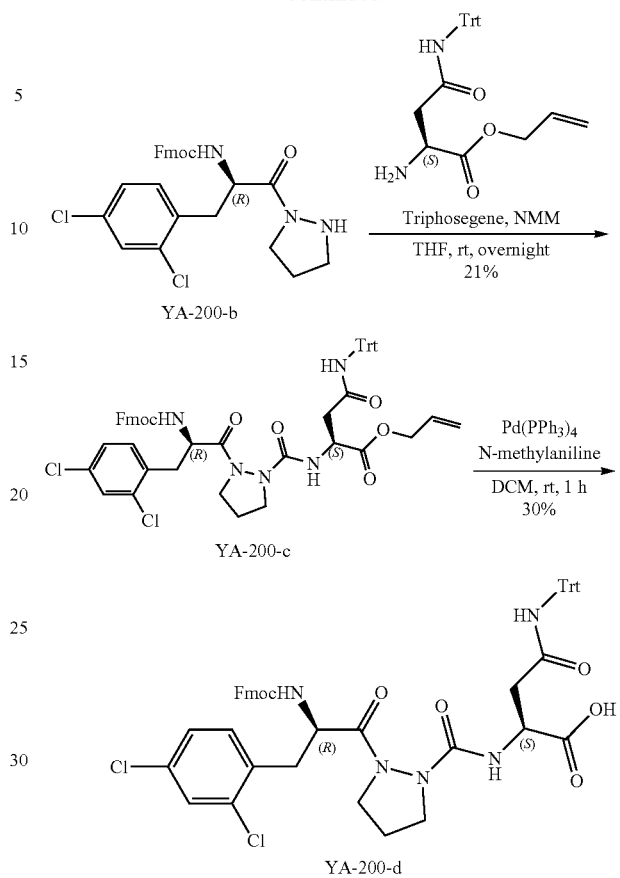

Step 1: (R)-2-(2-((9H-fluorene-9-yl) methoxy) carbonylamino)-3-phenylpropionyl)-3-(2,4-dichlorophenyl) propionyl) pyrazolone-1-carboxylic acid tert-butyl ester (Compound YA-200-a)

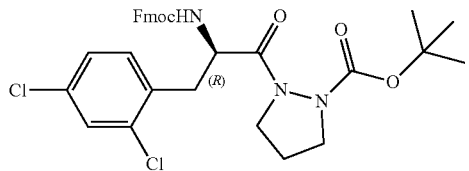

(R)-2((9H-fluorene-9-yl) methoxy) carbonylamino)-3-(2,4-dichlorophenyl) propionic acid (1 g, 2.2 mmol) was dissolved in N,N-dimethylformamide (20 mL), and HATU (1.25 g, 3.3 mmol), HOAt (0.36 g, 2.64 mmol) and triethylamine (667 mg, 6.6 mmol) were added sequentially at room temperature. After the mixture was stirred at room temperature for 0.5 hours, pyrazolone-1,2-diacid mono-tert-butyl ester (0.45 g, 2.64 mmol) was added, and the reaction mixture was stirred at room temperature for 3 hours. Then, water (30 mL) was added to the reaction mixture to precipitate a large amount of solid. The solid was filtered off and dried to give the captioned compound (1.2 g, 95%) as a white solid. LCMS (ESI) [M+Na]$^+$=632.2.

Step 2: (R)-2-(2-((9H-fluorene-9-yl) methoxy) carbonylamino)-3-phenylpropionyl)-3-(2,4-dichlorophenyl) propionyl) pyrazolone (Compound YA-200-b)

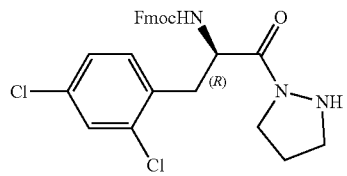

The compound (R)-2-(2-((9 hydrogen-fluorene-9-yl) methoxy) carbonylamino)-3-phenylpropionyl)-3-(2,4-dichlorophenyl) propionyl) pyrazolone-1-carboxylic acid tert-butyl ester (1.2 g, 1.97 mmol) was dissolved in methylene chloride (30 mL), and HCl/dioxane (4M, 2 mL) was then added. The reaction mixture was stirred overnight at room temperature. Then, the reaction mixture was washed with saturated aqueous sodium bicarbonate solution (20 mL×2), saturated saline solution (50 mL×2) and water (50 mL×2), respectively. The organic phase was isolated, dried over anhydrous sodium sulfate, filtered and concentrated. The residue was isolated and purified by high-speed chromatography (petroleum ether/ethyl acetate=1/0-0/1) to give the captioned compound (1 g, 85%) as a white solid. LCMS (ESI) [M+H]+=510.2.

Step 3: (S)-2-(2-((R)-2-((9H-fluorene-9-yl) methoxy) carbonylamino)-3-(2,4-dichlorophenyl) propionyl) pyrazolone-1-carboxamido)-4-oxo-4-(tritylamino) allyl butyrate (Compound YA-200-c)

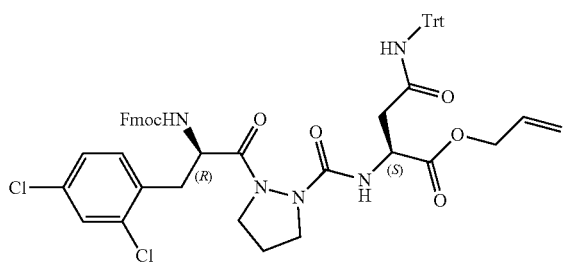

The compound (R)-2-(2-((9 hydrogen-fluorene-9-yl) methoxy) carbonylamino)-3-phenylpropionyl)-3-(2,4-dichlorophenyl) propionyl) pyrazolidine (1.5 g, 2.95 mmol) was dissolved in tetrahydrofuran (60 mL), and N-methyl-morpholine (299 mg, 2.95 mmol) and triphosgene (292 mg, 0.98 mmol) were added under nitrogen protection in an ice water bath. The reaction mixture was stirred at 0° C. for 1 hour. Then, tetrahydrofuran (10 mL) solution of (S)-2-amino-4-oxo-4-(tritylamino) allyl butyrate (1.22 g, 2.95 mmol) was added dropwise, and the reaction mixture was stirred overnight at room temperature. The reaction mixture was concentrated, and the residue was isolated and purified by high-speed chromatography (petroleum ether/ethyl acetate=10/1-0/1) to give the captioned compound (570 mg, 21%) as a white solid. LCMS (ESI) [M+Na]+=972.3.

Step 4: (S)-2-(2-((R)-2-((9H-fluorene-9-yl) methoxy) carbonylamino)-3-phenylpropionyl)-3-(2,4-dichlorophenyl) propionyl) pyrazolone-1-carboxamido)-4-oxo-4-(tritylamino) butyric acid (Compound YA-200-d)

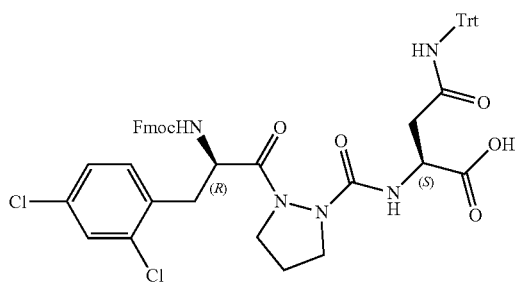

The compound (S)-2-(2-((R)-2-((9H-fluorene-9-yl) methoxy) carbonylamino)-3-(2,4-dichlorophenyl) propionyl) pyrazolone-1-carboxamido)-4-oxo-4-(tritylamino) allyl butyrate (570 mg, 0.6 mmol) was dissolved in dichloromethane (20 mL), subsequently, PD (PPh3) 4 (277 mg, 0.24 mmol) and N-methylaniline (64 mg, 0.6 mmol) were added, and stirred at room temperature for 1 hour. The solvent was evaporated to dryness, and the residue obtained was purified by high-speed chromatography (dichloromethane/methanol=1/0-10/1) to give crude product, and then the captioned compound (170 mg, 30%) was prepared by reverse phase as a white solid. LCMS (ESI) [M+Na]+=932.

Preparation Embodiment 5: (S)-2-(1-(((9H-fluorene-9-yl) methoxy) carbonyl) amino)-2-phenethyl)-1-H-imidazole-5-carboxylic acid (Compound YA-208-e)

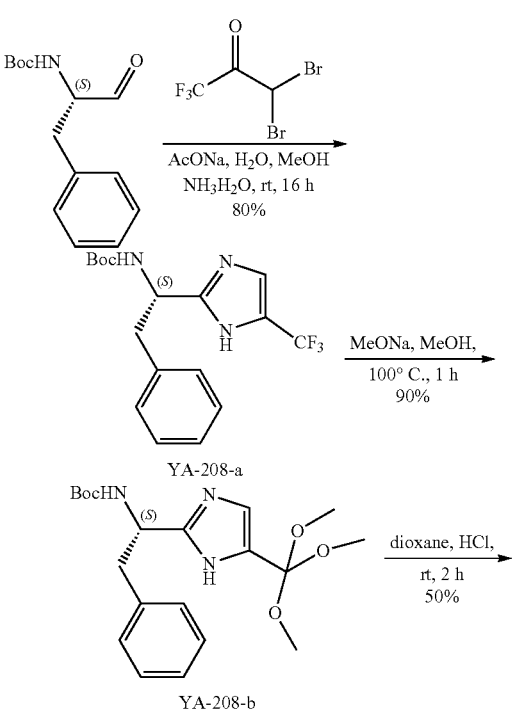

Step 2: Tert-butyl (S)-(2-phenyl-1-(5-(trimethoxymethyl)-1-hydrogen-imidazole-2-yl) ethyl) carbonate (Compound YA-208-b)

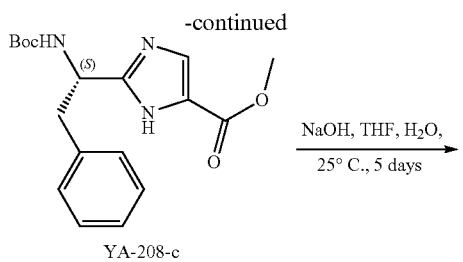

YA-208-c

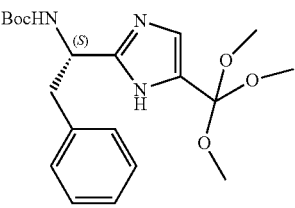

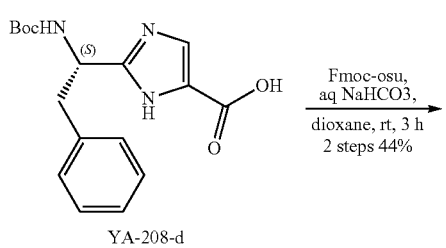

YA-208-d

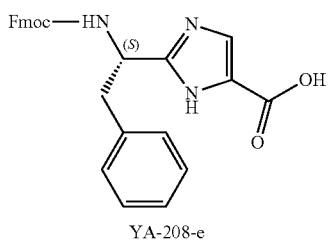

YA-208-e

Step 1: Tert-butyl (S)-(2-phenyl-1-(5-(trifluoromethyl)-1-hydrogen-imidazole-2-yl) ethyl) carbonate (Compound YA-208-a)

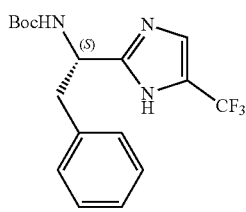

3,3-dibromo-1,1,1-trifluoromethyl acetone (0.87 g, 3.2 mmol) and sodium acetate (0.53 g, 6.4 mmol) were added to methanol (5 ml), the reaction mixture was stirred at 9° C. for 1 hour, and then cooled to room temperature. A solution of N-tert-butoxycarbonyl-L-phenylpropanal (0.73 g, 2.9 mmol) in methanol solution (10 mL) and concentrated ammonia water (2 mL) were added and stirred at room temperature for 16 h. The mixture was filtered and the solid was washed with water (20 mL) to give the captioned compound (0.8 g, yield 80%) as a white solid. LCMS (ESI): $[M+H]^+$=356.1.

Tert-butyl (S)-(2-phenyl-1-(5-(trifluoromethyl)-1-hydrogen-imidazole-2-yl) ethyl) carbonate ((0.8 g, 2.2 mmol) and a solution of sodium methoxide in methanol (25%) (20 mL) were dissolved in methanol (20 mL). The mixture was heated at 100° C. for 2 hours and then concentrated. The residue was dissolved in ethyl acetate (100 mL), washed with water, the organic phase was dried over anhydrous sodium sulfate, filtered, and concentrated to give the captioned compound (0.88 g, 100%) as a yellow oil. LCMS (ESI) $[M+H]^+$=346.1.

Step 3: (S)-2-(1-amino-2-phenethyl)-1-hydrogen-imidazole-5-methyl carbonate (Compound YA-208-c)

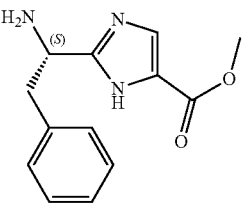

Tert-butyl (S)-(2-phenyl-1-(5-(trimethoxymethyl)-1-hydrogen-imidazole-2-yl) ethyl) carbonate (0.8 g, 2.0 mmol) was dissolved in dioxane hydrochloride (20 mL), the reaction mixture was stirred at room temperature for 2 hours, and then concentrated. The residue was isolated and purified by high-speed chromatography (dichloromethane/methanol=95/5) to give the captioned compound (250 mg, 50%) as a brown solid. LCMS (ESI) $[M+H]^+$=246.1.

Step 4: (S)-2-(1-amino-2-phenylethyl)-1-hydrogen-imidazole-5-carboxylic acid (Compound YA-208-d)

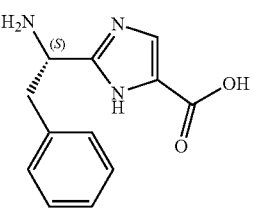

The compound (S)-2-(1-amino-2-phenethyl)-1-hydrogen-imidazole-5-methyl carbonate (250 mg, 1.0 mmol) was dissolved in tetrahydrofuran (5 mL) and water (5 mL), then strong sodium oxide (400 mg, 10.0 mmol) was added and stirred at room temperature for 120 hours. The pH value of the mixed solution was adjusted to 7, which was directly used in the next reaction. LCMS (ESI) [M+H]⁺=232.1.

Step 5: (S)-2-(1-(((9H-fluorene-9-yl) methoxy) carbonyl) amino)-2-phenethyl)-1-H-imidazole-5-carboxylic acid (Compound YA-208-e)

(S)-2-(1-amino-2-phenethyl)-1-hydrogen-imidazole-5-carboxylic acid (231 mg, 1.0 mmol) and 9-fluorenyl-N-succinimidyl carbonate (337 mg, 1.0 mmol) were dissolved in saturated aqueous sodium bicarbonate solution (20 mL) and dioxane (20 mL), and the mixture was stirred at room temperature for 3 hours. The mixture was extracted with ethyl acetate (50 mL), the organic phase was dried with anhydrous sodium sulfate, filtered, concentrated, and the residue was isolated and purified by high-speed chromatography (dichloromethane/methanol=80/20) to give the captioned compound (200 mg, 44%) as a white solid. LCMS (ESI): [M+H]+=454.2; 1H NMR (400 MHz, DMSO) δ 12.68 (s, 1H), 12.40 (s, 1H), 8.09-7.75 (m, 3H), 7.73-7.59 (m, 2H), 7.41 (t, J=7.4 Hz, 2H), 7.39-6.96 (m, 8H), 4.87 (s, 1H), 4.37-3.95 (m, 3H), 3.19 (d, J=16.9 Hz, 1H), 3.10-2.70 (m, 1H).

Preparation Embodiment 6: (S)-8-benzyl((R)-1-tert-butoxyethyl)-1-(9H-fluorene-9-yl)-3,6,9-tricarbonyl-2-oxa-4,7,8,10-tetraazadodecane-12-carboxylic acid (Compound YA-241-d)

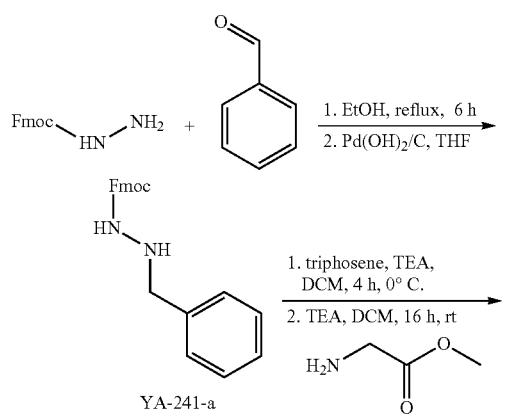

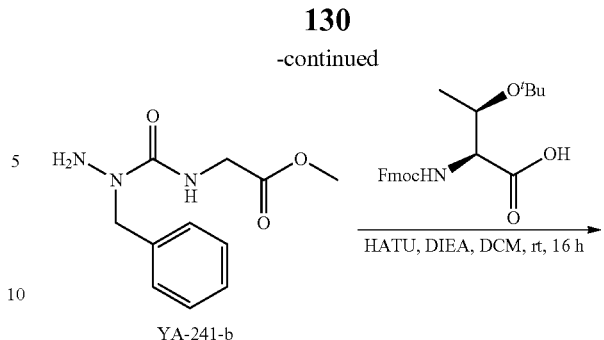

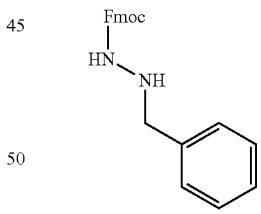

Step 1: (9H-fluorene-9-yl) methyl 2-benzylhydrazine carbonate (Compound YA-241-a)

Fmoc-hydrazine (20 g, 78.7 mmol) was dissolved in ethanol (300 mL), and benzaldehyde (8.35 g, 78.7 mmol) was added at room temperature. The reaction mixture was heated under reflux and stirred for 6 hours, then concentrated and dissolved in tetrahydrofuran (300 mL). Then, Pd (OH)₂/C (4 g, content 20%) was added at room temperature, and the mixture was ventilated with hydrogen for five times, and then reacted in hydrogen at five atmospheres for 16 hours. Then the mixture was filtered and concentrated, and the residue was isolated and purified by high-speed chromatography (petroleum ether/ethyl acetate=3/2) to give the captioned compound (20 g, 74%) as a white solid. LCMS (ESI) [M+Na]⁺=367.1.

Step 2: Methyl 2-(1-benzylhydrazine amido) acetate (Compound YA-241-b)

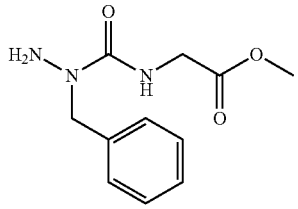 [SMILES: COC(=O)CNC(=O)N(N)Cc1ccccc1]

Triphosgene (1.82 g, 6.1 mmol) was dissolved in methylene chloride (10 mL), and then a solution of methyl glycinate hydrochloride (1.5 g, 12.2 mmol) dissolved in methylene chloride (30 mL) was added dropwise at 0° C. The reaction mixture was stirred at 0° C. for 4 hours, then triethylamine (4.95 g, 48.9 mmol) was added and stirred for another 20 minutes. Then, (9 hydrogen-fluorene-9-yl) methyl 2-benzylhydrazine carbonate (5.5 g, 15.9 mmol) and triethylamine (6.81 g, 61.2 mmol) were added, and the reaction mixture was stirred overnight at room temperature. Then the reaction liquid was directly concentrated, and the residue was isolated and purified by high-speed chromatography (dichloromethane/ethyl acetate=1/3) to give the captioned compound (900 mg, 91%) as a white solid. LCMS (ESI) [M+H]$^+$=238.2.

Step 3: (S)-8-benzyl-5-((R)-1-tert-butoxyethyl)-1-(9-hydrogen-fluorene-9-yl)-3,6,9-tricarbonyl-2-oxa-4,7,8,10-tetraazadodecane-12-methyl formate (Compound YA-241-c)

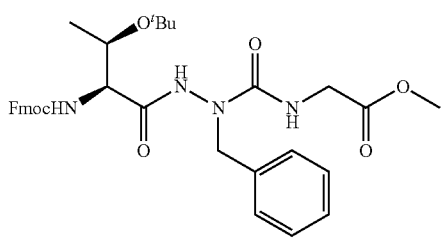

Fmoc-O-tert-butyl-L-threonine (1.51 g, 3.8 mmol) and methyl 2-(1-benzylhydrazine amido) acetate (900 mg, 3.8 mmol) were dissolved in dichloromethane (80 mL), then HATU (1.73 g, 4.6 mmol) and diisopropylethylamine (1.47 g, 11.4 mmol) were added. The reaction mixture was stirred overnight at room temperature and then concentrated. The residue was isolated and purified by high-speed chromatography (petroleum ether/ethyl acetate=3/1) to give the captioned compound (300 mg, 13%) as a white solid. LCMS (ESI) [M+H]$^+$=617.4.

Step 4: (S)-8-benzyl-5-((R)-1-tert-butoxyethyl)-1-(9-hydrogen-fluorene-9-yl)-3,6,9-tricarbonyl-2-oxa-4,7,8,10-tetraazadodecane-12-formic acid (Compound YA-241-d)

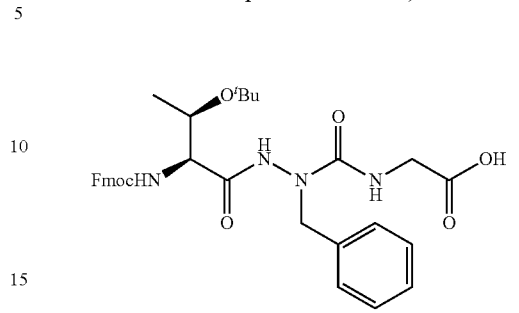

(S)-8-benzyl-5-((R)-1-tert-butoxyethyl)-1-(9-hydrogen-fluorene-9-yl)-3,6,9-tricarbonyl-2-oxa-4,7,8,10-tetraazadodecane-12-methyl formate (300 mg, 0.49 mmol) was dissolved in a mixed solution of tetrahydrofuran (5 mL) and water (5 mL), then lithium hydroxide monohydrate (123 mg, 2.92 mmol) was added at room temperature and stirred overnight at room temperature. The reaction mixture was evaporated to dryness under vacuum and the PH was adjusted to 4 with 1 mol/L hydrochloric acid. Dioxane (8 mL), FMOC-OSU (164 mg, 0.49 mmol) and sodium carbonate (103 mg, 0.97 mmol) were added at room temperature, followed by stirring at room temperature for one night. The reaction mixture was adjusted to PH=3-4 with 1 mol/L hydrochloric acid, then extracted with ethyl acetate (200 mL×3) and washed with saturated saline (100 mL). The organic phase was isolated, dried over anhydrous sodium sulfate, filtered and concentrated. The residue was eluted with a linear concentration gradient (30 minutes) at a flow rate of 50 ml/minute. Eluent A/B: 90/10-40/60 use: eluent A: 0.1% TFA aqueous solution, eluent B: acetonitrile, on preparative HPLC, using Boston ODS 120 g Flash, CV 60 ml-100 ml/min, PMAX: 200 psi. The fractions containing the product were collected and lyophilized to give the captioned compound (240 mg, 82%) as a white solid. LCMS (ESI) [M+Na]+=625.0; 1H NMR (400 MHz, DMSO-d6) δ 10.01 (s, 1H), 7.90-7.78 (m, 5H), 7.74-7.29 (m, 10H), 6.85 (s, 1H), 4.66-4.11 (m, 6H), 3.79-3.70 (m, 3H), 1.18 (s, 9H), 1.06 (d, J=44.4, 3H).

Preparation Embodiment 7: 3-(4-(1 hydrogen-pyrazol-1-yl) phenyl)-2-((9 hydrogen-fluoren-9-yl) methoxy) carbonylamino) propionic acid (Compound YA-242-C)

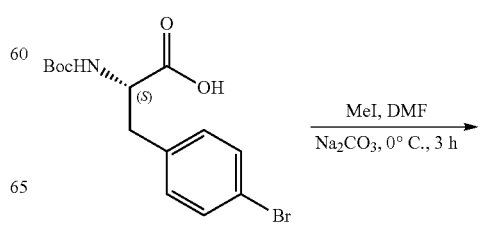

133

-continued

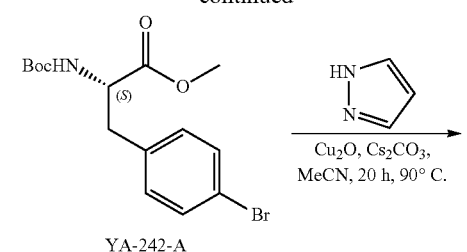

YA-242-A

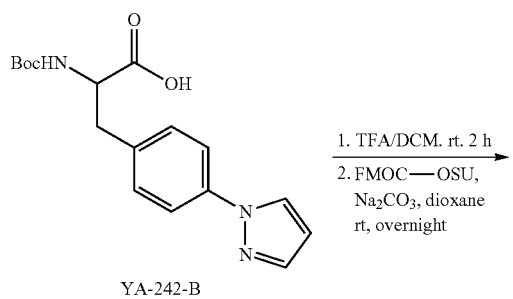

YA-242-B

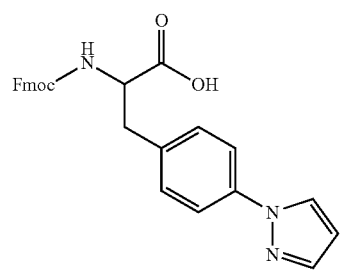

YA-242-C

Step 1:
Tert-butoxycarbonyl-4-bromo-L-phenylalanine methyl ester (Compound YA-242-A)

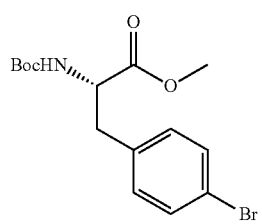 [SMILES: COC(=O)[C@H](Cc1ccc(Br)cc1)NC(=O)OC(C)(C)C]

Tert-butoxycarbonyl-4-bromo-L-phenylalanine (2.21 g, 6.4 mmol) and sodium carbonate (1.37 g, 12.9 mmol) were dissolved in N,N-dimethylformamide (60 mL), cooled to 0° C. and then methyl iodide (4.57 g, 32.2 mmol) was added. The reaction mixture was stirred at 0° C. for 2 hours and then diluted with ethyl acetate (500 mL). The mixed solution was washed with water (150 mL×4) and saturated saline (150 mL), respectively. The organic phase was isolated, dried over anhydrous sodium sulfate, filtered and concentrated. The crude product was isolated and purified by high-speed chromatography (petroleum ether/ethyl acetate=5/1) to give the captioned compound (2.16 g, 94%) as a white solid. LCMS (ESI) [M+H]$^+$=380.0.

134

Step 2: 3-(4-(1-hydrogen-pyrazol-1-yl) phenyl)-2-(tert-butoxycarbonylamino) propionic acid (Compound YA-242-B)

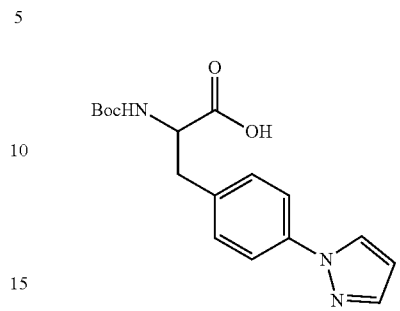

Tert-butoxycarbonyl-4-bromo-L-phenylalanine methyl ester (500 mg, 1.4 mmol), pyrazole (475 mg, 7 mmol) and cesium carbonate (907 mg, 2.8 mmol) were dissolved in acetonitrile (40 mL), and cuprous oxide (399 mg, 2.8 mmol) was added under nitrogen protection. The reaction mixture was heated under nitrogen protection, refluxed and stirred for 24 hours, cooled to room temperature, and diluted with ethyl acetate (100 mL). The mixed solution was filtered and concentrated, and the crude product was eluted with a linear concentration gradient (30 minutes) at a flow rate of 50 ml/minute. Eluent AB was used at a ratio of 90/10-50/50: eluent A:0.1% TFA aqueous solution, eluent B: Acetonitrile, on preparative HPLC, use Boston ODS 120 g Flash, CV 60 ml-100 ml/min, PMAX: 200 psi. The fractions containing the product were collected and lyophilized to give the captioned compound (150 mg, 32%) as a white solid. LCMS (ESI) [M+Na]$^+$=354.1.

Step 3: 3-(4-(1-hydrogen-pyrazol-1-yl) phenyl)-2-((9-hydrogen-fluoren-9-yl) methoxy) methoxyamino) propionic acid (Compound YA-242-C)

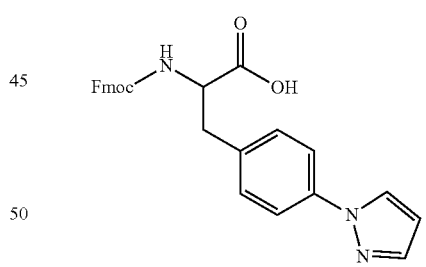

3-(4-(1-hydrogen-pyrazol-1-yl) phenyl)-2-(tert-butoxycarbonylamino) propionic acid (370 mg, 1.1 mmol) was dissolved in a mixture of dichloromethane (8 mL) and trifluoroacetic acid (2 mL) and stirred at room temperature for 2 hours. The reaction mixture was evaporated to dryness under vacuum and the PH was adjusted to 8 with saturated sodium bicarbonate. Then, water (10 mL), dioxane (10 mL), 9-fluorenylmethyl-N-succinimidyl carbonate (377 mg, 1.1 mmol) and sodium carbonate (237 mg, 2.2 mmol) were added at room temperature and stirred overnight at room temperature. The reaction mixture was adjusted to pH 3-4 with 1 mol/L hydrochloric acid, then extracted with ethyl acetate (100 mL×3) and washed with saturated saline (150 mL). Separate organic phase, dry with anhydrous sodium sulfate, filter and concentrate. The crude product was isolated and purified by high-speed chromatography (petroleum ether/ethyl acetate=1/1) to give the captioned compound (316 mg, 61%) as a white solid. LCMS (ESI) [M+H]$^+$= 454.2; 1H NMR (400 MHz, DMSO-d6) δ 12.77 (s, 1H), 8.45 (d, J=2.4, 1H), 7.87 (d, J=7.6, 2H), 7.78-7.73 (m, 4H), 7.64 (t, J=7.4, 2H), 7.41-7.36 (m, 4H), 7.32-7.25 (m, 2H), 6.53 (s, 1H), 4.22-4.15 (m, 4H), 3.15-3.10 (m, 1), 2.93-2.87 (m, 1H).

Preparation Embodiment 8: (2-((((9H-fluorene-9-yl) methoxycarbonyl)-L-phenylalaninyl)-2-methylhydrazine)-1-carbonyl-L-leucine (Compound YA-247-E)

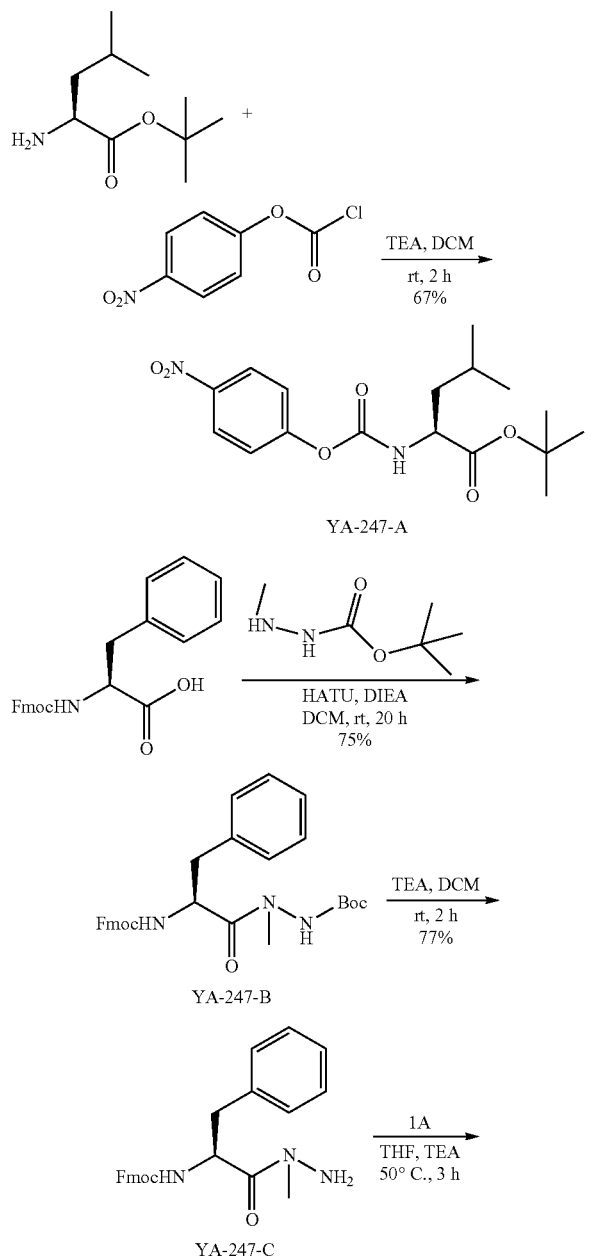

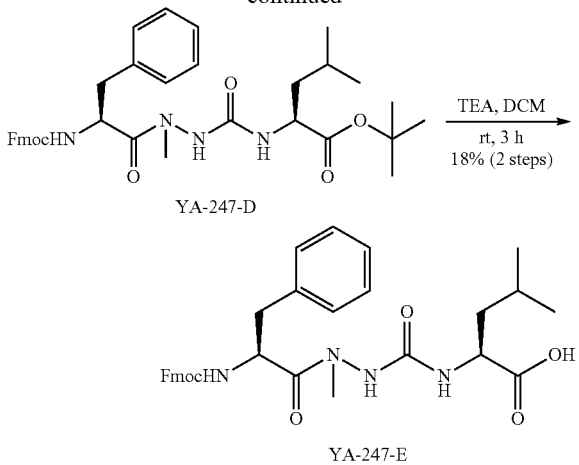

Step 1: P-Nitrophenoxycarbonyl-L-Leucine tert-butyl ester (Compound YA-247-A)

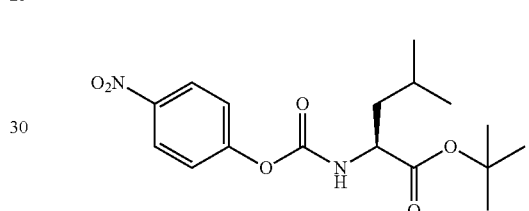

L-leucine tert-butyl ester (1.87 g, 10 mmol) was dissolved in methylene chloride (50 mL), and then triethylamine (1.1 g, 11 mmol) and p-nitrophenyl chloroformate (2 g, 10 mmol) were added at room temperature. The reaction mixture was stirred for 2 hours under nitrogen protection and then diluted with ethyl acetate (200 mL). The mixture was washed with water (100 mL) and saturated brine (100 mL), respectively. The organic phase was dried over anhydrous sodium sulfate, filtered and concentrated. The crude product was isolated and purified by high-speed chromatography (petroleum ether/ethyl acetate=4/1) to give the captioned compound (2.1 g, 59%) as a white solid. LCMS (ESI) [M+H]$^+$=375.2.

Step 2: (2-((((9H-fluorene-9-yl) methoxy) carbonyl))-L-phenylalaninyl)-2-methylhydrazine-1-carbonyl) tert-butyl ester (Compound YA-247-B)

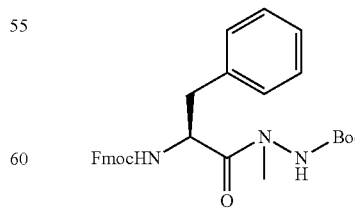

N-fluorenylmethoxycarbonyl-L-phenylalanine (5.38 g, 13.7 mmol) and tert-butyl 2-methylhydrazinocarboxylate (2 g, 13.7 mmol) were dissolved in methylene chloride (100 mL), then HATU (5.72 g, 15.1 mmol) and diisopropylethylamine (5.3 g, 41 mmol) were added. The reaction mixture was stirred overnight at room temperature and then concentrated. The crude product was isolated and purified by high-speed chromatography (petroleum ether/ethyl acetate=2/1) to give the captioned compound (5 g, 75%) as a white solid. LCMS (ESI) [M+H]$^+$=538.3.

Step 3: (2-((((9H-fluorene-9-yl) methoxy) carbonyl)-L-phenylalaninyl)-2-methylhydrazine-1-carbonyl (Compound YA-247-C)

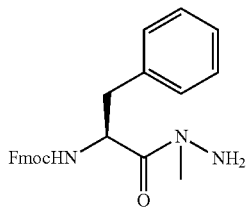

The compound (2-((((9 hydrogen-fluoren-9-yl) methoxy) carbonyl)-L-phenylalaninyl)-2-methylhydrazine-1-carbonyl) tert-butyl ester (4.0 g, 7.77 mmol) was dissolved in methylene chloride (100 mL), followed by adding with trifluoroacetic acid (25 mL). The reaction mixture was stirred at room temperature for 2 hours and then concentrated. The crude product was isolated and purified by high-speed chromatography (petroleum ether/ethyl acetate=1/2) to give the captioned compound (2.5 g, 77%) as a white solid. LCMS (ESI) [M+H]$^+$=416.2.

Step 4: (2-((((9H-fluorene-9-yl) methoxy) carbonyl)-L-phenylalaninyl)-2-methylhydrazine-1-carbonyl)-L-leucine tert-butyl ester (Compound YA-247-D)

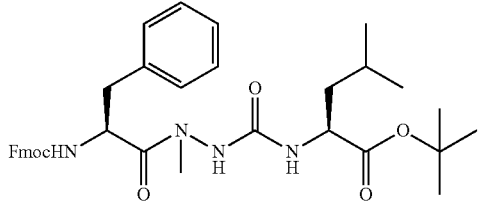

The compound 2-((((9 hydrogen-fluorene-9-yl) methoxy) carbonyl)-L-phenylalaninyl)-2-methylhydrazine-1-carbonyl (1.0 g, 2.4 mmol) was dissolved in tetrahydrofuran (10 mL), then p-nitrophenoxycarbonyl-L-leucine tert-butyl ester (2.0 g, 5.7 mmol) was added, stirred at 50° C. under nitrogen protection for 3 hours, and then concentrated. The residue was dissolved in ethyl acetate, washed with saturated brine, the organic phase was dried with anhydrous sodium sulfate, filtered and concentrated to give the crude product of the captioned compound (1.0 g), a yellow solid, which was directly used in the next reaction without purification. LCMS (ESI) [M-55]$^+$=573.3.

Step 5: (2-((((9H-fluorene-9-yl) methoxy) carbonyl)-L-phenylalaninyl)-2-methylhydrazine-1-carbonyl)-L-leucine (Compound YA-247-E)

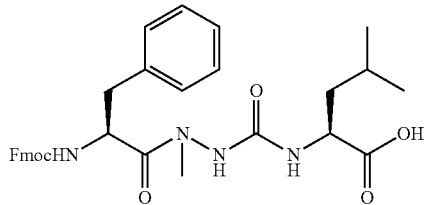

The compound 2-((((9 hydrogen-fluorene-9-yl) methoxy) carbonyl)-L-phenylalaninyl)-2-methylhydrazine-1-carbonyl)-L-leucine tert-butyl ester (1.0 g, 6.0 mmol) was dissolved in methylene chloride (20 mL), followed by trifluoroacetic acid (10 mL). The reaction mixture was stirred at room temperature for 3 hours and then concentrated. The crude product was isolated and purified by high-speed chromatography (petroleum ether/ethyl acetate=1/5) to give the captioned compound (250 mg, 18% two-step yield) as a white solid. LCMS (ESI) [M+H]$^+$=573.3; 1H NMR (400 MHz, DMSO-d6) δ 12.64 (s, 1H), 8.59 (s, 1H), 7.87 (m, 2H), 7.70-7.63 (m, 2H), 7.43-7.38 (m, 2H), 7.27-7.14 (m, 8H), 4.79 (s, 1H), 4.20 (s, 1H), 4.15-4.09 (m, 3H), 3.11-2.81 (m, 5H), 1.67-1.46 (m, 3H), 0.87 (s, 6H).

Preparation Embodiment 9: (5-((S)-1-((2S, 3R)-2-(((9H-fluorene-9-yl) methoxy) carbonyl) amino)-3-(tert-butoxybutylamino)-2-phenylethyl)-4H-1,2,4-triazol-3-carbonyl)-L-leucine (Compound YA-209-H)

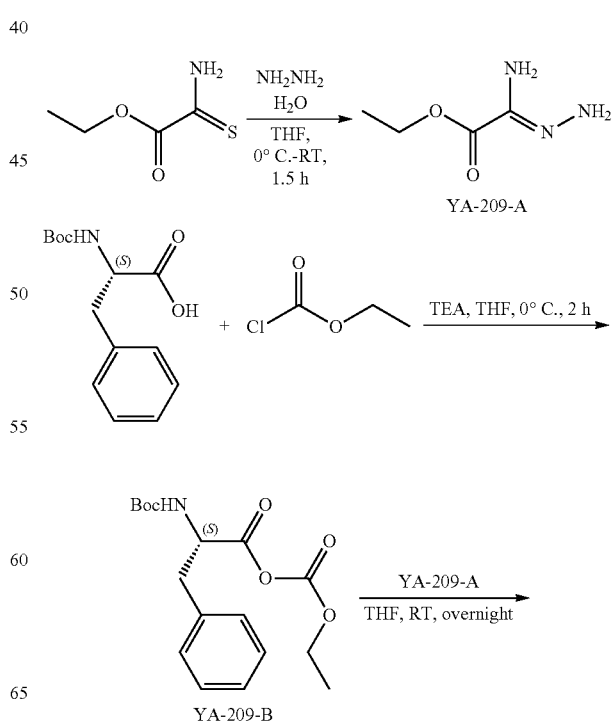

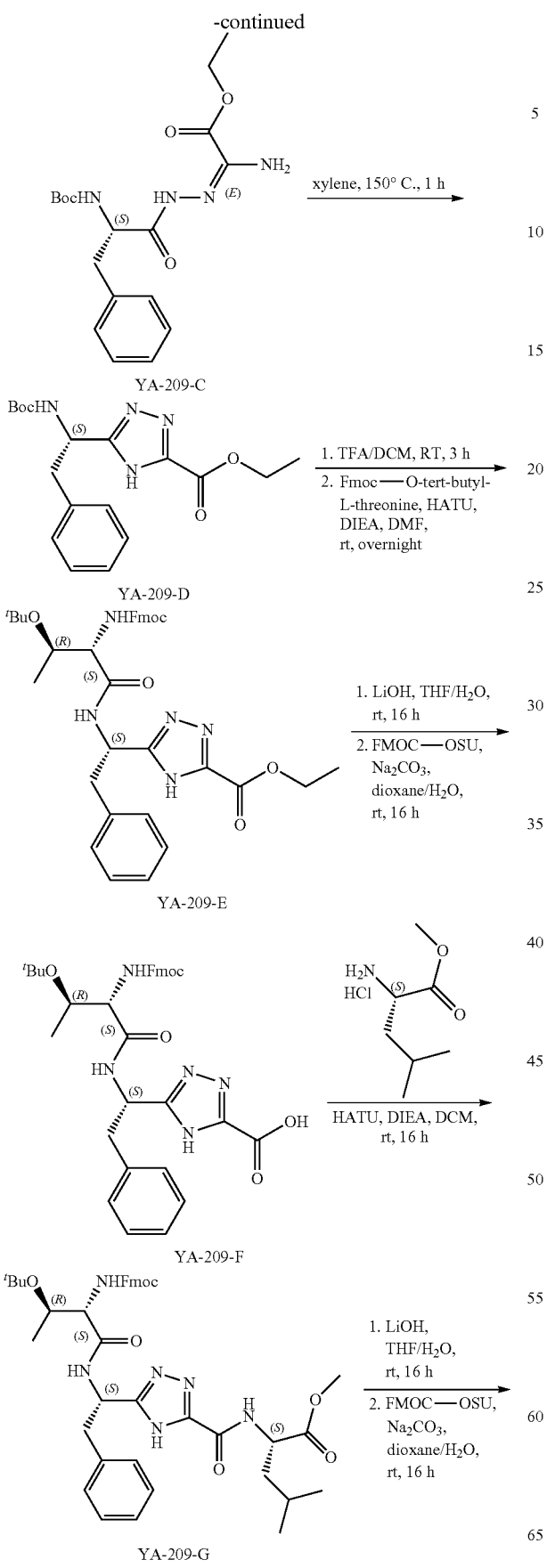

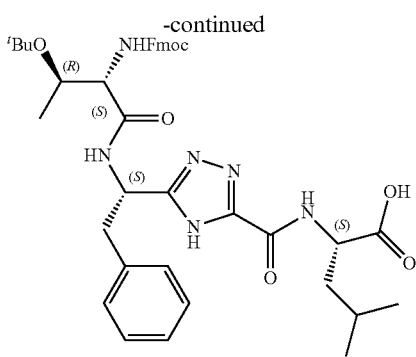

Step 1: Ethyl 2-amino-2-hydrazone acetate (YA-209-A)

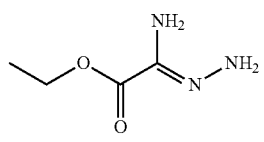

Ethyl thiooxalate (5.27 g, 39.6 mmol) was dissolved in tetrahydrofuran (40 mL), then hydrazine hydrate (1.89 g, 37.7 mmol) was added dropwise at 0° C., and the reaction mixture was stirred at room temperature for 1.5 hours. The reaction mixture was concentrated and directly used in the next step.

Step 2: (S)-(S)-2-((tert-butoxycarbonyl) amino)-3-phenylpropionic acid acetic anhydride (YA-209-B)

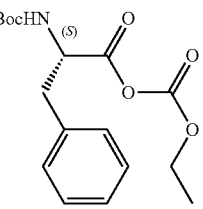

N-tert-butoxycarbonyl-L-phenylalanine (10 g, 37.7 mmol) and triethylamine (7.62 g, 75.5 mmol) were dissolved in tetrahydrofuran (100 mL), then ethyl chloroformate (6.11 g, 56.6 mmol) was added dropwise at 0° Celsius, and the reaction mixture was stirred at 0° C. for 2 hours. The reaction mixture was concentrated and directly used in the next step.

Step 3: (E)-2-amino-2-(2-((tert-butoxycarbonyl)-L-phenylpropyl) hydrazonyl) ethyl acetate (YA-209-C)

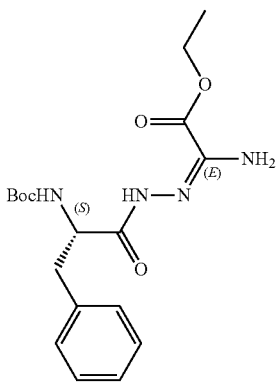

Ethyl 2-amino-2-hydrazone acetate (5.19 g, 39.6 mmol) was dissolved in tetrahydrofuran (50 mL), then (S)-(S)-2-((tert-butoxycarbonyl) amino)-3-phenylpropionic acid acetic anhydride (12.7 g, 37.7 mmol) was added at room temperature, and the reaction mixture was stirred overnight at room temperature. The reaction mixture was directly filtered, the white solid was washed with tetrahydrofuran (30 mL), and dried to give the captioned compound (3.4 g, 24%) as a white solid. LC-MS (ESI) [M+H]$^+$=379.1.

Step 4: (S)-5-(1-((tert-butoxycarbonyl) amino)-2-phenethyl)-4H-1,2,4-triazol-3-ethyl formate (YA-209-D)

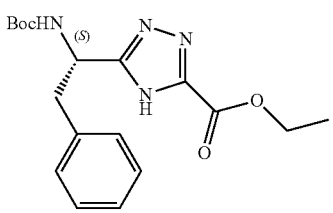

Ethyl (E)-2-amino-2-(2-((tert-butoxycarbonyl)-L-phenylpropyl) hydrazone group) ethyl acetate (3.4 g, 9 mmol) was dissolved in toluene (40 mL), the reaction mixture was stirred at 150° C. for 1 hour, and then at 185° C. for 5 hours. The reaction mixture was directly concentrated to give the crude captioned compound (3 g, 94%) as a yellow solid. LC-MS (ESI) [M+Na]$^+$=383.1.

Step 5: 5-((S)-1-((2S, 3R)-2-(((9H-fluorene-9-yl) methoxy) carbonyl) amino)-3-(tert-butoxy) butylamino)-2-phenethyl)-4H-1,2,4-triazol-3-ethyl formate (YA-209-E)

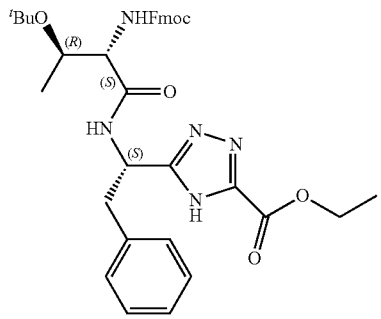

(S)-5-(1-((tert-butoxycarbonyl) amino)-2-phenylethyl)-4H-1,2,4-triazol-3-ethyl formate (3 g, 8.3 mmol) was dissolved in a mixture of dichloromethane (40 mL) and trifluoroacetic acid (10 mL) and stirred at room temperature for 3 hours. The reaction mixture was directly concentrated and then dissolved in dimethylformamide (50 mL). Fmoc-O-tert-butyl-L-threonine (4.97 g, 12.5 mmol), HATU (4.75 g, 12.5 mmol) and diisopropylethylamine (5.38 g, 41.7 mmol) were then added. The reaction mixture was stirred overnight at room temperature and diluted with ethyl acetate (800 mL). The mixed solution was washed with water (300 mL×4) and saturated saline (300 mL), respectively. Isolate organic phase, dry with anhydrous sodium sulfate, filter and concentrate. The residue was eluted with a linear concentration gradient (30 minutes) at a flow rate of 50 ml/minute, eluent A/B was used at a ratio of 90/10-30/70: eluent A: 0.1% TFA aqueous solution, eluent B: Acetonitrile, on preparative HPLC, use Boston ODS 120 g Flash, CV 60 ml-100 ml/min, PMAX: 200 psi. The fractions containing the product were collected and lyophilized to give the captioned compound (2.2 g, 42%) as a white solid. LC-MS (ESI) [M+H]$^+$=640.3.

Step 6: 5-((S)-1-((2S, 3R)-2-(((9H-fluorene-9-yl) methoxy) carbonyl) amino)-3-(tert-butoxy) butylamino)-2-phenethyl)-4H-1,2,4-triazol-3-carboxylic acid (YA-209-F)

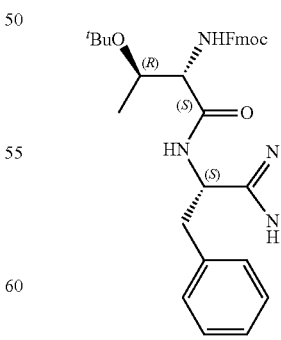

5-((S)-1-((2S, 3R)-2-(((9H-fluorene-9-yl) methoxy) carbonyl) amino)-3-(tert-butoxy) butylamino)-2-phenethyl)-4H-1,2,4-triazol-3-ethyl formate (2 g, 3.1 mmol) was dissolved in a mixed solution of tetrahydrofuran (30 mL) and water (30 mL), then lithium hydroxide monohydrate (1.05 g, 25 mmol) was added at room temperature and stirred overnight at room temperature. The reaction mixture was dried in vacuo and the PH was adjusted to 4 with 0.5 mol/L hydrochloric acid. Then dioxane (50 mL), Fmoc-OSu (1.05 g, 3.1 mmol) and sodium carbonate (664 mg, 6.3 mmol) were added at room temperature, and then stirred overnight at room temperature. The reaction mixture was adjusted to PH 3-4 with 1 mol/L hydrochloric acid, extracted with ethyl acetate (200 mL×3), and washed with saturated saline (100 mL). The organic phase was isolated, dried over anhydrous sodium sulfate, filtered and concentrated to give the crude captioned compound (2.5 g, 60%) as a white solid. LC-MS (ESI) [M+H]$^+$=612.3.

Step 7: (5-((S)-1-((2S, 3R)-2-((9H-fluorene-9-yl) methoxy) carbonyl) amino)-3-(tert-butoxybutylamino)-2-phenylethyl)-4H-1,2,4-triazol-3-carbonyl)-L-leucine methyl ester (YA-209-G)

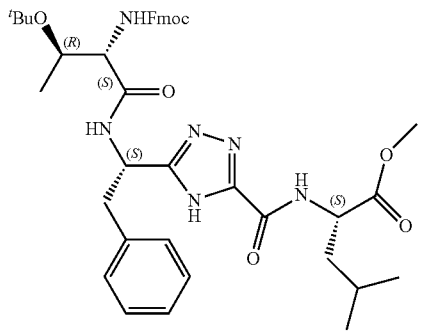

5-((S)-1-((2S, 3R)-2-(((9H-fluorene-9-yl) methoxy) carbonyl) amino)-3-(tert-butoxy) butylamino)-2-phenethyl)-4H-1,2,4-triazol-3-carboxylic acid (1.9 g, 3.1 mmol) and L-leucine methyl ester hydrochloride (734 mg, 4 mmol) was dissolved in dichloromethane (60 mL), and HATU (1.42 g, 3.7 mmol) and diisopropylethylamine (1.2 g, 9.3 mmol) was added. The reaction mixture was stirred overnight at room temperature and then concentrated. The residue was isolated and purified by high-speed chromatography (dichloromethane/methanol 20/1) to give the captioned compound (970 mg, 42%) as a white solid. LC-MS (ESI) [M+H]$^+$=739.4.

Step 8: (5-((S)-1-((2S, 3R)-2-((9H-fluorene-9-yl) methoxy) carbonyl) amino)-3-(tert-butoxybutylamino)-2-phenylethyl)-4H-1,2,4-triazol-3-carbonyl)-L-leucine (YA-209-H)

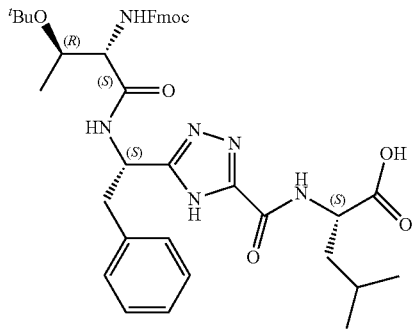

(5-((S)-1-((2S, 3R)-2-(((9H-fluorene-9-yl) methoxy) carbonyl) amino)-3-(tert-butoxybutylamino)-2-phenylethyl)-4H-1,2,4-triazol-3-carbonyl)-L-leucine methyl ester (970 mg, 1.31 mmol) was dissolved in a mixed solution of tetrahydrofuran (10 mL) and water (10 mL), then lithium hydroxide monohydrate (442 mg, 10.5 mmol) was added at room temperature and stirred overnight at room temperature. The reaction mixture was evaporated to dryness under vacuum and the PH was adjusted to 4 by 0.5 mol/hydrochloric acid. Then dioxane (10 mL), Fmoc-OSu (443 mg, 1.31 mmol) and sodium carbonate (229 mg, 2.62 mmol) were added at room temperature, and the reaction mixture was stirred at room temperature for one night. The reaction mixture was adjusted to PH 3-4 with 1 mol/L hydrochloric acid, then extracted with ethyl acetate (300 mL×3) and washed with saturated saline (200 mL). The organic phase was isolated, dried over anhydrous sodium sulfate, filtered and concentrated. The crude product was isolated and purified by high-speed chromatography (ethyl acetate) to give the captioned compound (400 mg, 42%) as a white solid. LC-MS (ESI) [M+H]$^+$=725.3; 1H NMR (400 MHz, DMSO-d6) δ 7.77-6.96 (m, 17H), 5.91 (s, 0.5H), 5.58 (s, 0.5H), 4.73-4.35 (m, 2H), 4.22-4.04 (m, 4H), 3.37-3.21 (m, 1H), 2.05 (s, 1H), 1.82-1.71 (m, 2H), 1.28-0.66 (m, 20H).

Preparation Embodiment 10: (s)-2-(1h-indole-3-yl)-1-(1H-tetrazole-5-yl) ethylamine (Compound YA-250-d)

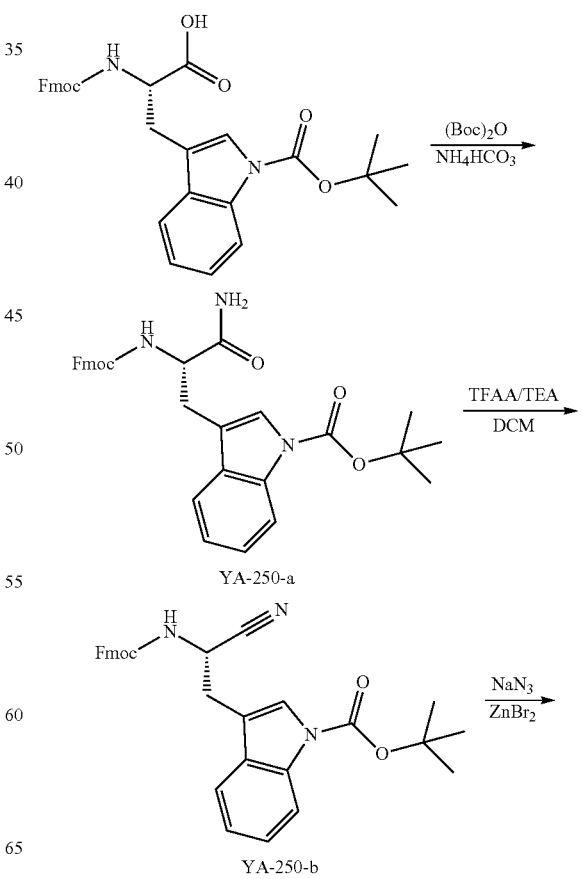

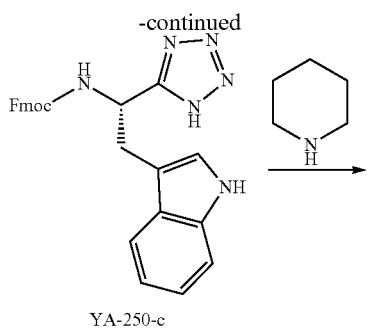

YA-250-c

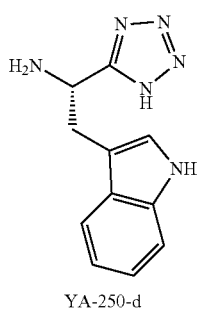

YA-250-d

Step 1: (S)-3-(2-((((9H-fluorene-9-yl) methoxy) carbonyl) amino)-3-amino-3-oxapropyl)-1-hydro-indole-1-tert-butyl carbonate (Compound YA-250-a)

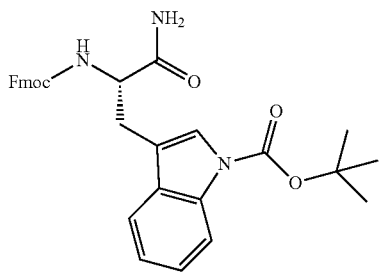

Fmoc-L-tryptophan (Boc) (10.0 g, 18.99 mmol) was dissolved in DMF (50 mL), then ammonium bicarbonate (1.88 g, 23.30 mmol), pyridine (0.9 mL, 11.3 mmol) and (Boc)$_2$O (5.39 g, 24.69 mmol) were added. The reaction mixture was stirred at room temperature for 16 hours. The reaction mixture was poured into water (200 mL) to precipitate a white solid. Filter and fix the aqueous body. The solid was dissolved in ethyl acetate (200 mL), petroleum ether (500 mL) was slowly added to the solution, and stirred at room temperature for 30 minutes. After filtration, the solid was washed with petroleum ether to give the captioned compound (9.9 g, 99.5%) as a white solid. LC-MS (ESI) [M−99]$^+$=426.1.

Step 2: (S)-3-(2-((((9H-fluorene-9-yl) methoxy) carbonyl) amino)-2-cyanoethyl)-1-hydro-indole-1-tert-butyl carbonate (Compound YA-250-b)

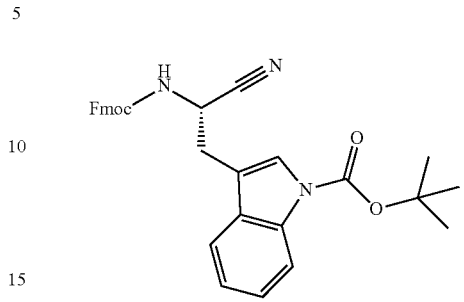

(S)-3-(2-((((9H-fluorene-9-yl) methoxy) carbonyl) amino)-3-amino-3-oxapropyl)-1-hydro-indole-1-tert-butyl carbonate (Compound YA-250-a, 9.9 g, 18.8 mmol) was dissolved in methylene chloride (150 mL), cooled to 0° C., triethylamine (10.6 mL, 75.2 mmol) and trifluoroacetic anhydride (7.8 mL, 56.4 mmol) were added simultaneously, and the reaction mixture was stirred at room temperature for 4 hours. The mixture was washed with saturated brine (20 mL×2), dried over anhydrous sodium sulfate, filtered and concentrated. The crude product was isolated and purified by high-speed chromatography (petroleum ether/ethyl acetate=3/1) to give the captioned compound (5.6 g, 58%) as a white solid. LC-MS (ESI) [M+18]$^+$=525.3.

Step 3: (9H-fluorene-9-yl) methyl) (s)-(2-1h-indole-3-yl)-1-(1h-tetrazole-5-yl) carbonate (Compound YA-250-c)

(S)-3-(2-((((9H-fluorene-9-yl) methoxy) carbonyl) amino)-2-cyanoethyl)-1-hydro-indole-1-tert-butyl carbonate (Compound YA-250-b, 3.0 g, 5.91 mmol), ZnBr$_2$ (665 mg, 3.0 mmol) and NaN$_3$ (768 mg, 11.8 mmol) were dissolved in isopropanol (80 mL) and water (80 mL), and the reaction mixture was stirred at 85° C. for 72 hours. The reaction mixture was concentrated to remove isopropyl alcohol, then extracted with dichloromethane (100 mL×2), the organic phase was dried over anhydrous sodium sulfate, filtered and concentrated. The crude product was isolated and purified by high-speed chromatography (dichloromethane/methanol=10/1) to give the captioned compound (1.9 g, 58%) as brown solid LC-MS (ESI) [M+H]$^+$=451.2.

Step 4: (S)-2-(1H-indole-3-yl)-1-(1H-tetrazole-5-yl) ethylamine (Compound YA-250-d)

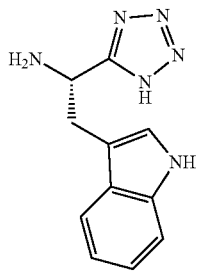 [SMILES: N[C@@H](Cc1c[nH]c2ccccc12)c1nnn[nH]1]

(9H-fluorene-9-yl) methyl) (s)-(2-1h-indole-3-yl)-1-(1h-tetrazole-5-yl) carbonate (900 mg, 2.0 mmol) was dissolved in dichloromethane (10 mL), piperidine (2 mL) was added, and stirred at room temperature for 1 hour. The reaction mixture was poured into water, precipitated, the solid was filtered out, washed with water, and dried in vacuum to give the target compound (420 mg, 92%) as a brown solid. LC-MS (ESI) [M+H]$^+$=229.0. 1H NMR (400 MHz, DMSO-d6) δ 11.00 (s, 1H), 7.58 (d, J=7.6 Hz, 1H), 7.41 (d, J=8.0 Hz, 1H), 7.24 (s, 1H), 7.13 (dd, J=6.8, 7.6 Hz, 1H), 7.04 (dd, J=7.6, 8.0 Hz, 1H), 4.47 (br, 1H), 3.60-3.30 (m, 3H), 3.10-3.00 (m, 1H).

Preparation Embodiment 11: (5S)-5-benzyl-1-(9-hydrogen-fluoren-9-yl)-11-isobutyl-3,6,-dioxo-10-thio-2-oxa-4,7,9-triazadecane-12-carboxylic acid (Compound YA-254-E)

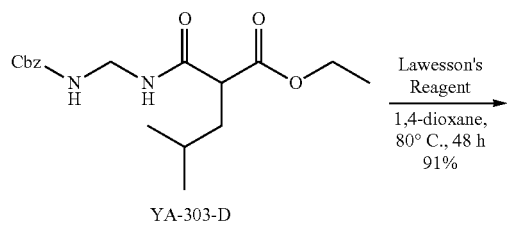

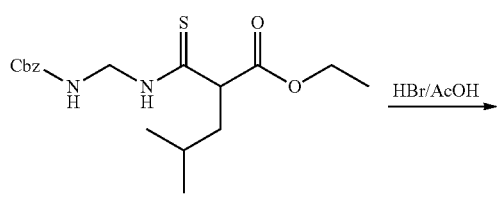

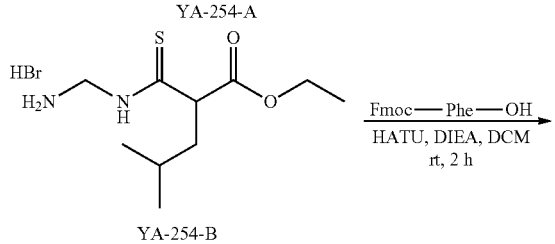

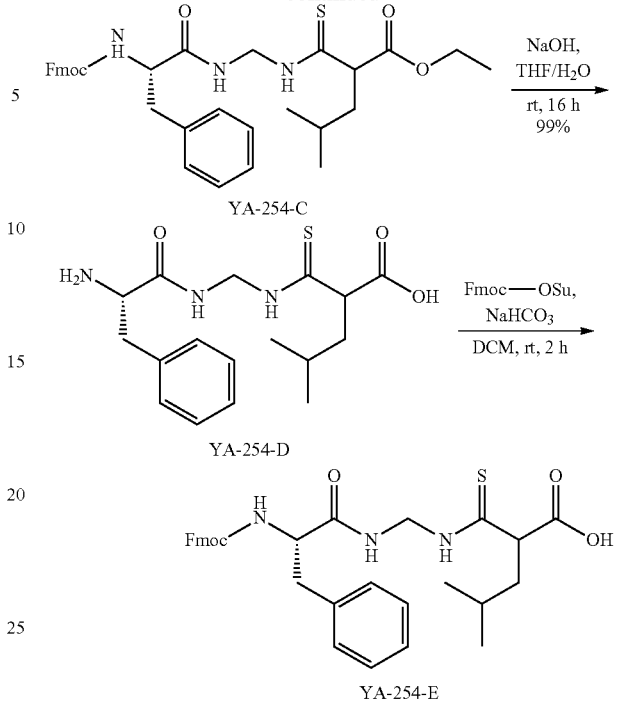

Step 1: 2-((benzyloxycarbonylamino) methylamino methionyl)-4-methyl ethyl valerate (YA-254-A)

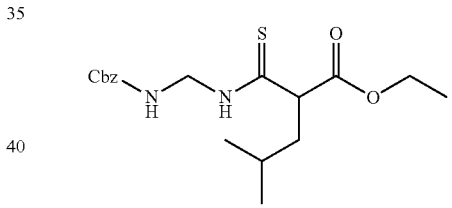

2-((benzyloxycarbonylamino) methylaminoformyl)-4-methyl ethyl valerate (YA-303-D) (1.1 g, 3.14 mmol) and Lawesson reagent (1.40 g, 3.46 mmol) were dissolved in 1,4-dioxane (30 mL) and stirred at 80° C. for 48 hours. The reaction mixture was concentrated, and the residue was isolated and purified by high-speed chromatography (petroleum ether/ethyl acetate=5/1) to give the captioned compound (1.05 g, 91%). LCMS (ESI) [M+H]$^+$=367.1.

Step 2: 2-(aminomethylaminothioacyl)-4-methyl ethyl valerate hydrobromide (YA-254-B)

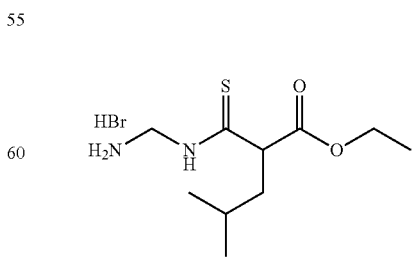

33% acetic hydrobromide solution (3 mL) and dichloromethane (2 mL) were added into 2-((benzyloxycarbonylamino) methylamino thioacyl)-4-methyl ethyl valerate (700 mg, 1.91 mmol), and the reaction was stirred at room temperature for 30 minutes. The reaction mixture was concentrate and dried to give crude product which was directly used as the next reaction. LC-MS (ESI) [M+H-29]$^+$=204.1.

Step 3: (5S)-5-benzyl-1-(9-hydrogen-fluoren-9-yl)-11-isobutyl-3,6-dioxo-10-thio-2-oxa-4,7,9-triazadecane-12-carboxylic acid ethyl ester (YA-254-C)

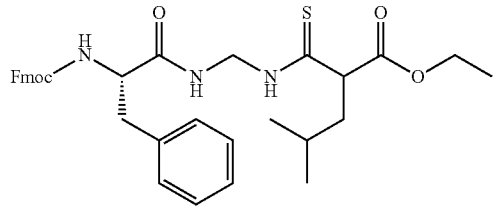

2-(aminomethylaminothioacyl)-4-methyl ethyl valerate hydrobromide (crude product, about 1.91 mmol), (S)-2-((9 hydrogen-fluorene-9-yl) methoxy) carbonylamino)-3-phenylalanine (739 mg, 1.74 mmol), HATU (726 mg, 1.74 mmol), HOAt (261 mg, 1.91 mmol) were dissolved in dichloromethane (20 mL), and N,N-diisopropylethylamine (1.23 g, 9.55 mmol) was added, and the reaction mixture was stirred at room temperature for 2 hours. The reaction mixture was concentrated and the crude product was isolated and purified by high-speed chromatography (petroleum ether/ethyl acetate=1/1) to give the captioned compound (452 mg, 39%) as a pale yellow oil. LC-MS (ESI) [M+H]$^+$=602.3.

Step 4: 2-((S)-2-amino-3-phenylpropanamide) methylaminothioacyl)-4-methylpentanoic acid (YA-254-D)

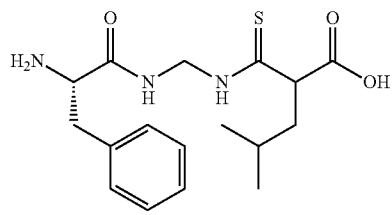

(5 S)-5-benzyl-1-(9-hydrogen-fluorene-9-yl)-11-isobutyl-3,6-dioxo-10-thio-2-oxa-4,7,9-triazadecane-12-carboxylic acid ethyl ester (0.45 g, 0.75 mmol) was dissolved in tetrahydrofuran (10 mL) and water (10 mL), lithium hydroxide monohydrate (158 mg, 3.75 mmol) was then added, and the mixed solution was stirred and reacted at 0° C. for 5 hours. The reaction mixture was acidified with 2N hydrochloric acid until the ph value=2-3, extracted with ethyl acetate, dried and concentrated, then the obtained crude product was directly used in the next reaction without purification. LC-MS (ESI) [M+H]$^+$=352.1.

Step 5: (5S)-5-benzyl-1-(9H-fluoren-9-yl)-11-isobutyl-3,6,-dioxo-10-thio-2-oxa-4,7,9-triazadecane-12-carboxylic acid (YA-254-E)

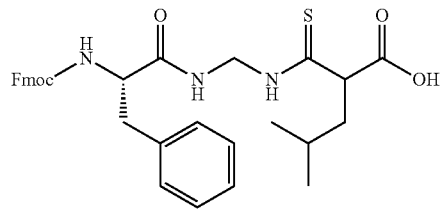

2-((S)-2-amino-3-phenylpropanamide) methylaminothioacyl)-4-methylpentanoic acid (crude product, about 0.75 mmol) and fluorenylmethyloxycarbonylsuccinimide (304 mg, 0.90 mmol) were dissolved in the mixture of 30 mL of acetone: water=1:1, sodium bicarbonate (630 mg, 7.5 mmol) was added in batches, and the reaction mixture was stirred at room temperature for 4 hours. The mixture was acidified with 2 N hydrochloric acid until pH=5-6, extracted with ethyl acetate (50 mL×2), washed with saturated salt, dried over anhydrous sodium sulfate, and filtered and concentrated. The residue was isolated and purified by high-speed chromatography (petroleum ether/ethyl acetate=1/5) to give the captioned compound (226 mg, 52% in both steps) as a pale yellow solid. LCMS (ESI) [M+H]$^+$=574.3.

Preparation Embodiment 12: ((((S)-2-(((9H-fluorene-9-yl) methoxy) carbonyl) amino)-3-phenylpropanamine) methyl) carbonylurea)-L-leucine (Compound YA-256-f)

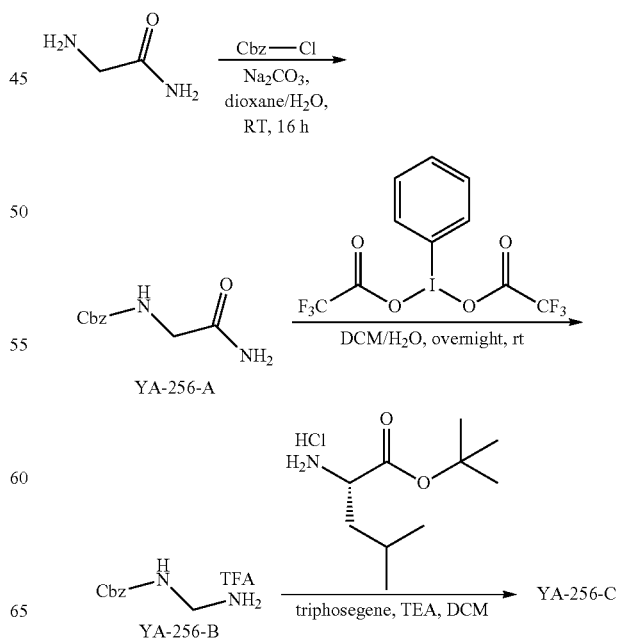

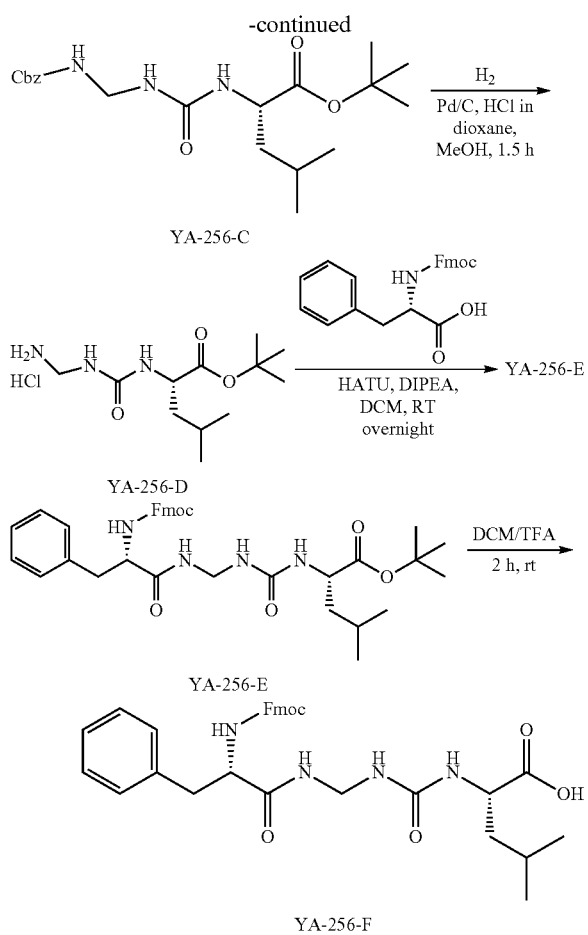

YA-256-C

YA-256-D

YA-256-E

YA-256-F

Step 1: Benzyl 2-amino-2-oxaethyl carbonate (YA-256-A)

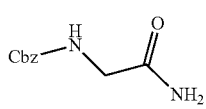

2-glycinamide (10 g, 90.5 mmol) and sodium carbonate (10 g, 90.5 mmol) were dissolved in dioxane (100 mL) and water (100 mL), cooled to 0° C., benzyl chloroformate (15.43 g, 90.5 mmol) was then added, and stirred at room temperature for 16 hours. The mixture was concentrated and filtered. The solid was washed with water and dried to give the captioned compound (12 g, 64%) as a white solid. LC-MS (ESI) [M-55]$^+$=209.1.

Step 2: Benzoxycarbonylaminomethylamine (YA-256-B)

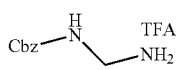

Benzyl 2-amino-2-oxaethyl carbonate (6 g, 28.9 mmol) was dissolved in methylene chloride (180 mL) and water (10 mL), bistrifluoroacetyl iodobenzene (14.9 g, 34.6 mmol) was added, and the mixture was stirred overnight at room temperature. The reaction liquid was cooled to 0° C. and the solid was precipitated. The filtered solid was washed with n-heptane (100 ml) and dried naturally to give the captioned compound (6.7 g, 79%) as a white solid. LC-MS (ESI) [M-55]$^+$=181.1.

Step 3: ((benzyloxycarbonylaminomethyl) carbamoyl)-L-leucine tert-butyl ester (YA-256-C)

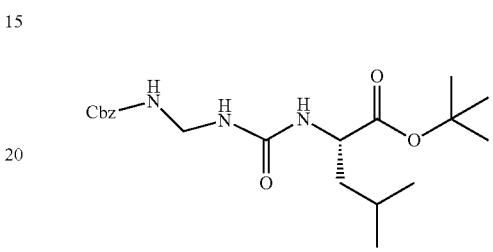

Triphosgene (3.38 g, 11.4 mmol) was dissolved in dichloromethane (40 mL), and then a solution of L-leucine tert-butyl hydrochloride (5.09 g, 22.8 mmol) in dichloromethane (30 mL) was added dropwise at 0° C. The reaction mixture was stirred at 0° C. for 1 hour, then triethylamine (6.91 g, 68.4 mmol) was added and stirred for 20 minutes. The reaction mixture was concentrated and dissolved in dichloromethane (50 mL). Benzyloxycarbonylaminomethylamine trifluoroacetate (6.7 g, 22.8 mmol) and triethylamine (4.6 g, 45.6 mmol) were added, and the reaction mixture was stirred overnight at room temperature. The reaction mixture was concentrated, and the crude product was isolated and purified by high-speed chromatography (petroleum ether/ethyl acetate=2/3) to give the captioned compound (3.1 g, 35%) as a white solid. LC-MS (ESI) [M+H]$^+$=394.0.

Step 4: (aminomethyl carbamoyl)-L-leucine tert-butyl Ester (YA-256-D)

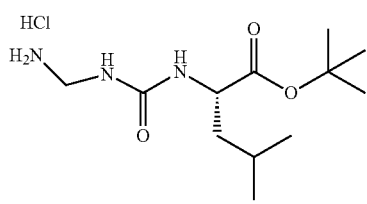 [SMILES: Cl ; CC(C)C[C@H](NC(=O)NCN)C(=O)OC(C)(C)C]

((Benzyloxycarbonylaminomethyl) carbamoyl)-L-leucine tert-butyl ester (3.3 g, 8.4 mmol) was dissolved in methanol (100 mL), the Pd/C (1 g, 10% on C) and HCl/dioxane (4.2 ml, 16.8 mmol, 4 mol/1) were added. The reaction mixture was stirred at room temperature for 1.5 hours in a hydrogen atmosphere. The mixture was filtered and concentrated to give the captioned compound (2.3 g, 90%) as a white solid. LCMS (ESI) [M+Na-29]$^+$=253.0.

Step 5: ((((S)-2-(((9H-fluorene-9-yl) methoxy) carbonyl) amino)-3-phenylpropamino) methyl) carbonylurea)-L-leucine tert-butyl ester (YA-256-E)

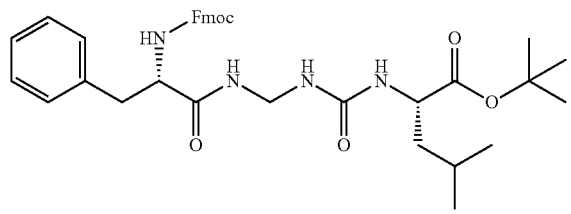

Fmoc-L-phenylalanine (3 g, 7.8 mmol) and (aminomethyl carbamoyl)-L-leucine tert-butyl ester (2.3 g, 7.8 mmol) were dissolved in dichloromethane (100 mL), then HATU (2.96 g, 7.8 mmol) and diisopropylethylamine (2 g, 15.6 mmol) were added. The reaction mixture was stirred overnight at room temperature and concentrated. The crude product was eluted with a linear concentration gradient (30 minutes) at a flow rate of 50 ml/minute, eluent A/B was applied at the ratio of 90/10-10/90 (eluent A:0.1% TFA aqueous solution, eluent B: acetonitrile) on a preparative HPLC using Boston ODS 120 g Flash, CV 60 ml-100 ml/min, PMAX: 200 psi. The fractions containing the product were collected and lyophilized to give the captioned compound (2.5 g, 51%) as a white solid. LC-MS (ESI) [M+H]$^+$=629.1.

Step 6: ((((S)-2-(((9H-fluorene-9-yl) methoxy) carbonyl) amino)-3-phenylpropamino) methyl) carbonylurea)-L-leucine (YA-256-F)

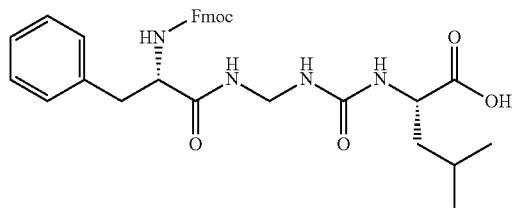

(((S)-2-(((9H-fluorene-9-yl) methoxy) carbonyl) amino)-3-phenylpropamino) methyl) carbonylurea)-L-leucine tert-butyl ester (500 mg, 0.8 mmol) was dissolved in methylene chloride (15 mL) and trifluoroacetic acid (15 mL), stirred at room temperature for 2 hours, and concentrated. The crude product was eluted with a linear concentration gradient (30 minutes) at a flow rate of 50 ml/minute, eluent A/B was applied at the ratio of 90/10-30/70 (eluent A:0.1% TFA aqueous solution, eluent B: acetonitrile) on a preparative HPLC using Boston ODS 120 g Flash, CV 60 ml-100 ml/min, PMAX: 200 psi. The fractions containing the product were collected and lyophilized to give the captioned compound (340 mg, 75%) as a white solid. LC-MS (ESI) [M+H]$^+$=573.1.

Preparation Embodiment 13: (s)-5-(((9H-fluorene-9-yl) methoxy) carbonyl) amino)-4-oxa-6-phenyl-hexanoic acid (Compound YA-274-f)

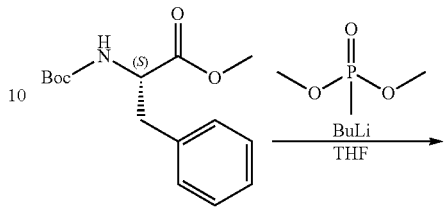

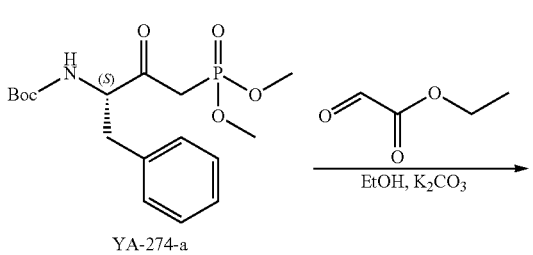

YA-274-a

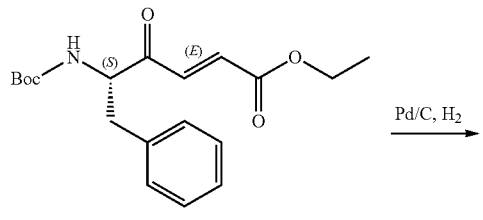

YA-274-b

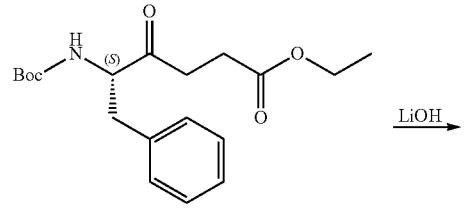

YA-274-c

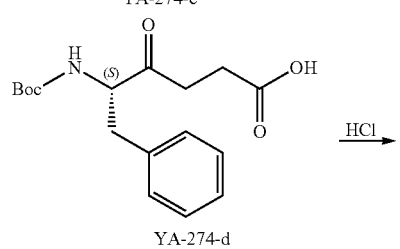

YA-274-d

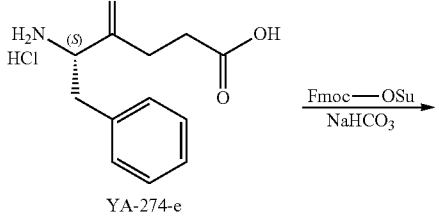

YA-274-e

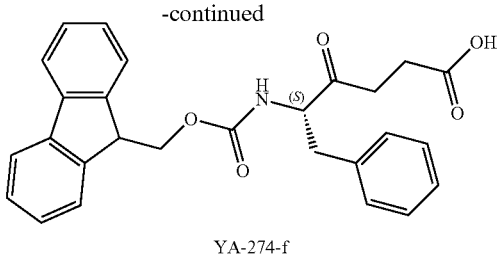

YA-274-f

Step 1: (S)-(4-(dimethoxyphosphate)-3-oxa-1-phenylbutyl-2-yl) tert-butyl carbamate (Compound YA-274-a)

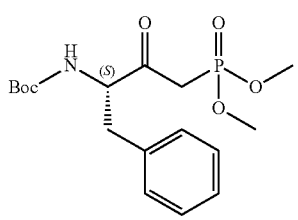

Dimethyl methylphosphate (14.2 g, 114.5 mmol) was dissolved in dry tetrahydrofuran (100 mL), cooled to −78° C., Buli (2.5 N in hexane, 45.8 mL, 114.5 mmol) was added dropwise, and the mixture was reacted at −78° C. for 1 hour. A solution of Boc-L-phenylalanine methyl ester (6.4 g, 22.9 mmol) in tetrahydrofuran (50 mL) was then added dropwise, and the mixture was reacted at −78° C. for 2 hours. Saturated ammonium chloride solution (150 mL) was added to the reaction mixture, extracted with ethyl acetate (200 mL×2), and the organic phase was isolated. The organic phase was washed with saturated brine (50 mL), dried over anhydrous sodium sulfate, filtered and concentrated. The crude product was isolated and purified by high-speed chromatography (petroleum ether/ethyl acetate=5/1) to give the captioned compound (6.5 g, 76%) as a white solid. LC-MS (ESI) [M+H]⁺=370.1.

Step 2: (S,E)-5-((tert-butoxycarbonyl) amino)-4-oxa-6-phenylhexyl-2-enoic acid ethyl ester (Compound YA-274-b)

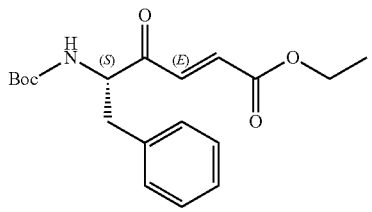

(S)-(4-(dimethoxyphosphate)-3-oxa-1-phenylbutyl-2-yl) carbamic acid tert-butyl ester (6.5 g, 17.5 mmol) and ethyl glyoxylate (50% w/w in toluene, 3.57 g, 17.5 mmol) were dissolved in absolute ethanol (100 mL), then potassium carbonate (2.42 g, 17.5 mmol) was added, and the reaction mixture was stirred at room temperature for 4 hours. Filtering, neutralizing the filtrate with acetic acid (0.5 mL), concentrating, and separating and purifying the crude product by high-speed chromatography (petroleum ether/ethyl acetate=5/1) to give the captioned compound (trans-isomer, 4.5 g, 74%) as a pale yellow solid. LC-MS (ESI) [M−H]⁺=346.2. 1H NMR (400 MHz, CDCl3) δ 7.25-7.13 (m, 3H), 7.08 (d, J=15.6 Hz, 1H), 7.06-7.00 (m, 2H), 6.69 (d, J=15.6 Hz, 1H), 5.09 (d, J=8.0 Hz, 1H), 4.75-4.68 (m, 1H), 4.18 (q, J=7.2 Hz, 2H), 3.09 (dd, J=6.4, 14.0 Hz, 1H), 2.91 (dd, J=6.4, 14.0 Hz, 1H), 1.34 (s, 9H), 1.25 (t, J=7.2 Hz, 3H).

Meanwhile, another isomer (cis-isomer, 1.5 g, 24%) was obtained as a yellow oil. LC-MS (ESI) [M−H]−=346.2. 1H NMR (400 MHz, CDCl3) δ 7.32-7.16 (m, 5H), 6.43 (d, J=12.0 Hz, 1H), 6.05 (d, J=12.0 Hz, 1H), 5.16 (d, J=8.0 Hz, 1H), 4.76-4.68 (m, 1H), 4.21 (q, J=7.6 Hz, 2H), 3.25 (dd, J=6.0, 10.0 Hz, 1H), 3.01 (dd, J=6.0, 10.0 Hz, 1H), 1.39 (s, 9H), 1.28 (t, J=7.6 Hz, 3H).

Step 3: (S)-5-((tert-butoxycarbonyl) amino)-4-oxa-6-phenylhexanoate ethyl ester (Compound YA-274-c)

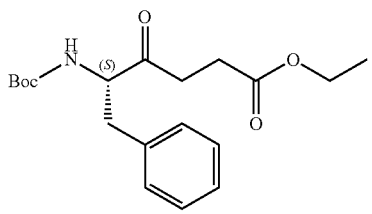

(S,E)-5-((tert-butoxycarbonyl) amino)-4-oxa-6-phenylhexyl-2-enoic acid ethyl ester (trans-isomer, 990 mg, 2.85 mmol) was dissolved in ethyl acetate (25 mL), then Pd/C (10% Pd, 100 mg) was added and stirred at room temperature for 2 hours in a hydrogen atmosphere. The mixture was filtered, the filtrate was concentrated, and the crude product was isolated and purified by high-speed chromatography (petroleum ether/ethyl acetate=5/1) to give the captioned compound (0.88 g, 88%) as a yellow solid. LC-MS (ESI) [M−99]⁺=250.1

Step 4: (S)-5-((tert-butoxycarbonyl) amino)-4-oxa-6-phenylhexanoic acid (Compound YA-274-d)

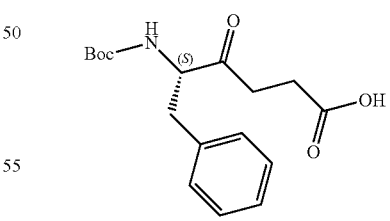

Ethyl (S)-5-((tert-butoxycarbonyl) amino)-4-oxa-6-phenylhexanoate (850 mg, 2.43 mmol) was dissolved in methanol (7 mL) and tetrahydrofuran (27 mL), then an aqueous solution of lithium hydroxide (0.5 N, 34 mL, 17.0 mmol) was added and stirred at room temperature for 3 hours. The mixture was adjusted to pH=4-5 with acetic acid and extracted with ethyl acetate (100 mL×2). The organic phase was washed with saturated brine (30 mL), dried over anhydrous sodium sulfate, filtered, and concentrated. 830 mg of captioned compound (0.78 g, 100%) was obtained as a pale yellow solid. LC-MS (ESI) [M−H]−=320.2

Step 5: (S)-5-((((9H-fluorene-9-yl) methoxy) carbonyl) amino)-4-oxa-6-phenylhexanoic acid (Compound YA-274-e)

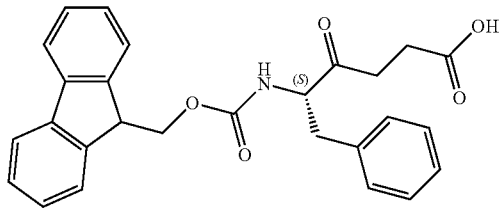

(S)-5-((tert-butoxycarbonyl) amino)-4-oxa-6-phenylhexanoic acid (830 mg, 2.43 mmol) was dissolved in dichloromethane (10 mL), then HCl (4 n in 1,4-dioxane, 10 ml, 40 mmol) was added and stirred at room temperature for 4 hours. The mixture was concentrated and then acetone (50 mL), water (25 mL), NaHCO$_3$ (202 mg, 2.41 mmol), 9-fluorenylmethyl-N-succinimidyl carbonate (811 mg, 2.41 mmol) were sequentially added and stirred at room temperature for 4 hours. The mixture was adjusted to pH=2-3 with 2N HCl, acetone was removed by rotary evaporation, and dichloromethane was extracted (100 mL×2). The organic phase was dried over anhydrous sodium sulfate, filtered and concentrated. The crude product was isolated and purified by high-speed chromatography (dichloromethane/ethyl acetate=5/1-1/5) to give the captioned compound (0.65 g, 56%) as a white solid. LCMS (ESI) [M+H]$^+$=444.1. 1H NMR (400 MHz, CDCl3) δ 7.75 (d, J=7.6 Hz, 2), 7.53 (d, J=7.6, 8.0 Hz, 2H), 7.39 (dd, J=7.2, 8.0 Hz, 2H), 7.32-7.20 (m, 5H), 7.13 (d, J=7.2 Hz, 2H), 5.36 (d, J=7.6 Hz, 1H), 4.66-4.52 (m, 1H), 4.40-4.31 (m, 2H), 4.19-4.15 (m, 2H), 3.14 (dd, J=6.0, 14.0 Hz, 1H), 2.98 (dd, J=6.8, 14.0 Hz, 1H), 2.74-2.67 (m, 2H), 2.64-2.57 (m, 2H).

Preparation Embodiment 14: 4-(2-((9H-fluorene-9-yl) methoxy) carbonyl-1-benzylhydrazino)-4-oxobutyric acid (Compound YA-275-b)

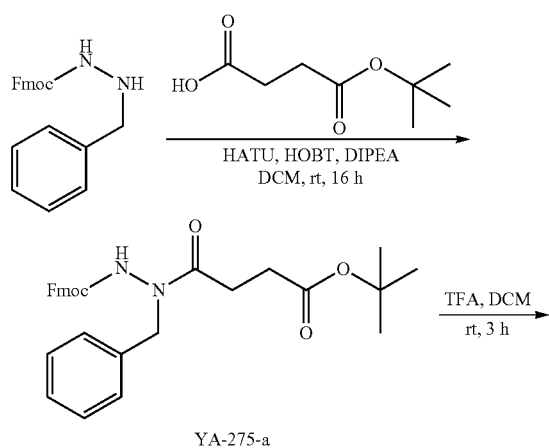

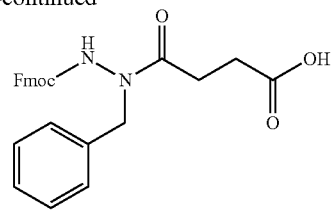

Step 1: 4-(2-((9H-fluoren-9-yl) methoxy) carbonyl)-1-benzylhydrazino)-4-oxobutanoic acid tert-butyl ester (Compound YA-275-a)

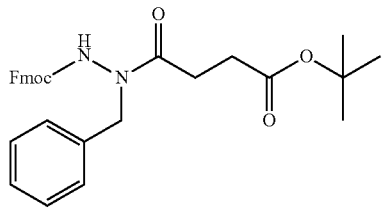

Methyl (9-hydrogen-fluorene-9-yl) 2-benzylhydrazine formate (1 g, 2.9 mmol), mono-tert-butyl 1,4-succinate (1 g, 5.8 mmol), HOBt (0.59 g, 4.35 mmol) and HATU (1.65 g, 4.35 mmol) were dissolved in dichloromethane (25 mL), and then N,N-diisopropylethylamine (0.75 g, 5.8 mmol) was added at room temperature. The reaction mixture was stirred at room temperature for 16 hours and then concentrated. The residue was isolated and purified by high-speed chromatography (petroleum ether/ethyl acetate=4/1) to give the captioned compound (1 g, 69%) as a white solid. LC-MS (ESI) [M−55]$^+$=445.0.

Step 2: 4-(2-((9H-fluoren-9-yl) methoxy) carbonyl)-1-benzylhydrazino)-4-oxobutyric acid (Compound YA-275-b)

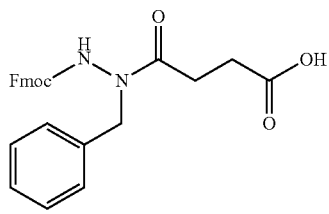

The compound 4-(2-((9 hydrogen-fluorene-9-yl) methoxy) carbonyl)-1-benzylhydrazino)-4-oxobutyric acid tert-butyl ester (1 g, 2.0 mmol) was dissolved in dichloromethane (15 mL), trifluoroacetic acid (15 mL) was added under ice-water bath, and the reaction mixture was stirred at room temperature for 3 hours. The reaction mixture was concentrated and the crude product was isolated and purified by high-speed chromatography (petroleum ether/ethyl acetate=35/65) to give the captioned compound (800 mg, 90%) as a white solid. LC-MS (ESI) [M+H]$^+$=445.0.

Preparation Embodiment 15: (5S)-5-benzyl-1-(9H-fluoren-9-yl)-11-isobutyl-3,6,10-trioxy-2-oxa-4,7,9-triazadecane-12-carboxylic acid (Compound YA-303-h)

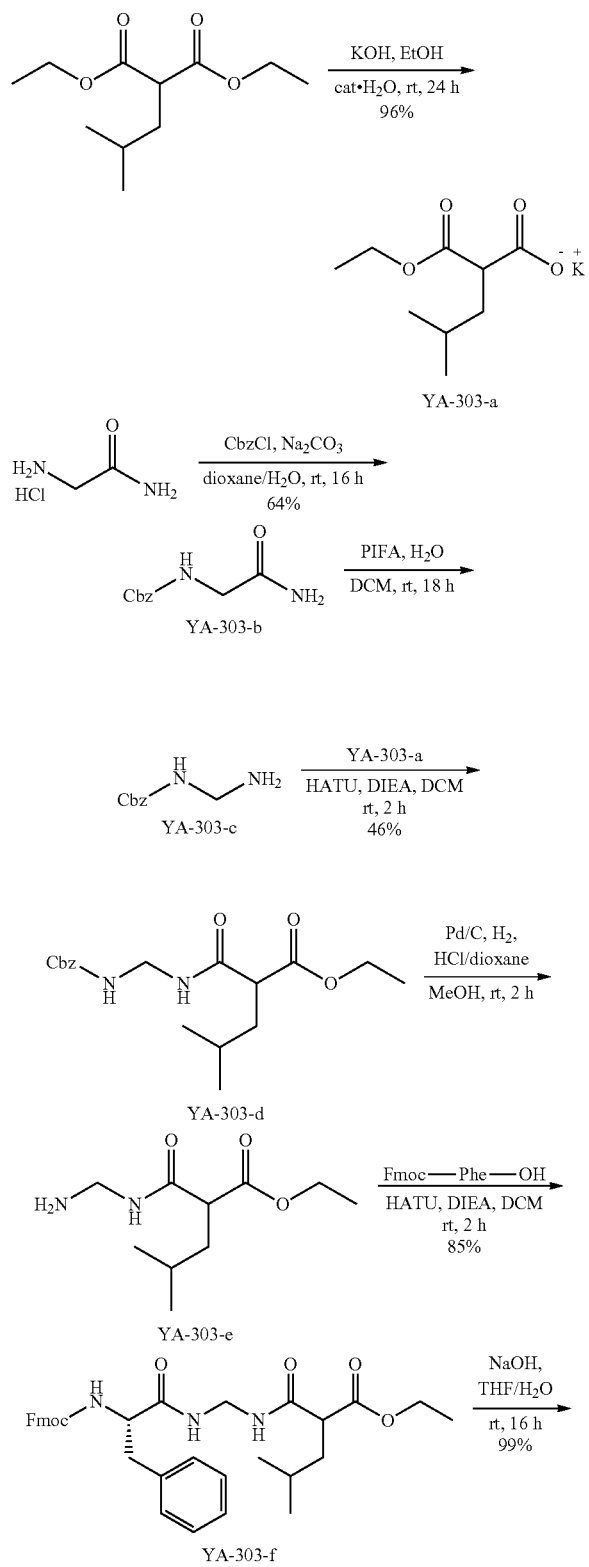

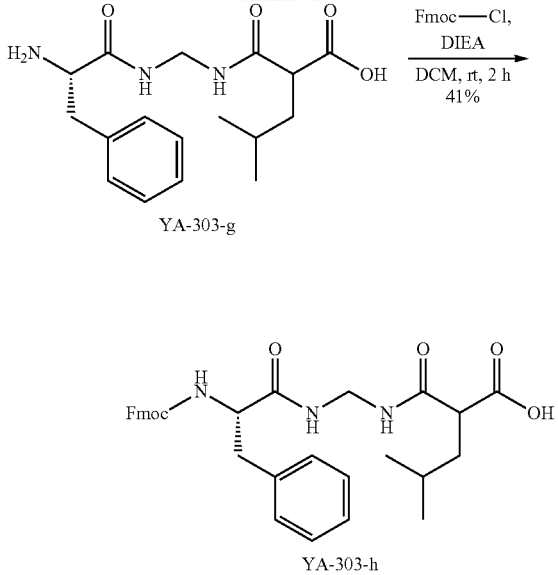

Step 1: Isobutyl Malonate Monoethyl Potassium Salt (YA-303-A)

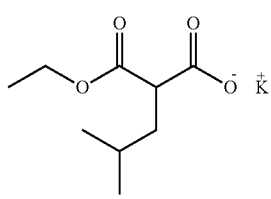

Diethyl 2-isobutylmalonate (2.16 g, 10 mmol) and potassium hydroxide (560 mg, 10 mmol) were dissolved in ethanol (50 mL) and a drop of water was added. The reaction mixture was stirred at room temperature for 24 hours. The reaction mixture was then concentrated to give the captioned compound (1.8 g, 96%) as a white solid.

Step 2: 2-benzyloxycarbonylaminoacetamide (YA-303-B)

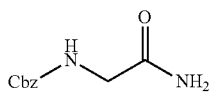

The hydrochloride (10 g, 90.5 mmol) of 2-aminoacetamide and sodium carbonate (9.59 g, 90.5 mmol) were dissolved in 1,4-dioxane/water (1/1, 200 mL), cooled to 0° C., then benzyl chloroformate (15.43 g, 90.5 mmol) was added dropwise, and the mixture was stirred at room temperature for 16 hours. The reaction liquid was concentrated, water (20 mL) was added to the residue, the solid was filtered off and the filter cake was washed with water, and after drying, the captioned compound (12 g, 64%) was obtained as a white solid. LC-MS (ESI) [M+H]$^+$=209.1.

Step 3: 2-benzyloxycarbonylaminomethylamine Trifluoroacetate (YA-303-C)

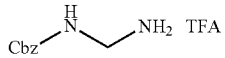

2-benzyloxycarbonylaminoacetamide (1 g, 5 mmol) and bis (trifluoroacetoxy) iodobenzene (2.4 g, 5.5 mmol) were dissolved in dichloromethane (50 mL), then a drop of water was added, and the reaction mixture was stirred at room temperature for 18 hours. The reaction mixture was concentrated to give the captioned compound (1.39 g, 99%) as a white solid. LC-MS (ESI) [M+H]$^+$=181.3.

Step 4: 2-((benzyloxycarbonylamino) methylaminoformyl)-4-methyl ethyl valerate (YA-303-D)

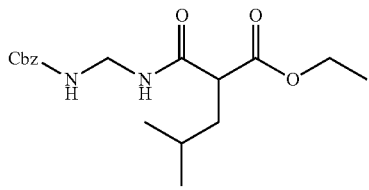

2-benzyloxycarbonylaminomethylamine trifluoroacetate (1.39 g, 5 mmol), potassium isobutylmalonate monoethyl ester (1.05 g, 5 mmol), HATU (1.9 g, 5 mmol) and N,N-diisopropylethylamine (1.29 g, 10 mmol) were dissolved in dichloromethane (50 mL), and the mixture was stirred at room temperature for 2 hours. The reaction mixture was concentrated, and the residue was isolated and purified by high-speed chromatography (petroleum ether/ethyl acetate=5/1) to give the captioned compound (800 mg, 46%) as a white solid. LC-MS (ESI) [M+H]$^+$=351.2.

Step 5: 2-(aminomethyl carbamoyl)-4-methyl ethyl valerate (YA-303-E)

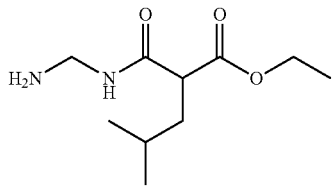

Ethyl 2-((benzyloxycarbonylamino) methylaminoformyl)-4-methylpentanoate (700 mg, 2 mmol), Pd/C (70 mg) and hydrochloric acid/1,4-dioxane solution (4 M, 1 mL) were dissolved in methanol (10 mL), and the reaction system was ventilated 3 times with hydrogen. The reaction mixture was stirred for 2 hours at room temperature under the protection of hydrogen. The filtrate was filtered and concentrated to give the captioned compound (432 mg, 99%) as colorless oil. LC-MS (ESI) [M+Na]$^+$=239.2.

Step 6: (5 S)-5-benzyl-1-(9-hydrogen-fluoren-9-yl)-11-isobutyl-3,6,10-trioxy-2-oxa-4,7,9-triazadecane-12-carboxylic acid ethyl ester (YA-303-F)

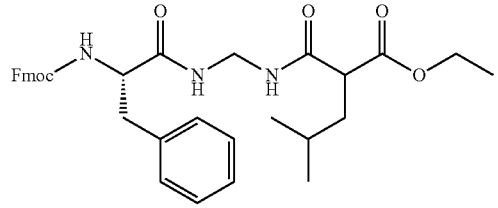

Ethyl 2-(aminomethylcarbamoyl)-4-methylpentanoate (432 mg, 2 mmol), (S)-2-((9 hydrogen-fluorene-9-yl) methoxy) carbonylamino)-3-phenylalanine (774 mg, 2 mmol), HATU (760 mg, 2 mmol) and N,N-diisopropylethylamine (516 mg, 4 mmol) were dissolved in dichloromethane (20 mL), and the reaction mixture was stirred at room temperature for 2 hours. The reaction mixture was concentrated and the crude product was isolated and purified by high-speed chromatography (petroleum ether/ethyl acetate=1/1) to give the captioned compound (1 g, 85%) as a white solid. LC-MS (ESI) [M+H]$^+$=586.3.

Step 7: 2-((S)-2-amino-3-phenylpropanamide) methylaminoacyl)-4-methylpentanoic acid (YA-303-G)

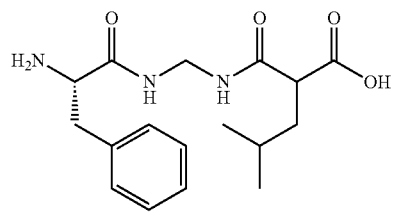 [SMILES: CC(C)CC(C(=O)O)C(=O)NCNC(=O)[C@@H](N)Cc1ccccc1]

(5 S)-5-benzyl-1-(9-hydrogen-fluoren-9-yl)-11-isobutyl-3,6,10-trioxy-2-oxa-4,7,9-triazadecane-12-carboxylic acid ethyl ester (1 g, 1.7 mmol) and sodium hydroxide (340 mg, 8.5 mmol) were dissolved in tetrahydrofuran (50 mL) and water (20 mL), and the reaction mixture was stirred at room temperature for 16 hours. The reaction mixture was concentrated, and the resulting crude product (570 mg, 99%) was directly used for the next reaction without purification. LC-MS (ESI) [M+H]$^+$=336.4.

Step 8: (5S)-5-benzyl-1-(9H-fluoren-9-yl)-11-isobutyl-3,6,10-trioxy-2-oxa-4,7,9-triazadecane-12-carboxylic acid (YA-303-H)

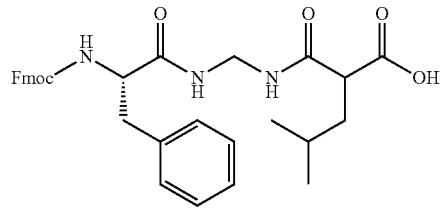

2-((S)-2-amino-3-phenylpropanamide) methylaminoacyl)-4-methylpentanoic acid (570 mg, 1.7 mmol), chloroformate (9 hydrogen-fluorene-9-yl) methyl ester (570 mg, 1.7 mmol) and N,N-diisopropylethylamine (440 mg, 3.4 mmol) were dissolved in dichloromethane (20 mL). The reaction mixture was stirred at room temperature for 2 hours and then concentrated. The residue was isolated and purified by high-speed chromatography (dichloromethane/methanol=10/1) to give the captioned compound (400 mg, 41%) as a white solid. LC-MS (ESI) [M+H]$^+$=558.4.

Preparation Embodiment 16: (5S)-5-benzyl-1-(9-hydrogen-fluoren-9-yl)-11-isobutyl-3,6,-dioxo-10-thio-2-oxa-4,7,9-triazadecane-12-carboxylic acid (Compound YA-326-B)

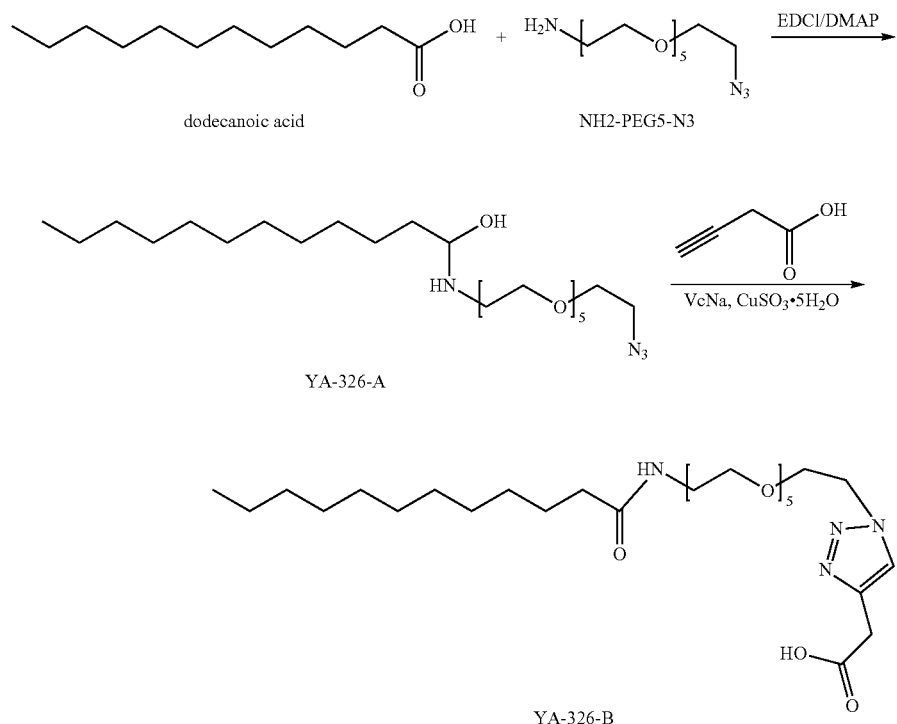

Step 1: Cinnamamide-PEG5-Azide (YA-326-A)

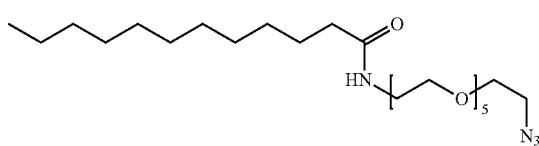

Cinnamic acid (273 mg, 1.36 mmol), EDCI (261 mg, 1.36 mmol), DMAP (166 mg, 1.36 mmol) and NH$_2$-PEG5-N3 (347 mg, 1.13 mmol) were dissolved in dichloromethane (10 mL) and stirred overnight at room temperature. The reaction mixture was concentrated, water (50 mL) was added, extracted with ethyl acetate (50 mL×2), washed with saturated saline solution, dried over anhydrous sodium sulfate, filtered, and concentrated. The crude product obtained was directly used for the next reaction. LC-MS (ESI) [M+H]$^+$= 489.3

Step 2: (1-(cinnamamide-PEG5)-1,2,3-triazine file)-4-acetic acid (YA-326-B)

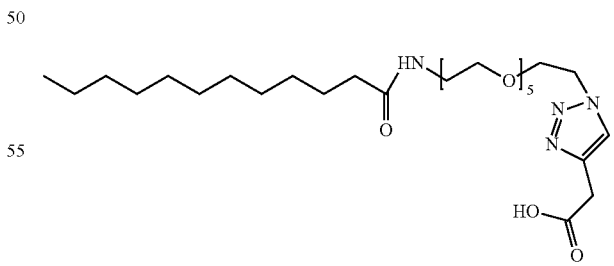

To a solution of YA-326-A (1.13 mmol) in N,N-dimethylformamide (10 mL), 3-butynic acid (190 mg, 2.26 mmol), sodium vitamin C salt (448 mg, 2.26 mmol), copper sulfate pentahydrate (282 mg, 1.13 mmol) and water (1 mL) were added, and the reaction was stirred at room temperature for 3 hours. The reaction mixture was poured into 30 mL of water, extracted with ethyl acetate (100 mL), washed with saturated brine, dried over anhydrous sodium sulfate, filtered, and concentrated. The crude product was isolated and purified by reversed-phase column. The eluent was acetonitrile:water=70:30. The product was collected and lyophilized to give the captioned compound (389 mg, total yield of two steps: 60%). LC-MS (ESI) [M−H]⁻=571.4

Preparation Embodiment 17:
hexadecyl-1,2,3-triazine file-1-PEG8-propionic acid (Compound YA-367-A)

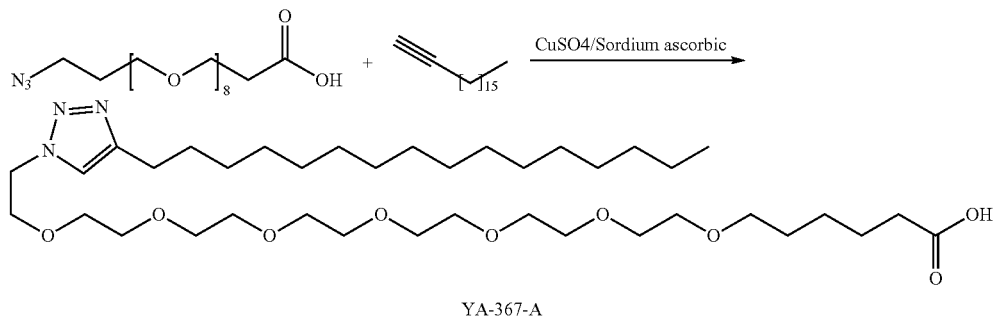

YA-367-A

N,N-dimethylformamide (10 mL), 1-octadecyne (376 mg, 1.5 mmol), sodium vitamin C salt (297 mg, 1.5 mmol), copper sulfate pentahydrate (240 mg, 1.5 mmol) and water (1 mL) were added to a solution of PEG8-N3 (468 mg, 1.0 mmol), and the reaction was stirred at room temperature for 3 hours. The reaction mixture was poured into 30 mL of water, extracted with ethyl acetate (100 mL), washed with saturated brine, dried over anhydrous sodium sulfate, filtered, and concentrated. The crude product was isolated and purified by reverse phase column. The eluent was acetonitrile:water=70:30. The product was collected and lyophilized to give 300 mg of the captioned compound with a yield of 41%. LC-MS (ESI) [M+H]+=718.4

Embodiment 1

Preparation of Ac-Tyr-Asn-Trp-Asn-Ser-Phe-Gly-Leu-Arg-Phe-NH₂ (Compound YA-2)

Step 1: Polypeptides were synthesized by standard Fmoc chemistry. The basic operations were as follows. 5.0 g of commercially available Rink Amide MBHA resin (0.5 mmol/g) was swollen in DMF, and the resin was treated with 20 mL 20% piperidine/DMF for 20 minutes to remove Fmoc, repeated twice. The obtained resin was washed with DMF, 20 mL DMF solution of Fmoc-Phe-OH (2.9 g, 7.5 mmol), HATU (2.85 g, 7.5 mmol) and HOAt (1.04 g, 7.5 mmol) were added, then DIPEA (2.6 mL, 15 mmol) was added, the resin was treated at room temperature for 40 minutes, and the resin was washed with DMF to give Fmoc-Phe-Rink Amide MBHA resin. The resin was treated with 20 ml of 20% piperidine/DMF for 20 minutes to remove Fmoc, and the operation was repeated twice. The resin was washed with DMF, and a 20 mL DMF solution of Fmoc-Arg (PBF)—OH (5.0 g, 7.5 mmol), DIC (945 mg, 7.5 mmol) and HOBt (1.01 g, 7.5 mmol) was added to react overnight at room temperature. In a similar manner, amino acids such as Leu, Gly, Phe, SER (tBu), Asn (Trt), trp (Boc, Asn (Trt), D-Tyr (tBu) and the like were sequentially introduced to give NH₂-D-Tyr (tBu)-Asn (Trt)-Trp (Boc)-Asn (Trt)-Thr(tBu)-Phe-Gly-Leu-Arg-Phe-Rinkamide MBHA resin. The mixture was washed with DMF, added 10 mL DMF solution of AcOH (44 μL, 7.5 mmol), DIC (945 mg, 7.5 mmol) and HOBt (1.01 g, 7.5 mmol), reacted overnight at room temperature, then AC group was introduced. The resin was washed with DMF, DCM, methanol and methyl tert-butyl ether, and then drained to give 8.5 g of Ac-D-Tyr (tBu)-Asn(Trt)-Trp(Boc-Asn(Trt)-Thr(tBu)-Phe-Gly-Leu-Arg-Phe-Rinkamide MBHA resin.

Step 2: dried resin was added into 85 mL of TFA/TIS/EDT/H2O (94/2/2/2) solution, the mixture was stirred for 2 hours, filtered to remove the resin, and the resin was washed with 20 mL of TFA/TIS/EDT/H₂O (94/2/2/2) solution. The filtrates were combined, cold diethyl ether (1000 mL) was added to the filtrate, and the resulting mixture was centrifuged at 3000 rpm for 3 minutes to remove the supernatant, and the solid was washed twice with diethyl ether and drained.

Step 3: The obtained crude polypeptide was dissolved with DMF, and then linear gradient elution (10 minutes) was performed with a flow rate of 25 mL/minute. Eluent AB was applied at a ratio of 74/26-64/36 using: eluent A: 0.05% TFA aqueous solution and eluent B: acetonitrile solution of 0.05% TFA, Sunfire C18, 10 μm, 120 column (19×250 mm) was applied on a preparative HPLC. The fractions containing the product were collected and lyophilized to give 1.1 g of white solid.

Embodiment 2

Preparation of Ac-(D-Tyr)-Hyp-Asn-Thr-Phe-azaGly-Leu-Arg(Me)-trp-NH₂ (Compound YA-3)

Step 1:5.0 g of commercially available Rink Amide MBHA resin (0.5 mmol/g) was swollen in DMF, and the resin was treated with 20 mL 20% piperidine/DMF for 20 minutes to remove Fmoc, repeated twice. The obtained resin was washed with DMF, 20 mL DMF solution of Fmoc-Trp (Boc)-OH (4.0 g, 7.5 mmol), HATU (2.85 g, 7.5 mmol) and HOAt (1.04 g, 7.5 mmol) was added, then DIPEA (2.6 mL, 15 mmol) was added, the resin was treated at room temperature for 40 minutes, and the resin was washed with DMF to give Fmoc-Trp(Boc)-Rink Amide MBHA resin. The resin was treated with 20 ml of 20% piperidine/DMF for 20 minutes to remove Fmoc, repeated twice. The resin was washed with DMF, and a solution of Fmoc-Arg (Me, Pbf)-OH (2.08 g, 3.0 mmol) in 20 mL DMF, DIC (945 mg, 7.5 mmol) and HOBt (1.01 g, 7.5 mmol) were added to react overnight at room temperature. The resin was treated with 20 mL 20% piperidine/DMF for 20 minutes to remove Fmoc, repeated twice. The resin was washed with DMF to give Arg (Me, Pbf)-Trp (Boc)-Rink amide MBHA resin. The obtained resin was added with 15 mL DMF solution of Fmoc-Phe-azaGly-Leu-OH (1.68 g, 3.0 mmol), DIC (945 mg, 7.5 mmol) and HOBt (1.01 g, 7.5 mmol), and reacted overnight at room temperature. The resin was treated with 20 mL 20% piperidine/DMF for 20 minutes to remove Fmoc, repeated twice. The resin was washed with DMF to give Phe-azaGly-Leu-Arg (Me, Pbf)-Trp (Boc)-Rink Amide MBHA resin. In a similar manner, amino acids such as Thr(tBu), Asn(Trt), Hyp(tBu), D-Tyr(tBu) and the like were sequentially introduced to give NH$_2$-D-Tyr(tBu)-Hyp(tBu)-Asn(Trt)-Thr(tBu)-Phe-azaGly-Leu-Arg(Me, Pbf)-Trp (Boc)-Rink Amide MBHA resin. The mixture was washed with DMF, then 10 mL DMF solution of AcOH (44 ml, 7.5 mmol), DIC (945 mg, 7.5 mmol) and HOBt (1.01 g, 7.5 mmol) were added, the reaction was performed overnight at room temperature to introduce Ac group. The resin was washed with DMF, DCM, methanol and methyl tert-butyl ether, and then drained to finally give 8.6 g of Ac-D-Tyr (tBu)-Hyp(tBu)-Asn(Trt)-Thr(tBu)-Phe-azaGly-Leu-Arg (Me, Pbf)-Trp(Boc)-Rink Amide MBHA resin.

Step 2: The dried resin was added into 85 mL of TFA/TIS/EDT/H$_2$O (94/2/2/2) solution, the mixture was stirred for 2 hours, filtered to remove the resin, and the resin was washed with 20 mL of TFA/TIS/EDT/H$_2$O (94/2/2/2) solution. The filtrates were pooled, cold diethyl ether (1000 mL) was added to the filtrate, and the resulting mixture was centrifuged at 3000 rpm for 3 minutes to remove the supernatant, and the solid was washed twice with diethyl ether and drained.

Step 3: The obtained crude precipitate was dissolved with DMF, and then linear gradient elution (17 minutes) was performed at a flow rate of 25 mL/minute. Eluent A/B: 79/21-69/31 using: eluent A: 0.05% TFA aqueous solution, eluent B: 0.05% TFA acetonitrile solution was applied on a preparative HPLC using Phenomenex Gemini 10μ, 110 Å column (21.2×250 mm). The fractions containing the product were collected and lyophilized to give 1.2 g of trifluoroacetate, and 1.0 g of acetate was obtained by salt conversion, all of which were white solids.

Embodiment 3

Preparation of Ac-Dap(Dnp)-Hyp-Asn-Thr-Phe-azaGly-Leu-Arg(Me)-Trp-NH$_2$ (Compound YA-41)

Similar to the synthesis method of Embodiment 2, while Fmoc-Dap(Dnp)-OH (3 equivalents) was used instead of Fmoc-D-Tyr(tBu)—OH condensation, HBTU/HOBt/DIPEA was used as condensation conditions, DMF was used as solvent, and the mixture was reacted at room temperature for 3 hours. The resin was washed and dried. The target polypeptide was cleaved from the resin and deprotected by the method of Step 2 of Embodiment 2. The crude product YA-41 was isolated and purified by HPLC, and eluted with linear gradient (10 minutes) at a flow rate of 25 mL/minute. Eluent A/B: 70/30-62/38, using: eluent A: 0.05% TFA aqueous solution, eluent B: 0.05% TFA acetonitrile solution, Sunfire C18, 10 μm, 120 column (19×250 mm) was applied on a preparative HPLC. The fractions containing the product were collected and lyophilized to give 10.0 mg of white solid.

Embodiment 4

Preparation of Ac-[D-Phe(2,4-DiCl)]-Hyp-Asn-Thr-Phe-azaGly-Leu-Arg(Me)-Trp-NH$_2$ (Compound YA-42)

Similar to the synthesis method of Embodiment 2, while Fmoc-[D-Phe (2,4-diCl)]—OH (3 equivalents) was used instead of Fmoc-D-Tyr(tBu)-OH condensation, HBTU/HOBt/DIPEA was used as condensation condition, DMF was used as solvent, and the mixture was reacted at room temperature for 3 hours. The resin was washed and dried. The target polypeptide was claeved from the resin and deprotected by the method of Step 2 of Embodiment 2. The crude product YA-42 was isolated and purified by HPLC, and eluted with a linear gradient (10 minutes) at a flow rate of 25 mL/minute. Eluent A/B: 73/27-63/37, using: eluent A: 0.05% TFA aqueous solution, eluent B: 0.05% TFA acetonitrile solution, Sunfire C18, 5 μm, 120 column (19×150 mm) was applied on a preparative HPLC. The fractions containing the product were collected and lyophilized to give 68.8 mg of white solid.

Embodiment 5

Preparation of Ac-(D-2Fua)-Hyp-Asn-Thr-Phe-azaGly-Leu-Arg(Me)-Trp-NH$_2$ (Compound YA-43)

Similar to the synthesis method of Embodiment 2, while Fmoc-(D-2Fua)-OH (3 equivalents) was used instead of Fmoc-D-Tyr(tBu)—OH condensation, HBTU/HOBt/DIPEA was used as condensation conditions, DMF was used as solvent, and the mixture was reacted at room temperature for 3 hours. The resin was washed and dried. The target polypeptide was cleaved from the resin according to the method of Step 2 of Embodiment 2 and deprotected. The solution for cleavage was TFA/TIS/H2O (94/3/3) solution without containing EDT, and the other operations were consistent with previous methods. The crude product YA-43 was isolated and purified by HPLC, and eluted with a linear gradient (10 minutes) at a flow rate of 20 mL/minute. Eluent A/B: 78/22-70/30, using: eluent A: 0.05% TFA aqueous solution, eluent B: 0.05% TFA acetonitrile solution, Sunfire C18, 5 μm, 120 column (19×150 mm) was applied on a preparative HPLC. The fractions containing the product were collected and lyophilized to give 6.2 mg of white solid.

Embodiment 6

Preparation of Ac-Pro(5Ph)-Hyp-Asn-Thr-Phe-azaGly-Leu-Arg(Me)-Trp-NH$_2$ (Compound YA-44)

Similar to the synthesis method of Embodiment 2, while Fmoc-Pro(5Phe)-OH (3 equivalents) was used instead of Fmoc-D-Tyr(tBu)—OH condensation, HBTU/HOBt/DIPEA was used as condensation conditions, DMF was used as solvent, and the mixture was reacted at room temperature for 3 hours. The resin was washed and dried. The target polypeptide was cleaved from the resin and deprotected by the method of Step 2 of Embodiment 2. The crude product YA-44 was isolated and purified by HPLC, and eluted with a linear gradient (10 minutes) at a flow rate of 25 mL/minute, and eluent A/B: 73/27-67/33, using: eluent A: 0.05% TFA aqueous solution, eluent B: 0.05% TFA acetonitrile solution, Sunfire C18, 10 μm, 120 column (19×250 mm) was applied on a preparative HPLC. The fractions containing the product were collected and lyophilized to give 28.0 mg of white solid.

Embodiment 7

Preparation of Ac-D-Tyr-Thz-Asn-Thr-Phe-azaGly-Leu-Arg(Me)-Trp-NH$_2$ (Compound YA-45)

Similar to the synthesis method of Embodiment 2, while Fmoc-Thz-OH (3 equivalents) was used instead of Fmoc-Hyp (tBu)—OH condensation, HBTU/HOBt/DIPEA was used as condensation conditions, DMF was used as solvent, and the mixture was reacted at room temperature for 3 hours. The resin was washed and dried. The target polypeptide was cleaved from the resin and deprotected by the method of Step 2 of Embodiment 2. The crude product YA-45 was isolated and purified by HPLC, and eluted with linear gradient (10 minutes) at a flow rate of 25 mL/minute, and eluent A/B: 75/25-68/32, using: eluent A: 0.05% TFA aqueous solution, eluent B: 0.05% TFA acetonitrile solution, Sunfire C18, 10 μm, 120 column (19×250 mm) was applied on a preparative HPLC. The fractions containing the product were collected and lyophilized to give 10.0 mg of white solid.

Embodiment 8

Preparation of Ac-3Pal-Hyp-Asn-Thr-Phe-azaGly-Leu-Arg(Me)-Trp-NH$_2$ (Compound YA-69)

Similar to the synthesis method of Embodiment 2, while Fmoc-3Pal-OH (3 equivalents) was used instead of Fmoc-D-Tyr(tBu)—OH, HBTU/HOBt/DIPEA was used as condensation conditions, DMF was used as solvent, and the mixture was reacted at room temperature for 3 hours. The resin was washed and dried. The target polypeptide was cleaved from the resin and deprotected by the method of Step 2 of Embodiment 2. The crude product YA-69 was isolated and purified by HPLC, and eluted with linear gradient (10 minutes) at a flow rate of 25 mL/minute, and eluent A/B: 85/15-75/25, using: eluent A: 0.05% TFA aqueous solution, eluent B: 0.05% TFA acetonitrile solution, Sunfire C18, 10 μm, 120 column (19×250 mm) was applied on preparative HPLC. The fractions containing the product were collected and lyophilized to give 21.6 mg of white solid.

Embodiment 9

Preparation of Ac-Phe(3-Cl)-Hyp-Asn-Thr-Phe-azaGly-Leu-Arg(Me)-Trp-NH$_2$ (Compound YA-70)

Similar to the synthesis method of Embodiment 2, while Fmoc-Phe(3-Cl)—OH (3 equivalents) was used instead of Fmoc-D-Tyr(tBu)—OH, HBTU/HOBt/DIPEA was used as condensation conditions, DMF was used as solvent, and the mixture was reacted at room temperature for 3 hours. The resin was washed and dried. The target polypeptide was cleaved from the resin and deprotected by the method of Step 2 of Embodiment 2. The crude product YA-70 was isolated and purified by HPLC, and eluted with linear gradient (10 minutes) at a flow rate of 25 mL/minute, and eluent A/B: 73/27-64/36, using: eluent A: 0.05% TFA aqueous solution, eluent B: 0.05% TFA acetonitrile solution, Sunfire C18, 10 μm, 120 column (19×250 mm) was applied on a preparative HPLC. The fractions containing the product were collected and lyophilized to give 11.0 mg of white solid.

Embodiment 10

Preparation of Ac-Phe(4-F)-Hyp-Asn-Thr-Phe-azaGly-Leu-Arg(Me)-Trp-NH$_2$ (Compound YA-71)

Similar to the synthesis method of Embodiment 2, while Fmoc-Phe(4-F)—OH (3 equivalents) was used instead of Fmoc-D-Tyr(tBu)—OH, HBTU/HOBt/DIPEA was used as condensation conditions, DMF was used as solvent, and the mixture was reacted at room temperature for 3 hours. The resin was washed and dried. The target polypeptide was cleaved from the resin and deprotected by the method of Step 2 of Embodiment 2. The crude product YA-71 was isolated and purified by HPLC, and eluted with linear gradient (10 minutes) at a flow rate of 30 mL/minute, and eluent A/B: 68/32-62/38, using: eluent A: 0.05% TFA aqueous solution, eluent B: 0.05% TFA acetonitrile solution, Sunfire C18, 10 μm, 120 column (19×250 mm) was applied on preparative HPLC. The fractions containing the product were collected and lyophilized to give 7.6 mg of white solid.

Embodiment 11

Preparation of Ac-Phe(4-Cl)-Hyp-Asn-Thr-Phe-azaGly-Leu-Arg(Me)-Trp-NH$_2$ (Compound YA-72)

Similar to the synthesis method of Embodiment 2, while Fmoc-Phe(4-Cl)—OH (3 equivalents) was used instead of Fmoc-D-Tyr(tBu)—OH, HBTU/HOBt/DIPEA was used as condensation conditions, DMF was used as solvent, and the mixture was reacted at room temperature for 3 hours. The resin was washed and dried. The target polypeptide was cleaved from the resin and deprotected by the method of Step 2 of Embodiment 2. The crude product YA-72 was isolated and purified by HPLC, and eluted with linear gradient (10 minutes) at a flow rate of 30 mL/minute, and eluent A/B: 61/39-54/46, using: eluent A: 0.05% TFA aqueous solution, eluent B: 0.05% TFA acetonitrile solution, Sunfire C18, 10 μm, 120 column (19×250 mm) was applied on a preparative HPLC. The fractions containing the product were collected and lyophilized to give 12.4 mg of white solid.

Embodiment 12

Preparation of Ac-Tyr(Me)-Hyp-Asn-Thr-Phe-azaGly-Leu-Arg(Me)-Trp-NH$_2$ (Compound YA-73)

Similar to the synthesis method of Embodiment 2, while Fmoc-Tyr(Me)-OH (3 equivalents) was used instead of Fmoc-D-Tyr(tBu)—OH, HBTU/HOBt/DIPEA was used as condensation conditions, DMF was used as solvent, and the mixture was reacted at room temperature for 3 hours. The resin was washed and dried. The target polypeptide was cleaved from the resin and deprotected by the method of Step 2 of Embodiment 2. The crude product YA-73 was isolated and purified by HPLC, and eluted with linear gradient (10 minutes) at a flow rate of 25 mL/minute, and eluent A/B: 76/24-68/32, using: eluent A: 0.05% TFA aqueous solution, eluent B: 0.05% TFA acetonitrile solution, Sunfire C18, 10 μm, 120 column (19×250 mm) was applied on a preparative HPLC. The fractions containing the product were collected and lyophilized to give 4.7 mg of white solid.

Embodiment 13

Preparation of Ac-Phe(4-Me)-Hyp-Asn-Thr-Phe-azaGly-Leu-Arg(Me)-Trp-NH$_2$ (Compound YA-74)

Similar to the synthesis method of Embodiment 2, while Fmoc-Phe(4-Me)-OH (3 equivalents) was used instead of Fmoc-D-Tyr(tBu)—OH, HBTU/HOBt/DIPEA was used as condensation conditions, DMF was used as solvent, and the mixture was reacted at room temperature for 3 hours. The resin was washed and dried. The target polypeptide was cleaved from the resin and deprotected by the method of Step 2 of Embodiment 2. The crude product YA-74 was isolated and purified by HPLC, and eluted with linear gradient (10 minutes) at a flow rate of 25 mL/minute. Eluent A/B: 73/27-65/35, using: eluent A: 0.05% TFA aqueous solution, eluent B: 0.05% TFA acetonitrile solution, Sunfire C18, 10 μm, 120 column (19×250 mm) was applied on a preparative HPLC. The fractions containing the product were collected and lyophilized to give 5.1 mg of white solid.

Embodiment 14

Preparation of Ac-Phe(4-tBu)-Hyp-Asn-Thr-Phe-azaGly-Leu-Arg(Me)-Trp-NH$_2$ (Compound YA-75)

Similar to the synthesis method of Embodiment 2, while Fmoc-Phe(4-tBu)—OH (3 equivalents) was used instead of Fmoc-D-Tyr(tBu)—OH, HBTU/HOBt/DIPEA was used as condensation conditions, DMF was used as solvent, and the mixture was reacted at room temperature for 3 hours. The resin was washed and dried. The target polypeptide was cleaved from the resin and deprotected by the method of Step 2 of Embodiment 2. The crude product YA-75 was isolated and purified by HPLC, and eluted with linear gradient (10 minutes) at a flow rate of 30 mL/minute. Eluent A/B: 62/38-56/44, using: eluent A: 0.05% TFA aqueous solution, eluent B: 0.05% TFA acetonitrile solution, Sunfire C18, 10 μm, 120 column (19×250 mm) was applied on a preparative HPLC. The fractions containing the product were collected and lyophilized to give 5.9 mg of white solid.

Embodiment 15

Preparation of Ac-D-Tyr-Pro(diF)-Asn-Thr-Phe-azaGly-Leu-Arg(Me)-Trp-NH$_2$ (Compound YA-80)

Similar to the synthesis method of Embodiment 2, while Fmoc-Pro(diF)-OH (3 equivalents) was used instead of Fmoc-Hyp(tBu)—OH condensation, HATU/HOAt/DIPEA was used as condensation conditions, DMF was used as solvent, and the mixture was reacted at room temperature for 3 hours. The resin was washed and dried. The target polypeptide was cleaved from the resin and deprotected by the method of Step 2 of Embodiment 2. The crude product YA-80 was isolated and purified by HPLC, and eluted with linear gradient (10 minutes) at a flow rate of 30 mL/minute. Eluent A/B: 67/33-59/41, using: eluent A: 0.05% TFA aqueous solution, eluent B: 0.05% TFA acetonitrile solution, Sunfire C18, 10 μm, 120 column (19×250 mm) was applied on a preparative HPLC. The fractions containing the product were collected and lyophilized to give 8.8 mg of white solid.

Embodiment 16

Preparation of Ac-D-Tyr-Hyp-Asn-Thr-Phe-azaGly-Leu-Arg(Me)-2Nal-NH$_2$ (Compound YA-81)

Similar to the synthesis method of Embodiment 2, while Fmoc-2Nal-OH (3 equivalents) was used instead of Fmoc-Trp(Boc)-OH condensation, HATU/HOAt/DIPEA was used as condensation condition, DMF was used as solvent, and the mixture was reacted at room temperature for 3 hours. The resin was washed and dried. The target polypeptide was cleaved from the resin and deprotected by the method of Step 2 of Embodiment 2. The crude product YA-81 was isolated and purified by HPLC, and eluted with linear gradient (10 minutes) at a flow rate of 30 mL/minute. Eluent A/B: 61/39-54/46, using: eluent A: 0.05% TFA aqueous solution, eluent B: 0.05% TFA acetonitrile solution, Sunfire C18, 10 μm, 120 column (19×250 mm) was applied on a preparative HPLC. The fractions containing the product were collected and lyophilized to give 11.6 mg of white solid.

Embodiment 17

Preparation of Ac-D-Tyr-Pro(4-NH2)-Asn-Thr-Phe-azaGly-Leu-Arg(Me)-Trp-NH$_2$ (Compound YA-83)

Similar to the synthesis method of Embodiment 2, while Fmoc-Pro(4-NH$_2$)—OH (3 equivalents) was used instead of Fmoc-Hyp(tBu)—OH condensation, HATU/HOAt/DIPEA was used as condensation conditions, DMF was used as solvent, and the mixture was reacted at room temperature for 3 hours. The resin was washed and dried. The target polypeptide was cleaved from the resin and deprotected by the method of Step 2 of Embodiment 2. The crude product YA-83 was isolated and purified by HPLC, and eluted with linear gradient (10 minutes) at a flow rate of 25 mL/minute. Eluent A/B: 82/18-72/28, using: eluent A: 0.05% TFA aqueous solution, eluent B: 0.05% TFA acetonitrile solution, Sunfire C18, 10 μm, 120 column (19×250 mm) was applied on a preparative HPLC. The fractions containing the product were collected and lyophilized to give 29.8 mg of white solid.

Embodiment 18

Preparation of Ac-D-Tyr-Thi-Asn-Thr-Phe-azaGly-Leu-Arg(Me)-Trp-NH$_2$ (Compound YA-84)

Similar to the synthesis method of Embodiment 2, while Fmoc-Thi-OH (3 equivalents) was used instead of Fmoc-Hyp(tBu)—OH condensation, HATU/HOAt/DIPEA was used as condensation condition, DMF was used as solvent, and the mixture was reacted at room temperature for 3 hours. The resin was washed and dried. The target polypeptide was cleaved from the resin and deprotected by the method of Step 2 of Embodiment 2. The crude product YA-84 was isolated and purified by HPLC, and eluted with linear gradient (10 minutes) at a flow rate of 30 mL/minute. Eluent A/B: 67/33-61/39, using: eluent A: 0.05% TFA aqueous solution, eluent B: 0.05% TFA acetonitrile solution, Sunfire C18, 10 μm, 120 column (19×250 mm) was applied on a preparative HPLC. The fractions containing the product were collected and lyophilized to give 15.0 mg of white solid.

Embodiment 19

Preparation of Ac-D-Tyr-(S-Pip)-Asn-Thr-Phe-azaGly-Leu-Arg(Me)-Trp-NH$_2$ (Compound YA-85)

Similar to the synthesis method of Embodiment 2, while Fmoc-(S-Pip)-OH (3 equivalents) was used instead of Fmoc-Hyp (tBu)—OH for condensation, HATU/HOAt/DIPEA was used as condensation condition, DMF was used as solvent, and the mixture was reacted at room temperature for 3 hours. The resin was washed and dried. The target polypeptide was cleaved from the resin and deprotected by the method of Step 2 of Embodiment 2. The crude product YA-85 was isolated and purified by HPLC, and eluted with linear gradient (10 minutes) at a flow rate of 30 mL/minute. Eluent A/B: 67.5/32.5-59/41, using: eluent A: 0.05% TFA aqueous solution, eluent B: 0.05% TFA acetonitrile solution, Sunfire C18, 10 μm, 120 column (19×250 mm) was applied on a preparative HPLC. The fractions containing the product were collected and lyophilized to give 6.2 mg of white solid.

Embodiment 20

Preparation of Ac-Ala(dip)-Hyp-Asn-Thr-Phe-azaGly-Leu-Arg(Me)-Trp-NH$_2$ (Compound YA-132)

Similar to the synthesis method of Embodiment 2, while Fmoc-Ala(dip)-OH (3 equivalents) was used instead of Fmoc-D-Tyr(tBu)—OH, HBTU/HOBt/DIPEA was used as condensation conditions, DMF was used as solvent, and the mixture was reacted at room temperature for 3 hours. The resin was washed and dried. The target polypeptide was cleaved from the resin and deprotected by the method of Step 2 of Embodiment 2. The crude product YA-132 was isolated and purified by HPLC, and eluted with a linear gradient (10 minutes) at a flow rate of 20 mL/minute. Eluent A/B: 71/29-65/35, using: eluent A: 0.05% TFA aqueous solution, eluent B: 0.05% TFA acetonitrile solution, Sunfire C18, 5 μm, 120 column (19×150 mm) was applied on a preparative HPLC. The fractions containing the product were collected and lyophilized to give 4.6 mg of white solid.

Embodiment 21

Preparation of Ac-D-Tyr-Hyp-Asn-2Fua-Phe-azaGly-Leu-Arg(Me)-Trp-NH$_2$ (Compound YA-143)

Similar to the synthesis method of Embodiment 2, while Fmoc-2Fua-OH (3 equivalents) was used instead of Fmoc-Thr (tBu)—OH, HBTU/HOBt/DIPEA was used as condensation condition, DMF was used as solvent, and the mixture was reacted at room temperature for 3 hours. The resin was washed and dried. The target polypeptide was cleaved from the resin according to the method of Step 2 of Embodiment 2 and deprotected. The solution for cleavage was TFA/TIS/H$_2$O (94/3/3) solution without containing EDT, the other operations were consistent with above methods. The crude product YA-143 was isolated and purified by HPLC, and eluted with a linear gradient (10 minutes) at a flow rate of 25 mL/minute. Eluent A/B: 75/25-67/33, using: eluent A: 0.05% TFA aqueous solution, eluent B: 0.05% TFA acetonitrile solution, Sunfire C18, 10 μm, 120 column (19×250 mm) was applied on a preparative HPLC. The fractions containing the product were collected and lyophilized to give 4.2 mg of white solid.

Embodiment 22

Preparation of Ac-D-Tyr-ACPA-Asn-Thr-Phe-azaGly-Leu-Arg(Me)-Trp-NH$_2$ (Compound YA-145)

Similar to the synthesis method of Embodiment 2, while Fmoc-ACPA-OH (3 equivalents) was used instead of Fmoc-Hyp(tBu)—OH condensation, HATU/HOAt/DIPEA was used as condensation condition, DMF was used as solvent, and the mixture was reacted at room temperature for 3 hours. The resin was washed and dried. The target polypeptide was cleaved from the resin and deprotected by the method of Step 2 of Embodiment 2. The crude product YA-145 was isolated and purified by HPLC, and eluted with a linear gradient (10 minutes) at a flow rate of 25 mL/minute. Eluent A/B: 78/22-68/32, using: eluent A: 0.05% TFA aqueous solution, eluent B: 0.05% TFA acetonitrile solution, was applied on a HPLC using Phenomenex Gemini C18, 10 μm, 110 column (21.2×250 mm). The fractions containing the product were collected and lyophilized to give 17.9 mg of white solid.

Embodiment 23

Preparation of Ac-D-Tyr-Hyp-Asn-Thr-Phe-ACPO-Leu-Arg(Me)-Trp-NH$_2$ (Compound YA-152)

Step 1: Polypeptides were synthesized by standard Fmoc chemistry. The basic operation was as follows. 1.0 g of commercially available Rink Amide MBHA resin (0.5 mmol/g) was swollen in DMF, and the resin was treated with 10 mL of 20% piperidine/DMF for 20 minutes to remove Fmoc, repeated twice. The obtained resin was washed with DMF, 10 mL DMF solution of Fmoc-Trp (Boc)-OH (0.8 g, 1.5 mmol), Hatu (0.57 g, 1.5 mmol) and HOAt (0.208 g, 1.5 mmol) was added, then DIPEA (0.52 mL, 3 mmol) was added, the resin was treated at room temperature for 40 minutes, and the resin was washed with DMF to give Fmoc-Trp (Boc)-Rink Amide MBHA resin. The resin was treated with 10 ml of 20% piperidine/DMF for 20 minutes to remove Fmoc, repeated twice. The resin was washed with DMF, and 10 mL DMF solution of mixture was washed with DMF, added 10 mL DMF solution of AcOH (88 μL, 1.5 mmol), DIC (189 mg, 1.5 mmol) and HOBt (0.202 g, 1.5 mmol), reacted overnight at room temperature, then Ac group was introduced. The resin was washed with DMF, DCM, methanol and methyl tert-butyl ether, and then drained to give 1.3 g of Ac-D-Tyr(tBu)-Asn(Trt)-Thr(tBu)-Phe-ACPO-Leu-Arg-Phe-Rink Amide MBHA resin.

Step 2: The dried resin was added to 20 mL of TFA/TIS/EDT/H$_2$O (94/2/2/2) solution, the mixture was stirred for 2 hours, the resin was removed by filtration, and the resin was washed with 4 mL of TFA/TIS/EDT/H$_2$O (94/2/2/2) solution. The filtrates were combined, cold diethyl ether (200 mL) was added to the filtrate, and the resulting mixture was centrifuged at 3000 rpm for 3 minutes to remove the supernatant, and the solid was washed twice with diethyl ether and drained.

Step 3: The obtained crude polypeptide was dissolved with DMF, and then linear gradient elution (10 minutes) was performed at a flow rate of 30 mL/minute. Eluent A/B: 77/23-67/33, using: eluent A: 0.05% TFA aqueous solution, eluent B: 0.05% TFA acetonitrile solution, on a HPLC using Xtimate C18, 10 μm, 120 column (20×250 mm). The fractions containing the product were collected and lyophilized to give 7.1 mg of white solid.

Embodiment 24

Preparation of Ac-D-Tyr-Hyp-Asn-Thr-Phe-Aze-Leu-Arg(Me)-Trp-NH$_2$ (Compound YA-153)

Similar to the synthesis method of Embodiment 23, Fmoc-Aze-OH (3 equivalents) was used instead of Fmoc-ACPO-OH condensation, HATU/HOAt/DIPEA was used as condensation condition, DMF was used as solvent, and the mixture was reacted at room temperature for 3 hours. The resin was washed and dried. The target polypeptide was cleaved from the resin and deprotected by the method of Step 23 of Embodiment 2. The crude product YA-153 was isolated and purified by HPLC, and eluted with linear gradient (10 minutes) at a flow rate of 30 mL/minute. Eluent A/B: 78/22-68/32, using: eluent A: 0.05% TFA aqueous solution, eluent B: 0.05% TFA acetonitrile solution, was applied on a HPLC using Xtimate C18, 10 μm, 120 column (20×250 mm). The fractions containing the product were collected and lyophilized to give 24.4 mg of white solid.

Embodiment 25

Preparation of Ac-D-Tyr-(D-2Fua)-Asn-Thr-Phe-azaGly-Leu-Arg(Me)-Trp-NH$_2$ (Compound YA-165)

Similar to the synthesis method of Embodiment 2, while Fmoc-(D-2Fua)-OH (3 equivalents) was used instead of Fmoc-Hyp(tBu)—OH condensation, HATU/HOAt/DIPEA was used as condensation condition, DMF was used as solvent, and the mixture was reacted at room temperature for 3 hours. The resin was washed and dried. The target polypeptide was cleaved from the resin according to the method of Step 2 of Embodiment 2 and deprotected. The solution for cleavage was TFA/TIS/H$_2$O (94/3/3) solution without containing EDT, and the other operations were consistent with previous methods. The crude product YA-165 was isolated and purified by HPLC.

Embodiment 26

Preparation of Ac-(D-Tyr)-Hyp-Asn-Thr-(D-2Fua)-azaGly-Leu-Arg(Me)-Trp-NH$_2$ (Compound YA-167)

The polypeptide was synthesized by standard solid-phase polypeptide synthesis operation and Fmoc strategy, the basic operation was the same as the preparation method of Embodiment 2 (synthesis of YA-3), except that the raw material Fmoc-(D-2Fua)-azaGly-Leu-OH was different. The target polypeptide was cleaved from the resin according to the method of Step 2 of Embodiment 2 and deprotected. The solution for cleavage was TFA/TIS/H$_2$O (94/3/3) solution without containing EDT, and the other operations were consistent with previous methods. The crude product YA-167 was isolated and purified by HPLC and eluted by linear gradient (10 minutes). Flow rate was 25 mL/min, eluent A/B: 78/22-68/32, using: eluent A: 0.05% TFA aqueous solution, eluent B: 0.05% TFA acetonitrile solution, was applied on a HPLC using Phenomenex Gemini C18, 10 μm, 110 column (21.2×250 mm). The fractions containing the product were collected and lyophilized to give 19.1 mg of white solid.

Embodiment 27

Preparation of Ac-D-Tyr-Hyp-Asn-Thr-Phe-(D-2Fua)-Leu-Arg(Me)-Trp-NH$_2$ (Compound YA-168)

Similar to the synthesis method of Embodiment 23, Fmoc-(D-2Fua)-OH (3 equivalents) was used instead of Fmoc-ACPO-OH condensation, HATU/HOAt/DIPEA was used as condensation condition, DMF was used as solvent, and the mixture was reacted at room temperature for 3 hours. The resin was washed and dried. The target polypeptide was cleaved from the resin according to the method of Step 2 of Embodiment 2 and deprotected. The solution for cleavage was TFA/TIS/H2O (94/3/3) solution without containing EDT, and the other operations were consistent with previous methods. The crude product YA-168 was isolated and purified by HPLC, and eluted with linear gradient (10 minutes) at a flow rate of 30 mL/minute. Eluent A/B: 73/27-63/37, using: eluent A: 0.05% TFA aqueous solution, eluent B: 0.05% TFA acetonitrile solution, was applied on a HPLC using Xtimate C18, 10 μm, 120 column (20×250 mm). The fractions containing the product were collected and lyophilized to give 8.4 mg of white solid.

Embodiment 28

Preparation of Ac-[D-Phe(4-F)]-Hyp-Asn-Thr-Phe-azaGly-Leu-Arg(Me)-Trp-NH$_2$ (Compound YA-170)

Similar to the synthesis method of Embodiment 2, while Fmoc-[D-Phe (4-F)]—OH (3 equivalents) was used instead of Fmoc-D-Tyr (tBu)—OH, HBTU/HOBt/DIPEA was used as condensation condition, DMF was used as solvent, and the mixture was reacted at room temperature for 3 hours. The resin was washed and dried. The target polypeptide was cleaved from the resin and deprotected by the method of Step 2 of Embodiment 2. The crude product YA-170 was isolated and purified by HPLC, and eluted with a linear gradient (10 minutes) at a flow rate of 20 mL/minute. Eluent A/B: 71/29-65/35, using: eluent A: 0.05% TFA aqueous solution, eluent B: 0.05% TFA acetonitrile solution, Sunfire C18, 5 μm, 120 column (19×150 mm) was applied on a preparative HPLC. The fractions containing the product were collected and lyophilized to give 4.6 mg of white solid.

Embodiment 29

Preparation of Ac-D-Tyr-A6c-Asn-Thr-Phe-azaGly-Leu-Arg(Me)-Trp-NH$_2$ (Compound YA-172)

Similar to the synthesis method of Embodiment 2, while Fmoc-A6c-OH (3 equivalents) was used instead of Fmoc-Hyp(tBu)—OH condensation, HATU/HOAt/DIPEA was used as condensation condition, DMF was used as solvent, and the mixture was reacted at room temperature for 3 hours. The resin was washed and dried. The target polypeptide was cleaved from the resin and deprotected by the method of Step 2 of Embodiment 2. The crude product YA-172 was isolated and purified by HPLC, and then eluted with linear concentration gradient (10 minutes) at a flow rate of 25 mL/minute. Eluent A/B: 67/33-57/43 using: eluent A: 0.05% TFA aqueous solution, eluent B: 0.05% TFA acetonitrile solution, was applied on a HPLC using Shimada Zu C18 10 μm, 120 column (2×21.2×250 mm). Fractions containing the product were collected and lyophilized to give 12.2 mg of white solid.

Embodiment 30

Preparation of Ac-D-Tyr-Hyp-Asn-Thr-Phe-A6c-Leu-Arg(Me)-Trp-NH$_2$ (Compound YA-175)

Similar to the synthesis method of Embodiment 23, Fmoc-A6c-OH (3 equivalents) was used instead of Fmoc-ACPO-OH condensation, HATU/HOAt/DIPEA was used as condensation condition, DMF was used as solvent, and the mixture was reacted at room temperature for 3 hours. The resin was washed and dried. The target polypeptide was cleaved from the resin and deprotected by the method of Step 23 of Embodiment 2. The crude product YA-175 was isolated and purified by HPLC, and eluted with linear gradient (10 minutes) at a flow rate of 25 mL/minute. Eluent A/B: 73/27-65/35, using: eluent A: 0.05% TFA aqueous solution, eluent B: 0.05% TFA acetonitrile solution, was applied on a HPLC using Xtimate C18, 10 μm, 120 column (20×250 mm). The fractions containing the product were collected and lyophilized to give 16.4 mg of white solid.

Embodiment 31

Preparation of Ac-[D-Phe(2,4-DiCl)]-Thi-Asn-Thr-Phe-azaGly-Leu-Arg(Me)-Trp-NH$_2$ (Compound YA-178)

Similar to the synthesis method of Embodiment 2, while Fmoc-Thi-OH (3 equivalents) was used instead of Fmoc-Hyp(tBu)—OH condensation, HATU/HOAt/DIPEA was used as condensation condition, DMF was used as solvent, and the mixture was reacted at room temperature for 3 hours. Fmoc-[D-Phe (2,4-DiCl)]—OH (3 equivalents) was used replacing Fmoc-Tyr(tBu)—OH for condensation, HATU/HOAt/DIPEA was used as condensation condition, DMF was used as solvent, and the mixture was reacted for 3 hours at room temperature. The resin was washed and dried. The target polypeptide was cleaved from the resin and deprotected by the method of Step 2 of Embodiment 2. The crude product YA-178 was isolated and purified by HPLC. Linear gradient elution (10 minutes) was performed at a flow rate of 25 mL/minute, and eluent A/B: 59/41-49/51, using: eluent A: 0.05% TFA aqueous solution, eluent B: 0.05% TFA acetonitrile solution, was applied on a HPLC using Phenomenex Gemini C18, 10 μm, 110 column (21.2×250 mm). The fractions containing the product were collected and lyophilized to give 20.1 mg of white solid.

Embodiment 32

Preparation of Ac-[D-Phe(2,4-DiCl)]-Pro(diF)-Asn-Thr-Phe-azaGly-Leu-Arg(Me)-Trp-NH$_2$ (Compound YA-180)

Similar to the synthesis method of Embodiment 2, while Fmoc-Pro(diF)-OH (3 equivalents) was used instead of Fmoc-Hyp(tBu)—OH condensation, HATU/HOAt/DIPEA was used as condensation conditions, DMF was used as solvent, and the mixture was reacted at room temperature for 3 hours. Fmoc-[D-Phe (2,4-DiCl)]—OH (3 equivalents) was used to replace Fmoc-Tyr(tBu)—OH for condensation, HATU/HOAt/DIPEA was used as condensation condition, DMF was used as solvent, and the mixture was reacted for 3 hours at room temperature. The resin was washed and dried. The target polypeptide was cleaved from the resin and deprotected by the method of Step 2 of Embodiment 2. The crude product YA-180 was isolated and purified by HPLC. Linear gradient elution (10 minutes) was performed at a flow rate of 25 mL/minute, and eluent A/B: 68/32-58/42, using: eluent A: 0.05% TFA aqueous solution, eluent B: 0.05% TFA acetonitrile solution, Sunfire C18, 10 μm, 120 column (19×250 mm) was applied on a preparative HPLC. The fractions containing the product were collected and lyophilized to give 115.4 mg of white solid.

Embodiment 33

Preparation of Ac-(D-2Fua)-(S-Pip)-Asn-Thr-Phe-azaGly-Leu-Arg(Me)-Trp-NH$_2$ (Compound YA-181)

Similar to the synthesis method of Embodiment 2, while Fmoc-S-Pip-OH (3 equivalents) was used instead of Fmoc-Hyp(tBu)—OH condensation, HATU/HOAt/DIPEA was used as condensation condition, DMF was used as solvent, and the mixture was reacted at room temperature for 3 hours. Fmoc-(D-2Fua)-OH (3 equivalents) was used to replace Fmoc-Tyr(tBu)—OH for condensation, HATU/HOAt/DIPEA was used as condensation condition, DMF was used as solvent, and the mixture was reacted for 3 hours at room temperature. The resin was washed and dried. The target polypeptide was cleaved from the resin according to the method of Step 2 of Embodiment 2 and deprotected. The solution for cleavage was TFA/TIS/H2O (94/3/3) solution without containing EDT, and the other operations were consistent with previous methods. The crude product YA-181 was isolated and purified by HPLC. Linear gradient elution (10 minutes) was performed at a flow rate of 25 mL/minute, and eluent A/B: 68/32-58/42, using: eluent A: 0.05% TFA aqueous solution, eluent B: 0.05% TFA acetonitrile solution, was applied on a HPLC using Phenomenex Gemini C18, 10 μm, 110 column (21.2×250 mm). The fractions containing the product were collected and lyophilized to give 20.7 mg of white solid.

Embodiment 34

Preparation of Ac-[D-Phe(2,4-DiCl)]—(S-Pip)-Asn-Thr-Phe-azaGly-Leu-Arg(Me)-Trp-NH$_2$ (Compound YA-182)

Similar to the synthesis method of Embodiment 2, while Fmoc-S-Pip-OH (3 equivalents) was used instead of Fmoc-Hyp(tBu)—OH condensation, HATU/HOAt/DIPEA was used as condensation condition, DMF was used as solvent, and the mixture was reacted at room temperature for 3 hours. Fmoc-[D-Phe (2,4-DiCl)]—OH (3 equivalents) was used to replace Fmoc-Tyr(tBu)—OH for condensation, HATU/HOAt/DIPEA was used as condensation condition, DMF was used as solvent, and the mixture was reacted for 3 hours at room temperature. The resin was washed and dried. The target polypeptide was cleaved from the resin and deprotected by the method of Step 2 of Embodiment 2. The crude product YA-182 was isolated and purified by HPLC. Linear gradient elution (10 minutes) was performed at a flow rate of 25 mL/minute, and eluent A/B: 59/41-49/51, using: eluent A: 0.05% TFA aqueous solution, eluent B: 0.05% TFA acetonitrile solution, was applied on a HPLC using Phenomenex Gemini C18, 10 μm, 110 column (21.2×250 mm). The fractions containing the product were collected and lyophilized to give 20.2 mg of white solid.

Embodiment 35

Preparation of Ac-(D-2Fua)-Pro(diF)-Asn-Thr-Phe-azaGly-Leu-Arg(Me)-Trp-NH$_2$ (Compound YA-183)

Similar to the synthesis method of Embodiment 2, while Fmoc-Pro(diF)-OH (3 equivalents) was used instead of Fmoc-Hyp(tBu)—OH condensation, HATU/HOAt/DIPEA was used as condensation conditions, DMF was used as solvent, and the mixture was reacted at room temperature for 3 hours. Fmoc-(D-2Fua)-OH (3 equivalents) was used to replace Fmoc-Tyr(tBu)—OH for condensation, HATU/HOAt/DIPEA was used as condensation condition, DMF was used as solvent, and the mixture was reacted for 3 hours at room temperature. The resin was washed and dried. The target polypeptide was cleaved from the resin according to the method of Step 2 of Embodiment 2 and deprotected. The solution for cleavage was TFA/TIS/H2O (94/3/3) solution without containing EDT, and the other operations were consistent with previous methods. The crude product YA-183 was isolated and purified by HPLC. Linear gradient elution (10 minutes) was performed at a flow rate of 25 mL/minute, and eluent A/B: 71/29-61/39, using: eluent A: 0.05% TFA aqueous solution, eluent B: 0.05% TFA acetonitrile solution, was applied on a HPLC using Xtimate C18, 10 μm, 120 column (20×250 mm). The fractions containing the product were collected and lyophilized to give 19.6 mg of white solid.

Embodiment 36

Preparation of Ac-[D-Phe(2,4-DiCl)]-Hyp-Asn-Thr-Phe-azaPro-Leu-Arg(Me)-Trp-NH$_2$ (Compound YA-184)

Step 1: 0.4 g of commercially available Rink Amide MBHA resin (0.5 mmol/g) was swollen in DCM, and the resin was treated with 12 ml of 20% piperidine/DMF for 20 minutes to remove Fmoc, repeated twice. The obtained resin was washed with DMF, 10 mL DMF solution of Fmoc-Trp (Boc)-OH (320 mg, 0.6 mmol), HBTU (227 mg, 0.6 mmol) and HOBt (81 mg, 0.6 mmol) were added, then DIPEA (155 mg, 1.2 mmol) was added and treated at room temperature for 40 minutes. The resin was washed with DMF to give Fmoc-Trp(Boc)-Rink Amide MBHA resin. The resin was treated with 12 ml of 20% piperidine/DMF for 20 minutes to remove Fmoc, repeated twice. The resin was washed with DMF, 7 mL DMF solution of Fmoc-Arg (Me, Pbf)-OH (180 mg, 0.3 mmol), HATU (113 mg, 0.3 mmol) and HOAt (27 mg, 0.2 mmol) were added, then DIPEA (78 mg, 0.6 mmol) was added and treated at room temperature for 40 minutes. The resin was treated with 12 ml of 20% piperidine/DMF for 20 minutes to remove Fmoc, repeated twice. The resin was washed with DMF to give NH2-Arg (Me, Pbf)-Trp (Boc)-Rink Amide MBHA resin. Fmoc-Phe-Azap-Leu (150 mg, 0.24 mmol), DIC (60 mg, 0.48 mmol) and HOBt (67 mg, 0.48 mmol) were added in 10 mL DMF solution. After overnight reaction at room temperature, HATU (182 mg, 0.48 mmol), HOAt (67 mg, 0.48 mmol) and DIPEA (62 mg, 0.48 mmol), and the reaction was continued at room temperature for 40 minutes. The resin was washed with DMF, and the resin was treated with 12 ml of 20% piperidine/DMF for 20 minutes to remove Fmoc, repeated twice. NH$_2$-Phe-Azap-Leu-Arg (Me, Pbf)-Trp (Boc)-Rink Amide resin was obtained. Thr(tBu), Asn(Trt), Hyp(tBu) and D-Phe(2,4-DiCl) were sequentially and gradually introduced in a Trp-like manner. The obtained resin was washed with DMF, Ac2O (184 mg, 1.8 mmol) and DIPEA (460 mg, 3.6 mmol) were added, the reaction was carried out at room temperature for 30 minutes, Ac groups were introduced, and the resin was washed by DMF, DCM, methanol and methyl tert-butyl ether and then drained to finally give Ac-[D-Phe (2,4-diCl)]-Hyp(tBu)-Asn(Trt)-Thr(tBu)-Phe-Azap-Leu-Arg(Me,Pbf) Trp(Boc)-Rink Amide MBHA resin.

Step 2: The dried resin was added to 10 mL of TFA/TIS/EDT/H$_2$O (94/2/2/2) solution, then the mixture was stirred for 2 hours, filtered to remove the resin, and the resin was washed with 2 mL of TFA/TIS/EDT/H$_2$O (94/2/2/2) solution. The filtrates were combined, ether (70 mL) was added to the filtrate, and the resulting mixture was centrifuged at 3000 rpm for 3 minutes to remove the supernatant, and the solid was washed twice with ether and drained. The obtained precipitate was dissolved in DMF and then eluted with a linear concentration gradient (10 minutes) at a flow rate of 25 mL/minute. Eluent A/B: 66/34-58/42, using: eluent A: 0.05% TFA aqueous solution, eluent B: 0.05% TFA acetonitrile solution, was applied on a HPLC using Xtimate C18, 10 μm, 120 column (20×250 mm). The fractions containing the product were collected and lyophilized to give 5.9 mg of white solid.

Embodiment 37

Preparation of Ac-[D-Phe(2,4-DiCl)]-Hyp-Asn-Thr-Phe-Aze-Leu-Arg(Me)-Trp-NH$_2$ (Compound YA-188)

Similar to the synthesis method of Embodiment 24, Fmoc-[D-Phe (2,4-DiCl)]—OH (3 equivalents) was used instead of Fmoc-Tyr(tBu)—OH condensation, HATU/HOAt/DIPEA was used as condensation condition, DMF was used as solvent, and the mixture was reacted at room temperature for 3 hours. The resin was washed and dried. The target polypeptide was cleaved from the resin and deprotected by the method of Embodiment 24. The crude product YA-188 was isolated and purified by HPLC. Linear gradient elution (10 minutes) was performed at a flow rate of 25 mL/minute, and eluent A/B: 73/27-65/35, using: eluent A: 0.05% TFA aqueous solution, eluent B: 0.05% TFA acetonitrile solution, was applied on a HPLC using Xtimate C18, 10 μm, 120 column (20×250 mm). The fractions containing the product were collected and lyophilized to give 11.2 mg of white solid.

Embodiment 38

Preparation of Ac-D-Tyr-Thi-Asn-Thr-Phe-Aze-Leu-Arg(Me)-Trp-NH$_2$ (Compound YA-191)

Similar to the synthesis method of Embodiment 24, Fmoc-Thi-OH (3 equivalents) was used instead of Fmoc-Hyp(tBu)—OH condensation, HATU/HOAt/DIPEA was used as condensation condition, DMF was used as solvent, and the mixture was reacted at room temperature for 3 hours. The resin was washed and dried. The target polypeptide was cleaved from the resin according to the method of Step 2 of Embodiment 2 and deprotected. The solution for cleavage was TFA/TIS/H$_2$O (94/3/3) solution without containing EDT, and the other operations were consistent with previous methods. The crude product YA-191 was isolated and purified by HPLC. Linear gradient elution (10 minutes) was performed at a flow rate of 25 mL/minute, and eluent A/B: 71/29-63/37, using: eluent A: 0.05% TFA aqueous solution, eluent B: 0.05% TFA acetonitrile solution, was applied on a HPLC using Xtimate C18, 10 μm, 120 column (20×250 mm). The fractions containing the product were collected and lyophilized to give 3.8 mg of white solid.

Embodiment 39

Preparation of Ac-D-Tyr-(S-Pip)-Asn-Thr-Phe-Aze-Leu-Arg(Me)-Trp-NH$_2$ (Compound YA-194)

Similar to the synthesis method of Embodiment 24, Fmoc-(S-Pip)-OH (3 equivalents) was used instead of Fmoc-Hyp(tBu)—OH for condensation, HATU/HOAt/DIPEA was used as condensation condition, DMF was used as solvent, and the mixture was reacted at room temperature for 3 hours. The resin was washed and dried. The target polypeptide was cleaved from the resin according to the method of Step 2 of Embodiment 2 and deprotected. The solution for cleavage was TFA/TIS/H$_2$O (94/3/3) solution without containing EDT, and the other operations were consistent with previous methods. The crude product YA-194 was isolated and purified by HPLC. Linear gradient elution (10 minutes) was performed at a flow rate of 25 mL/minute, and eluent A/B: 76/24-68/32, using: eluent A: 0.05% TFA aqueous solution, eluent B: 0.05% TFA acetonitrile solution, was applied on a HPLC using Xtimate C18, 10 μm, 120 column (20×250 mm). The fractions containing the product were collected and lyophilized to give 6.5 mg of white solid.

Embodiment 40

Preparation of Ac-[D-Phe(4-F)]-Hyp-Asn-Thr-Phe-A6c-Leu-Arg(Me)-Trp-NH$_2$ (Compound YA-195)

Similar to the synthesis method of Embodiment 30, Fmoc-[D-Phe(4-F)]—OH (3 equivalents) was used instead of Fmoc-Tyr(tBu)—OH condensation, HATU/HOAt/DIPEA was used as condensation condition, DMF was used as solvent, and the mixture was reacted at room temperature for 3 hours. The resin was washed and dried. The target polypeptide was cleaved from the resin and deprotected by the method of Step 2 of Embodiment 2. The crude product YA-195 was isolated and purified by HPLC, and eluted with a linear gradient (10 minutes) at a flow rate of 25 mL/minute, and eluent A/B: 68/32-58/42, using: eluent A: 0.05% TFA aqueous solution, eluent B: 0.05% TFA acetonitrile solution, was applied on a HPLC using Xtimate C18, 10 μm, 120 column (20×250 mm). The fractions containing the product were collected and lyophilized to give 12.6 mg of white solid.

Embodiment 41

Preparation of Ac-[D-Phe(2,4-DiCl)]-Hyp-Asn-Thr-Phe-A6c-Leu-Arg (Me)-Trp-NH$_2$ (Compound YA-196)

Similar to the synthesis method of Embodiment 30, Fmoc-[D-Phe(2,4-DiCl)]—OH (3 equivalents) was used instead of Fmoc-Tyr(tBu)—OH condensation, HATU/HOAt/DIPEA was used as condensation condition, DMF was used as solvent, and the mixture was reacted at room temperature for 3 hours. The resin was washed and dried. The target polypeptide was cleaved from the resin and deprotected by the method of Step 2 of Embodiment 2. The crude product YA-196 was isolated and purified by HPLC, and eluted with linear gradient (10 minutes) at a flow rate of 25 mL/minute, and eluent A/B: 65/35-55/45, using: eluent A: 0.05% TFA aqueous solution, eluent B: 0.05% TFA acetonitrile solution, was applied on a HPLC using Xtimate C18, 10 μm, 120 column (20×250 mm). The fractions containing the product were collected and lyophilized to give 22.4 mg of white solid.

Embodiment 42

Preparation of Ac-(D-2Fua)-Hyp-Asn-Thr-Phe-A6c-Leu-Arg(Me)-Trp-NH$_2$ (Compound YA-197)

Similar to the synthesis method of Embodiment 30, Fmoc-(D-2Fua)-OH (3 equivalents) was used instead of Fmoc-Tyr(tBu)—OH for condensation, HATU/HOAt/DIPEA was used as condensation condition, DMF was used as solvent, and the mixture was reacted at room temperature for 3 hours. The resin was washed and dried. The target polypeptide was cleaved from the resin according to the method of Step 2 of Embodiment 2 and deprotected. The solution for cleavage was TFA/TIS/H$_2$O (94/3/3) solution without containing EDT, and the other operations were consistent with previous methods. The crude product YA-197 was isolated and purified by HPLC, and eluted with linear gradient (10 minutes) at a flow rate of 25 mL/minute, and eluent A/B: 71/29-61/39, using: eluent A: 0.05% TFA aqueous solution, eluent B: 0.05% TFA acetonitrile solution, was applied on a HPLC using Xtimate C18, 10 μm, 120 column (20×250 mm). The fractions containing the product were collected and lyophilized to give 18.3 mg of white solid.

Embodiment 42'

Preparation of Ac-D-Phe(2,4-DiCl)-azaPro-Asn-Thr-Phe-A6c-Leu-Arg(Me)-Trp-NH$_2$ (Compound YA-200)

0.4 g of commercially available Rink Amide MBHA resin (0.5 mmol/g) was swollen in DCM, and the resin was treated with 12 ml of 20% piperidine/DMF for 20 minutes to remove Fmoc, repeated twice. The obtained resin was washed with DMF, 10 mL DMF solution of Fmoc-Trp (Boc)-OH (320 mg, 0.6 mmol), HBTU (227 mg, 0.6 mmol) and HOBt (81 mg, 0.6 mmol) were added, then DIPEA (155 mg, 1.2 mmol) was added and treated at room temperature for 40 minutes. The resin was washed with DMF to give Fmoc-Trp(Boc)-Rink Amide MBHA resin. The resin was treated with 12 ml of 20% piperidine/DMF for 20 minutes to remove Fmoc, repeated twice. The resin was washed with DMF, 7 mL DMF solution of Fmoc-Arg (Me, Pbf)-OH (180 mg, 0.3 mmol), HATU (113 mg, 0.3 mmol) and HOAt (27 mg, 0.2 mmol) were added, then DIPEA (78 mg, 0.6 mmol) was added and treated at room temperature for 40 minutes. The resin was treated with 12 ml of 20% piperidine/DMF for 20 minutes to remove Fmoc, repeated twice. The resin was washed with DMF to give NH2-Arg(Me,Pbf)-Trp(Boc)-Rink Amide MBHA resin.

Amino acids such as Leu, A6c, Phe, Thr(tBu) were introduced in a Trp-like manner, and the resin was washed with DMF to give NH2-Thr(tBu)-Phe-A6c-Leu-Arg(Me, Pbf)-Trp(Boc)-Rink Amide MBHA resin. 7 mL DMF solution of D-Phe (2,4-diCl)-azaPro-ASN (TRT) (219 mg, 0.24 mmol), hatu (91 mg, 0.48 mmol) and HOAt (67 mg, 0.48 mmol) were added, then DIPEA (62 mg, 0.48 mmol) were also added and treated at room temperature for 40 minutes. The resin was treated with 10 mL 20% piperidine/DMF for 20 minutes to remove Fmoc, repeated twice. The resin was washed with DMF to give NH2-D-Phe(2,4-diCl)-azaPro-Asn(Trt)-Thr(tBu)-Phe-A6c-Leu-Arg(Me,Pbf)-Trp(Boc)-Rink Amide MBHA resin. Ac$_2$O (61 mg, 0.6 mmol) and DIPEA (77 mg, 0.6 mmol) were added and reacted at room temperature for 30 minutes, then Ac groups were introduced, the resin was washed with DMF, DCM, methanol and methyl tert-butyl ether, and then drained to finally give Ac[D-Phe(2,4-diCl)]-azaPro-Asn(Trt)-Thr(tBu)-Phe-A6c-Leu-Arg(Me,Pbf)-Trp(Boc)-Rink Amide MBHA resin.

The dried resin was added to 10 mL of TFA/TIS/PhSMe/EDT (84/6/6/4) solution, the mixture was stirred for 40 minutes, the resin was removed by filtration, and the resin was washed with 2 mL of TFA/TIS/PhSMe/EDT (84/6/6/4)

solution. The filtrates were combined, ether (70 mL) was added to the filtrate, and the resulting mixture was centrifuged at 3000 rpm for 1 minute to remove the supernatant, and the solid was washed twice with ether and drained. The obtained precipitate was dissolved in DMF and then eluted with a linear concentration gradient (10 minutes) at a flow rate of 25 mL/minute, and eluent A/B: 65/35-55/45 using: eluent A: 0.05% TFA aqueous solution, eluent B: Acetonitrile with 0.05% TFA was applied on a preparative HPLC using Phenomenex Gemini 10µ, 110 Å column (21.2 mm×250 mm). The fractions containing the product were collected and lyophilized to give 12 mg of white solid.

Embodiment 43

Preparation of Ac-(D-2Fua)-Pro(diF)-Asn-Thr-Phe-A6c-Leu-Arg(Me)-Trp-NH$_2$ (Compound YA-201)

Similar to the synthesis method of Embodiment 30, Fmoc-Pro(diF)-OH (3 equivalents) was used instead of Fmoc-Hyp(tBu)—OH condensation, HATU/HOAt/DIPEA was used as condensation condition, DMF was used as solvent, and the mixture was reacted at room temperature for 3 hours. Fmoc-(D-2Fua)-OH (3 equivalents) was used instead of Fmoc-Tyr(tBu)—OH for condensation, HATU/HOAt/DIPEA was used as condensation condition, DMF was used as solvent, and the mixture was reacted for 3 hours at room temperature. The resin was washed and dried. The target polypeptide was cleaved from the resin according to the method of Step 2 of Embodiment 2 and deprotected. The solution for cleavage was TFA/TIS/H2O (94/3/3) solution without containing EDT, and the other operations were consistent with previous methods. The crude product YA-201 was isolated and purified by HPLC, and eluted with linear gradient (10 minutes) at a flow rate of 25 mL/minute, with eluent A/B: 68/32-58/42, using: eluent A: 0.05% TFA aqueous solution, eluent B: 0.05% TFA acetonitrile solution, applying on a HPLC using Xtimate C18, 10 µm, 120 column (20×250 mm). The fractions containing the product were collected and lyophilized to give 11.6 mg of white solid.

Embodiment 44

Preparation of Ac-(D-Tyr)-Hyp-Asn-Thr-{(S)-2-(1-amino-2-phenylethyl)-1H-imidazole-5-carboxylic acid}-Leu-Arg(Me)-Trp-NH$_2$ (Compound YA-208)

Step 1: 0.4 g of commercially available Rink Amide MBHA resin (0.5 mmol/g) was swollen in DMF, and the resin was treated with 8 ml of 20% piperidine/DMF for 20 minutes to remove Fmoc, repeated twice. The obtained resin was washed with DMF, 10 mL DMF solution of Fmoc-Tro(Boc)-OH (320 mg, 0.6 mmol), HBTU (227 mg, 0.6 mmol) and HOBt (81 mg, 0.6 mmol) were added, then DIPEA (155 mg, 1.2 mmol) was added and treated at room temperature for 40 minutes. The resin was treated with 8 ml of 20% piperidine/DMF for 20 minutes to remove Fmoc, repeated twice. The resin was washed with DMF, 10 mL DMF solution of the second amino acid Fmoc-Arg (Me, PBF)—OH (180 mg, 0.3 mmol), HATU (113 mg, 0.3 mmol), HOBt (27 mg, 0.2 mmol) were added, followed by adding with DIPEA (78 mg, 0.6 mmol). Fmoc-Arg(Me,Pbf)-Trp(Boc)-Rink Amide MBHA resin was obtained by treatment at room temperature for 2 hours. Leu was introduced by introducing Trp(Boc) to give Fmoc-Leu-Arg(Me,Pbf)-Trp(Boc)-Rink Amide MBHA resin. The resin was treated with 8 ml of 20% piperidine/DMF for 20 minutes to remove Fmoc, repeated twice. The resin was washed with DMF, then 10 mL DMF solution of Fmoc-(S)-2-(1-Amino-2-Phenylethyl)-1H-Imidazole-5-carboxylic acid (120 mg, 0.3 mmol), HATU (113 mg, 0.3 mmol), HOBt (27 mg, 0.2 mmol) were added, and then DIPEA (78 mg, 0.6 mmol) was added and treated at room temperature for 2 hours. The resin was treated with 8 ml of 20% piperidine/DMF for 20 minutes to remove Fmoc, and the operation was repeated twice. The resin was washed with DMF to give {(S)-2-(1-amino-2-phenylethyl)-1H-imidazole-5-carboxylic acid}-Leu-Arg(Me,Pbf)-Trp(Boc)-Rink Amide MBHA resin. Other amino acids [Fmoc-Thr(OtBu)—OH, Fmoc-Asn(Trt)-OH, Fmoc-Hyp(OtBu)—OH, Fmoc-D-Tyr(OtBu)—OH] were introduced to give Fmoc-(D-Tyr)-Hyp-Asn-Thr-{(S)-2-(1-amino-2-phenylethyl)-1H-imidazole-5-carboxylic acid}-Leu-Arg(Me)-Trp-Rink Amide resin. The resin was treated with 5 ml of 20% piperidine/DMF for 20 minutes to remove Fmoc, repeated twice. The resin was washed with DMF, then 10 mL DMF DMF, acetic acid (100 mg, 1.6 mmol), DIC (76 mg, 0.6 mmol) were sequentially added, treated at room temperature for 60 minutes, and Ac groups were introduced. The resin was washed with DMF, DCM, methanol and methyl tert-butyl ether, and then drained to finally give Ac-D-Tyr(tBu)-Hyp(tBu)-Asn(Trt)-Thr(tBu)-{(S)-2-(1-amino-2-phenylethyl)-1H-imidazole-5-carboxylic acid}-Leu-Arg(Me,Pbf)-Trp(Boc)-Rink Amide MBHA resin.

Step 2: The dried resin was added to 10 mL of TFA/TIS/EDT/H2O (94/2/2/2) solution, the mixture was stirred for 2 hours, filtered to remove the resin, and the resin was washed with 2 mL of TFA/TIS/EDT/H$_2$O (94/2/2/2) solution. The filtrates were pooled and added with ether (50 mL), the resulting mixture was centrifuged at 3000 rpm for 1 minute to remove the supernatant, and the solid was washed twice with ether and drained. The obtained precipitate was dissolved in DMF and then eluted with a linear concentration gradient (10 minutes) at a flow rate of 25 mL/minute, and eluent A/B: 76/24-66/34 using: Elution A: 0.05% TFA aqueous solution, eluent B: 0.05% TFA acetonitrile solution was applied on a preparative HPLC using Phenomenex Gemini 10 µt, 110 Å column (21.2×250 mm). The fractions containing the product were collected and lyophilized to give 40 mg of white solid.

Embodiment 45

Preparation of Ac-[D-Phe(4-F)]-Pro(diF)-Asn-Thr-Phe-A6c-Leu-Arg(Me)-Trp-NH$_2$ (Compound YA-212)

Similar to the synthesis method of Embodiment 30, Fmoc-Pro(diF)-OH (3 equivalents) was used instead of Fmoc-Hyp(tBu)—OH condensation, HATU/HOAt/DIPEA was used as condensation condition, DMF was used as solvent, and the mixture was reacted at room temperature for 3 hours. Fmoc-[D-Phe(4-F)]—OH (3 equivalents) was used instead of Fmoc-Tyr(tBu)—OH for condensation, HATU/HOAt/DIPEA was used as condensation condition, DMF was used as solvent, and the mixture was reacted for 3 hours at room temperature. The resin was washed and dried. The target polypeptide was cleaved from the resin and deprotected by the method of Step 2 of Embodiment 2. The crude product YA-212 was isolated and purified by HPLC, and eluted with linear gradient (10 minutes) at a flow rate of 25 mL/minute with eluent A/B: 66/34-56/44, using: eluent A: 0.05% TFA aqueous solution, eluent B: 0.05% TFA acetonitrile solution applying on a HPLC using Xtimate C18, 10 μm, 120 column (20×250 mm). The fractions containing the product were collected and lyophilized to give 20.2 mg of white solid.

Embodiment 46

Preparation of Ac-[D-Phe(4-F)]-Pro(diF)-Asn-Thr-Phe-Aze-Leu-Arg(Me)-Trp-NH$_2$ (Compound YA-213)

Similar to the synthesis method of Embodiment 24, Fmoc-Pro(diF)-OH (3 equivalents) was used instead of Fmoc-Hyp(tBu)—OH condensation, HATU/HOAt/DIPEA was used as condensation condition, DMF was used as solvent, and the mixture was reacted at room temperature for 3 hours. Fmoc-[D-Phe(4-F)]—OH (3 equivalents) was used instead of Fmoc-Tyr(tBu)—OH for condensation, HATU/HOAt/DIPEA was used as condensation condition, DMF was used as solvent, and the mixture was reacted for 3 hours at room temperature. The resin was washed and dried. The target polypeptide was cleaved from the resin and deprotected by the method of Step 2 of Embodiment 2. The crude product YA-213 was isolated and purified by HPLC, and eluted with a linear gradient (10 minutes) at a flow rate of 25 mL/minute with eluent A/B: 70/30-60/40 using: eluent A: 0.05% TFA aqueous solution, eluent B: 0.05% TFA acetonitrile solution applying on a preparative HPLC using Phenenex Gemini C18 10 μm, 110 column (21.2×250 mm). Fractions containing the product were collected and lyophilized to give 39.8 mg of white solid.

Embodiment 47

Preparation of Ac-[D-Phe(4-Cl)]-Hyp-Asn-Thr-Phe-azaGly-Leu-Arg(Me)-Trp-NH$_2$ (Compound YA-214)

Similar to the synthesis method of Embodiment 2, while Fmoc-[D-Phe(4-Cl)]—OH (3 equivalents) was used instead of Fmoc-Tyr(tBu)—OH for condensation, HATU/HOAt/DIPEA was used as condensation condition, DMF was used as solvent, and the mixture was reacted at room temperature for 3 hours. The resin was washed and dried. The target polypeptide was cleaved from the resin and deprotected by the method of Step 2 of Embodiment 2. The crude product YA-214 was isolated and purified by HPLC, and eluted with linear gradient (10 minutes) at a flow rate of 25 mL/minute with eluent A/B: 72/28-62/38, using: eluent A: 0.05% TFA aqueous solution, eluent B: 0.05% TFA acetonitrile solution applying on a HPLC using Phenenex Gemini C18 10 μm, 110 column (21.2×250 mm). Fractions containing the product were collected and lyophilized to give 32.1 mg of white solid.

Embodiment 48

Preparation of Ac-[D-Phe(3-Cl)]-Hyp-Asn-Thr-Phe-azaGly-Leu-Arg(Me)-Trp-NH$_2$ (Compound YA-215)

Similar to the synthesis method of Embodiment 2, while Fmoc-[D-Phe(3-Cl)]—OH (3 equivalents) was used instead of Fmoc-Tyr(tBu)—OH for condensation, HATU/HOAt/DIPEA was used as condensation condition, DMF was used as solvent, and the mixture was reacted at room temperature for 3 hours. The resin was washed and dried. The target polypeptide was cleaved from the resin and deprotected by the method of Step 2 of Embodiment 2. The crude product YA-215 was isolated and purified by HPLC, and was subjected to linear gradient elution (10 minutes), followed by linear gradient elution (10 minutes), with a flow rate of 25 mL/minute, and eluent A/B: 73/27-65/35, using: eluent A: 0.05% TFA aqueous solution, eluent B: 0.05% TFA acetonitrile solution, was applied on a HPLC using Phenenex Gemini C18 10 μm, 110 column (21.2×250 mm). Fractions containing the product were collected and lyophilized to give 28.1 mg of white solid.

Embodiment 49

Preparation of Ac-D-Tyr-Hyp-Asn-Thr-Phe-Ind-Leu-Arg(Me)-Trp-NH$_2$ (Compound YA-221)

Similar to the synthesis method of Embodiment 23, Fmoc-Idn-OH (3 equivalents) was used instead of Fmoc-ACPO-OH condensation, HATU/HOAt/DIPEA was used as condensation condition, DMF was used as solvent, and the mixture was reacted at room temperature for 3 hours. The resin was washed and dried. The target polypeptide was cleaved from the resin and deprotected by the method of Step 2 of Embodiment 2. The crude product YA-221 was isolated and purified by HPLC, and eluted with linear gradient (10 minutes) at a flow rate of 25 mL/minute with eluent A/B: 70/30-60/40, using: eluent A: 0.05% TFA aqueous solution, eluent B: 0.05% TFA acetonitrile solution applying on a HPLC using Phenenex Gemini C18 10 μm, 110 column (21.2×250 mm). Fractions containing the product were collected and lyophilized to give 16.5 mg of white solid.

Embodiment 50

Preparation of Ac-D-Tyr-(S-Pip)-Asn-Thr-Phe-A6c-Leu-Arg(Me)-Trp-NH$_2$ (Compound YA-228)

Similar to the synthesis method of Embodiment 30, Fmoc-(S-Pip)-OH (3 equivalents) was used instead of Fmoc-Hyp(tBu)—OH for condensation, HATU/HOAt/DIPEA was used as condensation condition, DMF was used as solvent, and the mixture was reacted at room temperature for 3 hours. The resin was washed and dried. The target polypeptide was cleaved from the resin and deprotected by the method of Step 2 of Embodiment 2. The crude product YA-228 was isolated and purified by HPLC, and eluted with a linear gradient (10 minutes) at a flow rate of 25 mL/minute with eluent A/B: 74/26-64/36, using: eluent A: 0.05% TFA aqueous solution, eluent B: 0.05% TFA acetonitrile solution, Sunfire C18, 10 μm, 120 column (19×250 mm) applying on a preparative HPLC. The fractions containing the product were collected and lyophilized to give 32.2 mg of white solid.

Embodiment 51

Preparation of Ac-D-Tyr-Oic-Asn-Thr-Phe-azaGly-Leu-Arg(Me)-Trp-NH$_2$ (Compound YA-230)

Similar to the synthesis method of Embodiment 2, while Fmoc-Oic-OH (3 equivalents) was used instead of Fmoc-Hyp(tBu)—OH condensation, HATU/HOAt/DIPEA was used as condensation condition, DMF was used as solvent, and the mixture was reacted at room temperature for 3 hours. The resin was washed and dried. The target polypeptide was cleaved from the resin and deprotected by the method of Step 2 of Embodiment 2. The crude product YA-230 was isolated and purified by HPLC, and eluted with a linear gradient (10 minutes) at a flow rate of 25 mL/minute with eluent A/B: 75/25-67/33, using: eluent A: 0.05% TFA aqueous solution, eluent B: 0.05% TFA acetonitrile solution, Sunfire C18, 10 μm, 120 column (19×250 mm) applying on a preparative HPLC. The fractions containing the product were collected and lyophilized to give 20.1 mg of white solid.

Embodiment 52

Preparation of Ac-D-Tic-Hyp-Asn-Thr-Phe-azaGly-Leu-Arg(Me)-Trp-NH$_2$ (Compound YA-236)

Similar to the synthesis method of Embodiment 2, while Fmoc-D-Tic-OH (3 equivalents) was used instead of Fmoc-Tyr(tBu)—OH condensation, HATU/HOAt/DIPEA was used as condensation condition, DMF was used as solvent, and the mixture was reacted at room temperature for 3 hours. The resin was washed and dried. The target polypeptide was cleaved from the resin and deprotected by the method of Step 2 of Embodiment 2. The crude product YA-236 was isolated and purified by HPLC, and eluted with a linear gradient (10 minutes) at a flow rate of 25 mL/minute. Eluent A/B: 75/25-65/35, using: eluent A: 0.05% TFA aqueous solution, eluent B: 0.05% TFA acetonitrile solution, Sunfire C18, 10 μm, 120 column (19×250 mm) was applied on a preparative HPLC. The fractions containing the product were collected and lyophilized to give 16.0 mg of white solid.

Embodiment 52-1

Preparation of a Ac-[D-Phe(2,4-diCl)]—(S-Pip)-Asn-Thr-azaPhe-Gly-Leu-Arg(Me)-Trp-NH$_2$ (Compound YA-241)

0.26 g of commercially available Rink Amide MBHA resin (0.5 mmol/g) was swollen in DMF, and the resin was treated with 5 ml of 20% piperidine/DMF for 20 minutes to remove Fmoc, repeated twice. The obtained resin was washed with DMF, 10 mL DMF solution of Fmoc-Trp (Boc)-OH (205 mg, 0.39 mmol), HBTU (148 mg, 0.39 mmol), HOBt (53 mg, 0.39 mmol) were added, and then DIPEA (100 mg, 0.78 mmol) was added. Treatment was carried out at room temperature for 40 minutes, and the resin was washed with DMF to give Fmoc-Trp(Boc)-Rink Amide MBHA resin. The resin was treated with 5 ml of 20% piperidine/DMF for 20 minutes to remove Fmoc, repeated twice. The obtained resin was washed with DMF, and 10 mL DMF solution of Fmoc-Arg (Me, PBF)—OH (100 mg, 0.15 mmol), DIC (57 mg, 0.45 mmol) and HOBt (60 mg, 0.45 mmol) were added to react overnight at room temperature. The resin was treated with 20 mL 20% piperidine/DMF for 20 minutes to remove Fmoc, and the operation was repeated twice. The resin was washed with DMF to give NH2-Arg (Me,Pbf)-Trp(Boc)-Rink Amide MBHA resin. Leu was introduced in a similar manner. The resin was washed with DMF, 5 mL DMF solution of Fmoc-Thr (TBU)-Azaphe-Gly-OH (94 mg, 0.16 mmol), HATU (61 mg, 0.16 mmol) and HOAt (22 mg, 0.16 mmol) were added, then DIPEA (41 mg, 0.32 mmol) was added and treated at room temperature for 40 minutes. The resin was treated with 8 ml of 20% piperidine/DMF for 20 minutes to remove Fmoc, and the operation was repeated twice. The resin was washed with DMF to give NH2-Thr(tBu)-azaPhe-Gly-Leu-Arg(Me, Pbf)-Trp(Boc)-MBHA resin. Asn, S-Pip and D-Phe(2,4-diCl) were introduced in a Trp-like manner, the resin was washed with DMF, and a 5 mL DMF solution of AcOH (47 mg, 0.78 mmol), DIC (98 mg, 0.78 mmol) and HOBt (108 mg, 0.78 mmol) were added to react overnight at room temperature to introduce AC groups. The resin was washed with DMF, DCM, methanol and methyl tert-butyl ether, and then drained to finally give Ac[D-Phe(2,4-diCl)]—(S-Pip)-Asn(Trt)-Thr(tBu)-azaPhe-Gly-Leu-Arg(Me, Pbf)-Trp (Boc)-Rink Amide MBHA resin.

The dried resin was added to 10 mL of TFA/TIS/EDT/H$_2$O (94/2/2/2) solution, the mixture was stirred for 2 hours, the resin was removed by filtration, and the resin was washed with 2 mL of TFA/TIS/EDT/H$_2$O (94/2/2/2) solution. The filtrates were pooled and added with ether (70 mL), the resulting mixture were centrifuged at 3000 rpm for 1 minute to remove the supernatant, and the solid were washed twice with ether and drained. The obtained precipitate were dissolved in DMF and then eluted with a linear concentration gradient (10 minutes) at a flow rate of 25 mL/minute, and eluent AB: 67/33-57/43 Use: eluent A: 0.05% TFA aqueous solution, eluent B: 0.05% TFA acetonitrile solution, were applied on preparative HPLC using Phenomenex Gemini 10μ, 110 Å column (21.2×250 mm). The fraction containing the product were collected and lyophilized to give 45 mg of white solid.

Embodiment 52-2

Preparation of Ac-[D-Phe(2,4-diCl)]—(S-Pip)-Asn-Thr-Phe-azaGly-Leu-Phe(4-Pyrazol)-Trp-NH$_2$ (Compound YA-242)

0.26 g of commercially available Rink Amide MBHA resin (0.5 mmol/g) were swollen in DMF, and the resin were treated with 5 ml of 20% piperidine/DMF for 20 minutes to remove Fmoc, repeated twice. The obtained resin was washed with DMF, 10 mL DMF solution of Fmoc-TRP (Boc)-OH (205 mg, 0.39 mmol), HBTU (148 mg, 0.39 mmol), HOBt (53 mg, 0.39 mmol) were added, then DIPEA (100 mg, 0.78 mmol) was added, the resin was treated at room temperature for 40 minutes, and the resin was washed with DMF to give Fmoc-Trp(Boc)-Rink Amide MBHA resin. The resin was treated with 5 ml of 20% piperidine/DMF for 20 minutes to remove Fmoc, repeated twice. The obtained resin was washed with DMF, and a 5 mL DMF solution of Fmoc-Phe(4-Pyrazol)-OH (54 mg, 0.12 mmol), DIC (30 mg, 0.24 mmol) and HOBt (33 mg, 0.24 mmol) was added to react overnight at room temperature. The resin was treated with 8 ml of 20% piperidine/DMF for 20 minutes to remove Fmoc, and the operation was repeated twice. The resin was washed with DMF to give NH2-Phe (4-Pyrazol)-Trp (Boc)-Rink Amide MBHA resin. Fmoc-Phe-azaGly-Leu-OH (67 mg, 0.3 mmol), DIC (76 mg, 0.6 mmol) and HOBt (83 mg, 0.6 mmol) 5 mL DMF solution were added to react overnight at room temperature. The resin was treated with 8 ml of 20% piperidine/DMF for 20 minutes to remove Fmoc, repeated twice. The resin was washed with DMF to give NH2-Phe-azaGly-Leu-Phe(4-Pyrazol)-Trp(Boc)-Rink Amide MBHA resin. Thr(tBu), Asn(Trt), S-Pip and D-Phe (2,4-diCl) were introduced in a Trp-like manner, the resin was washed with DMF, and a 5 mL DMF solution of AcOH (47 mg, 0.78 mmol), DIC (98 mg, 0.78 mmol) and HOBt (108 mg, 0.78 mmol) were added to react overnight at room temperature to introduce Ac groups. The resin was washed with DMF, DCM, methanol and methyl tert-butyl ether, and then drained to finally give Ac[D-Phe(2,4-diCl)]—(S-Pip)-Asn(Trt)-Thr(tBu)-Phe-azaGly-Leu-Phe(4-Pyrazol)-Trp (Boc)-Rink Amide MBHA resin.

The dried resin was added to 10 mL of TFA/TIS/EDT/H$_2$O (94/2/2/2) solution, the mixture was stirred for 2 hours, the resin was removed by filtration, and the resin was washed with 2 mL of TFA/TIS/EDT/H$_2$O (94/2/2/2) solution. The filtrates were pooled and added with ether (70 mL), the resulting mixture was centrifuged at 3000 rpm for 1 minute to remove the supernatant, and the solid was washed twice with ether and drained. The obtained precipitate was dissolved in DMF and then eluted with a linear concentration gradient (10 minutes) at a flow rate of 45 mL/minute, and eluent AB: 50/50-43/57 using: eluent A: 0.05% TFA aqueous solution, eluent B: 0.05% TFA acetonitrile solution was applied on a preparative HPLC using Phenomenex Gemini 10μ, 110 Å column (30 mm×250 mm). The fractions containing the product were collected and lyophilized to give 80 mg of white solid.

Embodiment 53

Preparation of Ac-D-Tyr-A6c-Asn-Thr-Phe-A6c-Leu-Arg(Me)-Trp-NH$_2$ (Compound YA-243)

Similar to the synthesis method of Embodiment 30, Fmoc-A6c-OH (3 equivalents) was used instead of Fmoc-Hyp(tBu)—OH condensation, HATU/HOAt/DIPEA was used as condensation condition, DMF was used as solvent, and the mixture was reacted at room temperature for 3 hours. The resin was washed and dried. The target polypeptide was cleaved from the resin and deprotected by the method of Step 2 of Embodiment 2. The crude product YA-243 was subjected to HPLC separation and purification, linear gradient elution (10 minutes), flow rate of 25 mL/minute, and eluent A/B: 67/33-57/43, using: eluent A: 0.05% TFA aqueous solution, eluent B: 0.05% TFA acetonitrile solution, was applied on a HPLC using Phenomenex Gemini C18, 10 110 column (21.2×250 mm). The fractions containing the product were collected and lyophilized to give 30.7 mg of white solid.

Embodiment 53-1

Preparation of Ac-(D-Tyr)-Hyp-Asn-Thr-Phe-azaN-MeGly-Leu-Arg(Me)-Trp-NH$_2$ (Compound YA-247)

0.26 g of commercially available Rink Amide MBHA resin (0.5 mmol/g) was swollen in DMF, and the resin was treated with 5 ml of 20% piperidine/DMF for 20 minutes to remove Fmoc, repeated twice. The obtained resin was washed with DMF, 10 mL DMF solution of Fmoc-TRP (Boc)-OH (205 mg, 0.39 mmol), HBTU (148 mg, 0.39 mmol), HOBt (53 mg, 0.39 mmol) was added, then DIPEA (100 mg, 0.78 mmol) was added, the resin was treated at room temperature for 40 minutes, and the resin was washed with DMF to give Fmoc-Trp(Boc)-Rink Amide MBHA resin. The resin was treated with 5 ml of 20% piperidine/DMF for 20 minutes to remove Fmoc, repeated twice. The obtained resin was washed with DMF, and 10 mL DMF solution of Fmoc-Arg (Me, PBF)—OH (100 mg, 0.15 mmol), DIC (57 mg, 0.45 mmol) and HOBt (60 mg, 0.45 mmol) were added to react overnight at room temperature. The resin was treated with 20 mL 20% piperidine/DMF for 20 minutes to remove Fmoc, and the operation was repeated twice. The resin was washed with DMF to give Arg (Me, Pbf)-Trp (Boc)-Rinkamide MBHA resin. The obtained resin was added with 15 mL DMF solution of Fmoc-Phe-azaN-MeGly-Leu-OH (110 mg, 0.15 mmol), DIC (57 mg, 0.45 mmol) and HOBt (60 mg, 0.45 mmol), and reacted overnight at room temperature. The resin was treated with 20 mL 20% piperidine/DMF for 20 minutes to remove Fmoc, repeated twice. The resin was washed with DMF to give NH2-Phe-azaNMeGly-Leu-Arg(Me,Pbf)-Trp(Boc)-Rink Amide MBHA resin. Other amino acids [Fmoc-Thr(OtBu)—OH, Fmoc-Asn(Trt)-OH, Fmoc-Hyp(OtBu)—OH, Fmoc-D-Tyr (OtBu)—OH] were introduced in a similar manner to give NH2-D-Tyr(tBu)-Hyp(tBu)-Asn (Trt)-Thr(tBu)-Phe-azaN-MeGly-Leu-Arg(Me, Pbf)-Trp(Boc)-Rink Amide MBHA resin. Then 10 mL DMF DMF, acetic acid (25 mg, 0.4 mmol), DIC (49 mg, 0.39 mmol) were added, treated at room temperature for 40 minutes, and Ac groups were introduced. The resin was washed with DMF, DCM, methanol and methyl tert-butyl ether, and then drained to give Ac-D-Tyr(tBu)-Hyp(tBu)-Asn(Trt)-Thr(tBu)-Phe-azaN-MeGly-Leu-Arg(Me,Pbf)-Trp(Boc)-Rink Amide MBHA resin.

The dried resin was added to 10 mL of TFA/TIS/EDT/H$_2$O (94/2/2/2) solution, the mixture was stirred for 2 hours, the resin was removed by filtration, and the resin was washed with 2 mL of TFA/TIS/EDT/H$_2$O (94/2/2/2) solution. The filtrates were pooled and added with ether (70 mL), the resulting mixture was centrifuged at 3000 rpm for 1 minute to remove the supernatant, and the solid was washed twice with ether and drained. The obtained precipitate was dissolved in DMF and then subjected to linear gradient elution (10 minutes) at a flow rate of 25 mL/minute, and eluent A/B: 79/21-69/31, using: eluent A: 0.05% TFA aqueous solution, eluent B: 0.05% TFA acetonitrile solution was applied on a preparative HPLC using Phenomenex Gemini 10μ, 110 Å column (21.2×250 mm). The fractions containing the product were collected and lyophilized to give 11.5 mg of white solid.

Embodiment 54

Preparation of Ac-[D-Phe(2,4-diCl)]-Pro(diF)-Asn-Thr-Phe-A6c-Leu-Arg(Me)-Trp-NH$_2$ (Compound YA-248)

Similar to the synthesis method of Embodiment 30, Fmoc-Pro(diF)-OH (3 equivalents) was used instead of Fmoc-Hyp(tBu)—OH condensation, HATU/HOAt/DIPEA was used as condensation condition, DMF was used as solvent, and the mixture was reacted at room temperature for 3 hours. Fmoc-[D-Phe(2,4-diCl)]—OH (3 equivalents) was used instead of Fmoc-Tyr(tBu)—OH for condensation, HATU/HOAt/DIPEA was used as condensation condition, DMF was used as solvent, and the mixture was reacted for 3 hours at room temperature. The resin was washed and dried. The target polypeptide was cleaved from the resin and deprotected by the method of Step 2 of Embodiment 2. The crude product YA-248 was isolated and purified by HPLC, and eluted with a linear gradient (10 minutes) at a flow rate of 25 mL/minute. Eluent A/B: 64/36-56/44 using: Elution A: 0.05% TFA aqueous solution, eluent B: 0.05% TFA Acetonitrile solution, was applied on a preparative HPLC using Sunfire C18 10 μm, 120 column (19×250 mm). Fractions containing the product were collected and lyophilized to give 25.2 mg of white solid.

Embodiment 55

Preparation of Ac-D-Tyr-Pro(diF)-Asn-Thr-Phe-A6c-Leu-Arg(Me)-Trp-NH$_2$ (Compound YA-251)

Similar to the synthesis method of Embodiment 30, Fmoc-Pro(diF)-OH (3 equivalents) was used instead of Fmoc-Hyp(tBu)—OH condensation, HATU/HOAt/DIPEA was used as condensation conditions, DMF was used as solvent, and the mixture was reacted at room temperature for 3 hours. The resin was washed and dried. The target polypeptide was cleaved from the resin and deprotected by the method of Step 2 of Embodiment 2. The crude product YA-251 was isolated and purified by HPLC, and eluted with linear gradient (10 minutes) at a flow rate of 25 mL/minute. Eluent A/B: 66/34-63/37 using: eluent A: 0.05% TFA aqueous solution, eluent B: 0.05% TFA acetonitrile solution was applied on a preparative HPLC using Boston C18 10 μm, 120 column (21.2×250 mm). Fractions containing the product were collected and lyophilized to give 28.3 mg of white solid.

Embodiment 56

Preparation of Ac-[D-Phe(2,4-DiCl)]-A6c-Asn-Thr-Phe-azaGly-Leu-Arg(Me)-Trp-NH$_2$ (Compound YA-260)

Similar to the synthesis method of Embodiment 2, while Fmoc-A6c-OH (3 equivalents) was used instead of Fmoc-Hyp(tBu)—OH condensation, HATU/HOAt/DIPEA was used as condensation condition, DMF was used as solvent, and the mixture was reacted at room temperature for 3 hours. Fmoc-[D-Phe(2,4-DiCl)]—OH (3 equivalents) was used to replace Fmoc-Tyr(tBu)—OH for condensation, HATU/HOAt/DIPEA was used as condensation condition, DMF was used as solvent, and the mixture was reacted for 3 hours at room temperature. The resin was washed and dried. The target polypeptide was cleaved from the resin and deprotected by the method of Step 2 of Embodiment 2. The crude product YA-260 was isolated and purified by HPLC. Linear gradient elution (10 minutes) was performed at a flow rate of 25 mL/minute, and eluent A/B: 60/40-56/44 using: eluent A: 0.05% TFA aqueous solution, eluent B: 0.05% TFA acetonitrile solution was applied on a preparative HPLC using Boston C18 10 μm, 120 column (21.2×250 mm). Fractions containing the product were collected and lyophilized to give 12.8 mg of white solid.

Embodiment 57

Preparation of Ac-(D-2Fua)-A6c-Asn-Thr-Phe-azaGly-Leu-Arg(Me)-Trp-NH$_2$ (Compound YA-271)

Similar to the synthesis method of Embodiment 2, while Fmoc-A6c-OH (3 equivalents) was used instead of Fmoc-Hyp(tBu)—OH condensation, HATU/HOAt/DIPEA was used as condensation condition, DMF was used as solvent, and the mixture was reacted at room temperature for 3 hours. Fmoc-(D-2Fua)-OH (3 equivalents) was used to replace Fmoc-Tyr(tBu)—OH for condensation, HATU/HOAt/DIPEA was used as condensation condition, DMF was used as solvent, and the mixture was reacted for 3 hours at room temperature. The resin was washed and dried. The target polypeptide was cleaved from the resin and deprotected by the method of Step 2 of Embodiment 2. The crude product YA-271 was isolated and purified by HPLC. Linear gradient elution (10 minutes) was performed at a flow rate of 25 mL/minute, and eluent A/B: 72/28-62/38 using: eluent A: 0.05% TFA aqueous solution, eluent B: 0.05% TFA acetonitrile solution was applied on a preparative HPLC using Sunfire C18 10 um, 120 column (19×250 mm). Fractions containing the product were collected and lyophilized to give 19.4 mg of white solid.

Embodiment 58

Preparation of Ac-[D-Phe(4-F)]-Hyp-Asn-Thr-Phe-A6c-Leu-Arg(Me)-Trp-NH$_2$ (Compound YA-195)

Similar to the synthesis method of Embodiment 30, Fmoc-[D-Phe(4-F)]—OH (3 equivalents) was used instead of Fmoc-Tyr(tBu)—OH condensation, HATU/HOAt/DIPEA was used as condensation condition, DMF was used as solvent, and the mixture was reacted at room temperature for 3 hours. The resin was washed and dried. The target polypeptide was cleaved from the resin and deprotected by the method of Step 2 of Embodiment 2. The crude product YA-195 was isolated and purified by HPLC, and eluted with a linear gradient (10 minutes) at a flow rate of 25 mL/minute. Eluent A/B: 68/32-58/42, using: eluent A: 0.05% TFA aqueous solution, eluent B: 0.05% TFA acetonitrile solution, was applied on a HPLC using Xtimate C18, 10 μm, 120 column (20×250 mm). The fractions containing the product were collected and lyophilized to give 12.6 mg of white solid.

Embodiment 59

Preparation of Ac-PEG4-(D-Tyr)-Hyp-Asn-Thr-Phe-azaGly-Leu-Arg(Me)-Trp-NH$_2$ (Compound YA-150)

Step 1: 0.26 g of commercially available Rink Amide MBHA resin (0.5 mmol/g) was swollen in DMF to give NH2-D-Tyr(tBu)-Hyp(tBu)-Asn(Trt)-Thr(tBu)-Phe-azaGly-Leu-Arg(Me,Pbf)-Trp(Boc)-Rink Amide MBHA resin according to Embodiment 2. The resin was washed with DMF, 10 mL DMF solution of Fmoc-PEG4-CH$_2$CH$_2$—COOH (94 mg, 0.19 mmol), HBTU (227 mg, 0.6 mmol), HOBt (81 mg, 0.6 mmol) were added, then DIPEA (209 μL, 1.2 mmol) was added, treated at room temperature for 40 minutes, and added with PEG 4. The resin was treated with 5 ml of 20% piperidine/DMF for 20 minutes to remove Fmoc, repeated twice. The resin was washed with DMF, 5 mL DMF solution of AcOH (47 mg, 0.78 mmol), DIC (98 mg, 0.78 mmol) and HOBt (108 mg, 0.78 mmol) were added, and the reaction was carried out overnight at room temperature to introduce Ac groups. The resin was washed with DMF, DCM, methanol and methyl tert-butyl ether, and then drained to give Ac-PEG4-D-Tyr(tBu)-Hyp(tBu)-Asn(Trt)-Thr(tBu)-Phe-azaGly-Leu-Arg(Me, Pbf)-Trp(Boc)-Rink Amide MBHA resin.

Step 2: The dried resin was added to 10 mL of TFA/TIS/H$_2$O (95/2.5/2.5) solution, the mixture was stirred for 2 hours, the resin was removed by filtration, and the resin was washed with 2 mL of TFA/TIS/H$_2$O (95/2.5/2.5) solution. The filtrates were combined, and ice methyl tert-butyl ether (70 mL) was added to the filtrate. The resulting mixture was centrifuged at 3000 rpm for 3 minutes, and the solid was washed twice with ice ethyl ether and drained. The obtained precipitate was dissolved in DMF and then eluted with a linear concentration gradient (10 minutes) at a flow rate of 25 mL/minute. Eluent A/B: 80/20-70/30 use: eluent A: 0.05% TFA aqueous solution, eluent B: 0.05% TFA acetonitrile solution, was applied on a preparative HPLC, Sunfire 10μ, 120 Å column (19 mm×250 mm). The fractions containing the product were collected and lyophilized to give 12.0 mg of white solid.

Embodiment 60

Preparation of Ac-PEG8-(D-Tyr)-Hyp-Asn-Thr-Phe-azaGly-Leu-Arg (Me)-Trp-NH$_2$ (Compound YA-151)

Similar to the synthesis method of Embodiment 59, Fmoc-PEG8-CH$_2$CH$_2$—COOH (1.5 equivalent) was used instead of Fmoc-PEG8-CH$_2$CH$_2$—COOH condensation, HBTU/HOBt/DIPEA was used as condensation condition, DMF was used as solvent, and the mixture was reacted at room temperature for 40 minutes. The resin was washed and dried. The target polypeptide was cleaved from the resin and deprotected by the method of step 2 of Embodiment 59. The crude product YA-151 was isolated and purified by HPLC, and eluted with linear gradient (10 minutes) at a flow rate of 25 mL/minute. Eluent A/B: 80/20-70/30 use: eluent A: 0.05% TFA aqueous solution, eluent B: 0.05% TFA acetonitrile solution was applied on a preparative HPLC using Boston C18 10 µm, 120 column (21.2×250 mm). Fractions containing the product were collected and lyophilized to give 34.5 mg of white solid.

Embodiment 61

Preparation of Palm-PEG8-Gly-Gly-(D-Tyr)-Hyp-Asn-Thr-Phe-azaGly-Leu-Arg(Me)-Trp-NH$_2$ (Compound YA-156)

Step 1: 0.26 g of commercially available Rink Amide MBHA resin (0.5 mmol/g) was swelled in DMF to give NH2-Gly-Gly-D-Tyr(tBu)-Hyp(tBu)-Asn(Trt)-Thr(tBu)-Phe-azaGly-Leu-Arg(Me,Pbf)-Trp(Boc)-Rink Amide resin according to Embodiment 2. The resin was washed with DMF, 10 mL DMF solution of Fmoc-PEG8-CH$_2$CH$_2$—COOH (126 mg, 0.19 mmol), HBTU (227 mg, 0.6 mmol), HOBt (81 mg, 0.6 mmol) were added, then DIPEA (209 µL, 1.2 mmol) was added, and treated at room temperature for 40 minutes, and added with PEG 8. The resin was treated with 5 ml of 20% piperidine/DMF for 20 minutes to remove Fmoc, repeated twice. The obtained resin was washed with DMF, 10 mL DMF solution of Palm Acid (61.5 mg, 0.24 mmol), HBTU (227 mg, 0.6 mmol), HOBt (81 mg, 0.6 mmol) were added, and then DIPEA (209 µL, 1.2 mmol) was added and treated at room temperature for 40 minutes. Palm-PEG8-Gly-Gly-D-Tyr-Asn-Trp-Asn-Ser-Tic-Gly-Leu-Arg-Phe-MBHA was obtained. The resin was washed with DMF, DCM, methanol and methyl tert-butyl ether, and then drained to give Ac-PEG4-D-Tyr(tBu)-Hyp(tBu)-Asn(Trt)-Thr(tBu)-Phe-azaGly-Leu-Arg(Me,Pbf)-Trp(Boc)-Rinkamide MBHA resin.

Step 2: The dried resin was added to 10 mL of TFA/TIS/H$_2$O (95/2.5/2.5) solution, the mixture was stirred for 2 hours, the resin was removed by filtration, and the resin was washed with 2 mL of TFA/TIS/H$_2$O (95/2.5/2.5) solution. The filtrates were combined, and ice methyl tert-butyl ether (70 mL) was added to the filtrate. The resulting mixture was centrifuged at 3000 rpm for 3 minutes, and the solid was washed twice with ice ethyl ether and drained. The obtained precipitate was dissolved in DMF and then eluted with a linear concentration gradient (10 minutes) at a flow rate of 25 mL/minute, and eluent A/B: 47/53-37/63, using: eluent A: 0.05% TFA aqueous solution, eluent B: 0.05% TFA acetonitrile solution, was applied on a HPLC using Xtimate C18, 10 µm, 120 column (20×250 mm). The fractions containing the product were collected and lyophilized to give 20.4 mg of white solid.

Embodiment 62

Preparation of Ac-Lys(Palm-PEG8)-Gly-Gly-(D-Tyr)-Hyp-Asn-Thr-Phe-azaGly-Leu-Arg(Me)-Trp-NH$_2$ (Compound YA-157)

Step 1: 0.26 g (0.5 mmol/g) of commercially available Rink Amide MBHA resin was swollen in DMF, and the resin was treated with 5 ml of 20% piperidine/DMF for 20 minutes to remove Fmoc, repeated twice. The obtained resin was washed with DMF, 10 mL DMF solution of Fmoc-Trp (Boc)-OH (205 mg, 0.39 mmol), HBTU (148 mg, 0.39 mmol), HOBt (53 mg, 0.39 mmol) were added, then DIPEA (100 mg, 0.78 mmol) was added, treated at room temperature for 40 minutes, and TRP (Boc) was introduced thereto to give Fmoc-Trp(Boc)-MBHA resin. The resin was treated with 5 ml of 20% piperidine/DMF for 20 minutes to remove Fmoc, repeated twice. The obtained resin was washed with Fmoc, and 10 mL DMF solution of Fmoc-Arg (Me, Pbf)-OH (100 mg, 0.15 mmol), DIC (57 mg, 0.45 mmol) and HOBt (60 mg, 0.45 mmol) was added to react overnight at room temperature. The resin was treated with 20 mL 20% piperidine/DMF for 20 minutes to remove Fmoc, repeated twice to give Arg(Me,Pbf)-Trp(Boc)-MBHA resin. The obtained resin was washed with DMF, and 15 mL DMF solution of Fmoc-phe-azaGly-leu-oh (104 mg, 0.15 mmol), DIC (57 mg, 0.45 mmol) and HOBt (60 mg, 0.45 mmol) was added to react overnight at room temperature. The resin was treated with 20 mL 20% piperidine/DMF for 20 minutes to remove Fmoc, repeated twice. Phe-azaGly-Leu-Arg (Me, Pbf)-Trp (Boc)-MBHA resin was obtained. Other amino acids (Fmoc-Thr(OtBu)—OH, Fmoc-Asn(Trt)-OH, Fmoc-Hyp(OtBu)—OH, Fmoc-D-Tyr(OtBu)—OH), Fmoc-Gly-OH, Fmoc-GLy-OH, Ac-Lys(Fmoc)-OH) was introduced to give Ac-Lys-Gly-Gly-(D-Tyr)-Hyp-Asn-Thr-Phe-azaGly-Leu-Arg(Me)-Trp-MBHA resin. Then 10 mL DMF solution of Fmoc-PEG8-CH$_2$CH$_2$—COOH (172 mg, 0.26 mmol), HBTU (148 mg, 0.39 mmol), HOBt (53 mg, 0.39 mmol) were added, followed by DIPEA (100 mg, 0.78 mmol), treated at room temperature for 40 minutes, and PEG 8 was introduced thereto. The resin was treated with 5 ml of 20% piperidine/DMF for 20 minutes to remove Fmoc, repeated twice. The obtained resin was washed with DMF, 10 mL DMF solution of Palm Acid (103 mg, 0.4 mmol), HBTU (227 mg, 0.6 mmol) and HOBt (81 mg, 0.6 mmol) were added, then DIPEA (155 mg, 1.2 mmol) was added and treated at room temperature for 40 minutes. Ac-Lys(Palm-PEG8)-Gly-Gly-(D-Tyr)-Hyp-Asn-Thr-Phe-azaGly-Leu-Arg(Me)-Trp-MBHA resin was obtained.

The resin was washed with DCM, methanol and methyl tert-butyl ether and then drained to give 400 mg of resin. The dried resin was added to 10 mL of TFA/TIS/EDT/H$_2$O (94/2/2/2) solution, followed by shaking for 2 hours, filtering to remove the resin, and washing the resin with 2 mL of TFA/TIS/EDT/H$_2$O (94/2/2/2) solution. The filtrates were combined, diethyl ether (70 mL) was added to the filtrate, and the resulting precipitate was centrifuged to remove the supernatant. The obtained precipitate was dissolved in DMF, and on a preparative HPLC using Phenomenex Gemini 10µ, 110 Å column (21.2×250 mm) was used. The fractions containing the product were collected and lyophilized to give 31 mg of white solid.

Step 2: The dried resin was added to 10 mL of TFA/TIS/H$_2$O (95/2.5/2.5) solution, the mixture was stirred for 2 hours, the resin was removed by filtration, and the resin was washed with 2 mL of TFA/TIS/H$_2$O (95/2.5/2.5) solution. The filtrates were combined, and ice methyl tert-butyl ether (70 mL) was added to the filtrate. The resulting mixture was centrifuged at 3000 rpm for 3 minutes, and the solid was washed twice with ice ethyl ether and drained. The obtained precipitate was dissolved in DMF and then eluted with a linear concentration gradient (10 minutes) at a flow rate of 25 mL/minute, and eluent A/B: 47/53-37/63, using: eluent A: 0.05% TFA aqueous solution, eluent B: 0.05% TFA acetonitrile solution, was applied on a HPLC using Xtimate C18, 10 μm, 120 column (20×250 mm). The fractions containing the product were collected and lyophilized to give 20.4 mg of white solid.

Embodiment 63

Preparation of Palm-PEG8-Gly-Gly-Tyr-Asn-Trp-Asn-Ser-Phe-Gly-Leu-Arg-Phe-NH$_2$ (Compound YA-158)

0.26 g of commercially available Rink Amide MBHA resin (0.5 mmol/g) was swollen in DMF, and NH$_2$-D-Tyr(tBu)-Asn(Trt)-Trp(Boc)-Asn(Trt)-Thr(tBu)-Phe-Gly-Leu-Arg-Phe-Rink Amide MBHA resin was obtained according to the method of step 1 of Embodiment 1. Gly, Gly, PEG8 and Palm were introduced according to the method of Step 1 of Embodiment 61 to give Palm-PEG8-D-Tyr(tBu)-Asn(Trt)-Trp(Boc)-Asn(Trt)-Thr(tBu)-Phe-Gly-Leu-Arg-Phe-Rink Amide MBHA resin. The resin was washed and dried. The target polypeptide was cleaved from the resin and deprotected by the method of Step 61 of Embodiment 2. The crude product YA-158 was isolated and purified by HPLC, and eluted with linear gradient (10 minutes) at a flow rate of 25 mL/minute. Eluent A/B: 48/52-38/62, using: eluent A: 0.05% TFA aqueous solution, eluent B: 0.05% TFA acetonitrile solution, was applied on a HPLC using Xtimate C18, 10 μm, 120 column (20×250 mm). The fractions containing the product were collected and lyophilized to give 10.9 mg of white solid.

Embodiment 65

Preparation of Palm-PEG8-Gly-Gly-D-3Fua-Pro(diF)-Asn-Thr-Phe-A6c-Leu-Arg(Me)-Trp-NH$_2$ (Compound YA-220)

NH$_2$-3Fua-Pro(diF)-Asn(Trt)-Thr(tBu)-Phe-A6c-Leu-Arg(Me,Pbf)-Trp(Boc)-Rink Amide MBHA resin was obtained according to the method of Embodiment 43. Gly, Gly, PEG8 and Palm were introduced respectively according to the method of Step 1 of Embodiment 61 to give Palm-PEG8-Gly-Gly-3Fua-Pro(diF)-Asn(Trt)-Thr(tBu)-Phe-A6c-Leu-Arg(Me,Pbf)-Trp(Boc)-Rink Amide MBHA resin. The resin was washed and dried. The target polypeptide was cleaved from the resin and deprotected by the method of Step 61 of Embodiment 2. The crude product YA-220 was isolated and purified by HPLC, and eluted with a linear gradient (10 minutes) at a flow rate of 25 mL/minute. Eluent A/B: 45/55-25/75, using: eluent A: 0.05% TFA aqueous solution, eluent B: 0.05% TFA acetonitrile solution, was applied on a HPLC using Xtimate C18, 10 μm, 120 column (20×250 mm). The fractions containing the product were collected and lyophilized to give 24.5 mg of white solid.

Embodiment 66

Preparation of Palm-PEG 8-Gly-Gly-D-Tyr-Hyp-Asn-Thr-Phe-A6C-Leu-Arg(Me)-Trp-NH$_2$ (Compound YA-264)

Similar to the synthesis method of Embodiment 30, NH$_2$-D-Tyr(tBu)-Hyp (tBu)-Asn(Trt)-Thr(tBu)-Phe-A6c-Leu-Arg(Me,Pbf)-Trp(Boc)-Rink Amide MBHA resin was obtained. Gly, Gly, PEG8 and Palm were introduced respectively according to the method of Step 1 of Embodiment 61 to give Palm-PEG8-D-Tyr(tBu)-Hyp(tBu)-Asn(Trt)-Thr(tBu)-Phe-A6c-Leu-Arg(Me,Pbf)-Trp(Boc)-Rink Amide MBHA resin. The resin was washed and dried. The target polypeptide was cleaved from the resin and deprotected by the method of Step 61 of Embodiment 2. The crude product YA-264 was isolated and purified by HPLC, and eluted with linear gradient (10 minutes) at a flow rate of 25 mL/minute. Eluent A/B: 43/57-33/67, using: eluent A: 0.05% TFA aqueous solution, eluent B: 0.05% TFA acetonitrile solution, was applied on a HPLC using Xtimate C18, 10 μm, 120 column (20×250 mm). The fractions containing the product were collected and lyophilized to give 13.0 mg of white solid.

Embodiment 67

Preparation of Palm-PEG8-D-3Fua-Pro(diF)-Asn-Thr-Phe-A6c-Leu-Arg(Me)-Trp-NH$_2$ (Compound YA-267)

NH$_2$-3Fua-Pro(diF)-Asn(Trt)-Thr(tBu)-Phe-A6c-Leu-Arg(Me,Pbf)-Trp(Boc)-Rink Amide MBHA resin was obtained according to the method of Embodiment 43. Gly, Gly, PEG8 and Palm were introduced respectively according to the method of Step 1 of Embodiment 61 to give Palm-PEG 8-3 Fua-Pro(diF)-Asn(Trt)-Thr(tBu)-Phe-A6c-Leu-Arg(Me,Pbf)-Trp(Boc)-Rink Amide MBHA resin. The resin was washed and dried. The target polypeptide was cleaved from the resin and deprotected by the method of Step 61 of Embodiment 2. The crude product YA-267 was isolated and purified by HPLC, and eluted with a linear gradient (10 minutes) at a flow rate of 25 mL/minute. Eluent A/B: 40/60-30/70, use: eluent A: 0.05% TFA aqueous solution, eluent B: 0.05% TFA acetonitrile solution, was applied on a HPLC using Phenomenex Gemini C18, 10 μm, 110 column (21.2×250 mm). The fractions containing the product were collected and lyophilized to give 41.3 mg of white solid.

Embodiment 68

C 18 preparation of diacid-OEG-OEG-D-Tyr-Hyp-Asn-Thr-Phe-azaGly-Leu-Arg(Me)-Trp-NH$_2$ (Compound YA-273)

NH$_2$-D-Tyr(tBu)-Hyp(tBu)-Asn(Trt)-Thr(tBu)-Phe-azaGly-Leu-Arg(Me,Pbf)-Trp(Boc)-Rink Amide MBHA resin was obtained according to the method of Step 1 of Embodiment 2. OEG, OEG and C18 diacid(monotBu) were introduced according to the method of step 1 of Embodiment 61 to give C18diacid(tBu)-OEG-OEG-D-Tyr(tBu)-Hyp(tBu)-Asn(Trt)-Thr(tBu)-Phe-A6c-Leu-Arg(Me,Pbf)-Trp(Boc)-Rink Amide resin. The resin was washed and dried. The target polypeptide was cleaved from the resin and deprotected by the method of Step 61 of Embodiment 2. The crude product YA-273 was isolated and purified by HPLC and eluted by linear gradient (10 minutes) with a flow rate of 25 mL/minute. Eluent A/B: 58/42-42/52 was used: eluent a: 0.05% TFA aqueous solution, eluent B: 0.05% TFA acetonitrile solution was applied on a preparative HPLC using Utimate C8 10 μm, 120 column (21.2×250 mm). Fractions containing the product were collected and lyophilized to give 30.4 mg of white solid.

Embodiment 69

Preparation of Palm-PEG 8-Gly-Gly-D-Tyr-Hyp-Asn-Thr-(S)-2-{(1-Amino-2-Phenylethyl)-1H-Imidazole-5-Carboxylic Acid}-Leu-Arg(Me)-Trp-NH$_2$ (Compound YA-286)

Similar to the synthesis method of Embodiment 44, NH$_2$-D-Tyr(tBu)-Hyp(tBu)-Asn(Trt)-Thr(tBu)-(S)-2-{(1-amino-2-phenylethyl)-1H-imidazole-5-carboxylic acid}-Leu-Arg(Me,Pbf)-Trp(Boc)-Rink Amide MBHA resin was obtained. Gly, Gly, PEG8 and Palm were introduced according to the method of Step 1 of Embodiment 61 to give Palm-PEG8-D-Tyr(tBu)-Hyp(tBu)-Asn(Trt)-Thr(tBu)-Phe-(S)-2-{(1-amino-2-phenylethyl)-1H-imidazole-5-carboxylic acid}-Leu-Arg(Me,Pbf)-Trp(Boc)-Rink Amide MBHA resin. The resin was washed and dried. The target polypeptide was cleaved from the resin and deprotected by the method of Step 61 of Embodiment 2. The crude product YA-286 was isolated and purified by HPLC and eluted by linear gradient (10 minutes) with a flow rate of 25 mL/minute, and eluent A/B: 53/47-43/57 using: eluent A: 0.05% TFA aqueous solution, eluent B: 0.05% TFA Acetonitrile solution was applied on preparative HPLC using Phenenex Gemini C18 10 μm, 110 column (21.2×250 mm). Fractions containing the product were collected and lyophilized to give 2.1 mg of white solid.

Embodiment 70

Preparation of Palm-PEG 8-Gly-Gly-D-Tyr-Hyp-Asn-Thr-Phe-Aze-Leu-Arg(Me)-Trp-NH$_2$ (Compound YA-287)

Similar to the synthesis method of Embodiment 24, NH$_2$-D-Tyr(tBu)-Hyp(tBu)-Asn(Trt)-Thr(tBu)-Phe-Aze-Leu-Arg (Me, Pbf)-Trp(Boc)-Rink Amide MBHA resin was obtained. Gly, Gly, PEG8 and Palm were introduced according to the method of Step 1 of Embodiment 61 to give Palm-PEG8-D-Tyr(tBu)-Hyp(tBu)-Asn(Trt)-Thr(tBu)-Phe-Aze-Leu-Arg(Me,Pbf)-Trp(Boc)-Rink Amide MBHA resin. The resin was washed and dried. The target polypeptide was cleaved from the resin and deprotected by the method of Step 61 of Embodiment 2. The crude product YA-287 was isolated and purified by HPLC, and eluted with linear gradient (10 minutes) at a flow rate of 25 mL/minute. Eluent A/B: 47/53-37/63, using: eluent A: 0.05% TFA aqueous solution, eluent B: 0.05% TFA acetonitrile solution, was applied on a HPLC using Xtimate C18, 10 μm, 120 column (20×250 mm). The fractions containing the product were collected and lyophilized to give 2.4 mg of white solid.

Embodiment 71

Preparation of Palm-PEG 8-Gly-Gly-D-Tyr-Hyp-Asn-Thr-Phe-(D-2Fua)-Leu-Arg(Me)-Trp-NH$_2$ (Compound YA-288)

Similar to the synthesis method of Embodiment 27, NH$_2$-D-Tyr(tBu)-Hyp(tBu)-Asn(Trt)-Thr(tBu)-Phe-(D-2Fua)-Leu-Arg(Me,Pbf)-Trp(Boc)-Rink Amide MBHA resin was obtained. Gly, Gly, PEG8 and Palm were introduced respectively according to the method of Step 1 of Embodiment 61 to give Palm-PEG8-D-Tyr(tBu)-Hyp(tBu)-Asn(Trt)-Thr(tBu)-Phe-(D-2Fua)-Leu-Arg(Me,Pbf)-Trp(Boc)-Rink Amide MBHA resin. The resin was washed and dried. The target polypeptide was cleaved from the resin and deprotected by the method of Step 61 of Embodiment 2. The crude product YA-288 was isolated and purified by HPLC, and eluted with linear gradient (10 minutes) at a flow rate of 25 mL/minute. Eluent A/B: 45/55-35/65, using: eluent A: 0.05% TFA aqueous solution, eluent B: 0.05% TFA acetonitrile solution, was applied on a HPLC using Xtimate C18, 10 μm, 120 column (20×250 mm). The fractions containing the product were collected and lyophilized to give 13.4 mg of white solid.

Embodiment 72

Preparation of Hexanoyl-D-Tyr-Hyp-Asn-Thr-Phe-azaGly-Leu-Arg(Me)-Trp-NH$_2$ (Compound YA-294)

NH$_2$-D-Tyr(tBu)-Hyp(tBu)-Asn(Trt)-Thr(tBu)-Phe-azaGly-Leu-Arg(Me,Pbf)-Trp(Boc)-Rink Amide MBHA resin was obtained according to the method of Step 1 of Embodiment 2. Hexanoyl groups were respectively introduced according to the method of Step 1 of Embodiment 61 to give Hexanoyl-Tyr(tBu)-Hyp(tBu)-Asn(Trt)-Thr(tBu)-Phe-A6c-Leu-Arg(Me,Pbf)-Trp(Boc)-Rink Amide MBHA resin. The resin was washed and dried. The target polypeptide was cleaved from the resin and deprotected by the method of Step 61 of Embodiment 2. The crude product YA-294 was isolated and purified by HPLC, and eluted with a linear gradient (10 minutes) at a flow rate of 25 mL/minute. Eluent A/B: 70/30-60/40, use: eluent A: 0.05% TFA aqueous solution, eluent B: 0.05% TFA acetonitrile solution, was applied on a HPLC using Phenenex Gemini C18 10 μm, 110 column (21.2×250 mm). Fractions containing the product were collected and lyophilized to give 6.5 mg of white solid.

Embodiment 73

Preparation of Nonanoyl-OEG-D-Tyr-Hyp-Asn-Thr-Phe-azaGly-Leu-Arg(Me)-Trp-NH$_2$ (Compound YA-295)

NH$_2$-D-Tyr(tBu)-Hyp(tBu)-Asn(Trt)-Thr(tBu)-Phe-azaGly-Leu-Arg(Me,Pbf)-Trp(Boc)-Rink Amide MBHA resin was obtained according to the method of Step 1 of Embodiment 2. OEG and Nonanoyl groups were respectively introduced according to the method of Step 1 of Embodiment 61 to give Nonanoyl-OEG-Tyr(tBu)-Hyp(tBu)-Asn(Trt)-Thr(tBu)-Phe-A6c-Leu-Arg(Me, Pbf)-Trp(Boc)-Rink Amide MBHA resin. The resin was washed and dried. The target polypeptide was cleaved from the resin and deprotected by the method of Step 61 of Embodiment 2. The crude product YA-295 was isolated and purified by HPLC, and eluted with linear gradient (10 minutes) at a flow rate of 25 mL/minute. Eluent A/B: 63/37-53/47, using: eluent A: 0.05% TFA aqueous solution, eluent B: 0.05% TFA acetonitrile solution was applied on a preparative HPLC using Utimate C8, 10 μm, 120 column (21.2×250 mm). Fractions containing the product were collected and lyophilized to give 5.5 mg of white solid.

Embodiment 74

Preparation of Dodecanoyl-PEG4-PEG4-D-Tyr-Hyp-Asn-Thr-Phe-azaGly-Leu-Arg(Me)-Trp-NH₂ (Compound YA-296)

NH₂-D-Tyr(tBu)-Hyp(tBu)-Asn(Trt)-Thr(tBu)-Phe-azaGly-Leu-Arg(Me,Pbf)-Trp(Boc)-Rink Amide MBHA resin was obtained according to the method of Step 1 of Embodiment 2. PEG, PEG and Dodecanoyl groups were respectively introduced according to the method of Step 1 of Embodiment 61 to give Dodecanoyl-PEG4-PEG4-Tyr(tBu)-Hyp(tBu)-Asn(Trt)-Thr(tBu)-Phe-A6c-Leu-Arg(Me,Pbf)-Trp(Boc)-Rink Amide MBHA resin. The resin was washed and dried. The target polypeptide was cleaved from the resin and deprotected by the method of Step 61 of Embodiment 2. The crude product YA-296 was isolated and purified by HPLC, and eluted with a linear gradient (10 minutes) at a flow rate of 25 mL/minute. Eluent A/B: 60/40-50/50, use: eluent A: 0.05% TFA aqueous solution, eluent B: 0.05% TFA acetonitrile solution, was applied on a HPLC using Phenomenex Gemini C18, 10 μm, 110 column (21.2×250 mm). The fractions containing the product were collected and lyophilized to give 14.5 mg of white solid.

Embodiment 75

Preparation of Palm-D-Tyr-Hyp-Asn-Thr-Phe-azaGly-Leu-Arg(Me)-Trp-NH₂ (Compound YA-297)

NH₂-D-Tyr(tBu)-Hyp(tBu)-Asn(Trt)-Thr(tBu)-Phe-azaGly-Leu-Arg(Me,Pbf)-Trp(Boc)-Rink Amide MBHA resin was obtained according to the method of Step 1 of Embodiment 2. Palm groups were respectively introduced according to the method of Step 1 of Embodiment 61 to give Palm-Tyr(tBu)-Hyp(tBu)-Asn(Trt)-Thr(tBu)-Phe-A6c-Leu-Arg(Me,Pbf)-Trp(Boc)-Rink Amide MBHA resin. The resin was washed and dried. The target polypeptide was cleaved from the resin and deprotected by the method of Step 61 of Embodiment 2. The crude product YA-297 was isolated and purified by HPLC, and eluted with linear gradient (10 minutes) at a flow rate of 25 mL/minute. Eluent A/B: 34/66-24/76, using: eluent A: 0.05% TFA aqueous solution, eluent B: 0.05% TFA acetonitrile solution, was applied on a HPLC using Phenomenex Gemini C18, 10 μm, 110 column (21.2×250 mm). The fractions containing the product were collected and lyophilized to give 40.0 mg of white solid.

Embodiment 76

Preparation of Palm-PEG8-D-Tyr-Hyp-Asn-Thr-Phe-azaGly-Leu-Arg(Me)-Trp-NH₂ (Compound YA-298)

NH₂-D-Tyr(tBu)-Hyp(tBu)-Asn(Trt)-Thr(tBu)-Phe-azaGly-Leu-Arg(Me,Pbf)-Trp(Boc)-Rink Amide MBHA resin was obtained according to the method of Step 1 of Embodiment 2. PEG8 and Palmitoyl groups were respectively introduced according to the method of Step 1 of Embodiment 61 to give Palm-PEG 8-D-Tyr(tBu)-Hyp(tBu)-Asn(Trt)-Thr(tBu)-Phe-A6c-Leu-Arg(Me,Pbf)-Trp(Boc)-Rink Amide MBHA resin. The resin was washed and dried. The target polypeptide was cleaved from the resin and deprotected by the method of Step 61 of Embodiment 2. The crude product YA-298 was isolated and purified by HPLC, and eluted with linear gradient (10 minutes) at a flow rate of 25 mL/minute. Eluent A/B: 46/54-36/64, using: eluent A: 0.05% TFA aqueous solution, eluent B: 0.05% TFA acetonitrile solution, was applied on a HPLC using Xtimate C18, 10 μm, 120 column (20×250 mm). The fractions containing the product were collected and lyophilized to give 16.0 mg of white solid.

Embodiment 78

Preparation of Dodecanoyl-

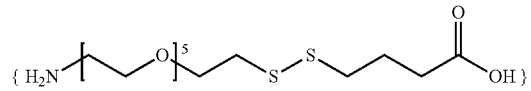

-D-Tyr-Hyp-Asn-Thr-Phe-azaGly-Leu-Arg(Me)-Trp-NH₂ (Compound YA-296)

Step 1: 0.1 g of commercially available Rink Amide MBHA resin (0.5 mmol/g) was swollen in DMF, and the resin was treated with 2 mL 20% piperidine/DMF for 20 minutes to remove Fmoc, repeated twice. NH₂-D-Tyr(tBu)-Hyp(tBu)-Asn(Trt)-Thr(tBu)-Phe-azaGly-Leu-Arg(Me,Pbf)-Trp(Boc)-Rink Amide MBHA resin was obtained according to the method of Step 1 of Embodiment 2. The resin was washed with DMF and 2.5 mL DMF solution of 4-(Pyridin-2-yldisulfaneyel) butanoic acid (34 mg, 0.15 mmol), HATU (57 mg, 0.15 mmol), HOAt (20 mg, 0.15 mmol) was added. Then DIPEA (53 μL, 0.3 mmol) was added, treated at room temperature for 2 hours, and the resin was washed with DMF to give 4-(Pyridin-2-yldisulfaneyl) butanoyl-D-Tyr(tBu)-Hyp(tBu)-Asn(Trt)-Thr(tBu)-Phe-azaGly-Leu-Arg(Me,Pbf)-Trp(Boc)-Rink Amide MBHA resin. A 2.0 mL DMF solution of NH₂-PEG5-SH hydrochloride (33 mg, 0.1 mmol) was added to the resin and treated at room temperature for 36 hours. The resin was washed with DMF to give NH₂-PEG5-S—S-butanoyl-D-Tyr(tBu)-Hyp(tBu)-Asn(Trt)-Thr(tBu)-Phe-azaGly-Leu-Arg(Me,Pbf)-Trp(Boc)-Rink Amide MBHA resin. The obtained resin was added with 2.5 mL DMF solution of Dodecanoic Acid (30 mg, 0.15 mmol), Hatu (57 mg, 0.15 mmol), HOAt (20 mg, 0.15 mmol), then DIPEA (53 μL, 0.3 mmol) was added and treated at room temperature for 40 minutes. The resin was washed with DMF, DCM, methanol and methyl tert-butyl ether, and then drained to give Dodecanoyl-

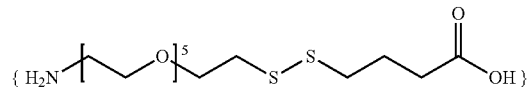

-D-Tyr(tBu)-Hyp(tBu)-Asn(Trt)-Thr(tBu)-Phe-azaGly-Leu-Arg(Me, Pbf)-Trp(Boc)-Rink Amide MBHA resin.

Step 2: Add the dried resin to 4 mL of TFA/TIS/phenol/H₂O (94/2/2/2) solution, stir the mixture for 2 hours, filter to remove the resin, and wash the resin with 1 mL of TFA/TIS/phenol/H₂O (94/2/2/2) solution. The filtrates were combined, and ice methyl tert-butyl ether (20 mL) was added to the filtrate. The resulting mixture was centrifuged at 3000 rpm for 3 minutes, and the solid was washed twice with ice ethyl ether and drained. The obtained precipitate was dissolved in DMF and then eluted with a linear concentration gradient (11 minutes) at a flow rate of 25 mL/minute, AND eluent A/B: 53/47-43/57 Use: eluent A: 0.05% TFA aqueous solution, eluent B: 0.05% TFA acetonitrile solution was applied on a preparative HPLC using Xtimate, 10μ, 120 Å column (20 mm×250 mm). Fractions containing the product were collected and lyophilized to give 2.7 mg of white solid.

Embodiment 79

Preparation of Ac-(D-Tyr)-Hyp-Asn-Thr-Phe-azaG-Leu-Arg(Me)-Trp-2H-tetrazol-5-yl (Compound YA-250)

1. g of commercially available 2-CTC resin (1.36 mmol/g) was swollen in DCM (10 mL), Fmoc-Arg (Me, PBF)—OH (332 mg, 0.5 mmol) and DIPEA (387 mg, 3 mmol) were added, treated at room temperature for 3 hours, then methanol (1.5 mL) was added, shaken for 1 hour, and the unreacted resin was blocked. Filter, resin washed with DCM. The resulting Fmoc-Arg (Me, Pbf)-CTC resin was treated with 5 ml of 20% piperidine/DMF for 20 minutes to remove Fmoc, repeated twice. The obtained resin was washed with DMF, 10 mL DMF solution of the second amino acid Fmoc-Phe-azaGly-Leu-OH (335 mg, 0.6 mmol), HATU (456 mg, 1.2 mmol), HOBt (162 mg, 1.2 mmol) was added, and then DIPEA (310 mg, 2.4 mmol), treated at room temperature for 1 hour, and the resin was washed with DMF to give Fmoc-Phe-azaGly-Leu-Arg (Me, Pbf)-CTC resin. Other amino acids Fmoc-Thr (tBu)—OH, Fmoc-Asn (Trt)-OH, Fmoc-Hyp (tBu)—OH, Fmoc-D-Tyr (tBu)—OH were sequentially introduced in a similar manner to give Fmoc-D-Tyr (tBu)-Hyp (tBu)-Asn (Trt)-Thr (tBu)-Phe-azaG-Leu-Arg (Me, Pbf)-CTC resin. The resin was treated with 5 ml of 20% piperidine/DMF for 20 minutes to remove Fmoc, repeated twice. The resin was washed with DMF, 10 mL DMF solution of DIPEA (3096 mg, 24 mmol) was added, then $(Ac)_2O$ (816 mg, 8 mmol) was added, and the process was repeated at room temperature for 30 minutes. The resin was washed with DMF, DCM, methanol and methyl tert-butyl ether, and then drained to finally give Ac-D-Tyr(tBu)-Hyp(tBu)-Asn(Trt)-Thr(tBu)-Phe-azaG-Leu-Arg(Me, Pbf)-CTC resin.

The dried 1346 mg resin was added to 10 mL of HFIP/DCM (3/7) solution, the mixture was stirred for 2 hours, and the resin was removed by filtration. The filtrate was concentrated to give fully protected polypeptide Ac-D-Tyr(tBu)-Hyp(tBu)-Asn(Trt)-Thr(tBu)-Phe-azaG-Leu-Arg(Me, Pbf)-OH (63 mg, 0.037 mmol). The crude peptide was dissolved in DCM (10 mL), then HATU (21 mg, 0.055 mmol), DIPEA (14 mg, 0.11 mmol) and (s)-2-(1h-indol-3-yl)-1-(2h-tetrazol-5-yl) ethanamine (Compound YA-250-d, 17 mg, 0.074 mmol) were added and stirred at room temperature for 4 hours. Water (5 mL) was added to the reaction mixture, the aqueous layer was extracted with DCM, the combined organic phases were washed with water, dried over anhydrous sodium sulfate, and concentrated to give fully protected amide (100 mg), which was directly used in the next reaction without purification.

The obtained amide crude product was added to 10 mL of TFA/EDT/TIS/$H_2O$ (92/2/2/2) solution, the mixture was stirred for 2 hours, cold diethyl ether (100 mL) was added to the solution, the obtained mixture was centrifuged at 3000 rpm for 1 minute, the supernatant was removed, the solid was washed twice with diethyl ether and drained. The obtained precipitate was dissolved in DMF and then eluted with a linear concentration gradient (10 minutes) at a flow rate of 25 mL/minute, and eluent A/B: 69/31-64/36, using: eluent A: 0.05% TFA aqueous solution, eluent B: 0.05% TFA acetonitrile solution was applied on a preparative HPLC using Phenomenex, 10 120 Å columns (21.2 mm×250 mm). Fractions containing the product were collected and lyophilized to give compound YA-250-A (1.8 mg) as a white solid and compound YA-250-B (0.4 mg) as a white solid.

Embodiment 80

Preparation of Ac-(D-Tyr)-Hyp-Asn-Thr-Phe-ψ(NHCS)Gly-Leu-Arg(Me)-Trp-$NH_2$ (Compound YA-254)

313 mg of commercially available Rink Amide MBHA resin (0.32 mmol/g) was swollen in DMF, and the resin was treated with 5 ml of 20% piperidine/DMF for 20 minutes to remove Fmoc, repeated twice. The obtained resin was washed with DMF, 5 mL DMF solution of Fmoc-Trp (Boc)-OH (158 mg, 0.3 mmol), HATU (114 mg, 0.3 mmol), HOAt (41 mg, 0.3 mmol) was added, and then DIPEA (77 mg, 0.6 mmol) was added. Treatment was carried out at room temperature for 40 minutes, and Trp(Boc) was introduced thereto to give Fmoc-Trp(Boc)-Rink Amide MBHA resin. The resin was treated with 5 ml of 20% piperidine/DMF for 20 minutes to remove Fmoc, repeated twice. The obtained resin was washed with DMF, 5 mL DMF solution of Fmoc-Arg (Me, Pbf)-OH (99 mg, 0.15 mmol), HATU (57 mg, 0.15 mmol), HOAt (21 mg, 0.15 mmol) was added, and then DIPEA (39 mg, 0.3 mmol) was added. After treatment at room temperature for 1 hour, the resin was washed with DMF to give Fmoc-Arg (Me, Pbf)-Trp (Boc)-Rinkamide MBHA resin. Other amino acids Fmoc-Phe-ψ(NHCS)Gly-Leu-OH, Fmoc-Thr(OtBu)—OH, Fmoc-Asn(Trt)-OH, Fmoc-Hyp (OtBu)—OH, Fmoc-[D-Tyr(OtBu)]—OH were introduced in a similar manner. Fmoc-[D-Tyr(OtBu)]-Hyp (OtBu)-Asn(Trt)-Thr(OtBu)-Phe-ψ(NHCS)Gly-Leu-Arg (Me)-Trp(Boc)-Rink Amide MBHA resin was obtained. The resin was treated with 5 ml of 20% piperidine/DMF for 20 minutes to remove Fmoc, repeated twice. The resin was washed with DMF, 5 mL DMF solution of glacial acetic acid (36 mg, 0.6 mmol), HBTU (227 mg, 0.6 mmol), HOBt (81 mg, 0.6 mmol) were added, then DIPEA (155 mg, 1.2 mmol) was added, the resin was treated at room temperature for 40 minutes, DMF, DCM, Methanol and methyl tert-butyl ether were washed and then drained to give Ac-[D-Tyr(OtBu)]-Hyp(OtBu)-Asn(Trt)-Thr(OtBu)-Phe-ψ(NHCS)Gly-Leu-Arg(Me)-Trp(Boc)-Rink Amide MBHA resin.

The dried resin was added to 10 mL of TFA/TIS/$H_2O$ (92/4/4) solution, the mixture was stirred for 2 hours, the resin was removed by filtration, and the resin was washed with 1 mL of TFA/TIS/$H_2O$ (92/4/4) solution. The filtrates were combined, methyl tert-butyl ether (110 mL) was added to the filtrate, the resulting mixture was centrifuged at 3000 rpm for 1 minute, and the solid was washed twice with cold diethyl ether and drained. The obtained precipitate was dissolved in DMF and then eluted with a linear concentration gradient (10 minutes) at a flow rate of 25 mL/minute, and eluent A/B: 75/25-65/35 using: eluent A: 0.05% TFA aqueous solution, eluent B: 0.05% TFA acetonitrile solution was applied on a preparative HPLC using XTIMATE, 10 μm, 120 columns (20×250 mm). The fraction containing the product (the peak with the later retention time of the two peaks of the same molecular weight) was collected and lyophilized to give 5.0 mg of white solid.

Embodiment 81

Preparation of Ac-[D-Phe(2,4-DiCl)]-DiFluorPro-Asn-Thr-Phe-ψ(NHCS) Gly-Leu-Arg(Me)-Trp-NH$_2$ (Compound YA-255)

313 mg of commercially available Rink Amide MBHA resin (0.32 mmol/g) was swollen in DMF, and the resin was treated with 5 ml of 20% piperidine/DMF for 20 minutes to remove Fmoc, repeated twice. The obtained resin was washed with DMF, 5 mL DMF solution of Fmoc-Trp (Boc)-OH (158 mg, 0.3 mmol), HATU (114 mg, 0.3 mmol), HOAt (41 mg, 0.3 mmol) were added, and then DIPEA (77 mg, 0.6 mmol) was added. Treatment was carried out at room temperature for 40 minutes, and Trp (Boc) was introduced thereto to give Fmoc-Trp (Boc)-Rink Amide MBHA resin. The resin was treated with 5 ml of 20% piperidine/DMF for 20 minutes to remove Fmoc, repeated twice. The obtained resin was washed with DMF, 5 mL DMF solution of Fmoc-Arg (Me, Pbf)-OH (99 mg, 0.15 mmol), Hatu (57 mg, 0.15 mmol), HOAt (21 mg, 0.15 mmol) was added, and then DIPEA (39 mg, 0.3 mmol) was added. After treatment at room temperature for 1 hour, the resin was washed with DMF to give Fmoc-Arg (Me, Pbf)-Trp (Boc)-Rinkamide MBHA resin. Other amino acids Fmoc-Phe-ψ(NHCS)Gly-Leu-OH, Fmoc-Thr(OtBu)—OH, Fmoc-Asn(Trt)-OH, Fmoc-DiFluorPro-OH, Fmoc[D-Phe(2,4-DiCl)]—OH were introduced in a similar manner to give Fmoc-[D-Phe(2,4-DiCl)]-DiFluorPro-Asn(Trt)-Thr(OtBu)-Phe-ψ(NHCS)Gly-Leu-Arg(Me)-Trp(Boc)-Rink Amide MBHA resin. The resin was treated with 5 ml of 20% piperidine/DMF for 20 minutes to remove Fmoc, repeated twice. The resin was washed with DMF, 5 mL DMF solution of glacial acetic acid (36 mg, 0.6 mmol), HBTU (227 mg, 0.6 mmol), HOBt (81 mg, 0.6 mmol) were added, then DIPEA (155 mg, 1.2 mmol) was added, the resin was treated at room temperature for 40 minutes, DMF, DCM, methanol and methyl tert-butyl ether were washed and then drained to give Ac-[D-Phe(2,4-DiCl)]-DiFluorPro-Asn(Trt)-Thr(OtBu)-Phe-ψ(NHCS)Gly-Leu-Arg(Me)-Trp(Boc)-Rink Amide MBHA resin.

The dried resin was added to 10 mL of TFA/TIS/H$_2$O (92/4/4) solution, the mixture was stirred for 2 hours, the resin was removed by filtration, and the resin was washed with 1 mL of TFA/TIS/H$_2$O (92/4/4) solution. The filtrates were combined, methyl tert-butyl ether (110 mL) was added to the filtrate, the resulting mixture was centrifuged at 3000 rpm for 1 minute, and the solid was washed twice with cold diethyl ether and drained. The obtained precipitate was dissolved in DMF and then eluted with a linear concentration gradient (10 minutes) at a flow rate of 25 mL/minute. Eluent A/B: 64/36-54/46 Use: Elution A: 0.05% TFA aqueous solution, eluent B: 0.05% TFA acetonitrile solution was applied on a preparative HPLC using XTIMATE, 10 120 columns (20×250 mm). The fraction containing the product (the peak with the later retention time of the two peaks of the same molecular weight) was collected and lyophilized to give 3.8 mg of white solid.

Embodiment 82

Preparation of Ac-(D-Tyr)-Hyp-Asn-Thr-Phe-ψ(NH—CO—NH)Gly-Leu-Arg(Me)-Trp-NH$_2$ (Compound YA-256)

617 mg of commercially available Rink Amide MBHA (0.324 mmol/g) resin was swollen in DMF, and the resin was treated with 10 mL 20% piperidine/DMF for 20 minutes to remove Fmoc, repeated twice. The obtained resin was washed with DMF, 10 mL DMF solution of Fmoc-Trp (Boc)-OH (316 mg, 0.6 mmol), HATU (228 mg, 0.6 mmol), HOBt (81 mg, 0.6 mmol) were added, then DIPEA (155 mg, 1.2 mmol) was added, the resin was treated at room temperature for 40 minutes, and the resin was washed with DMF to give Fmoc-Trp(Boc)-Rink Amide MBHA resin. The resin was treated with 10 mL 20% piperidine/DMF for 20 minutes to remove Fmoc, repeated twice. Other amino acids (Fmoc-Arg (Me, Pbf)-OH, Fmoc-Phe-ψ(NH—CO—NH)Gly-Leu-OH, Fmoc-Thr(tBu)—OH, Fmoc-Asn(Trt)-OH, Fmoc-Hyp (tBu)—OH, Fmoc-D-Tyr (tBu)—OH were introduced to give Fmoc-D-Tyr(tBu)-Hyp(tBu)-Asn(Trt)-Thr(tBu)-Phe-ψ(NH—CO—NH)Gly-Leu-Arg(Me, Pbf)-Trp(Boc)-Rink Amide MBHA resin. The resin was treated with 10 mL 20% piperidine/DMF for 20 minutes to remove Fmoc, repeated twice. The resin was washed with DMF, 10 mL DMF solution of DIPEA (774 mg, 6 mmol) was added, then (Ac)$_2$O (204 mg, 2 mmol) was added, and the process was repeated at room temperature for 30 minutes. The resin was washed with DMF, DCM, methanol and methyl tert-butyl ether, and then drained to give Ac-D-Tyr(tBu)-Hyp(tBu)-Asn(Trt)-Thr(tBu)-Phe-ψ(NH—CO—NH)Gly-Leu-Arg (Me, Pbf)-Trp(Boc)-Rink Amide MBHA resin.

The dried resin was added to 10 mL of TFA/TIS/EDT/H$_2$O (94/2/2/2) solution, the mixture was stirred for 2 hours, the resin was removed by filtration, and the resin was washed with 4 ml of TFA/TIS/EDT/H$_2$O (94/2/2/2) solution. The filtrates were pooled and added with methyl tert-butyl ether (200 mL), the resulting mixture was centrifuged at 3000 rpm for 1 minute, and the solid was washed twice with cold diethyl ether and drained. The obtained precipitate was dissolved in DMF and then eluted with a linear concentration gradient (10 minutes) at a flow rate of 25 mL/minute, and eluent A/B: 75/25-69/31, using: eluent A: 0.05% TFA aqueous solution, eluent B: 0.05% TFA acetonitrile, was applied on a preparative HPLC using Welch 10 μm, 110 A column (20×250 mm). The fractions containing the product were collected and lyophilized to give 32.8 mg of white solid.

Embodiment 83

Preparation of Ac-Gly-Arg-Lys-Lys-Arg-Arg-Gln-Arg-Arg-Pro-Gln-(Beta-Ala)-(Beta-Ala)-(D-Tyr)-Hyp-Asn-Thr-Phe-Azag-Leu-Arg(Me)-Trp-NH$_2$ (Compound YA-291)

313 mg of commercially available Rink Amide MBHA resin (0.32 mmol/g) was swollen in DMF, and the resin was treated with 5 ml of 20% piperidine/DMF for 20 minutes to remove Fmoc, repeated twice. The obtained resin was washed with DMF, 5 mL DMF solution of Fmoc-Trp (Boc)-OH (158 mg, 0.3 mmol), HATU (114 mg, 0.3 mmol), HOAt (41 mg, 0.3 mmol) was added, and then DIPEA (77 mg, 0.6 mmol) was added. Treatment was carried out at room temperature for 40 minutes, and Trp(Boc) was introduced thereto to give Fmoc-Trp(Boc)-Rink Amide MBHA resin. The resin was treated with 5 ml of 20% piperidine/DMF for 20 minutes to remove Fmoc, repeated twice. The obtained resin was washed with DMF, 5 mL DMF solution of Fmoc-Arg (Me, PBF)—OH (99 mg, 0.15 mmol), HATU (57 mg, 0.15 mmol), HOAt (21 mg, 0.15 mmol) were added, and then DIPEA (39 mg, 0.3 mmol) was added. After treatment at room temperature for 1 hour, the resin was washed with DMF to give Fmoc-Arg (Me, PBF)-Trp (Boc)-Rinkamide MBHA resin. Other amino acids Fmoc-Phe-azaG-Leu-OH, Fmoc-Thr(OtBu)—OH, Fmoc-Asn(Trt)-OH, Fmoc-Hyp (OtBu)—OH, Fmoc-[D-Tyr(OtBu)]—OH, Fmoc-beta-Ala-OH, Fmoc-beta-Ala-OH, Fmoc-Gln(Trt)-OH, Fmoc-Pro-OH, Fmoc-Arg(Pbf)-OH, Fmoc-Arg(Pbf)-OH, Fmoc-Arg (Pbf)-OH, Fmoc-Gln(Trt)-OH, Fmoc-Arg(Pbf)-OH, Fmoc-Arg (Pbf)-OH, Fmoc-Lys(Boc)-OH, FMoc-Lys(Boc)-OH, Fmoc-Arg(Pbf)-OH and Fmoc-Gly-OH were introduced to give Fmoc-Gly-Arg(Pbf)-Lys(Boc)-Lys(Boc)-Arg(Pbf)-Arg (Pbf)-GlnTrt)-Arg(Pbf)-Arg (Pbf)-Arg(Pbf)-Pro-Gln(Trt)-(beta-Ala)-(beta-Ala)-[D-Tyr(OtBul)]-Hyp(OtBu)-Asn (Trt)-Thr(OtBu)-Phe-azaG-Leu-Arg(Me)-Trp(Boc)-Rink Amide MBHA resin. The resin was treated with 5 ml of 20% piperidine/DMF for 20 minutes to remove Fmoc, repeated twice. The resin was washed with DMF, a 5 mL DMF solution of glacial acetic acid (36 mg, 0.6 mmol), HBTU (227 mg, 0.6 mmol), HOBt (81 mg, 0.6 mmol) were added, then DIPEA (155 mg, 1.2 mmol) was added, the resin was treated at room temperature for 40 minutes, DMF, DCM, methanol and methyl tert-butyl ether were washed and then drained. Ac-Gly-Arg(Pbf)-Lys(Boc)-Lys(Boc)-Arg(Pbf)-Arg(Pbf)-GlnTrt)-Arg(Pbf)-Arg(Pbf)-Arg(Pbf)-Pro-Gln(Trt)-(beta-Ala)-(beta-Ala)-[D-Tyr(OtBul)]-Hyp(OtBu)-Asn(Trt)-Thr(OtBu)-Phe-azaG-Leu-Arg(Me)-Trp(Boc)-Rink Amide MBHA resin was obtained.

The dried resin was added to 10 mL of TFA/TIS/H₂O (92/4/4) solution, the mixture was stirred for 2 hours, the resin was removed by filtration, and the resin was washed with 1 mL of TFA/TIS/H₂O (92/4/4) solution. The filtrates were combined, methyl tert-butyl ether (110 mL) was added to the filtrate, the resulting mixture was centrifuged at 3000 rpm for 1 minute, and the solid was washed twice with cold diethyl ether and drained. The obtained precipitate was dissolved in DMF and then eluted with a linear concentration gradient (10 minutes) at a flow rate of 25 mL/minute, and eluent A/B: 86/14-76/24 using: elution A: 0.05% TFA aqueous solution, eluent B: 0.05% TFA acetonitrile solution, was applied on a preparative HPLC using Phenonenex, 10 μm, 110 columns (21.2×250 mm). The fractions containing the product were collected and lyophilized to give 6.9 mg of white solid.

Embodiment 84

Preparation of Ac-(D-Tyr)-Hyp-Asn-Thr-[(S)-2-((2-amino-3-phenylpropyl)amino)-2-oxoacetyl]-Leu-Arg (Me)-Trp-NH₂ (Compound YA-302)

0.4 g of commercially available Rink Amide MBHA resin (0.5 mmol/g) was swollen in DMF, and the resin was treated with 5 ml of 20% piperidine/DMF for 20 minutes to remove Fmoc, repeated twice. The obtained resin was washed with DMF, and 5 mL DMF solution of Fmoc-Trp(Boc)-OH (0.53 g, 1 mmol), HOBt (0.162 g, 1.2 mmol) and DIC (0.486 mL, 1.2 mmol) were added. The resin was treated at room temperature for 55 minutes and washed with DMF to give Fmoc-Trp(Boc)-Rink Amide MBHA resin. The resin was treated with 5 ml of 20% piperidine/DMF for 30 minutes to remove Fmoc, the resin was washed with DMF, and 5 mL DMF solution of Fmoc-Arg (Me, Pbf)-OH (0.199 g, 0.3 mmol), DIC (0.055 mL, 0.36 mmol) and HOBt (0.048 g, 0.36 mmol) were added to react overnight at room temperature. The resin was treated with 5 ml of 20% piperidine/DMF for 30 minutes to remove Fmoc, and the resin was washed with DMF to give Arg (Me, Pbf)-Trp (Boc)-Rinkamide MBHA resin. The obtained resin was added with 5 mL DMF solution of Fmoc-Leu-OH (0.35 g, 1 mmol), DIC (0.181 ml, 1.2 mmol) and HOBt (0162 g, 1.2 mmol), treated at room temperature for 95 minutes, and the resin was washed with DMF. The resin was treated with 5 ml of 20% piperidine/DMF for 30 minutes to remove Fmoc, and the resin was washed with DMF to give NH2-Leu-Arg (Me, Pbf)-Trp (Boc)-Rink Amide MBHA resin. The obtained resin was added with 5 mL DMF solution of Fmoc-Thr (tBu)-[(S)-2-((2-Amino-3-phenylpropyl) Amino)-2-oxoacetyl]-OH (0.18 g, 0.3 mmol), DIC (0.055 ml, 0.36 mmol) and HOBt (0.048 g, 0.36 mmol), and reacted overnight at room temperature. The resin was treated with 20 mL 20% piperidine/DMF for 30 minutes to remove Fmoc, and the resin was washed with DMF to give NH2-THR (TBU)-[(S)-2-((2-amino-3-phenyl) amino)-2-oxoacetyl)-Leu-Arg (ME, PBF)-TRP (Boc)-rinkamide MBHA resin. In a similar manner, amino acids such as Asn(Trt), Hyp(tBu), D-Tyr (tBu) and the like were sequentially introduced, and the resin was washed with DMF to give NH₂-Thr(tBu)-[(S)-2-((2-amino-3-phenylpropyl)amino)-2-oxoacetyl]-Leu-Arg(Me, Pbf)-Trp(Boc)-Rink Amide MBHA resin. 5 mL DMF solution of AcOH (0.115 ml, 2 mmol) and DIC (0.309 ml, 2 mmol) was added, reacted at room temperature for 25 minutes, and Ac group was introduced. The resin was washed with DMF, DCM, methanol and methyl tert-butyl ether, and then drained to finally obtain Ac-D-Tyr(tBu)-Hyp (tBu)-Asn(Trt)-Thr(tBu)-[(S)-2-((2-amino-3-phenylpropyl) amino)-2-oxoacetyl]-Leu-Arg(Me, Pbf)-Trp(Boc)-Rink Amide MBHA resin.

The dried resin was added to 6 mL of TFA/TIS/Phenol/H₂O (88/2/5/5) solution, the mixture was stirred for 2 hours, the resin was removed by filtration, and the resin was washed with 2 mL of TFA/TIS/Phenol/H₂O (88/2/5/5) solution. The filtrates were pooled and added with ether (80 mL), the resulting mixture was centrifuged at 3000 rpm for 1 minute to remove the supernatant, and the solid was washed twice with ether and drained. The obtained precipitate was dissolved in DMF and then eluted with a linear concentration gradient (10 minutes) at a flow rate of 25 mL/minute. Eluent AB: 75/25-65/35, using: eluent A: 0.05% TFA aqueous solution, eluent B: 0.05% TFA acetonitrile solution was applied on a preparative HPLC using Phenomenex Gemini, 10 μm, 110 Å column (21.2×250 mm). The fractions containing the product were collected and lyophilized to give 43.5 mg of trifluoroacetate as a white solid.

Embodiment 85

Preparation of Ac-(D-Tyr)-Hyp-Asn-Thr-Phe-ψ (NHCO)Gly-Leu-Arg(Me)-Trp-NH₂ (Compound YA-303)

940 mg of commercially available Rink Amide MBHA resin (0.32 mmol/g) was swollen in DMF, and the resin was treated with 10 mL 20% piperidine/DMF for 20 minutes to remove Fmoc, repeated twice. The obtained resin was washed with DMF, 10 mL DMF solution of Fmoc-Trp(Boc)-OH (474 mg, 0.9 mmol), HATU (342 mg, 0.9 mmol), HOAt (122 mg, 0.9 mmol) was added, and then DIPEA (232 mg, 1.8 mmol) was added. Treatment was carried out at room temperature for 40 minutes, and Trp(Boc) was introduced thereto to give Fmoc-Trp(Boc)-Rink Amide MBHA resin. The resin was treated with 10 mL 20% piperidine/DMF for 20 minutes to remove Fmoc, repeated twice. The obtained resin was washed with DMF, 10 mL DMF solution of Fmoc-Arg (Me, Pbf)-OH (298 mg, 0.45 mmol), HATU (171 mg, 0.45 mmol), HOAt (61 mg, 0.45 mmol) was added, and then DIPEA (116 mg, 0.9 mmol) was added. After treatment at room temperature for 1 hour, the resin was washed with DMF to give Fmoc-Arg (Me, Pbf)-Trp (Boc)-Rinkamide MBHA resin. Other amino acids Fmoc-Phe-ψ(NHCO)Gly-Leu-OH, Fmoc-Thr(OtBu)—OH, Fmoc-Asn(Trt)-OH, Fmoc-Hyp(OtBu)—OH, Fmoc-[D-Tyr(OtBu)]—OH] were introduced in a similar manner. Fmoc-[D-Tyr(OtBu)]-Hyp (OtBu)-Asn(Trt)-Thr(OtBu)-Phe-ψ(NHCO)Gly-Leu-Arg (Me)-Trp(Boc)-Rink Amide MBHA resin was obtained. The resin was treated with 10 mL 20% piperidine/DMF for 20 minutes to remove Fmoc, repeated twice. The resin was washed with DMF, 10 mL DMF solution of glacial acetic acid (108 mg, 1.8 mmol), HBTU (671 mg, 1.8 mmol), HOBt (243 mg, 1.8 mmol) were added, then DIPEA (465 mg, 3.6 mmol) was added, the resin was treated at room temperature for 40 minutes, DMF, DCM, methanol and methyl tert-butyl ether were washed and then drained to give Ac-[D-Tyr (OtBu)]-Hyp(OtBu)-Asn(Trt)-Thr(OtBu)-Phe-ψ(NHCO) Gly-Leu-Arg(Me)-Trp(Boc)-Rink Amide MBHA resin.

The dried resin was added to 20 mL of TFA/TIS/H2O (92/4/4) solution, the mixture was stirred for 2 hours, the resin was removed by filtration, and the resin was washed with 2 mL of TFA/TIS/H$_2$O (92/4/4) solution. The filtrates were combined, methyl tert-butyl ether (220 mL) was added to the filtrate, the resulting mixture was centrifuged at 3000 rpm for 1 minute, and the solid was washed twice with cold diethyl ether and drained. The obtained precipitate was dissolved in DMF and then eluted with a linear concentration gradient (10 minutes) at a flow rate of 25 mL/minute, and eluent A/B: 75/25-72/28 Use: eluent A: 0.05% TFA aqueous solution, eluent B: 0.05% TFA acetonitrile solution was applied on a preparative HPLC using Phenonenex, 10 μm, 110 columns (21.2×250 mm). The fractions containing the product were collected and lyophilized to give 20.2 mg of white solid respectively with a retention time of 13.11 min.

Embodiment 86

Preparation of Dodecanoyl-(NH-PEG5-CH$_2$CH$_2$S)-(4-thiol-butanoyl)-(D-Tyr)-Hyp-Asn-Thr-Phe-azaG-Leu-Arg(Me)-Trp-NH$_2$ (Compound YA-324)

1. g of commercially available Rink Amide MBHA resin (0.5 mmol/g) was swollen in DMF, and the resin was treated with 2 mL 20% piperidine/DMF for 20 minutes to remove Fmoc, repeated twice. The obtained resin was washed with DMF, 2.5 mL DMF solution of Fmoc-Trp (Boc)-OH (79 mg, 0.15 mmol), HBTU (57 mg, 0.15 mmol), HOBt (20 mg, 0.15 mmol) were added, then DIPEA (39 mg, 0.3 mmol) was added, the resin was treated at room temperature for 40 minutes, and the resin was washed with DMF to give Fmoc-Trp(Boc)-Rink Amide MBHA resin. The resin was treated with 2 mL 20% piperidine/DMF for 20 minutes to remove Fmoc, and the operation was repeated twice. The resin was washed with DMF, and Fmoc-Arg (Me, Pbf)-OH (97.3 mg, 0.15 mmol), HATU (57 mg, 0.15 mmol), HOAt (20 mg, 0.15 mmol) of 2.5 mL DMF solution, then DIPEA (39 mg, 0.3 mmol) was added, treated at room temperature for 1 hour, and the resin was washed with DMF to give Fmoc-Arg (Me, Pbf)-Trp (Boc)-rinkamide mbha resin. The resin was treated with 2 mL 20% piperidine/DMF for 20 minutes to remove Fmoc, and the operation was repeated twice. The resin was washed with DMF, and Fmoc-phe-azaGly-leu-oh (56 mg, 0.1 mmol), hatu (57 mg, 0.15 mmol), HOAt(20 mg, 0.15 mmol) of 2.5 mL DMF solution, then DIPEA (39 mg, 0.3 mmol) was added, treated at room temperature for 1 hour, and the resin was washed with DMF to give Fmoc-Phe-azaG-Leu-Arg(Me,Pbf)-Trp(Boc)-Rink Amide MBHA resin. In a similar manner, amino acids such as Thr(OtBu), Asn(Trt), Hyp(OtBu), D-Tyr(OtBu) and the like were sequentially introduced to give Fmoc-[D-Tyr (OtBu)]-Hyp(OtBu)-Asn(Trt)-Thr(OtBu)-Phe-azaG-Leu-Arg(Me, Pbf)-Trp(Boc)-Rink Amide MBHA resin. The resin was treated with 2 mL 20% piperidine/DMF for 20 minutes to remove Fmoc, and the operation was repeated twice. The resin was washed with DMF, and 4-(pyridin-2-yldisulfaneyl) butanoic Acid (34 mg, 0.15 mmol), HATU (57 mg, 0.15 mmol), HOAt (20 mg, 0.15 mmol) of 2.5 mL DMF solution, then DIPEA (39 mg, 0.3 mmol) was added, treated at room temperature for 2 hours, and the resin was washed with DMF. 4-(pyridin-2-yldisulfaneyl)butanoyl-NH-[D-Tyr (OtBu)]-Hyp(OtBu)-Asn(Trt)-Thr(OtBu)-Phe-azaG-Leu-Arg(Me, Pbf)-Trp(Boc)-Rink Amide MBHA resin was obtained. The obtained resin was added with 2.0 mL DMF solution of hydrochloride (33 mg, 0.1 mmol) of $_{NH2}$-PEG5-CH$_2$CH$_2$SH, treated at room temperature for 36 hours, and the resin was washed with DMF. NH$_2$-PEG5-CH$_2$CH$_2$S-(4-thiol-butanoyl)-NH-[D-Tyr(OtBu)]-Hyp (OtBu)-Asn(Trt)-Thr(OtBu)-Phe-azaG-Leu-Arg(Me, Pbf)-Trp(Boc)-Rink Amide MBHA resin was obtained. To the obtained resin, 2.5 mL DMF solution of lauric acid (30 mg, 0.15 mmol), HATU (57 mg, 0.15 mmol), HOAt (20 mg, 0.15 mmol) were added, then DIPEA (39 mg, 0.3 mmol) was added, the resin was treated at room temperature for 40 minutes, DMF, DCM, Methanol and methyl tert-butyl ether were washed and then drained to give Dodecanoyl-(NH-PEG5-CH$_2$CH$_2$S)—(4-thiol-butanoyl)-[D-Tyr(OtBu)]-Hyp(OtBu)-Asn(Trt)-Thr (OtBu)-Phe-azaG-Leu-Arg(Me, Pbf)-Trp(Boc)-Rink Amide resin.

The dried resin was added to 4 mL of TFA/TIS/phenol/H$_2$O (94/2/2/2) solution, the mixture was stirred for 2 hours, the resin was removed by filtration, and the resin was washed with 1 mL of TFA/TIS/phenol/H$_2$O (94/2/2/2) solution. The filtrates were pooled and added with methyl tert-butyl ether (50 mL), the resulting mixture was centrifuged at 3000 rpm for 1 minute, and the solid was washed twice with cold diethyl ether and drained. The obtained precipitate was dissolved in DMF and then eluted with a linear concentration gradient (11 minutes) at a flow rate of 25 mL/minute, and eluent A/B: 53/47-43/57 Use: eluent A: 0.05% TFA aqueous solution, eluent B: 0.05% TFA acetonitrile solution was applied on a preparative HPLC using Welch, 10 120 column (20×250 mm). Fractions containing the product were collected and lyophilized to give 2.7 mg of white solid.

Embodiment 87

Preparation of Dodecanoy-(NH-PEG5-CH2CH2S)-(maleimide-butanoyl-)-(D-Tyr)-Hyp-Asn-Thr-Phe-azaG-Leu-Arg(Me)-Trp-NH$_2$ (Compound YA-325)

0.3 g of commercially available Rink Amide MBHA resin (0.5 mmol/g) was swollen in DMF, and the resin was treated with 5 ml of 20% piperidine/DMF for 20 minutes to remove Fmoc, repeated twice. The obtained resin was washed with DMF, 5 mL DMF solution of Fmoc-Trp (Boc)-OH (237 mg, 0.45 mmol), HBTU (171 mg, 0.45 mmol), HOBt (61 mg, 0.45 mmol) were added, then DIPEA (116 mg, 0.9 mmol) was added, the resin was treated at room temperature for 40 minutes, and the resin was washed with DMF to give Fmoc-Trp(Boc)-Rink Amide MBHA resin. The resin was treated with 5 ml of 20% piperidine/DMF for 20 minutes to remove Fmoc, and the operation was repeated twice. The resin was washed with DMF and Fmoc-Arg (Me, Pbf)-OH (199 mg, 0.3 mmol), HATU (114 mg, 0.3 mmol), HOAt (41 mg, 0.3 mmol) of 5 mL DMF solution, then DIPEA (77 mg, 0.6 mmol) was added and treated at room temperature for 1 hour. The resin was washed with DMF to give Fmoc-Arg (Me, Pbf)-Trp (Boc)-rinkamide mbha resin. The resin was treated with 5 ml of 20% piperidine/DMF for 20 minutes to remove Fmoc, and the operation was repeated twice. The resin was washed with DMF, and Fmoc-Phe-azaG-Leu-OH (168 mg, 0.3 mmol), Hatu (114 mg, 0.3 mmol), HOAt (41 mg, 0.3 mmol) of 5 mL DMF solution, then DIPEA (77 mg, 0.6 mmol) was added, treated at room temperature for 1 hour, and the resin was washed with DMF to give Fmoc-Phe-azaG-Leu-Arg(Me,Pbf)-Trp(Boc)-Rink Amide MBHA resin. In a similar manner, amino acids such as Thr(OtBu), Asn(Trt), Hyp(OtBu), D-Tyr(OtBu) and the like were sequentially introduced to give Fmoc-[D-Tyr(OtBu)]-Hyp (OtBu)-Asn(Trt)-Thr(OtBu)-Phe-azaG-Leu-Arg(Me, Pbf)-Trp(Boc)-Rink Amide MBHA resin. The resin was treated with 5 ml of 20% piperidine/DMF for 20 minutes to remove Fmoc, and the operation was repeated twice. The resin was washed with DMF, and 4-maleimidobutyric acid (82 mg, 0.45 mmol), Hatu (171 mg, 0.45 mmol), HOAt (61 mg, 0.45 mmol) of 5 mL DMF solution, then DIPEA (116 mg, 0.9 mmol) was added, treated at room temperature for 40 minutes, and the resin was washed with DMF to give 4-Maleimide-butanoyl-NH-[D-Tyr(OtBu)]-Hyp(OtBu)-Asn (Trt)-Thr(OtBu)-Phe-azaG-Leu-Arg(Me, Pbf)-Trp(Boc)-Rink Amide MBHA resin. The obtained resin was added with 5.0 mL DMF solution of hydrochloride (99 mg, 0.3 mmol) of $NH_2$-PEG5-$CH_2CH_2$SH, treated at room temperature for 16 hours, and the resin was washed with DMF. $NH_2$-PEG5-$CH_2CH_2$S-(4-maleimide-butanoyl)-NH-[D-Tyr (OtBu)]-Hyp(OtBu)-Asn(Trt)-Thr(OtBu)-Phe-azaG-Leu-Arg(Me, Pbf)-Trp (Boc)-Rink Amide MBHA resin was obtained. The obtained resin was added with 5 mL DMF solution of Dodecanoic Acid (90 mg, 0.45 mmol), Hatu (171 mg, 0.45 mmol) and HOAt (61 mg, 0.45 mmol), then DIPEA (116 mg, 0.9 mmol) was added and treated at room temperature for 1 hour. The resin was washed with DMF, DCM, methanol and methyl tert-butyl ether, and then drained to give Dodecanoyl-(NH-PEG5-CH2 CH2 S)-(4-maleimide-butanoyl)-[D-Tyr(OtBu)]-Hyp(OtBu)-Asn(Trt)-Thr(OtBu)-Phe-azaGly-Leu-Arg(Me, Pbf)-Trp(Boc)-Rink Amide MBHA resin.

The dried resin was added to 10 mL of TFA/TIS/phenol/$H_2O$ (94/2/2/2) solution, the mixture was stirred for 2 hours, the resin was removed by filtration, and the resin was washed with 2 mL of TFA/TIS/phenol/$H_2O$ (94/2/2/2) solution. The filtrates were combined, methyl tert-butyl ether (120 mL) was added to the filtrate, the resulting mixture was centrifuged at 3000 rpm for 1 minute, and the solid was washed twice with cold diethyl ether and drained. The obtained precipitate was dissolved in DMF and then eluted with a linear concentration gradient (11 minutes) at a flow rate of 25 mL/minute, and eluent A/B: 58/42-48/52 using eluent A: 0.05% TFA aqueous solution, eluent B: 0.05% TFA acetonitrile solution was applied on a preparative HPLC using XTIMATE, 10 μm, 120 columns (20 mm×250 mm). The fractions containing the product were collected and lyophilized to give 11.6 mg of white solid.

Embodiment 88

Preparation of Dodecanoyl-NH-PEG5-1,2,3-Triazole-Cyclic-Butanoyl-(D-Tyr)-Hyp-Asn-Thr-Phe-Azag-Leu-Arg(Me)-Trp-$NH_2$ (Compound YA-326)

1. g of commercially available Rink Amide MBHA resin (0.5 mmol/g) was swollen in DMF, and the resin was treated with 5 ml of 20% piperidine/DMF for 20 minutes to remove Fmoc, repeated twice. The obtained resin was washed with DMF, 5 mL DMF solution of Fmoc-Trp (Boc)-OH (237 mg, 0.45 mmol), HBTU (171 mg, 0.45 mmol), HOBt (61 mg, 0.45 mmol) were added, then DIPEA (116 mg, 0.9 mmol) was added, the resin was treated at room temperature for 40 minutes, and the resin was washed with DMF to give Fmoc-Trp(Boc)-Rink Amide MBHA resin. The resin was treated with 5 ml of 20% piperidine/DMF for 20 minutes to remove Fmoc, and the operation was repeated twice. The resin was washed with DMF and Fmoc-Arg (Me, Pbf)-OH (199 mg, 0.3 mmol), HATU (114 mg, 0.3 mmol), HOAt (41 mg, 0.3 mmol) of 5 mL DMF solution, then DIPEA (77 mg, 0.6 mmol) was added and treated at room temperature for 1 hour. The resin was washed with DMF to give Fmoc-Arg (Me,Pbf)-Trp(Boc)-Rink Amide MBHA resin. The resin was treated with 5 ml of 20% piperidine/DMF for 20 minutes to remove Fmoc, and the operation was repeated twice. The resin was washed with DMF, and Fmoc-Phe-Azag-Leu-OH (168 mg, 0.3 mmol), Hatu (114 mg, 0.3 mmol), HOAt (41 mg, 0.3 mmol) of 5 mL DMF solution, then DIPEA (77 mg, 0.6 mmol) was added, treated at room temperature for 1 hour, and the resin was washed with DMF to give Fmoc-Phe-azaGly-Leu-Arg(Me,Pbf)-Trp(Boc)-Rink Amide MBHA resin. In a similar manner, amino acids such as Thr(OtBu), Asn(Trt), Hyp(OtBu), D-Tyr(OtBu) and the like were sequentially introduced to give Fmoc-[D-Tyr(OtBu)]-Hyp (OtBu)-Asn(Trt)-Thr(OtBu)-Phe-azaG-Leu-Arg(Me, Pbf)-Trp(Boc)-Rink Amide MBHA resin. The resin was treated with 5 ml of 20% piperidine/DMF for 20 minutes to remove Fmoc, and the operation was repeated twice. The resin was washed with DMF, and Dodecanoyl-NH-PEG5-1,2,3-Triazole OLE-Cyclic-Butanoyl Acid (126 mg, 0.22 mmol), Hatu (171 mg, 0.45 mmol), HOAt (61 mg, 0.45 mmol) in 5 mL DMF solution, then DIPEA (116 mg, 0.9 mmol) was added, treated at room temperature for 2 hours, the resin was washed with DMF, DCM, methanol and methyl tert-butyl ether, and then drained to give Dodecanoyl-NH-PEG5-1,2,3-Triazole-cyclic-butanoyl-[D-Tyr (OtBu)]-Hyp(OtBu)-Asn(Trt)-Thr(OtBu)-Phe-azaG-Leu-Arg(Me, Pbf)-Trp(Boc)-Rink Amide MBHA resin.

The dried resin was added to 10 mL of TFA/TIS/phenol/$H_2O$ (94/2/2/2) solution, the mixture was stirred for 2 hours, the resin was removed by filtration, and the resin was washed with 2 mL of TFA/TIS/phenol/$H_2O$ (94/2/2/2) solution. The filtrates were combined, methyl tert-butyl ether (120 mL) was added to the filtrate, the resulting mixture was centrifuged at 3000 rpm for 1 minute, and the solid was washed twice with cold diethyl ether and drained. The obtained precipitate was dissolved in DMF and then eluted with a linear concentration gradient (11 minutes) at a flow rate of 25 mL/minute, and eluent A/B: 59/41-49/51 using eluent A: 0.05% TFA aqueous solution, eluent B: 0.05% TFA acetonitrile solution was applied on a preparative HPLC using XTIMATE, 10 μm and 120 columns (20×250 mm). Fractions containing the product were collected and lyophilized to give 15.5 mg of white solid.

Embodiment 89

Preparation of Ac-(D-Phe(2,4-DiCl))-HoPro-Asn-Thr-Phe-ψ(NHCO)Gly-Leu-Arg(Me)-Trp-$NH_2$ (Compound YA-332)

0.2 g of commercially available Rink Amide MBHA resin (0.5 mmol/g) was swollen in DMF, and the resin was treated with 3 ml of 20% piperidine/DMF for 20 minutes to remove Fmoc, repeated twice. The obtained resin was washed with DMF, 2.5 mL DMF solution of Fmoc-Trp (Boc)-OH (158 mg, 0.3 mmol), HATU (114 mg, 0.3 mmol), HOAt (27 mg, 0.3 mmol) was added, then DIPEA (78 mg, 0.6 mmol) was added, the resin was treated at room temperature for 40 minutes, and the resin was washed with DMF to give Fmoc-Trp(Boc)-Rink Amide MBHA resin. The resin was treated with 3 ml of 20% piperidine/DMF for 20 minutes to remove Fmoc, and the operation was repeated twice. The resin was washed with DMF, and 2.5 mL DMF solution of Fmoc-Arg (Me, Pbf)-OH (80 mg, 0.12 mmol) and DIC (19 mg, 0.15 mmol) was added. The resin was treated at room temperature for 16 hours, and the resin was washed with DMF to give Fmoc-Arg (Me, Pbf)-Trp (Boc)-Rink Amide MBHA resin. The resin was treated with 3 ml of 20% piperidine/DMF for 20 minutes to remove Fmoc, and the operation was repeated twice. The resin was washed with DMF, and Fmoc-Phe-Ψ (NHCO) Gly-Leu-OH (87 mg, 0.15 mmol), HATU (114 mg, 0.3 mmol), HOAt (27 mg, 0.3 mmol) of 2.5 mL DMF solution, then DIPEA (78 mg, 0.6 mmol) was added, treated at room temperature for 1 hour, and the resin was washed with DMF to give Fmoc-Phe-ψ (NHCO)Gly-Leu-Arg(Me,Pbf)-Trp(Boc)-Rink Amide MBHA resin. In a similar manner, amino acids such as Thr(tBu), Asn(Trt), HoPro, D-Phe(2,4-DiCl) and the like were introduced in sequence to give Fmoc-[D-Phe(2,4-DiCl)]-HoPro-Asn(Trt)-Thr(tBu)-Phe-ψ(NHCO)Gly-Leu-Arg(Me, Pbf)-Trp(Boc)-Rink Amide MBHA resin. The resin was treated with 3 ml of 20% piperidine/DMF for 20 minutes to remove Fmoc, and the operation was repeated twice. The resin was washed with DMF, and a 2.5 mL DMF solution of AcOH (18 mg, 0.3 mmol), DIC (38 mg, 0.3 mmol) and HOBt (41 mg, 0.3 mmol) was added to react overnight at room temperature to introduce AC groups. The resin was washed with DMF, DCM, methanol and methyl tert-butyl ether, and then drained to finally obtain Ac[D-Phe (2,4-DiCl)]-HoPro-Asn(Trt)-Thr(tBu)-Phe-ψ(NHCO)Gly-Leu-Arg(Me, Pbf)-Trp(Boc)-Rink Amide MBHA resin.

The dried resin was added to 4 mL of TFA/TIS/phenol/H$_2$O (94/2/2/2) solution, the mixture was stirred for 2 hours, the resin was removed by filtration, and the resin was washed with 1 mL of TFA/TIS/phenol/H$_2$O (94/2/2/2) solution. The filtrates were pooled and added with methyl tert-butyl ether (50 mL), the resulting mixture was centrifuged at 3000 rpm for 1 minute, and the solid was washed twice with cold diethyl ether and drained. The obtained precipitate was dissolved in DMF and then eluted with a linear concentration gradient (10 minutes) at a flow rate of 25 mL/minute, and eluent A/B: 63/37-53/47 using eluent A: 0.05% TFA aqueous solution, eluent B: 0.05% TFA acetonitrile solution was applied on a preparative HPLC using Utimate, 10 μm, 120 column (21.2×250 mm). Fractions containing the product were collected and lyophilized to give 9.0 mg of white solid.

Embodiment 90

Preparation of Ac-[3-(2-furyl)-D-Ala]-HoPro-Asn-Thr-Phe-ψ(NHCO) Gly-Leu-Arg(Me)-Trp-NH$_2$ (Compound YA-333)

0.2 g of commercially available Rink Amide MBHA resin (0.5 mmol/g) was swollen in DMF, and the resin was treated with 3 ml of 20% piperidine/DMF for 20 minutes to remove Fmoc, repeated twice. The obtained resin was washed with DMF, 2.5 mL DMF solution of Fmoc-Trp (Boc)-OH (158 mg, 0.3 mmol), HATU (114 mg, 0.3 mmol), HOAt (27 mg, 0.3 mmol) were added, then DIPEA (78 mg, 0.6 mmol) was added, the resin was treated at room temperature for 40 minutes, and the resin was washed with DMF to give Fmoc-Trp(Boc)-Rink Amide MBHA resin. The resin was treated with 3 ml of 20% piperidine/DMF for 20 minutes to remove Fmoc, and the operation was repeated twice. The resin was washed with DMF, and 2.5 mL DMF solution of Fmoc-Arg (Me, Pbf)-OH (80 mg, 0.12 mmol) and DIC (19 mg, 0.15 mmol) was added. The resin was treated at room temperature for 16 hours, and the resin was washed with DMF to give Fmoc-Arg (Me, Pbf)-Trp (Boc)-Rink Amide MBHA resin. The resin was treated with 3 ml of 20% piperidine/DMF for 20 minutes to remove Fmoc, and the operation was repeated twice. The resin was washed with DMF, and Fmoc-Phe-Ψ (NHCO) Gly-Leu-OH (87 mg, 0.15 mmol), HATU (114 mg, 0.3 mmol), HOAt (27 mg, 0.3 mmol) of 2.5 mL DMF solution, then DIPEA (78 mg, 0.6 mmol) was added, treated at room temperature for 1 hour, and the resin was washed with DMF to give Fmoc-Phe-Ψ (NHCO) Gly-Leu-Arg (Me, Pbf)-Trp (Boc)-Rink Amide MBHA resin. In a similar manner, amino acids such as Thr (OtBu), Asn (Trt), Ho Pro, 3-(2-furyl)-D-Alanine, etc. were introduced in sequence to give Fmoc-[3-(2-furyl)-D-Ala]-Ho Pro-Asn (Trt)-Thr (OtBu)-Phe-Ψ (NHCO) Gly-Leu-Arg (Me, Pbf)-Trp (Boc)-Rink Amide MBHA resin. The resin was treated with 3 ml of 20% piperidine/DMF for 20 minutes to remove Fmoc, and the operation was repeated twice. The resin was washed with DMF, and 2.5 mL DMF solution of AcOH (18 mg, 0.3 mmol), DIC (38 mg, 0.3 mmol) and HOBt (41 mg, 0.3 mmol) were added to react overnight at room temperature to introduce Ac groups. The resin was washed with DMF, DCM, methanol and methyl tert-butyl ether, and then drained to finally give Ac-[3-(2-furyl)-D-Ala]-Ho Pro-Asn (Trt)-Thr (OTBU)-Phe-Ψ (nhco) Gly-Leu-Arg (Me, Pbf)-Trp (Boc)-Rink Amide MBHA resin.

The dried resin was added to 4 mL of TFA/TIS/phenol/H$_2$O (94/2/2/2) solution, the mixture was stirred for 2 hours, the resin was removed by filtration, and the resin was washed with 1 mL of TFA/TIS/phenol/H$_2$O (94/2/2/2) solution. The filtrates were combined, methyl tert-butyl ether (50 mL) was added to the filtrate, the resulting mixture was centrifuged at 3000 rpm for 1 minute, and the solid was washed twice with cold diethyl ether and drained. The obtained precipitate was dissolved in DMF and then eluted with a linear concentration gradient (10 minutes) at a flow rate of 25 mL/minute, and eluent A/B: 69/31-59/41 using: eluent A: 0.05% TFA aqueous solution, eluent B: 0.05% TFA acetonitrile solution was applied on a preparative HPLC using Ultimate C8, 10 μm, 120 column (21.2 mm×250 mm). Fractions containing the product were collected and lyophilized to give 5.9 mg of white solid.

Embodiment 91

Preparation of Ac-[D-Phe (2,4-DiCl)]-DiFluoroPro-Asn-Thr-Phe-Ψ (NHCO) Gly-Leu-Arg(Me)-Trp-NH$_2$ (Compound YA-334)

0.2 g of commercially available Rink Amide MBHA resin (0.5 mmol/g) was swollen in DMF, and the resin was treated with 3 ml of 20% piperidine/DMF for 20 minutes to remove Fmoc, repeated twice. The obtained resin was washed with DMF, 2.5 mL DMF solution of Fmoc-Trp (Boc)-OH (158 mg, 0.3 mmol), HATU (114 mg, 0.3 mmol), HOAt (27 mg, 0.3 mmol) were added, then DIPEA (78 mg, 0.6 mmol) was added, the resin was treated at room temperature for 40 minutes, and the resin was washed with DMF to give Fmoc-Trp(Boc)-Rink Amide MBHA resin. The resin was treated with 3 ml of 20% piperidine/DMF for 20 minutes to remove Fmoc, and the operation was repeated twice. The resin was washed with DMF, and 2.5 mL DMF solution of Fmoc-Arg (Me, Pbf)-OH (80 mg, 0.12 mmol) and DIC (19 mg, 0.15 mmol) were added. The resin was treated at room temperature for 16 hours, and the resin was washed with DMF to give Fmoc-Arg (Me, Pbf)-Trp (Boc)-Rink Amide MBHA resin. The resin was treated with 3 ml of 20% piperidine/DMF for 20 minutes to remove Fmoc, and the operation was repeated twice. The resin was washed with DMF, and Fmoc-Phe-Ψ (NHCO) Gly-Leu-OH (87 mg, 0.15 mmol), HATU (114 mg, 0.3 mmol), HOAt (27 mg, 0.3 mmol) of 2.5 mL DMF solution, then DIPEA (78 mg, 0.6 mmol) was added, treated at room temperature for 1 hour, and the resin was washed with DMF to give Fmoc-Phe-Ψ (nhco) Gly-leu-Arg (Me, Pbf)-Trp (Boc)-rinkamide mbha resin. In a similar manner, amino acids such as Thr (OtBu), Asn (Trt), Difluoro, D-Phe (2,4-DiCl) and the like were introduced in sequence to give Fmoc-(D-Phe (2,4-DiCl))-Difluoro-Asn (Trt)-Thr (OtBu)-PhE-Ψ (NHCO) Gly-Leu-Arg (Me, Pbf)-Trp (Boc)-Rink amide MBHA resin. The resin was treated with 3 ml of 20% piperidine/DMF for 20 minutes to remove Fmoc, and the operation was repeated twice. The resin was washed with DMF, and a 2.5 mL DMF solution of AcOH (18 mg, 0.3 mmol), DIC (38 mg, 0.3 mmol) and HOBt (41 mg, 0.3 mmol) were added to react overnight at room temperature to introduce Ac groups. The resin was washed with DMF, DCM, methanol and methyl tert-butyl ether, and then drained to finally give Ac-[D-Phe (2,4-diCl)]-DiFluoroPro-Asn(Trt)-Thr(OtBu)-Phe-ψ (NHCO)Gly-Leu-Arg(Me, Pbf)-Trp(Boc)-Rink Amide MBHA resin.

The dried resin was added to 4 mL of TFA/TIS/phenol/ $H_2O$ (94/2/2/2) solution, the mixture was stirred for 2 hours, the resin was removed by filtration, and the resin was washed with 1 mL of TFA/TIS/phenol/$H_2O$ (94/2/2/2) solution. The filtrates were combined, methyl tert-butyl ether (50 mL) was added to the filtrate, the resulting mixture was centrifuged at 3000 rpm for 1 minute, and the solid was washed twice with cold diethyl ether and drained. The obtained precipitate was dissolved in DMF and then eluted with a linear concentration gradient (10 minutes) at a flow rate of 25 mL/minute. Eluent A/B: 64/36-54/46 Use: Elution A: 0.05% TFA aqueous solution, eluent B: 0.05% TFA acetonitrile solution was applied on a preparative HPLC using welche C8, 10 μm, 120 column (20.0 mm×250 mm). Fractions containing the product were collected and lyophilized to give 16.1 mg of white solid.

Embodiment 92

Preparation of Dodecanoyl-(NH-PEG5-)-(1,2,3-Triazole-cyclic-butanoyl)-(D-Tyr)-Hyp-Asn-Thr-Phe-ψ (NHCS)Gly-Leu-Arg(Me)-Trp-NH$_2$ (Compound YA-348)

3.13 g of commercially available Rink Amide MBHA resin (0.32 mmol/g) was swollen in DMF, and the resin was treated with 30 mL 20% piperidine/DMF for 20 minutes to remove Fmoc, repeated twice. The resulting resin was washed with DMF, and 30 mL DMF solution of Fmoc-Trp (Boc)-OH (1.58 g, 3.0 mmol), HATU (1.14 g, 3.0 mmol), HOAt (410 mg, 3.0 mmol) were added, followed by DIPEA (774 mg, 6.0 mmol). Treatment was carried out at room temperature for 40 minutes, and Trp(Boc) was introduced thereto to give Fmoc-Trp(Boc)-Rink Amide MBHA resin. The resin was treated with 30 mL 20% piperidine/DMF for 20 minutes to remove Fmoc, repeated twice. The resulting resin was washed with DMF, and 30 mL DMF solution of Fmoc-Arg (Me, Pbf)-OH (1.99 g, 3.0 mmol), HATU (1.14 g, 3.0 mmol), HOAt (410 mg, 3.0 mmol) were added, followed by DIPEA (774 mg, 6.0 mmol). After treatment at room temperature for 1 hour, the resin was washed with DMF to give Fmoc-Arg (Me, Pbf)-Trp (Boc)-Rink Amide MBHA resin. Other amino acids Fmoc-Phe-ψ(NHCS)Gly-Leu-OH, Fmoc-Thr(OtBu)—OH, Fmoc-Asn(Trt)-OH, Fmoc-Hyp (OtBu)—OH, Fmoc-D-Tyr(OtBu)—OH] were introduced in a similar manner. Fmoc-[D-Tyr(OtBu)]-Hyp(OtBu)-Asn (Trt)-Thr(OtBu)-Phe-ψ(NHC S)Gly-Leu-Arg(Me)-Trp (Boc)-Rink Amide resin was obtained. The resin was treated with 30 mL 20% piperidine/DMF for 20 minutes to remove Fmoc, repeated twice. The resin was washed with DMF, and Dodecanoyl-(NH-PEG5-)-(1,2,3-Triazole Olecycline-Butanoyl-OH (688 mg, 1.2 mmol), HATU (456 mg, 1.2 mmol), HOAt (163 mg, 1.2 mmol) of 30 mL DMF solution, then DIPEA (310 mg, 2.4 mmol) was added and treated at room temperature for 40 minutes. The resin was washed with DMF, DCM, methanol and methyl tert-butyl ether and then drained to give Dodecanoyl-(NH-PEG5-)-(1,2,3-Triazole cyclic-butanoyl-[D-Tyr(OtBu)]-Hyp(OtBu)-Asn(Trt)-Thr (OtBu)-Phe-ψ(NHC S)Gly-Leu-Arg(Me)-Trp(Boc)-Rink Amide MBHA resin.

The dried resin was added to 40 mL of TFA/TIS/$H_2O$ (92/4/4) solution, the mixture was stirred for 2 hours, the resin was removed by filtration, and the resin was washed with 5 mL of TFA/TIS/$H_2O$ (92/4/4) solution. The filtrates were combined, methyl tert-butyl ether (450 mL) was added to the filtrate, the resulting mixture was centrifuged at 3000 rpm for 1 minute, and the solid was washed twice with cold diethyl ether and drained. The obtained precipitate was dissolved in DMF and then eluted with a linear concentration gradient (10 minutes) at a flow rate of 25 mL/minute. Eluent A/B: 62/38-52/48 Use: Elution A: 0.05% TFA aqueous solution, eluent B: 0.05% TFA acetonitrile, on preparative HPLC, SunFire 10 U, 110 column (19×250 mm) was used. The fractions containing the product were collected and lyophilized to give 120 mg of white solid.

Embodiment 93

Preparation of Ac-(D-Tyr)-Hyp-Asn-Thr-Phe-Alg-Gly-Leu-Arg(Me)-Trp-NH$_2$ (Compound YA-350)

625 mg of commercially available Rink Amide MBHA resin (0.32 mmol/g) was swollen in DMF, and the resin was treated with 10 mL 20% piperidine/DMF for 20 minutes to remove Fmoc, repeated twice. The obtained resin was washed with DMF, 10 mL DMF solution of Fmoc-Trp (Boc)-OH (316 mg, 0.6 mmol), HATU (228 mg, 0.6 mmol), HOAt (82 mg, 0.6 mmol) were added, and then DIPEA (155 mg, 1.2 mmol) was added. Treatment was carried out at room temperature for 40 minutes, and Trp(Boc) was introduced thereto to give Fmoc-Trp(Boc)-Rink Amide MBHA resin. The resin was treated with 10 mL 20% piperidine/ DMF for 20 minutes to remove Fmoc, repeated twice. The obtained resin was washed with DMF, 10 mL DMF solution of Fmoc-Arg (Me, Pbf)-OH (199 mg, 0.3 mmol), HATU (114 mg, 0.3 mmol), HOAt (41 mg, 0.3 mmol) were added, and then DIPEA (77 mg, 0.6 mmol) was added. After treatment at room temperature for 1 hour, the resin was washed with DMF to give Fmoc-Arg (Me, Pbf)-Trp (Boc)-Rink Amide MBHA resin. Other amino acids Fmoc-Leu- OH, Fmoc-Alg-OH, Fmoc-Phe-OH, Fmoc-Thr(OtBu)—OH, Fmoc-Asn (Trt)-OH, Fmoc-Hyp(OtBu)—OH, Fmoc-D-Tyr(OtBu)—OH were introduced in a similar manner. Fmoc-[D-Tyr(OtBu)]-Hyp(OtBu)-Asn(Trt)-Thr(OtBu)-Phe-Alg-Gly-Leu-Arg(Me)-Trp(Boc)-Rink Amide resin was obtained. The resin was treated with 10 mL 20% piperidine/DMF for 20 minutes to remove Fmoc, repeated twice. The resin was washed with DMF, 10 mL DMF solution of glacial acetic acid (72 mg, 1.2 mmol), HBTU (454 mg, 1.2 mmol), HOBt (162 mg, 1.2 mmol) were added, then DIPEA (310 mg, 2.4 mmol) was added, the resin was treated at room temperature for 40 minutes, DMF, DCM, Methanol and methyl tert-butyl ether were washed and then drained to give Ac-[D-Tyr(OtBu)]-Hyp(OtBu)-Asn(Trt)-Thr(OtBu)-Phe-Alg-Leu-Arg(Me)-Trp(Boc)-Rink Amide MBHA resin.

The dried resin was added to 10 mL of TFA/TIS/$H_2O$ (92/4/4) solution, the mixture was stirred for 2 hours, the resin was removed by filtration, and the resin was washed with 1 mL of TFA/TIS/$H_2O$ (92/4/4) solution. The filtrates were combined, methyl tert-butyl ether (110 mL) was added to the filtrate, the resulting mixture was centrifuged at 3000 rpm for 1 minute, and the solid was washed twice with cold diethyl ether and drained. The obtained precipitate was dissolved in DMF and then eluted with a linear concentration gradient (10 minutes) at a flow rate of 25 mL/minute, and eluent A/B: 75/25-65/35 using eluent A: 0.05% TFA aqueous solution, eluent B: 0.05% TFA acetonitrile solution was applied onto a preparative HPLC, SUNFARE 10 μm, 110 column (19×250 mm) was used. The fractions containing the product were collected and lyophilized to give 32.7 mg of white solid.

Embodiment 94

Preparation of Palm-PEG 8-(D-Tyr)-Hyp-Asn-Thr-Phe-Alg-Gly-Leu-Arg (Me)-Trp-$NH_2$ (Compound YA-360)

625 mg of commercially available Rink Amide MBHA resin (0.32 mmol/g) was swollen in DMF, and the resin was treated with 10 mL 20% piperidine/DMF for 20 minutes to remove Fmoc, repeated twice. The obtained resin was washed with DMF, 10 mL DMF solution of Fmoc-TRP (Boc)-OH (316 mg, 0.6 mmol), HATU (228 mg, 0.6 mmol), HOAt (82 mg, 0.6 mmol) were added, and then DIPEA (155 mg, 1.2 mmol) was added. Treatment was carried out at room temperature for 40 minutes, and Trp(Boc) was introduced thereto to give Fmoc-Trp(Boc)-Rink Amide MBHA resin. The resin was treated with 10 mL 20% piperidine/DMF for 20 minutes to remove Fmoc, repeated twice. The obtained resin was washed with DMF, 10 mL DMF solution of Fmoc-Arg (Me, Pbf)-OH (199 mg, 0.3 mmol), HATU (114 mg, 0.3 mmol), HOAt (41 mg, 0.3 mmol) was added, and then DIPEA (77 mg, 0.6 mmol) was added. After treatment at room temperature for 1 hour, the resin was washed with DMF to give Fmoc-Arg (Me, PBF)-Trp (Boc)-Rink Amide MBHA resin. Other amino acids Fmoc-Leu-OH, Fmoc-Alg-OH, Fmoc-Phe-OH, Fmoc-Thr(OtBu)—OH, Fmoc-Asn(Trt)-OH, Fmoc-Hyp(OtBu)—OH, Fmoc-D-Tyr(OtBu)—OH, PEG 8 were introduced in a similar manner. Fmoc-PEG8-[D-Tyr(OtBu)]-Hyp(OtBu)-Asn(Trt)-Thr(OtBu)-Phe-Alg-Gly-Leu-Arg(Me)-Trp(Boc)-Rink Amide MBHA resin was obtained. The resin was treated with 10 mL 20% piperidine/DMF for 20 minutes to remove Fmoc, repeated twice. The resin was washed with DMF, 10 mL DMF solution of hexadecanoic acid (154 mg, 0.6 mmol), HBTU (228 mg, 0.6 mmol), HOBt (82 mg, 0.6 mmol) were added, then DIPEA (155 mg, 1.2 mmol) was added, the resin was treated at room temperature for 40 minutes, DMF, DCM, Methanol and methyl tert-butyl ether were washed and then drained to give Palm-PEG8-[D-Tyr (OtBu)]-Hyp(OtBu)-Asn(Trt)-Thr(OtBu)-Phe-Alg-Leu-Arg (Me)-Trp(Boc)-Rink Amide MBHA resin.

The dried resin was added to 10 mL of TFA/TIS/$H_2O$ (92/4/4) solution, the mixture was stirred for 2 hours, the resin was removed by filtration, and the resin was washed with 1 mL of TFA/TIS/$H_2O$ (92/4/4) solution. The filtrates were combined, methyl tert-butyl ether (110 mL) was added to the filtrate, the resulting mixture was centrifuged at 3000 rpm for 1 minute, and the solid was washed twice with cold diethyl ether and drained. The obtained precipitate was dissolved in DMF and then eluted with a linear concentration gradient (10 minutes) at a flow rate of 25 mL/minute, and eluent A/B: 50/50-40/60 using eluent A: 0.05% TFA aqueous solution, eluent B: 0.05% TFA acetonitrile solution was applied on a preparative HPLC using Phenonenex 10 μm, 110 columns (21.2×250 mm). The fractions containing the product were collected and lyophilized to give 28.5 mg of white solid.

Embodiment 95

Preparation of Hexadecyl-1,2,3-Triazole-PEG 8-Gly-Gly-(D-Tyr)-Hyp-Asn-Thr-Phe-Azag-Leu-Arg(Me)-Trp-$NH_2$ (Compound YA-367)

1.0 g of commercially available Rink Amide MBHA resin (0.31 mmol/g) was swollen in DMF, and the resin was treated with 10 mL 20% piperidine/DMF for 20 minutes to remove Fmoc, repeated twice. The obtained resin was washed with DMF, 10 mL DMF solution of Fmoc-Trp (Boc)-OH (474 mg, 0.9 mmol), HATU (342 mg, 0.9 mmol), HOAt (113 mg, 0.9 mmol) were added, then DIPEA (232 mg, 1.8 mmol) was added, the resin was treated at room temperature for 40 minutes, and the resin was washed with DMF to give Fmoc-Trp(Boc)-Rink Amide MBHA resin. The resin was treated with 10 ml of 20% piperidine/DMF for 20 minutes to remove Fmoc, and the operation was repeated twice. The resin was washed with DMF, and a 10 mL DMF solution of Fmoc-Arg (Me, Pbf)-OH (239 mg, 0.36 mmol) and DIC (57 mg, 0.45 mmol) were added. The resin was treated at room temperature for 16 hours, and the resin was washed with DMF to give Fmoc-Arg (Me, Pbf)-Trp (Boc)-Rink Amide MBHA resin. The resin was treated with 10 mL 20% piperidine/DMF for 20 minutes to remove Fmoc, and the operation was repeated twice. The resin was washed with DMF, and Fmoc-Phe-azaG-Leu-OH (251 mg, 0.45 mmol), HATU (171 mg, 0.45 mmol), HOAt (57 mg, 0.45 mmol) of 10 mL DMF solution, then DIPEA (116 mg, 0.9 mmol) was added, treated at room temperature for 1 hour, and the resin was washed with DMF to give Fmoc-Phe-azaG-Leu-Arg (Me, Pbf)-Trp(Boc)-Rink Amide MBHA resin. Other amino acids were sequentially introduced into Fmoc-Thr(OtBu)—OH, Fmoc-Asn(Trt)-OH, Fmoc-Hyp(OtBu)—OH, Fmoc-D-Tyr (OtBu)—OH, Fmoc-Gly-OH, Fmoc-Gly-OH and other amino acids in a similar manner. Fmoc-Gly-Gly-[D-Tyr (OtBu)]-Hyp(OtBu)-Asn(Trt)-Thr(OtBu)-Phe-azaG-Leu-Arg(Me,Pbf)-Trp(Boc)-Rink Amide MBHA resin was obtained. The resin was treated with 10 mL 20% piperidine/DMF for 20 minutes to remove Fmoc, repeated twice. The obtained resin was washed with DMF, 10 mL DMF solution of Hexadecyl-1,2,3-Triazole OLE-PEG 8-OH (300 mg, 0.418 mmol), HATU (159 mg, 0.418 mmol), HOAT (53 mg, 0.418 mmol) was added, then DIPEA (108 mg, 0.836 mmol)

was added, and treated at room temperature for 60 minutes. The resin was washed with DMF, methanol and methyl tert-butyl ether in sequence, and then drained to finally give Hexadecyl-1,2,3-Triazole-PEG8-Gly-Gly-[D-Tyr(OtBu)]-Hyp(OtBu)-Asn(Trt)-Thr(OtBu)-Phe-azaG-Leu-Arg(Me, Pbf)-Trp (Boc)-Rink Amide MBHA resin.

The above dried resin was added to 10 mL of TFA/TIS/phenol/H$_2$O (94/2/2/2) solution, the mixture was stirred for 2 hours, the resin was removed by filtration, and the resin was washed with 1 mL of TFA/TIS/phenol/H$_2$O (94/2/2/2) solution. The filtrates were combined, methyl tert-butyl ether (110 mL) was added to the filtrate, the resulting mixture was centrifuged at 3000 rpm for 1 minute, and the solid was washed twice with cold diethyl ether and drained. The obtained precipitate was dissolved in DMF and then eluted with a linear concentration gradient (10 minutes) at a flow rate of 25 mL/minute, and eluent A/B: 41/59-32/68 using Elution A: 0.05% TFA aqueous solution, eluent B: 0.05% TFA acetonitrile solution was applied on a preparative HPLC using Phenomenex C18 column (21.2 mm×250 mm). Fractions containing the product were collected and lyophilized to give 70.2 mg of white solid.

Embodiment 96

Preparation of Hexadecyl-S-maleimide-PEG8-Gly-Gly-(D-Tyr)-Hyp-Asn-Thr-Phe-azaG-Leu-Arg(Me)-Trp-NH$_2$ (Compound YA-368)

650 mg of commercially available Rink Amide MBHA resin (0.31 mmol/g) was swollen in DMF, and the resin was treated with 6 ml of 20% piperidine/DMF for 20 minutes to remove Fmoc, repeated twice. The obtained resin was washed with DMF, 6 mL DMF solution of Fmoc-Trp (Boc)-OH (316 mg, 0.6 mmol), HATU (228 mg, 0.6 mmol), HOAt (76 mg, 0.6 mmol) were added, then DIPEA (155 mg, 1.2 mmol) was added, the resin was treated at room temperature for 40 minutes, and the resin was washed with DMF to give Fmoc-Trp(Boc)-Rink Amide MBHA resin. The resin was treated with 6 ml of 20% piperidine/DMF for 20 minutes to remove Fmoc, and the operation was repeated twice. The resin was washed with DMF, and a 6 mL DMF solution of Fmoc-Arg (Me, Pbf)-OH (159 mg, 0.24 mmol) and DIC (38 mg, 0.3 mmol) were added. The resin was treated at room temperature for 16 hours, and the resin was washed with DMF to give Fmoc-Arg (Me, Pbf)-Trp (Boc)-Rinkamide MBHA resin. The resin was treated with 6 ml of 20% piperidine/DMF for 20 minutes to remove Fmoc, and the operation was repeated twice. The resin was washed with DMF, and Fmoc-Phe-azaGly-Leu-OH (167 mg, 0.3 mmol), HATU (114 mg, 0.3 mmol), HOAt (38 mg, 0.3 mmol) of 6 mL DMF solution, then DIPEA (75 mg, 0.6 mmol) was added, treated at room temperature for 1 hour, and the resin was washed with DMF to give Fmoc-Phe-azaG-Leu-Arg (Me, Pbf)-Trp (Boc)-Rink Amide MBHA resin. In a similar manner, Fmoc-Thr(OtBu)—OH, Fmoc-Asn(Trt)-OH, Fmoc-Hyp(OtBu)—OH, Fmoc-D-Tyr (OtBu)—OH, Fmoc-Gly-OH, Fmoc-Gly-OH and other amino acids were introduced in sequence. Fmoc-Gly-Gly-[D-Tyr(OtBu)]-Hyp(OtBu)-Asn(Trt)-Thr(OtBu)-Phe-azaG-Leu-Arg(Me, Pbf)-Trp(Boc)-Rink Amide MBHA resin was obtained. The resin was treated with 6 ml of 20% piperidine/DMF for 20 minutes to remove Fmoc, repeated twice. The obtained resin was washed with DMF, 6 mL DMF solution of Mal-PEG8-acid (125 mg, 0.24 mmol), HATU (91 mg, 0.24 mmol), HOAt (30 mg, 0.24 mmol) were added, then DIPEA (62 mg, 0.48 mmol) was added, and the resin was treated at room temperature for 60 minutes. The obtained resin was washed with DMF, DMF (6 ml), DIPEA (62 mg, 0.48 mmol) and hexadecane-1-thiol (124 mg, 0.48 mmol) were added in this order, and treated at room temperature for 3 hours. The resin was washed with DMF, methanol and methyl tert-butyl ether in sequence, and then drained to finally give Hexadecyl-S-maleimide-PEG8-Gly-Gly-[D-Tyr(OtBu)]-Hyp(OtBu)-Asn(Trt)-Thr(OtBu)-Phe-azaG-Leu-Arg(Me, Pbf)-Trp(Boc)-Rink Amide MBHA resin.

The above dried resin was added to 10 mL of TFA/TIS/phenol/H$_2$O (94/2/2/2) solution, the mixture was stirred for 2 hours, the resin was removed by filtration, and the resin was washed with 1 mL of TFA/TIS/phenol/H$_2$O (94/2/2/2) solution. The filtrates were combined, methyl tert-butyl ether (110 mL) was added to the filtrate, the resulting mixture was centrifuged at 3000 rpm for 1 minute, and the solid was washed twice with cold diethyl ether and drained. The obtained precipitate was dissolved in DMF and then eluted with a linear concentration gradient (10 minutes) at a flow rate of 25 mL/minute, and eluent A/B: 30/70-10/90 using eluent A: 0.05% TFA aqueous solution, eluent B: 0.05% TFA acetonitrile solution was applied on a preparative HPLC using Phenomenex C18 column (21.2 mm×250 mm). Fractions containing the product were collected and lyophilized to give 22.1 mg of white solid.

Embodiment 97

Preparation of Ac-(D-Tyr)-Hyp-Asn-Thr-Phe-(α-Me-Leu)-Leu-Arg(Me)-Trp-NH$_2$ (Compound YA-370)

0.4 g of commercially available Rink Amide MBHA resin (0.432 mmol/g) was swollen in DMF, and the resin was treated with 6 ml of 20% piperidine/DMF for 20 minutes to remove Fmoc, repeated twice. The obtained resin was washed with DMF, 6 mL DMF solution of Fmoc-Trp (Boc)-OH (273 mg, 0.52 mmol), HBTU (198 mg, 0.52 mmol), HOBt (71 mg, 0.52 mmol) were added, then DIPEA (185 µL, 1.04 mmol) was added, the resin was treated at room temperature for 40 minutes, and the resin was washed with DMF to give Fmoc-Trp(Boc)-Rink Amide MBHA resin. The resin was treated with 6 ml of 20% piperidine/DMF for 20 minutes to remove Fmoc, and the operation was repeated twice. The resin was washed with DMF and Fmoc-Arg (Me, Pbf)-OH (345 mg, 0.52 mmol), HATU (198 mg, 0.52 mmol), HOAt (71 mg, 0.52 mmol) of 6 mL DMF solution, then DIPEA (185 µL, 1.04 mmol) was added, treated at room temperature for 1 hour, and the resin was washed with DMF to give Fmoc-Arg (Me, Pbf)-Trp (Boc)-rinkamide mbha resin. The resin was treated with 6 ml of 20% piperidine/DMF for 20 minutes to remove Fmoc, and the operation was repeated twice. The resin was washed with DMF and 6 ml of DMF solution of Fmoc-Leu-OH (184 mg, 0.52 mmol), HATU (198 mg, 0.52 mmol), HOAt (71 mg, 0.52 mmol) were added. Then DIPEA (185 µL, 1.04 mmol) was added, treated at room temperature for 1 hour, and the resin was washed with DMF to give Fmoc-Leu-Arg(Me,Pbf)-Trp (Boc)-Rink Amide MBHA resin. In a similar way, α-Me-Leu, Phe, Thr(tBu), Asn(Trt), Hyp(tBu), D-Tyr(tBu) and other amino acids were introduced in sequence to give Fmoc-(D-Tyr(tBu))-Hyp(tBu)-Asn(Trt)-Thr(tBu)-Phe-(α-Me-Leu)-Leu-Arg(Me,Pbf)-Trp(Boc)-Rink-Amide MBHA resin. The resin was treated with 6 ml of 20% piperidine/DMF for 20 minutes to remove Fmoc, the resin was washed with DMF, a 6 mL DMF solution of acetic anhydride (49·mu·l, 0.52 mmol) and DIPEA (185·mu·l, 1.04 mmol) were added, the resin was treated at room temperature for 1 hour, and the resin was washed with DMF. Ac-(D-Tyr(tBu))-Hyp(tBu)-Asn(Trt)-Thr(tBu)-Phe-(α-Me-Leu)-Leu-Arg(Me,Pbf)-Trp(Boc)-Rink Amide MBHA resin was obtained. The resin was washed with DMF, DCM, methanol and methyl tert-butyl ether and then drained.

The dried resin was added to 15 mL of TFA/TIS/phenol/H$_2$O (94/2/2/2) solution, the mixture was stirred for 2 hours, the resin was removed by filtration, and the resin was washed with 3 mL of TFA/TIS/phenol/H$_2$O (94/2/2/2) solution. The filtrates were combined, methyl tert-butyl ether (150 mL) was added to the filtrate, and the resulting mixture was centrifuged at 4000 rpm for 1 minute, and the solid was washed twice with cold diethyl ether and drained to give 160 mg of precipitate. Dissolving the obtained precipitate with DMF, and then performing linear concentration gradient elution (10 minutes) at a flow rate of 25 mL/minute, using eluent A/B: 71/29-61/39: eluent A: 0.1% TFA aqueous solution, eluent B: acetonitrile, on a preparative HPLC,) (Bridge Peptide BEH C18 10 μm, 120 Å column (19 mm×250 mm). The components containing the product were collected and lyophilized to give 77.0 mg of white solid.

Embodiment 98

Preparation of Ac-(D-Tyr)-Hyp-Asn-A6c-Phe-azaGly-Leu-Arg(Me)-Trp-NH$_2$ (Compound YA-387)

0.5 g of commercially available Rink Amide MBHA resin (0.5 mmol/g) was swollen in DMF, and the resin was treated with 5 ml of 20% piperidine/DMF for 20 minutes to remove Fmoc, repeated twice. The obtained resin was washed with DMF, 8 mL DMF solution of Fmoc-Trp (Boc)-OH (316 mg, 0.60 mmol), HBTU (230 mg, 0.60 mmol), HOBt (81 mg, 0.60 mmol) were added, then DIPEA (160 μL, 0.9 mmol) was added, the resin was treated at room temperature for 40 minutes, and the resin was washed with DMF to give Fmoc-Trp(Boc)-Rink Amide MBHA resin. The resin was treated with 8 ml of 20% piperidine/DMF for 20 minutes to remove Fmoc, and the operation was repeated twice. The resin was washed with DMF, and Fmoc-Arg (Me, Pbf)-OH (130 mg, 0.30 mmol), HATU (230 mg, 0.60 mmol), HOAt (81 mg, 0.60 mmol) of 8 mL DMF solution, then DIPEA (107 μL, 0.60 mmol) was added, treated at room temperature for 1 hour, and the resin was washed with DMF to give Fmoc-Arg (Me, Pbf)-Trp (Boc)-Rink Amide MBHA resin. The resin was treated with 8 ml of 20% piperidine/DMF for 20 minutes to remove Fmoc, repeated twice. The resin was washed with DMF, and 5 mL of DMF solution containing Fmoc-Phe-azaGly-Leu-OH (200 mg, 0.3 mmol), HATU (114 mg, 0.30 mmol), HOAt (41 mg, 0.30 mmol) and DIPEA (106 μL, 0.6 mmol) was added successively, treated at room temperature for 1 hour, and the resin was washed with DMF to give Fmoc-Phe-azaGly-Leu-Arg (Me, Pbf)-Trp (Boc)-Rink Amide MBHA resin. In a similar manner, amino acids A6c, Asn(Trt), Hyp(tBu), D-Tyr(tBu) and the like were sequentially introduced to give Fmoc-(D-Tyr(tBu))-Hyp(tBu)-Asn(Trt)-A6c-Phe-azaGly-Leu-Arg(Me, Pbf)-Trp(Boc)-Rink Amide MBHA resin. The resin was treated with 5 ml of 20% piperidine/DMF for 20 minutes to remove Fmoc, and the operation was repeated twice. The resin was washed with DMF and 8 mL DMF solution of acetic anhydride (30 mg, 0.60 mmol), HATU (230 mg, 0.60 mmol), HOAt (81 mg, 0.60 mmol) were added. DIPEA (107 μL, 0.6 mmol) was then added and treated at room temperature for 2 hours. The resin was washed with DMF, DCM, methanol and methyl tert-butyl ether and then drained to give Ac-(D-Tyr(tBu))-Hyp(tBu)-Asn(Trt)-A6c-Phe-azaGly-Leu-Arg(Me, Pbf)-Trp(Boc)-Rink Amide MBHA resin.

The dried resin was added to 10 mL of TFA/TIS/H$_2$O (95/2.5/2.5) solution, the mixture was stirred for 2 hours, the resin was removed by filtration, and the resin was washed with 2 mL of TFA/TIS/H$_2$O (95/2.5/2.5) solution. The filtrates were combined, methyl tert-butyl ether (100 mL) was added to the filtrate, the resulting mixture was centrifuged at 3000 rpm for 1 minute, and the solid was washed twice with cold diethyl ether and drained. Dissolving the obtained precipitate with DMF, and performing linear concentration gradient elution (10 minutes) at a flow rate of 20 mL/minute, using eluent A/B: 70/30-65/35: eluent A: 0.1% TFA aqueous solution, eluent B: acetonitrile, on a preparative HPLC, Welch XB-C18 10 μm column (21.2 mm×250 mm). Fractions containing the product were collected and lyophilized to give 46.00 mg of white solid.

Embodiment 99

Preparation of Ac-(D-Tyr)-Hyp-Asn-Aze-Phe-azaGly-Leu-Arg(Me)-Trp-NH$_2$ (Compound YA-388)

0.5 g of commercially available Rink Amide MBHA resin (0.5 mmol/g) was swollen in DMF, and the resin was treated with 5 ml of 20% piperidine/DMF for 20 minutes to remove Fmoc, repeated twice. The obtained resin was washed with DMF, 8 mL DMF solution of Fmoc-TRP (Boc)-OH (316 mg, 0.60 mmol), HBTU (230 mg, 0.60 mmol), HOBT (81 mg, 0.60 mmol) was added, then DIPEA (160 μL, 0.9 mmol) was added, the resin was treated at room temperature for 40 minutes, and the resin was washed with DMF to give Fmoc-Trp(Boc)-Rink Amide MBHA resin. The resin was treated with 8 ml of 20% piperidine/DMF for 20 minutes to remove Fmoc, and the operation was repeated twice. The resin was washed with DMF, and Fmoc-Arg (Me, Pbf)-OH (130 mg, 0.30 mmol), HATU (230 mg, 0.60 mmol), HOAt (81 mg, 0.60 mmol) of 8 mL DMF solution, then DIPEA (107 μL, 0.60 mmol) was added, treated at room temperature for 1 hour, and the resin was washed with DMF to give Fmoc-Arg(Me, Pbf)-Trp(Boc)-Rink Amide MBHA resin. The resin was treated with 8 ml of 20% piperidine/DMF for 20 minutes to remove Fmoc, and the operation was repeated twice. The resin was washed with DMF, and Fmoc-Phe-azaGly-Leu-OH (41 mg, 0.30 mmol) of 5 mL DMF solution was added, then DIPEA (106 μL, 0.6 mmol) was added, treated at room temperature for 1 hour, and the resin was washed with DMF to give Fmoc-Phe-azaGly-Leu-Arg(Me, Pbf)-Trp(Boc)-Rink Amide MBHA resin. In a similar manner, amino acids such as Aze, Asn(Trt), Hyp(tBu), D-Tyr (tBu) and the like were introduced in sequence to give Fmoc-(D-Tyr(tBu))-Hyp(tBu)-Asn(Trt)-Aze-Phe-azaGly-Leu-Arg(Me,Pbf)-Trp(Boc)-Rink Amide MBHA resin. The resin was treated with 20% piperidine/DMF to remove Fmoc, and the operation was repeated twice. The resin was washed with DMF, and 8 mL DMF solution of acetic acid (30 mg, 0.60 mmol), HATU (230 mg, 0.60 mmol), HOAt (81 mg, 0.60 mmol) were added, followed by DIPEA (107 μL, 0.6 mmol), treated at room temperature for 2 hours, the resin was washed with DMF, DCM, methanol and methyl tert-butyl ether, and then drained to give Ac-(D-Tyr(tBu))-Hyp (tBu)-Asn(Trt)-Aze-Phe-azaGly-Leu-Arg(Me, Pbf)-Trp (Boc)-Rink Amide MBHA resin.

The dried resin was added to 10 mL of TFA/TIS/H$_2$O (95/2.5/2.5) solution, the mixture was stirred for 2 hours, the resin was removed by filtration, and the resin was washed with 2 mL of TFA/TIS/H$_2$O (95/2.5/2.5) solution. The filtrates were combined, methyl tert-butyl ether (100 mL) was added to the filtrate, the resulting mixture was centrifuged at 3000 rpm for 1 minute, and the solid was washed twice with cold diethyl ether and drained. Dissolving the obtained precipitate with DMF, and then performing linear concentration gradient elution (10 minutes) at a flow rate of 20 mL/minute, using eluent A/B:74/26-64/36: eluent a: 0.1% TFA aqueous solution, eluent B: acetonitrile, on a preparative HPLC using Welch XB-C18 10 μm column (21.2 mm×250 mm). The fractions containing the product were collected and lyophilized to give 7.00 mg of white solid.

The polypeptides prepared in the above the embodiments and the polypeptides prepared with reference to the above the embodiments were shown in Table 2 below. Table 2 also describes the purity analysis conditions, retention time, characterization data and effect data of each polypeptide (which were measured according to the method of effect Embodiment 1)

TABLE 2

| Compound number | | Sequence | Mw (obs.) [M + 2H]²⁺/2 | Mw (cal.) | Rt (min.) HPLC | HPLC purity analysis conditions | Preliminary measurement data (GPR54) EC50, nM |
|---|---|---|---|---|---|---|---|
| YA-150 | M10 [Ac, PEG4, D-Y45, Hyp46, des47, T49, azaGly51, R(Me)53, W54] | Ac-PEG4-(D-Tyr)-Hyp-Asn-Thr-Phe-azaGly-Leu-Arg(Me)-Trp-NH₂ | 737.1 | 1472.64 | 13.37 | C | 0.004 |
| YA-151 | M10 [Ac, PEG8, D-Y45, Hyp46, des47, T49, azaGly51, R(Me)53, W54] | Ac-PEG8-(D-Tyr)-Hyp-ASN-Thr-Phe-azaGly-Leu-Arg(Me)-Trp-NH₂ | 825.0 | 1648.85 | 15.24 | J | 0.045 |
| Ya-156 | M10 [Palm-PEG8, G43, G44, D-Y45, Hyp46, des47, T49, azaGly51, R(Me)53, W54] | Palm-PEG8-Gly-Gly-(D-Tyr)-Hyp-Asn-Thr-Phe-azaGly-Leu-Arg(Me)-Trp-NH₂ | 980.3 | 1958.32 | 9.28 | H | 0.045 |
| YA-157 | M10 [Ac, K(Palm-PEG8)42, G43, G44, D-Y45 Hyp46, des47, T49, azaGly51, R(Me)53, W54] | Ac-Lys(Palm-PEG8)-Gly-Gly-(D-Tyr)-Hyp-Asn-Thr-Phe-azaGly-Leu-Arg(Me)-Trp-NH₂ | 1065.3 | 2129.54 | 8.78 | H | 0.03 |
| YA-158 | M10 (Palm-PEG8, G43, G44) | Palm-PEG8-Gly-Gly-Tyr-Asn-Trp-Asn-Ser-Phe-Gly-Leu-Arg-Phe-NH₂ | 693.7 [M + 3H]+/3 | 2078.45 | 16.49 | 1 | 0.0478 |
| YA-220 | M10 [Palm-PEG8, G43, G44, D-2Fua45, Pro(diF)46, des47, T49, A6c51, R(Me)53, W54] | Palm-PEG8-Gly-Gly-[3-(2-furyl)-D-Ala]-DifluoroPro-Asn-Thr-Phe-A6c-Leu-Arg(Me)-Trp-NH₂ | 1011.0 | 2020.40 | 22.53 | L | 0.023 |
| YA-264 | M10 [Palm-PEG8-Gly-Gly, D-Tyr45, Hyp46, des47, Thr49, A6c51, Arg(Me)53, Trp54] | Palm-PEG8-Gly-Gly-DTyr-Hyp-Asn-Thr-Phe-A6c-Leu-Arg(Me)-Trp-NH₂ | 1014.0 | 2026.46 | 10.01 | H | 0.029 |
| YA-267 | M10 [Palm-PEG8, D-2Fua45, Pro(diF)46, des47, Thr49, A6c51, Arg(Me)53, Trp54] | Palm-PEG8-(D-2Fua)-Pro(diF)-Asn-Thr-Phe-A6c-Leu-Arg(Me)-Trp-NH₂ | 954.0 | 1906.33 | 12.97 | H | 0.03 |
| YA-268 | M10 [Palm-PEG8-Gly-Gly, D-Tyr45, A6c46, des47, Thr49, azaGly51, Arg(Me)53, Trp54] | Palm-PEG8-G-G-DY-A6c-Asn-Thr-Phe-azaG-Leu-Arg(Me)-Trp-NH₂ | 986.3 | 1971.38 | 10.41 | H | 0.02 |
| YA-273 | M10 [C18 diacid-OEG-OEG, D-Tyr45, Hyp46, des47, Thr49, azaGly51, Arg(Me)53, Trp54] | C18 diacid-OEG-OEG-DY-Hyp-Asn-Thr-Phe-azaG-Leu-Arg(Me)-Trp-NH₂ | 886.0 | 1770.11 | 16.02 | L | 0.05 |

TABLE 2-continued

| Compound number | | Sequence | Mw (obs.) [M + 2H]$^{2+}$/2 | Mw (cal.) | Rt (min.) HPLC | HPLC purity analysis conditions | Preliminary measure-ment data (GPR54) EC50, nM |
|---|---|---|---|---|---|---|---|
| YA-287 | M10 [Palm-PEG8-Gly-Gly, D-Tyr45, Hyp46, des47, Thr49, Aze51, Arg(Me)53, Trp54] | Palm-PEG8-Gly-Gly-(D-Tyr)-Hyp-Asn-Thr-Phe-Aze-Leu-Arg(Me)-Trp-NH$_2$ | 992.9 | 1984.38 | 14.47 | G | 0.038 |
| YA-288 | M10 [Palm-PEG8-Gly-Gly, D-Tyr45, Hyp46, des47, Thr49, D-2Fur51, Arg(Me)53, Trp54] | Palm-PEG8-Gly-Gly-(D-Tyr)-Hyp-Asn-Thr-Phe-(D-2Fua)-Leu-Arg(Me)-Trp-NH$_2$ | 1019.8 | 2038.42 | 21.56 | L | 0.018 |
| YA-294 | M10 [hexanoyl, D-Tyr45, Hyp46, des47, Thr49, azaGly51, Arg(Me)53, Trp54] | Hexanoyl-(D)-Tyr)-Hyp-Asn-Thr-Phe-azaGly-Leu-Arg(Me)-Trp-NH$_2$ | 641.5 | 1281.46 | 14.88 | E | 0.039 |
| YA-295 | M10 [nonanoyl-OEG, D-Tyr45, Hyp46, des47, Thr49, azaGly51, Arg(Me)53, Trp54] | Nonanoyl-OEG-(D-Tyr)-Hyp-Asn-Thr-Phe-azaGly-Leu-Arg(Me)-Trp-NH$_2$ | 735.2 | 1468.70 | 16.84 | E | 0.02 |
| YA-296 | M10 [dodecanoyl-PEG4-PEG4, D-Tyr45, Hyp46, des47, Thr49, azaGly51, Arg(Me)53, Trp54] | Dodecanoyl-PEG4-PEG4-(D-Tyr)-Hyp-Asn-Thr-Phe-azaGly-Leu-Arg(Me)-Tryp-NH$_2$ | 621.0 | 1860.2 | 18.98 | E | 0.011 |
| YA-297 | M10 [Palm, D-Tyr45, Hyp46, des47, Thr49, azaGly51, Arg(Me)53, Trp54] | Palm-DY-Hyp-N-T-F-azaG-L-R(Me)-W-NH$_2$ | 621.0 [M + 3H]+/3 | 1421.75 | 20.61 | L | 0.014 |
| YA-298 | M10 [Palm-PEG8, D-Tyr45, Hyp46, des47, Thr49, azaGly51, Arg(Me)53, Trp54] | Palm-PEG8-(D-Tyr)-Hyp-Asn-Thr-Phe-azaGly-Leu-Arg(Me)-Trp-NH$_2$ | 923.5 | 1845.23 | 14.89 | G | 0.016 |
| YA-324 | M10 [Dodecanoyl-PEG5-S-S-butanoyl, D-Tyr45, Hyp46, des47, Thr49, azaGly51, Arg(Me)53, Trp54] | Dodecanoyl- { H$_2$N-(O)$_5$-S-S-COOH } -(D-Tyr)-Hyp-Asn-Thr-Phe-azaGly-Leu-Arg(Me)-Trp-NH$_2$ | 882.5 | 1763.17 | 17.86 | L | 0.007 |

TABLE 2-continued

| Compound number | | Sequence | Mw (obs.) [M + 2H]²⁺/2 | Mw (cal.) | Rt (min.) HPLC | HPLC purity analysis conditions | Preliminary measurement data (GPR54) EC50, nM |
|---|---|---|---|---|---|---|---|
| YA-325 | M10 [Dodecanoyl-PEG5-S-maleimide-butanoyl, D-Tyr45, Hyp46, des47, Thr49, azaGly51, Arg(Me)53, Trp54] | Dodecanoyl- [structure] -(D-Tyr)-Hyp-Asn-Thr-Phe-azaGly-Leu-Arg(Me)-Trp-NH₂ | 914.8 | 1828.2 | 13.73 | 1 | 0.017 |
| YA-326 | M10 [Nonanoyl-PEG5-1,2,3-Triazole cyclic-butanoyl, D-Tyr45, Hyp46, des47, Thr49, azaGly51, Arg(Me)53, Trp54] | Nonanoyl- [structure] -(D-Tyr)-Hyp-Asn-Thr-Phe-azaGly-Leu-Arg(Me)-Trp-NH₂ | 869.8 | 1738.07 | 16.84 | L | 0.01 |
| YA-338 | M10 [Nonanoyl-PEG4, D-Tyr45, Hyp46, des47, Thr49, Aze51, Arg(Me)53, Trp54] | Nonanoyl-PEG4-(D-Tyr)-Hyp-Asn-Thr-Phe-Aze-Leu-Arg(Me)-Trp-NH₂ | 640.4 | 1278.48 | 13.60 | J | 0.057 |
| YA-339 | M10 [Dodecanoyl-PEG8, D-Tyr45, Hyp46, des47, Thr49, D-2Fua51, Arg(Me)53, Trp54] | Dodecanoyl-PEG4-(D-Tyr)-Hyp-Asn-Thr-Phe-(D-2Fua)-Leu-Arg(Me)-Trp-NH₂ | 584.5 | 1167.34 | 12.57 | J | 0.075 |
| YA-348 | M10 [Dodecanoyl-PEG5-1,2,3-Triazole cyclic-Acetyl, D-Tyr45, Hyp46, des47, Thr49, Gψ(NHCS)51, Arg(Me)53, Trp54] | Dodecanoyl- [structure] -(D-Tyr-Hyp-Asn-Thr-Phe-Ψ(NHCS)G-Leu-Arg(Me)-Trp-NH₂ | 585.5 [M + 3H]3+/3 | 1753.14 | 8.84/ 8.92 | I | 0.019 |
| YA-360 | M10 [Palm-PEG8, G43, G44, D-Y45, Hyp46, des47, T49, Alg51, R(Me)53, W54] | Palm-PEG8-Gly-Gly-(D-Tyr)-Hyp-Asn-Thr-Phe-Alg-Leu-Arg(Me)-Trp-NH₂ | 943.0 | 1884.33 | 14.54 | O | 0.006 |

TABLE 2-continued

| Compound number | | Sequence | Mw (obs.) [M + 2H]²⁺/2 | Mw (cal.) | Rt (min.) HPLC | HPLC purity analysis conditions | Preliminary measurement data (GPR54) EC50, nM |
|---|---|---|---|---|---|---|---|
| YA-366 | M10 [Palm-PEG8, G43, G44, D-Phe(4-I)45, Hyp46, des47, T49, azaGly51, R(Me)53, W54] | Palm-PEG8-Gly-Gly-(D-Phe(4-I))-Hyp-Asn-Thr-Phe-AzaGly-Leu-Arg(Me)-Trp-NH₂ | 1035.3 | 2069.26 | 14.85 | O | 0.048 |
| YA-367 | M10 (Hexadecyl-1,2,3-Triazole-PEG8, G43, G44, D-Tyr45, Hyp46, des47, T49, AzaGly51, R(Me)53, W54] | [Hexadecyl-triazole-PEG8-COOH]-Gly-Gly-(D-Tyr)-Hyp-Asn-Thr-Phe-azaGly-Leu-Arg(Me)-Trp-NH₂ | 999.1 | 1997.41 | 12.01 | K | 0.103 |
| YA-368 | M10 [Hexadecyl-S-maleimide-PEG8, G43, G44, D-Tyr45, Hyp46, des47, T49, AzaGly51, R(Me)53, W54] | [Hexadecyl-S-maleimide-PEG8-COOH]-Gly-Gly-(D-Tyr)-Hyp-Asn-Thr-Phe-azaGly-Leu-Arg(Me)-Trp-NH₂ | 1030.1 | 2059.50 | 14.25 | K | 0.051 |
| YA-41 | M10 [Ac, Dap(Dnp)45, Hyp46, des47, T49, azaGly51, R(Me)53, W54] | Ac-Dap(Dnp)-Hyp-Asn-Thr-Phe-azaGly-Leu-Arg(Me)-Trp-NH₂ | 658.0 | 1314.36 | 14.86 | C | 0.095 |
| YA-42 | M10 [Ac, D-Phe(2,4-diCl)45, Hyp46, des47, T49, azaGly51, R(Me)53, W54] | Ac-[D-Phe(2,4-DiCl)]-Hyp-Asn-Thr-Phe-azaGly-Leu-Arg(Me)-Trp-NH₂ | 640.3 | 1278.25 | 15.68 | C | 0.015 |
| YA-43 | M10 [Ac, D-2Fua45, Hyp46, des47, T49, azaGly51, R(Me)53, W54] | Ac-(D-2Fua)-Hyp-Asn-Thr-Phe-azaGly-Leu-Arg(Me)-Trp-NH₂ | 600.5 | 1199.32 | 13.50 | C | 0.095 |
| YA-44 | M10 [Ac, Pro(5Ph)45, Hyp46, des47, T49, azaGly51, R(Me)53, W54] | Ac-Pro(5Ph)-Hyp-Asn-Thr-Phe-azaGly-Leu-Arg(Me)-Trp-NH₂ | 618.5 | 1235.39 | 14.68 | C | 0.015 |
| YA-45 | M10 [Ac, D-Y45, thz46, des47, T49, azaGly51, R(Me)53, W54] | Ac-(D-Tyr)-Thz-Asn-Thr-Phe-azaGly-Leu-Arg(Me)-Trp-NH₂ | 614.5 | 1227.39 | 13.96 | C | 0.095 |
| YA-68 | M10 [Ac, 2Pal45, Hyp46, des47, T49, azaGly51, R(Me)53, W54] | Ac-2Pal-Hyp-Asn-Thr-Phe-azaGly-Leu-Arg(Me)-Trp-NH₂ | 606.0 | 1210.34 | 11.39 | C | 0.18 |
| YA-69 | M10 [Ac, 3Pal45, Hyp46, des47, T49, azaGly51, R(Me)53, W54] | Ac-3Pal-Hyp-Asn-Thr-Phe-azaGly-Leu-Arg(Me)-Trp-NH₂ | 606.0 | 1210.34 | 10.85 | C | 0.3 |

TABLE 2-continued

| Compound number | Sequence | | Mw (obs.) [M + 2H]²⁺/2 | Mw (cal.) | Rt (min.) HPLC | HPLC purity analysis conditions | Preliminary measurement data (GPR54) EC50, nM |
|---|---|---|---|---|---|---|---|
| YA-70 | M10 [Ac, Phe(3-Cl)45, Hyp46, des47, T49, azaGly51, R(Me)53, W54] | Ac-Phe(3-Cl)-Hyp-Asn-Thr-Phe-azaGly-Leu-Arg(Me)-Trp-NH₂ | 622.5 | 1243.80 | 14.68 | C | 0.245 |
| YA-71 | M10 [Ac, Phe(4-F)45, Hyp46, des47, T49, azaGly51, R(Me)53, W54] | Ac-Phe(4-F)-Hyp-Asn-Thr-Phe-azaGly-Leu-Arg(Me)-Trp-NH₂ | 614.2 | 1227.35 | 14.17 | C | 0.058 |
| YA-74 | M10 [Ac, Phe(4-Me)45, Hyp46, des47, T49, azaGly51, R(Me)53, W54] | Ac-Phe(4-Me)-Hyp-Asn-Thr-Phe-azaGly-Leu-Arg(Me)-Trp-NH₂ | 612.6 | 1223.38 | 14.60 | C | 0.921 |
| YA-80 | M10 [Ac, D-Y45, Pro(di-F)46, des47, T49, azaGly51, R(Me)53, W54] | Ac-(D-Tyr)-diFluorPro-Asn-Thr-Phe-azaGLy-Leu-Arg(Me)-Trp-NH₂ | 623.6 | 1245.34 | 14.09 | C | 0.007 |
| YA-81 | M10 [Ac, D-Y45, Hyp46, des47, T49, azaGly51, R(Me)53, 2Nal54] | Ac-(D-Tyr)-Hyp-Asn-Thr-Phe-azaGly-Leu-Arg(Me)-2Nal-NH₂ | 619.1 | 1236.38 | 15.11 | B | 0.011 |
| YA-83 | M10 [Ac, D-Y45, Pro(4-NH₂)46, des47, T49, azaGly51, R(Me)53, W54] | Ac-(D-Tyr)-Pro(4-NH₂)-Asn-Thr-Phe-azaGly-Leu-Arg(Me)-Trp-NH₂ | 613.0 | 1224.37 | 11.43 | C | 0.008 |
| YA-84 | M10 [Ac, D-Y45, thi46, des47, T49, azaGly51, R(Me)53, W54] | Ac-(D-Tyr)-Thi-Asn-Thr-Phe-azaGly-Leu-Arg(Me)-Trp-NH₂ | 633.5 | 1265.44 | 14.61 | C | 0.007 |
| YA-85 | M10 [Ac, D-Y45, S-Pip46, des47, T49, azaGly51, R(Me)53, W54] | Ac-(D-Tyr)-(S-Pip)-Asn-Thr-Phe-azaGly-Leu-Arg(Me)-Trp-NH₂ | 612.6 | 1223.38 | 13.94 | C | 0.026 |
| YA-132 | M10 [Ac, Ala(dip)45, Hyp46, des47, T49, azaGly51, R(Me)53, W54] | Ac-Ala(dip)-Hyp-Asn-Thr-Phe-azaGly-Leu-Arg(Me)-Trp-NH₂ | 643.7 | 1285.45 | 15.41 | C | 0.19 |
| YA-143 | M10 [Ac, D-Y45, Hyp46, des47, 2Fua49, azaGly51, R(Me)53, W54] | Ac-(D-Tyr)-Hyp-Asn-2Fua-Phe-azaGly-Leu-Arg(Me)-Trp-NH₂ | 631.5 | 1261.39 | 14.42 | C | 0.023 |
| YA-144 | M10 [Ac, D-Y45, Hyp46, des47, thi49, azaGly51, R(Me)53, W54] | Ac-(D-Tyr)-Hyp-Asn-Thi-Phe-azaGly-Leu-Arg(Me)-Trp-NH₂ | 639.5 | 1277.45 | 14.81 | C | 0.201 |
| YA-145 | M10 [Ac, D-Y45, ACPA46, des47, T49, azaGly51, R(Me)53, W54] | Ac-(D-Tyr)-ACPA-Asn-Thr-Phe-azaGly-Leu-Arg(Me)-Trp-NH₂ | 605.5 | 1209.36 | 13.50 | C | 0.034 |
| YA-153 | M10 (Ac, D-Y45, Hyp46, des47, T49, Aze51, R(Me)53, W54] | Ac-(D-Tyr)-Hyp-Asn-Thr-Phe-Aze-Leu-Arg(Me)-Trp-NH₂ | 626.0 | 1250.40 | 13.71 | C | 0.18 |
| YA-165 | M10 [Ac, D-Y45, D-2Fua46, des47, T49, azaGly51, R(Me)53, W54] | Ac-(D-Tyr)-(D-2Fua)-Asn-Thr-Phe-azaGly-Leu-Arg(Me)-Trp-NH₂ | 625.4 | 1249.38 | 14.26 | C | 0.025 |

TABLE 2-continued

| Compound number | | Sequence | Mw (obs.) $[M+2H]^{2+}/2$ | Mw (cal.) | Rt (min.) HPLC | HPLC purity analysis conditions | Preliminary measurement data (GPR54) EC50, nM |
|---|---|---|---|---|---|---|---|
| YA-166 | M10 (Ac, D-Y45, Hyp46, des47, D-2Fua50, azaGly51, R(Me)53, W54] | Ac-(D-Tyr)-Hyp-Asn-[3-(2-furyl)-D-Ala]-Phe-azaGly-L-Arg(Me)-Trp-NH₂ | 631.5 | 1261.39 | 14.47 | C | 0.86 |
| YA-167 | M10 (Ac, D-Y45, Hyp46, des47, T49, D-2Fua50, azaGly51, R(Me)53, W54] | Ac-(D-Tyr)-Hyp-Asn-Thr-(D-2Fua)-azaGly-L-Arg(Me)-Trp-NH₂ | 608.5 | 1215.32 | 12.93 | C | 0.33 |
| YA-168 | M10 [Ac, D-Y45, Hyp46, des47, T49, D-2Fua51, R(Me)53, W54] | Ac-(D-Tyr)-Hyp-Asn-Thr-Phe-[3-(2-furyl)-D-Ala]-Leu-Arg(Me)-Trp-NH₂ | 652.9 | 1304.45 | 14.77 | C | 0.531 |
| YA-170 | M10 [Ac, D-Phe(4-F)45, Hyp46, des47, T49, azaGly51, R(Me)53, W54] | Ac-[D-Phe(4-F)]-Hyp-Asn-Thr-Phe-azaGly-Leu-Arg(Me)-Trp-NH₂ | 614.4 | 1227.35 | 14.48 | C | 0.007 |
| YA-172 | M10 [Ac, D-Y45, A6c46, des47, T49, azaGly51, R(Me)53, W54] | Ac-(D-Tyr)-A6c-Asn-Thr-Phe-azaGly-Leu-Arg(Me)-Trp-NH₂ | 619.4 | 1237.41 | 15.10 | C | 0.012 |
| YA-175 | M10 [Ac, D-Y45, Hyp46, des47, T49, A6c51, R(Me)53, W54] | Ac-(D-Tyr)-Hyp-Asn-Thr-Phe-A6c-Leu-Arg(Me)-Trp-NH₂ | 647.0 | 1292.48 | 16.28 | D | 0.132 |
| YA-178 | M10 [Ac, D-Phe(2,4-diCl)45, thi46, des47, T49, azaGly51, R(Me)53, W54] | Ac-[D-Phe(2,4-DiCl)]-Thi-Asn-Thr-Phe-azaGly-Leu-Arg(Me)-Trp-NH₂ | 660.3 | 1318.33 | 19.95 | J | 0.011 |
| YA-180 | M10 [Ac, D-Phe(2,4-diCl)45, Pro(diF)46, des47, T49, azaGly51, R(Me)53, W54] | Ac-[D-Phe(2,4-DiCl)]-Pro(diF)-Asn-Thr-Phe-azaGly-Leu-Arg(Me)-Trp-NH₂ | 649.5 | 1298.23 | 16.88 | C | 0.015 |
| YA-181 | M10 [Ac, D-2Fua45, S-Pip46, des47, T49, azaGly51, R(Me)53, W54] | Ac-(D-2Fua)-(S-Pip)-Asn-Thr-Phe-azaGly-Leu-Arg(Me)-Trp-NH₂ | 599.8 | 1197.34 | 16.72 | J | 0.043 |
| YA-182 | M10 [Ac, D-Phe(2,4-diCl)45, S-Pip46, des47, T49, azaGly51, R(Me)53, W54] | Ac-[D-Phe(2,4-DiCl)]-(S-Pip)-Asn-Thr-Phe-azaGly-Leu-Arg(Me)-Trp-NH₂ | 638.5 | 1276.27 | 19.21 | J | 0.021 |
| YA-183 | M10 [Ac, D-2Fua45, Pro(diF)46, des47, T49, azaGly51, R(Me)53, W54] | Ac-(D-2Fua)-Pro(diF)-Asn-Thr-Phe-azaGly-Leu-Arg(Me)-Trp-NH₂ | 610.5 | 1219.30 | 14.78 | C | 0.029 |
| YA-188 | M10 [Ac, D-Phe(2,4-diCl)45, Hyp46, des47, T49, Aze51, R(Me)53, W54] | Ac-[D-Phe(2,4-DiCl)]-Hyp-Asn-Thr-Phe-Aze-Leu-Arg(Me)-Trp-NH₂ | 651.9 | 1303.29 | 16.00 | C | 0.477 |
| YA-191 | M10 [Ac, D-Y45, thi46, des47, T49, Aze51, R(Me)53, W54] | Ac-(D-Tyr)-Thi-Asn-Thr-Phe-Aze-Leu-Arg(Me)-Trp-NH₂ | 646.0 | 1290.49 | 15.13 | C | 0.521 |

TABLE 2-continued

| Compound number | | Sequence | Mw (obs.) [M + 2H]²⁺/2 | Mw (cal.) | Rt (min.) HPLC | HPLC purity analysis conditions | Preliminary measuremeant data (GPR54) EC50, nM |
|---|---|---|---|---|---|---|---|
| YA-194 | M10 (Ac D-Y45, S-Pip46, des47, T49, Aze51, R(Me)53, W54] | Ac-(D-Tyr)-(S-Pip)-Asn-Thr-Phe-Aze-Leu-Arg(Me)-Trp-NH₂ | 625.0 | 1248.43 | 14.26 | C | 0.544 |
| YA-195 | M10 [Ac, D-Phe(4-F)45, Hyp46, des47, T49, A6c51, R(Me)53, W54] | Ac-[D-Phe(4-F)]-Hyp-Asn-Thr-Phe-A6e-Leu-Arg(Me)-Trp-NH₂ | 648.0 | 1294.47 | 18.03 | J | 0.68 |
| YA-196 | Ma0 [Ac, D-Phe(2,4-diCl)45, Hyp46, des47, T49, A6c51, R(Me)53, W54] | Ac-[D-Phe(2,4-DiCl)]-Hyp-Asn-Thr-Phe-A6c-Leu-Arg(Me)-Trp-NH₂ | 673.8 | 1345.37 | 17.08 | C | 0.48 |
| YA-197 | M10 [Ac, D-2Fua45, Hyp46, des47, T49, A6c51, R(Me)53, W54] | Ac-(D-2Fua)-Hyp-Asn-Thr-Phe-A6c-Leu-Arg(Me)-Trp-NH₂ | 634.1 | 1266.45 | 17.18 | J | 0.57 |
| YA-201 | M10 [Ac, D-2Fua45, Pro(diF)46, des47, T49, A6c51, R(Me)53, W54] | Ac-[3-(2-furyl)-D-Ala]-DiFluorPro-Asn-Thr-Phe-A6c-Leu-Arg(Me)-Trp-NH₂ | 644.0 | 1286.43 | 16.57 | C | 0.39 |
| YA-208 | M10 [Ac, D-Y45, Hyp46, des47, T49, Imc51, R(Me)53, W54] | Ac-(D-Tyr)-Hyp-Asn-Thr-{(S)-2-(1-amino-2-phenylethyl)-1H-imidazole-5-carboxylic acid}-Leu-Arg(Me)-Trp-NH₂ | 617.5 | 1233.40 | 15.17 | J | 1.09 |
| YA-209 | M10 [Ac, D-Y45, Hyp46, des47, T49, tr3c51, R(Me)53, W54] | Ac-(D-Tyr)-Hyp-Asn-Thr-{(S)-5-(1-amino-2-phenylethyl)-4H-1,2,4-triazole-3-carboxylic acid}-Leu-Arg(Me)-Trp-NH₂ | 618.2 | 1234.70 | 15.28 | J | 1.4 |
| YA-212 | M10 [Ac, D-Phe(4-F)45, Pro(di-F)46, des47, T49, A6c51, R(Me)53, W54] | Ac-[D-Phe(4-F)]-DiFluorPro-Asn-Thr-Phe-A6c-Leu-Arg(Me)-Trp-NH₂ | 658.1 | 1314.46 | 17.41 | C | 0.50 |
| YA-213 | M10 [Ac, D-Phe(4-F)45, Pro(di-F)46, des47, T49, Aze51, R(Me)53, W54] | Ac-[D-Phe(4-F)]-DiFluorPro-Asn-Thr-Phe-Aza-Leu-Arg(Me)-Trp-NH₂ | 637.0 | 1272.38 | 15.97 | C | 0.40 |
| YA-214 | M10 [Ac, D-Phe(4-Cl)45, Hyp46, des47, T49, azaGly51, R(Me)53, W54] | Ac-[D-Phe(4-Cl)]-Hyp-Asn-Thr-Phe-azaGly-Leu-Arg(Me)-Trp-NH₂ | 622.5 | 1243.80 | 14.88 | C | 0.083 |
| YA-215 | M10 [Ac, D-Phe(3-Cl)45, Hyp46, des47, T49, azaGly51, R(Me)53, W54] | Ac-[D-Phe(3-Cl)]-Hyp-Asn-Thr-Phe-azaGly-Leu-Arg(Me)-Trp-NH₂ | 622.5 | 1243.80 | 14.80 | C | 0.122 |
| YA-216 | M10 [Ac, D-Y45, Hyp46, des47, T49, tic50, azaGly51, R(Me)53, W54] | Ac-(D-Tyr)-Hyp-Asn-Thr-Tic-azaGly-Leu-Arg(Me)-Trp-NH₂ | 619.4 | 1237.37 | 13.20 | C | 0.44 |
| YA-221 | M10 [Ac, D-Y45, Hyp46, des47, T49, Ind51, R(Me)53, W54] | Ac-(D-Tyr)-Hyp-Asn-Thr-Phe-Ind-Leu-Arg(Me)-Trp-NH₂ | 657.0 | 1312.47 | 151.0 | C | 0.64 |

TABLE 2-continued

| Compound number | | Sequence | Mw (obs.) [M + 2H]$^{2+}$/2 | Mw (cal.) | Rt (min.) HPLC | HPLC purity analysis conditions | Preliminary measurement data (GPR54) EC50, nM |
|---|---|---|---|---|---|---|---|
| YA-228 | M10 [Ac, D-Y45, S-Pip46, des47, T49, A6c51, R(Me)53, W54] | Ac-(D-Tyr)-S-Pip)-Asn-Thr-Phe-A6c-Leu-Arg(Me)-Trp-NH$_2$ | 646.2 | 1290.51 | 11.79 | I | 0.65 |
| YA-230 | M10 [Ac, D-Y45, Oic46, des47, T49, azaGly51, R(Me)53, W54] | Ac-(D-Tyr)-Oic-Asn-Thr-Phe-azaGly-Leu-Arg(Me)-Trp-NH$_2$ | 632.5 | 1263.45 | 14.54 | C | 0.04 |
| YA-236 | M10 [Ac, D-Tic45, Hyp46, des47, T49, azaGly51, R(Me)53, W54] | Ac-(D-Tic)-Hyp-Asn-Thr-Phe-azaGly-Leu-Arg(Me)-Trp-NH$_2$ | 611.5 | 1221.37 | 14.47 | C | 0.058 |
| YA-241 | M10 [Ac, D-Phe(2,4-DiCl)45, S-Pip46, des47, T49, azaPhe50, R(Me)53, W54] | Ac-[D-Phe(2,4-DiCl)]-(S-Pip)-Asn-Thr-azaPhe-Gly-Leu-Arg(Me)-Trp-NH$_2$ | 638.5 | 1276.27 | 17.12 | C | 0.93 |
| YA-248 | M10 [Ac, D-Phe(2,4-DiCl)45, Pro(diF)46, des47, T49, A6c51, R(Me)53, W54] | Ac-D-Phe(2,4-DiCl)-DiFluorPro-Asn-Thr-Phe-A6c-Leu-Arg(Me)-Trp-NH$_2$ | 683.6 | 1365.36 | 21.04 | J | 0.78 |
| YA-251 | M10 [Ac, D-Y45, Pro(diF)46, des47, T49, A6c51, R(Me)53, W54] | Ac-DTyr-DiFluorPro-Asn-Thr-Phe-A6c-Leu Arg(Me)-Trp-NH$_2$ | 657.0 | 1312.47 | 15.94 | C | 0.65 |
| YA-254 | M10 [Ac, D-Y45, Hyp46, des47, T49, Gψ(NHC)51, R(Me)53, W54] | Ac-DTyr-Hyp-Asn-Thr-Phe-ψ(NHC)G-Leu-Arg(Me)-Trp-NH$_2$ | 621.0 | 1240.45 | 13.38 | J | 0.03 |
| YA-255 | M10 [Ac, D-Phe(2,4-DiCl)45, Pro(diF)46, des47, T49, Gψ(NHCS)51, R(Me)53, W54] | Ac-D-Phe(2,4-DiCl)-DiFluorPro-Asn-Thr-Phe-ψ(NHCS)G-Leu-Arg(Me)-Trp-NH$_2$ | 657.4 | 1313.32 | 17.74 | J | 0.028 |
| YA-260 | M10 [Ac, D-Phe(2,4-diCl)45, A6c46, des47, T49, azaGly51, R(Me)53, W54] | Ac-D-Phe(2,4-DiCl)-A6c-Asn-Thr-Phe-azaG-Leu-Arg(Me)-Trp-NH$_2$ | 645.5 | 1290.30 | 18.27 | C | 0.027 |
| YA-266 | M10 [Ac, des45, A6c46, des47, Thr-49, azaGly51, Arg(Me)53, Trp54] | Ac-A6c-Asn-Thr-Phe-azaG-Leu-Arg(Me)-Trp-NH$_2$ | 538.1 | 1074.24 | 14.87 | C | 0.320 |
| YA-271 | M10 [Ac, D-2Fua45, A6c46, des47, Thr49, azaGly51, Arg(Me)53, Trp54] | Ac-(D-2Fua)-A6c-Asn-Thr-Phe-azaG-Leu-Arg(Me)-Trp-NH$_2$ | 606.5 | 1211.37 | 15.39 | J | 0.025 |

TABLE 2-continued

| Compound number | Sequence | | Mw (obs.) [M + 2H]²⁺/2 | Mw (cal.) | Rt (min.) HPLC | HPLC purity analysis conditions | Preliminary measurement data (GPR54) EC50, nM |
|---|---|---|---|---|---|---|---|
| YA-274 | M10 [Ac, D-Tyr45, Hyp46, des47, Thr49, (—CH2CH2CO—)51, Arg(Me)53, Trp54] | Ac-(D-Tyr)-Hyp-Asn-Thr-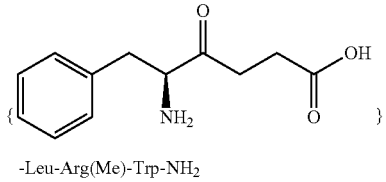-Leu-Arg(Me)-Trp-NH₂ | 612.6 | 1223.40 | 12.92 | J | 0.048 |
| YA-282 | M10 [Ac, D-Tyr45, Hyp46, des47, Thr49, cycloLeu51, Arg(Me)53, Trp54] | Ac-(D-Tyr)-Hyp-Asn-Thr-Phe-cycloLeu-Leu-Arg(Me)-Trp-NH₂ | 640.0 | 1278.46 | 13.83 | C | 0.46 |
| YA-291 | M10 [Ac-Gly-Arg-Lys-Lys-Arg-ArgGln-Arg-Arg-Arg-Pro-Gln-BetaAla-BetaAla-BataAla, D-Tyr45, Hyp46, des47, Thr49, azaGly51, Arg(Me)53, Trp54] | Ac-GRKKRRQRRRPQ-beta-Ala-beta-Ala-DY-Hyp-N-T-F-azaG-L-R(Me)-W-NH₂ | 743.9 [M + 4H]4/4 | 2971.45 | 8.08 | F | 0.31 |
| YA-303 | M10 [Ac, D-Tyr45, Hyp46, des47, Thr49, ψ(NHCO)Gly51, Arg(Me)53, Trp54] | Ac-(D-Tyr)-Hyp-Asn-Thr-Phe-ψ(NHCO)Gly-Leu-Arg(Me)-Trp-NH₂ | 612.9 | 1224.37 | 13.11 | F | 0.01 |
| YA-332 | M10 [Ac, D-Phe(2,4-diCl)45, HomoPro46, des47, Thr49, ψ(NHCO)Gly51, Arg(Me)53, Trp54] | Ac-[D-Phe(2,4-DiCl)]-HomoPro-Asn-Thr-Phe-ψ(NHCO)Gly-Leu-Arg(Me)-Trp-NH₂ | 638.00 | 1275.3 | 14.03 | J | 0.18 |
| YA-333 | M10 [Ac, D-2Fua45, HomoPro46, des47, Thr49, ψ(NHCO)Gly51, Arg(Me)53, Trp54] | Ac-(D-2Fua)-HomoPro-Asn-Thr-Phe-ψ(NHCO)Gly-Leu-Arg(Me)-Trp-NH₂ | 599.00 | 1196.38 | 16.77 | J | 0.066 |
| YA-334 | M10 [Ac, D-Phe(2,4-diCl)45, Pro(diF)46, des47, Thr49, ψ(NHCO)Gly51, Arg(Me)53, Trp54] | Ac-[D-Phe(2,4-diCl)]-Pro(diF)-Asn-Thr-Phe-ψ(NHCO)Gly-Leu-Arg(Me)-Trp-NH₂ | 649.7 | 1297.25 | 12.45 | M | 0.084 |
| YA-350 | M10 (Ac, D-Y45, Hyp46, des47, T49, Alg51, R(Me)53, W54] | Ac-(D-Tyr)-Hyp-Asn-Thr-Phe-Alg-Leu-Arg(Me)-Trp-NH₂ | 632.8 | 1264.45 | 12.80 | J | 0.17 |
| YA-354 | M10 [Ac, D-Tyr45, Hyp46, des47, Thr49, Morpholino cyclic amino acid51, Arg(Me)53, Trp54] | Ac-(D-Tyr)-Hyp-Asn-Thr-Phe-morpholino cyclic amino acid-Leu-Arg(Me)-Trp-NH₂ | 648.3 | 1294.48 | 13.24 | J | 0.26 |

TABLE 2-continued

| Compound number | Sequence | | Mw (obs.) [M + 2H]²⁺/2 | Mw (cal.) | Rt (min.) HPLC | HPLC purity analysis conditions | Preliminary measurement data (GPR54) EC50, nM |
|---|---|---|---|---|---|---|---|
| YA-357 | M10 [Ac, D-Phe(4-I)45, Hyp46, des47, T49, Beta-(thiazoly-4-yl)-L-Ala51, R(Me)53, W54] | Ac-(D-Tyr)-Hyp-Asn-Thr-Phe-Beta-(thiazoly-4-yl)-L-Ala-Leu-Arg(Me)-Trp-NH₂ | 661.5 | 1321.52 | 15.12 | J | 0.30 |
| YA-358 | M10 [Ac, D-Phe(4-I)45, Hyp46, des47, T49, AzaGly51, R(Me)53, W54] | Ac-(D-Phe(4-I)-Hyp-Asn-Thr-Phe-azaGly-Leu-Arg(Me)-Trp-NH₂ | 668.3 | 1335.27 | 15.58 | J | 0.032 |
| YA-379 | M10 [Ac, D-Tyr45, AlphaMeLeu46, des47, T49, azaGly51, R(Me)53, W54] | Ac-(D-Tyr)-AlphaMeLeu-Asn-Thr-Phe-azaGly-Leu-Arg(Me)-Trp-NH₂ | 620.5 | 1239.424 | 15.75 | J | 0.015 |
| YA-380 | M10 [Ac, D-Tyr45, Cba46, des47, T49 azaGly51, R(Me)53, W54] | Ac-(D-Tyr)-Cba-Asn-Thr-Phe-azaGly-Leu-Arg(Me)-Trp-NH₂ | 619.5 | 1237.43 | 15.27 | J | 0.191 |
| YA-381 | M10 [Ac, D-Tyr45, A6c46, des47, T49, azaGly51, R(Me)53, W54] | Ac-(D-Tyr)-A6c-Asn-Thr-Phe-azaGly-Leu-Arg(Me)-Trp-NH₂ | 619.8 | 1237.43 | 15.62 | J | 0.052 |
| YA-382 | M10 [Ac, D-Tyr45, Aze46, des47, T49, azaGly51, R(Me)53, W54] | Ac-(D-Tyr)-Aze-Asn-Thr-Phe-azaGly-Leu-Arg(Me)-Trp-NH₂ | 598.5 | 1195.35 | 13.72 | J | 0.175 |
| YA-383 | M10 [Ac, D-Tyr45, Cpa46, des47, T49, azaGly51, R(Me)53, W54] | Ac-(D-Tyr)-Cpa-Asn-Thr-Phe-azaGly-Leu-Arg(Me)-Trp-NH₂ | 612.7 | 1223.40 | 14.66 | J | 0.074 |
| YA-384 | M10 [Ac, D-Tyr45, ACBC 46, des47, T49, azaGly51, R(Me)53, W54] | Ac-(D-Tyr)-ACBC-Asn-Thr-Phe-azaGly-Leu-Arg(Me)-Trp-NH₂ | 605.5 | 1209.38 | 14.69 | J | 0.338 |
| YA-387 | M10 [Ac, D-Tyr45, Hyp46, des47, A6c49, azaGly51, R(Me)53, W54] | Ac-(D-Tyr)-Hyp-Asn-A6c-Phe-azaGly-Leu-Arg(Me)-Trp-NH₂ | 625.3 | 1249.42 | 12.54 | P | 0.041 |
| YA-388 | M10 [Ac, D-Tyr45, Hyp46, des47, Aze49, azaGly51, R(Me)53, W54] | Ac-(D-Tyr)-Hyp-Asn-Aze-Phe-azaGly-Leu-Arg(Me)-Trp-NH₂ | 604.3 | 1207.34 | 13.57 | Q | 0.058 |
| YA-403 | M10 [Ac, D-Tyr45, Hyp46, des47, beta, beta-diMe-L-serine49, azaGly51, R(Me)53, W54] | Ac-(D-Tyr)-Hyp-Asn-beta,beta-diMe-L-serine-Phe-azaGly-Leu-Arg(Me)-Trp-NH₂ | 620.5 | 1239.40 | 15.25 | J | 0.272 |
| YA-2 | M10 (Ac) | Ac-Tyr-Asn-Trp-Asn-Ser-Phe-Gly-Leu-Arg-Phe-NH₂ | 672.8 | 1344.48 | 14.94 | A | 10 |
| YA-3 | M10 [Ac, D-Y45, Hyp46, des47, T49, azaGly51, R(Me)53, W54] | Ac-(D-Tyr)-Hyp-Asn-Thr-Phe-azaGly-Leu-Arg(Me)-Trp-NH₂ | 613.3 | 1225.35 | 13.77 | A | 0.03 |

TABLE 2-continued

| Compound number | | Sequence | Mw (obs.) [M + 2H]²⁺/2 | Mw (cal.) | Rt (min.) HPLC | HPLC purity analysis conditions | Preliminary measurement data (GPR54) EC50, nM) |
|---|---|---|---|---|---|---|---|
| YA-72 | M10 [Ac, Phe(4-Cl)45, Hyp46, des47, T49, azaGly51, R(Me)53, W54] | Ac-Phe(4-Cl)-Hyp-Asn-Thr-Phe-azaGly-Leu-Arg(Me)-Trp-NH₂ | 622.5 | 1243.80 | 15.84 | B | 5.55 |
| YA-73 | M10 [Ac, tyr(Me)45, Hyp46, des47, T49, azaGly51, R(Me)53, W54] | Ac-Tyr(Me)-Hyp-Asn-Thr-Phe-azaGly-Leu-Arg(Me)-Trp-NH₂ | 620.5 | 1239.38 | 14.14 | C | 1.32 |
| YA-75 | M10 [Ac, Phe(4-tBu)45, Hyp46, des47, T49, azaGly51, R(Me)53, W54] | Ac-Phe(4-tBu)-Hyp-Asn-Thr-Phe-azaGly-Leu-Arg(Me)-Trp-NH₂ | 633.5 | 1265.46 | 16.24 | C | 18.7 |
| YA-82 | M10 [Ac, D-Y45, Hyp46, des47, T49, BataA51, NMeL52, R(Me)53, W54] | Ac-(D-Tyr)-Hyp-Asn-Thr-Phe-BetaAla-(NMe-Leu)-Arg(Me)-Trp-NH₂ | 627.0 | 1252.42 | 14.02 | C | 2.792 |
| YA-146 | M10 stapled(Ac, S5-48, S5-52) | Ac-Tyr-Asn-Trp-X-Ser-Phe-Gly-X-Arg-Phe-NH₂ (stapled) | 684.7 | 1367.55 | 17.21 | C | 544.8 |
| YA-152 | M10 (Ac D-Y45, Hyp46, des47, T49, ACPO51, R(Me)53, W54] | Ac-(D-Tyr)-Hyp-Asn-Thr-Phe-ACPO-Leu-Arg(Me)-Trp-NH₂ | 659.5 | 1317.45 | 13.62 | C | 1000 |
| YA-163 | M10 [Ac, Phe(4-F)45, Hyp46, des47, T49, BetaA51, NMeL52, R(Me)53, W54] | Ac-Phe(4-F)-Hyp-Asn-Thr-Phe-BetaAla-(NMe-Leu)-Arg(Me)-Trp-NH₂ | 628.0 | 1254.41 | 14.69 | C | 1000 |
| YA-164 | M10 [Ac, D-2Fua45, Hyp46, des47, T49, BetaA51, NMeL52, R(Me)53, W54] | Ac-[3-(2-furyl)-D-Ala]-Hyp-Asn-Thr-Phe-BetaAla-(NMe-Leu)-Arg(Me)-Trp-NH₂ | 614.0 | 1226.38 | 15.58 | D | 1.749 |
| YA-169 | M10 [Ac, D-Y45, Hyp46, des47, T49, azaGly51, R(Me)53, D-2Fua54] | Ac-(D-Tyr)-Hyp-Asn-Thr-Phe-azaGly-Leu-Arg(Me)-[3-(2-furyl)-D-Ala]-NH₂ | 589.0 | 1176.28 | 12.35 | C | 6.532 |
| YA-174 | M10 [Ac, D-Tyr45, Hyp46, des47, Thr49, A6c50, azaGly51, Arg(Me)53, Trp54] | Ac-(D-Tyr)-Hyp-Asn-Thr-A6c-azaGly-Leu-Arg(Me)-Trp-NH₂ | 602.5 | 1203.35 | 14.98 | J | 2.6 |
| YA-184 | M10 [Ac, D-Phe(2,4-diCl)45, Hyp46, des47, T49, azaPro51, R(Me)53, W54] | Ac-[D-Phe(2,4-DiCl)]-Hyp-Asn-Thr-Phe-azaPro-Leu-Arg(Me)-Trp-NH₂ | 660.5 | 1318.33 | 15.92 | C | 48 |
| YA-185 | M10 [Ac, D-Phe(2,4-diCl)45, S-Pip46, des47, T49, BetaA51, NMeL52, R(Me)53, W54] | Ac-[D-Phe(2,4-DiCl)]-(S-Pip)-Asn-Thr-Phe-BetaAla-NMeLeu-Arg(Me)-Trp-NH₂ | 652.5 | 1303.34 | 11.24 | I | 3.627 |

TABLE 2-continued

| Compound number | Sequence | | Mw (obs.) [M + 2H]²⁺/2 | Mw (cal.) | Rt (min.) HPLC | HPLC purity analysis conditions | Preliminary measurement data (GPR54) EC50, nM |
|---|---|---|---|---|---|---|---|
| YA-186 | M10 [Ac, D-2Fua45, Pro(diF)46, des47, T49, BetaA51, NMeL52, R(Me)53, W54] | Ac-[3-(2-Furyl)-D-Ala]-(DiFluorPro)-Asn-Thr-Phe-BetaAla-NMeLeu-Arg(Me)-Trp-NH₂ | 624.0 | 1246.36 | 17.01 | D | 3.893 |
| YA-187 | M10 [Ac, D-Phe(2,4-diCl)45, Hyp46, des47, T49, BetaA51, NMeL52, R(Me)53, W54] | Ac-[D-Phe(2,4-DiCl)]-Hyp-Asn-Thr-Phe-BetaAla-NMeLeu-Arg(Me)-Trp-NH₂ | 653.9 | 1305.31 | 17.61 | D | 1.854 |
| YA-189 | M10 [Ac, D-2Fua45, Hyp46, des47, T49, Aze51, R(Me)53, W54] | Ac-D-2Fua-Hyp-Asn-Thr-Phe-Aze-Leu-Arg(Me)-Trp-NH₂ | 613.0 | 1224.37 | 14.00 | C | 1.696 |
| YA-190 | M10 [Ac, Phe(4-F)45, Hyp46, des47, T49, Aze51, R(Me)53, W54] | Ac-Phe(4-F)-Hyp-Asn-Thr-Phe-Aze-Leu-Arg(Me)-Trp-NH₂ | 627.0 | 1252.39 | 14.73 | C | 3.893 |
| YA-192 | M10 [Ac, D-Y45, azaPro46, des47, T49, Aze51, R(Me)53, W54] | Ac-(D-Tyr)-azaPro-Asn-Thr-Phe-Aze-Leu-Arg(Me)-Trp-NH₂ | 618.4 | 1235.39 | 14.21 | C | 5.035 |
| YA-193 | M10 [Ac, D-Y45, Pro(diF)46, des47, T49, Aze51, R(Me)53, W54] | Ac-(D-Tyr)-Pro(diF)-Asn-Thr-Phe-Aze-Leu-Arg(Me)-Trp-NH₂ | 636.0 | 1270.39 | 14.36 | C | 1.365 |
| YA-198 | M10 [Ac, Phe(4-F)45, Hyp46, des47, T49, A6c51, R(Me)53, W54] | Ac-Phe(4-F)-Hyp-Asn-Thr-Phe-A6c-Leu-Arg(Me)-Trp-NH₂ | 648.0 | 1294.47 | 15.57 | C | 381.8 |
| YA-199 | M10 [Ac, D-Phe(4-F)45, thi46, des47, T49, A6c51, R(MKe)53, W54] | Ac-[D-Phe(4-F)]-Thi-Asn-Thr-Phe-A6c-Leu-Arg(Me)-Trp-NH₂ | 668.0 | 1334.56 | 17.83 | C | 15.56 |
| YA-200 | M10 [Ac, D-Phe(2,4-DiCl)45, azaPro46, des47, T49, A6c51, R(Me)53, W54] | Ac-[D-Phe(2,4-DiCl)]-azaPro-Asn-Thr-Phe-A6c-Leu-Arg(Me)-Trp-NH₂ | 666.3 | 1330.36 | 17.64 | C | 25.43 |
| YA-202 | M10 [Ac, Phe(4-F)45, S-Pip46, des47, T49, A6c51, R(Me)53, W54] | Ac-Phe(4-F)-(S-Pip)-Asn-Thr-Phe-A6c-Leu-Arg(Me)-Trp-NH₂ | 647.0 | 1292.50 | 17.02 | C | 9.60 |
| YA-203 | M10 [Ac, D-Y45, Hyp46, des47, 2Fua49, Aze51, R(Me)53, W54] | Ac-(D-Tyr)-Hyp-Asn-2Fua-Phe-Aze-Leu-Arg(Me)-Trp-NH₂ | 644.3 | 1286.44 | 14.77 | C | 1.19 |
| YA-204 | M10 [Ac, D-Y45, thi46, des47, 2Fua49, Aze51, R(Me)53, W54] | Ac-(D-Tyr)-Thi-Asn-2Fua-Phe-Aze-Leu-Arg(Me)-Trp-NH₂ | 664.2 | 1326.52 | 16.11 | C | 8.72 |
| YA-205 | M10 [Ac, D-Y45, Pro(diF)46, des47, 2Fua49, Aze51, R(Me)53, W54] | Ac-(D-Tyr)-DiFluorPro-Asn-2Fua-Phe-Aze-Leu-Arg(Me)-Trp-NH₂ | 654.2 | 1306.42 | 15.67 | C | 50.35 |

TABLE 2-continued

| Compound number | | Sequence | Mw (obs.) [M + 2H]$^{2+}$/2 | Mw (cal.) | Rt (min.) HPLC | HPLC purity analysis conditions | Preliminary measurement data (GPR54) EC50, nM |
|---|---|---|---|---|---|---|---|
| YA-206 | M10 [Ac, D-Phe(2,4-diCl)45, thi46, des47, T49, A6c51, R(Me)53, W54] | Ac-[D-Phe(2,4-DiCl)]-Thi-Asn-Thr-Phe-A6c-Leu-Arg(Me)-Trp-NH$_2$ | 693.7 | 1385.46 | 19.04 | C | 3.60 |
| YA-207 | M10 [Ac, D-Phe(2,4-diCl)45, thi46, T49, A6c51, R(Me)53, W54] | Ac-[D-Phe(2,4-DiCl)]-Thi-Trp-Asn-Thr-Phe-A6c-Leu-Arg(Me)-Trp-NH$_2$ | 786.5 | 1571.67 | 19.97 | C | 90.00 |
| YA-223 | M10 [Ac, D-2Fua45, Pro(diF)46, des47, T49, Ind51, R(Me)53, W54] | Ac-[3-(2-furyl)-D-Ala]-DifluoroPro-Asn-Thr-Phe-Ind-Leu-Arg(Me)-Trp-NH$_2$ | 654.1 | 1306.42 | 16.64 | C | 4.4 |
| YA-224 | M10 [Ac, D-2Fua45, Pro(diF)46, des47, T49, A6c51, R(Me)53, tic54] | Ac-[3-(2-furyl)-D-Ala]-DifluoroPro-Asn-Thr-Phe-A6C-Leu-Arg(Me)-Tic-NH$_2$ | 630.5 | 1259.40 | 16.11 | C | 6.5 |
| YA-210 | M10 [Ac, D-Phe(4-F)45, S-Pip46, des47, T49, A6c51, R(Me)53, W54] | Ac-[D-Phe(4-F)]-(S-Pip)-Asn-Thr-Phe-A6c-Leu-Arg(Me)-Trp-NH$_2$ | 647.1 | 1292.50 | 17.52 | C | 1.47 |
| YA-211 | M10 [Ac, D-Phe(4-F)45, S-Pip46, des47, T49, Aze51, R(Me)53, W54] | Ac-[D-Phe(4-F)]-(S-Pip)-Asn-Thr-Phe-Aze-Leu-Arg(Me)-Trp-NH$_2$ | 626.0 | 1250.42 | 15.92 | C | 1.13 |
| YA-226 | M10 [Ac, D-Y45, Hyp46, des47, T49, S-Pip51, R(Me)53, W54] | Ac-(D-Tyr)-Hyp-Asn-Thr-Phe-(S-Pip)-Leu-Arg(Me)-Trp-NH$_2$ | 640.1 | 1278.46 | 14.57 | C | 8.00 |
| YA-227 | M10 [Ac, D-Y45, Hyp46, des47, T49, R-Pip51, R(Me)53, W54] | Ac-(D-Tyr)-Hyp-Asn-Thr-Phe-(R-Pip)-Leu-Arg(Me)-Trp-NH$_2$ | 640.2 | 1278.46 | 14.44 | C | 1.89 |
| YA-229 | M10 [Ac, D-Y45, R-Pip46, des47, T49, A6c51, R(Me)53, W54] | Ac-(D-Tyr)-(R-Pip)-Asn-Thr-Phe-A6c-Leu-Arg(Me)-Trp-NH$_2$ | 646.1 | 1290.51 | 15.14 | C | 20.26 |
| YA-234 | M10 [Ac, D-Y45, Hyp46, des47, T49, Oic51, R(Me)53, W54] | Ac-(D-Tyr)-Hyp-Asn-Thr-Phe-Oic-Leu-Arg(Me)-Trp-NH$_2$ | 660.0 | 1318.52 | 14.95 | C | 202 |
| YA-239 | M10 [Ac, 3Pal(1-MePyridinium) 45, Hyp46, des47, T49, azaGly51, R(Me)53, W54] | Ac-[(S)-3-(2-amino-2-carboxyethyl)-1-methylpyridinium]-Hyp-Asn-Thr-Phe-azaGly-Leu-Arg(Me)-Trp-NH$_2$ | 613.0 | 1225.38 | 10.80 | C | 1.00 |
| YA-240 | M10 [Ac, D-Phe(2,4-diCl)45, S-Pip46, des47, T49, azaGly51, R(Me)53, W54, NHtBu] | Ac-[D-Phe(2,4-DiCl)]-(s-Pip)-Asn-Thr-Phe-azaGly-Leu-Arg(Me)-Trp-NHtBu | 667.2 | 1332.38 | 15.32 | L | 173 |

TABLE 2-continued

| Compound number | Sequence | | Mw (obs.) [M + 2H]$^{2+}$/2 | Mw (cal.) | Rt (min.) HPLC | HPLC purity analysis conditions | Preliminary measuremeant data (GPR54) EC50, nM |
|---|---|---|---|---|---|---|---|
| YA-242 mixture | M10 [Ac, D-Phe(2,4-diCl)45, S-Pip46, des47, T49, azaGly51, Phe(4-Pyra)53, W54] | Ac-[D-Phe(2,4-DiCl)]-(S-Pip)-Asn-Thr-Phe-azaGly-Leu-[(S)-3-(4-(1H-pyrazol-1-yl)phenyl)-2-aminopropanoic acid]-Trp-NH$_2$ | 659.8 | 1319.30 | 50.01%/ 42.71% (214 nm) RT = 16.9 7/17.14 min | 1 | 3.74 |
| YA-244 | M10 [Ac, D-Phe(4-F)45, A6c46, des47, T49, A6c51, R(Me)53, W54] | Ac-[D-Phe(4-F)]-A6c-Asn-Thr-Phe-A6c-Leu-Arg(Me)-Trp-NH$_2$ | 654.2 | 1306.53 | 18.64 | F | 1.17 |
| YA-245 | M10 [Ac, D-Y45, A6c46, des47, T49, Hyp51, R(Me)53, W54] | Ac-(D-Tyr)-A6c-Asn-Thr-Phe-Hyp-Leu-Arg(Me)-Trp-NH$_2$ | 647.0 | 1292.48 | 14.58 | C | 26 |
| YA-246 | M10 [Ac, D-Y45, Hyp46, des47, T49, azaGly51, R(Me)53, W54] | Ac-(D-Tyr)-Hyp-Asn-Thr-Phe-azaGly-Leu-Arg(Me)-Trp-OH | 614.0 | 1226.34 | 13.93 | C | 2.86 |
| YA-247 | M10 [Ac, D-Y45, Hyp46, des47, T49, azaNMeGly 51, R(Me)53, W54, OH] | Ac-(D-Tyr)-Hyp-Asn-Thr-Phe-azaNMeGly-Leu-Arg(Me)-Trp-NH$_2$ | 620.5 | 1239.38 | 14.87 | J | 11 |
| YA-250 | M10 [Ac, D-Y45, Hyp46, des47, T49, azaGly51, R(Me)53, W54, 2H-tetrazol-5-yl] | Ac-DY-Hyp-Asn-Thr-Phe-azaG-Leu-Arg(Me)-Trp-2H-tetrazol-5-yl | 625.7 | 1250.37 | 18.57 | J | 7.5/15.4 |
| YA-252 | M10 [Ac, D-Phe(2,4-diCl)45, Pro(diF)46, des47, T49, A6c51, R(Me)53, W54, NHEt] | Ac-D-Phe(2,4-DiCl)-DiFluorPro-Asn-Thr-Phe-A6c-Leu-Arg(Me)-Trp-NHet | 697.0 | 1393.41 | 16.22 | L | 1000 |
| YA-253 | M10 [Ac, D-Phe(2,4-diCl)45, Pro(diF)46, des47, T49, A6c51, R(Me)53, W54, NHMe] | Ac-D-Phe(2,4-DiCl)-DiFluorPro-Asn-Thr-Phe-A6c-Leu-Arg(Me)-Trp-NHMe | 690.7 | 1379.38 | 15.65 | L | 97.8 |
| YA-256 | M10 [Ac, D-Tyr45, Hyp46, des47, Thr49 ,ψ(NH—CO—NH)Gly51, Arg(Me)53, Trp54] | Ac-(D-Tyr)-Hyp-Asn-Thr-Phe-ψ(NH—CO—NH)Gly-Leu-Arg(Me)-Trp-NH$_2$ | 620.5 | 1239.38 | 14.90 | J | 2.6 |
| YA-259 | M10 [Ac, D-Phe(2,4-diCl)45, A6c46, des47, T49, A6c51, R(Me)53, W54] | Ac-D-Phe(2,4-DiCl)-A6c-Asn-Thr-Phe-Abc-Leu-Arg(Me)-Trp-NH$_2$ | 670.6 | 1357.43 | 16.52 | L | 3.2 |
| YA-272 | M10 [Ac, D-2Fua45, A6c46, des47, Thr49, A6c51, Arg(Me)53, Trp54] | Ac-3-(2-furyl)-D-alanine-A6c-Asn-Thr-Phe-A6c-Leu-Arg(Me)-Trp-NH$_2$ | 639.9 | 1278.52 | 14.49 | E | 7.95 |

TABLE 2-continued

| Compound number | Sequence | | Mw (obs.) [M + 2H]²⁺/2 | Mw (cal.) | Rt (min.) HPLC | HPLC purity analysis conditions | Preliminary measurement data (GPR54) EC50, nM |
|---|---|---|---|---|---|---|---|
| YA-284 | M10 [Ac, D-Tyr45, Hyp46, des47, Thr49, Cba51, Arg(Me)53, Trp54] | Ac-(D-Tyr)-Hyp-Asn-Thr-Phe-Cba-Leu-Arg(Me)-Trp-NH₂ | 647.0 | 1292.48 | 14.58 | F | 1.7 |
| YA-289 | M10 [Ac, D-Tyr45, Hyp46, des47, Thr49, ACPA51, Arg(Me)53, Trp54] | Ac-(D-Tyr)-Hyp-Asn-Thr-Phe-ACPA-Leu-Arg(Me)-Trp-NH₂ | 633.2 | 1264.45 | 17.03 | J | 42.6 |
| YA-336 | M10 [Ac, D-2Fua45, HomoPro46, des47, Thr49, A6c51, Arg(Me)53, Trp54] | Ac-(D-2Fua)-HomoPro-Asn-Thr-Phe-A6c-Leu-Arg(Me)-Trp-NH₂ | 633.2 | 1264.5 | 19.06 | J | 2.48 |
| YA-337 | M10 [Ac, D-Tyr45, Hyp46, des47, Thr49, BetaAla51, Arg(Me)53, Trp54] | Ac-(D-Tyr)-Hyp-Asn-Thr-Phe-BetaAla-Leu-Arg(Me)-Trp-NH₂ | 620.0 | 1238.42 | 13.19 | F | 2.20 |
| YA-355 | M10 [Ac, D-Tyr45, Hyp46, des47, Thr49, Deg51, Arg(Me)53, Trp54] | Ac-(D-Tyr)-Hyp-Asn-Thr-Phe-Deg-Leu-Arg(Me)-Trp-NH₂ | 641.0 | 1280.50 | 14.45 | J | 1.2 |
| YA-370 | M10 [Ac, D-Tyr45, Hyp46, des47, T49, AlphaMeLeu51, R(Me)53, W54] | Ac-(D-Tyr)-Hyp-Asn-Thr-Phe-AlphaMeLeu-Leu-Arg(Me)-Trp-NH₂ | 647.9 | 1294.50 | 12.29 | P | 1.563 |
| YA-396 | M10 [Ac, D-Tyr45, Hyp46 des47, T49, Cpg51, R(Me)53, W54] | Ac-(D-Tyr)-Hyp-Asn-Thr-Phe-Cpg-Leu-Leu-Arg(Me)-Trp-NH₂ | 633.2 | 1264.45 | 15.59 | J | 1.188 |

The HPLC purity analysis conditions in above Table 2 are as follows:

Condition A: Elution AB=95/5-35/65
Mobile phase: A: Water (0.01% TFA), B: ACN (0.01% TFA)
Mobile phase ratio: 5% B within 0-3 min, linear gradient elution 5-65% B within 20 min
Velocity: 1.2 ml/min
Column: Eclipse XDB-C18, 4.6*150 mm, 5 µm
Box temperature: 40° C.

Condition B: Elution AB=95/5-35/65
Mobile phase: A: Water (0.01% TFA), B: ACN (0.01% TFA)
Mobile phase ratio: 5% B within 0-3 min, linear gradient elution 5-65% B within 20 min
Velocity: 1.0 ml/min
Column: AGLIENT ZORBAX Eclipse XDB, C18, 4.6*150 mm, 5 µm
Temperature: 40° C.

Condition C: Elution A/B=95/5-35/65
Mobile phase: A: Water (0.01% TFA), B: ACN (0.01% TFA)
Mobile phase ratio: 5% B within 0-3 min, linear gradient elution 5-65% B within 20 min
Velocity: 1.0 ml/min
Column: SunFire C18, 4.6*150 mm, 3.5 µm
Temperature: 40° C.

Condition D: Elution A/B=95/5-35/65
Mobile phase: A: Water (0.05% TFA), B: ACN (0.05% TFA)
Mobile phase ratio: 5% B within 0-3 min, linear gradient elution 5-65% B within 20 min
Velocity: 1.2 ml/min
Column: Eclipse XDB-C18, 4.6*150 mm, 5 µm Condition E: Elution A/B=85/15-25/75
Mobile phase: A: Water (0.01% TFA), B: ACN (0.01% TFA)
Mobile phase ratio: 15% B within 0-3 min, linear gradient elution 15-75% B within 20 min
Velocity: 1.0 ml/min
Column: SunFire C18, 4.6*150 mm, 3.5 µm
Temperature: 40° C.

Condition F: Elution A/B=95/5-35/65
Mobile phase: A: Water (0.05% TFA), B: ACN (0.05% TFA)

Mobile phase ratio: 5% B within 0-3 min, linear gradient elution 5-65% B within 20 min
Velocity: 1.2 ml/min
Column: SunFire C18, 4.6*150 mm, 3.5 μm
Condition G: Elution A/B=80/20-20/80
Mobile phase: A: Water (0.01% TFA), B: ACN (0.01% TFA)
Mobile phase ratio: 20% B within 0-3 min, linear gradient elution 20-80% B within 20 min
Velocity: 1.0 ml/min
Column: SunFire C18, 4.6*150 mm, 3.5 μm
Temperature: 40° C.
Condition H: Elution A/B=50/50-0/100
Mobile phase: A: Water (0.05% TFA), B: ACN (0.05% TFA)
Mobile phase ratio: 50% B within 0-3 min, linear gradient elution 50-100% B within 20 min
Velocity: 1.0 mL/min
Column: XBridge Peptide BEH C18, 4.6*150 mm, 3.5 μm
Column temperature: 40° C.
Condition I: Elution A/B=80/20-5/95
Mobile phase: A: Water (0.01% TFA), B: ACN (0.01% TFA)
Mobile phase ratio: 20% B within 0-2 min, linear gradient elution 20-95% B within 25 min
Velocity: 1.0 mL/min
Column: SunFire C18, 4.6*150 mm, 3.5 μm
Column temperature: 40° C.
Condition J: Elution A/B=95/5-35/65
Mobile phase: Water (0.05% TFA), B: ACN (0.05% TFA)
Mobile phase ratio: 5% B within 0-3 min, linear gradient elution 5-65% B within 20 min
Velocity: 1.0 mL/min
Column: XBridge Peptide BEH C18, 4.6*150 mm, 3.5 μm
Column temperature: 40° C.
Condition K: Elution A/B=50/50-0/100
Mobile phase: A: A: Water (0.01% TFA), B: ACN (0.01% TFA)
Mobile phase ratio: 50% B within 0-3 min, linear gradient elution 50-100% B within 20 min
Velocity: 1.0 ml/min
Column: SunFire C18, 4.6*150 mm, 3.5 μm
Column temperature: 40° C.
Condition L: Elution A/B=80/20-5/95
Mobile phase: A: Water (0.05% TFA), B: ACN (0.05% TFA)
Mobile phase ratio: 20% B within 0-2 min, linear gradient elution 20-95% B within 25 min
Velocity: 1.0 ml/min
Column: XBridge Peptide BEH, 4.6*150 mm, 3.5 μm
Column temperature: 40° C.
Condition M: Elution A/B=80/20-20/80
Mobile phase: A: Water (0.05% TFA), B: ACN (0.05% TFA)
Mobile phase ratio: 20% B within 0-1 min, linear gradient elution 20-80% B within 20 min
Velocity: 1.0 mL/min
Column: XBridge Peptide BEH C18, 4.6*150 mm, 3.5 μm
Column temperature: 40° C.
Condition N: Elution A/B=70/30-0/100
Mobile phase: A: Water (0.05% TFA), B: ACN (0.05% TFA)
Mobile phase ratio: 30% B within 0-3 min, linear gradient elution 30-100% B within 20 min
Velocity: 1.0 mL/min
Column temperature: 40° C.
Column: XBridge Peptide BEH C18, 4.6*150 mm, 3.5 μm
Condition O: Elution A/B=65/35-0/100
Mobile phase: A: Water (0.05% TFA), B: ACN (0.05% TFA)
Mobile phase ratio: 35% B within 0-1 min, linear gradient elution 35-100% B within 20 min
Velocity: 1.0 mL/min
Column temperature: 40° C.
Column: XBridge Peptide BEH C18, 4.6*150 mm, 3.5 μm
Condition P: Elution AB=65/25-45/55
Mobile phase: A: Water (0.05% TFA), B: ACN (0.05% TFA)
Linear gradient elution 25-45% B within 30 min
Velocity: 1.0 mL/min
Column temperature: 40° C.
Column: XBridge Peptide BEH C18, 4.6*150 mm, 3.5 μm
Condition Q: Elution AB=82/18-52/48
Mobile phase: A: Water (0.05% TFA), B: ACN (0.05% TFA)
Linear gradient elution 25-45% B within 30 min
Velocity: 1.0 mL/min
Column temperature: 40° C.
Column: XBridge Peptide BEH C18, 4.6*150 mm, 3.5 μm Effect Embodiment 1 Determination of Kiss1 Receptor (GPR54) Binding Activity of Kiss1 Receptor (GPR54) Agonist The binding activity test of each compound from the above the embodiments with kiss1 receptor (GPR54) was performed by fluorescence energy resonance transfer (FRET) detection technology to detect $EC_{50}$ values of polypeptides and peptide analogs. The cells used in this experiment were NFAT-bla CHO-K1 cells (k1720, invitrogen, thermosher) that express human kiss1 receptor (GPR54). The specific operations were as follows:

Day 1: Seeding Cells in Plate

1. Microscope (CKX41, OLYMPUS), object lens×4 times, ocular lens×10 times. The cells were ensured in a good condition.

2. Digesting the cells, adding 3 ml of 0.05% pancreatin into a culture dish; cells were placed in a 37° C., 5% $CO_2$ incubator for 2 minutes (Thermo Fisher). After the cells became round under the microscope, 7 ml of culture medium was added. The formula of culture medium was as follows: DMEM 90%, dialzedfbS10, NEAA 0.1 mM, HEPES 25 mM, Penicillin 100 U/ml, Streptomycin 100 μm/ml, pH7.3. After blowing and stirring, it was transferred to 15 mL centrifuge tube (430790, Corning). Centrifuge at 1000 rpm for 5 min (5810R, Eppendorf) and the supernatant was discard.

3. Adding 7 mL of culture medium (DMEM+0.1% BSA), it was pipetting into single cell suspension, after counting with Bio-RAD counter, the cell density was adjusted to 312,500 cells/ml.

4. Cells were inoculated into 384 well plates at 32 μL per well, and the cell number was controlled at 10000 cells/well. 32 μl of culture medium was added into the blank control.

Day 2: Dosing and Data Analysis 1. 1000× Compound Plate Configuration

1) The compound to be tested was prepared into 50 mM working solution with DMSO.

2) 40 μl of the working solution of the compound to be tested was added into column 2 of row A-H of U-shaped 96-well plate (3797, comings), and 60 μl of DMSO was added into column 3-11. 20 μl of compound solution was sucked from the second column to the third column with a multichannel pipette blowing and stirring evenly; 20 μl of compound solution was absorbed from the third column with a multichannel pipette, then added into the fourth column, blowed and stirred to mix well; the compound was serially diluted 4-fold to a total of 10 concentrations. Column 1 and column 12 of 96-well plates were supplemented with 40 μl DMSO.

2. Intermediate Plate Configuration

1) AU-shaped 96-well plate was used, 199 μL of culture medium (DMEM+0.1% BSA) was added to each well, 1 μL of diluted compound (or DMSO) was sucked from 1000× compound plate and added into the 96-well plate at the corresponding position, blowed and stirred to mix well.

2) Homemade positive compounds and compounds to be tested were added. The cell culture plate was took out from the incubator and cells state was observed under microscope. Diluted compound in the intermediate plate or DMSO was added into the cell, 8 μl per well.

3) Cells were cultured in 37° C. and 5% $CO_2$ for 4 hours.

3. The Substrate was Added to Detect the Binding of the Drug to the Receptor 1) 1 μmol/L CCF-4AM solution and buffer solution B, C, D were equilibrated to room temperature. LiveBLAZER™-FRET B/G Loading Kit (K1095, thermo Fisher) containing CCF-4AM and solution B, solution C, solution D were also available from Invitrogen (K1157, thermo Fisher).

2) 6× loading solution was prepared: 6 μl of CCF-4AM dissolved solution A, 60 μl of solution b, 904 μl of solution c, and 30 μl of solution D were pipetted into EP tube, blowed and stirred to mix well.

3) 8 μl of the above-mentioned liquid was sucked with a multichannel pipette, added into a 96-well plate, and incubated for 2 hours at room temperature.

4) The PerkinElmer detector was used to detect the luminous signals of each hole. FI mode, λex=409 nm, λem1=460 nm, λem2=530 nm.

4. Data Processing Using Graphpad Prism 5 (GraphPad Software, Inc)

Effective rate %=(Signal−Min)/(Max−Min)×100%. Max: the maximum binding value of high concentration positive compound to kiss1 receptor. Min: Minimum value of no binding of 0.1% DMSO to receptor. Signal: the signal value at the corresponding concentration of the compound. The $EC_{50}$ of the corresponding compound was obtained by fitting the parameter curve with the concentration of the compound and the corresponding effective rate, as shown in Table 3.

TABLE 3

| | $EC_{50}$ of each polypeptide | | | | |
|---|---|---|---|---|---|
| Polypeptide number | GPR54 $EC_{50}$/nM | Polypeptide number | GPR54 $EC_{50}$/nM | Polypeptide number | GPR54 $EC_{50}$/nM |
| YA-1 | | YA-160 | 0.027 | YA-204 | 8.72 |
| YA-2 | 2.11 | YA-161 | 0.075 | YA-205 | 50.35 |
| YA-3 | 0.03 | YA-162 | 0.004 | YA-206 | 3.60 |
| YA-41 | 0.095 | YA-163 | 1000 | YA-207 | 90.00 |

TABLE 3-continued

| | $EC_{50}$ of each polypeptide | | | | |
|---|---|---|---|---|---|
| Polypeptide number | GPR54 $EC_{50}$/nM | Polypeptide number | GPR54 $EC_{50}$/nM | Polypeptide number | GPR54 $EC_{50}$/nM |
| YA-42 | 0.015 | YA-164 | 1.749 | YA-208 | 1.09 |
| YA-43 | 0.095 | YA-165 | 0.025 | YA-209 | 1.4 |
| YA-44 | 0.015 | YA-166 | 0.86 | YA-210 | 1.47 |
| YA-45 | 0.095 | YA-167 | 0.33 | YA-211 | 1.13 |
| YA-68 | 0.18 | YA-168 | 0.531 | YA-212 | 0.50 |
| YA-69 | 0.3 | YA-169 | 6.532 | YA-213 | 0.40 |
| YA-70 | 0.245 | YA-170 | 0.007 | YA-214 | 0.083 |
| YA-71 | 0.058 | YA-172 | 0.012 | YA-215 | 0.122 |
| YA-72 | 5.55 | YA-174 | 2.6 | YA-216 | 0.44 |
| YA-73 | 1.32 | YA-175 | 0.132 | YA-217 | 2.56 |
| YA-74 | 0.921 | YA-178 | 0.011 | YA-218 | 12.2 |
| YA-75 | 18.7 | YA-180 | 0.015 | YA-219 | 63.42 |
| YA-80 | 0.007 | YA-181 | 0.043 | YA-220 | 0.023 |
| YA-81 | 0.011 | YA-182 | 0.021 | YA-221 | 0.64 |
| YA-82 | 2.792 | YA-183 | 0.029 | YA-223 | 4.4 |
| YA-83 | 0.008 | YA-184 | 48 | YA-224 | 6.5 |
| YA-84 | 0.007 | YA-185 | 3.627 | YA-226 | 8.00 |
| YA-85 | 0.026 | YA-186 | 3.893 | YA-227 | 1.89 |
| YA-132 | 0.19 | YA-187 | 1.854 | YA-228 | 0.65 |
| YA-139 | 0.023 | YA-188 | 0.477 | YA-229 | 20.26 |
| YA-140 | 0.040 | YA-189 | 1.696 | YA-234 | 202 |
| YA-141 | 0.064 | YA-190 | 24.3 | YA-236 | 0.058 |
| YA-142 | 0.064 | YA-191 | 0.521 | YA-239 | 1.00 |
| YA-143 | 0.023 | YA-192 | 2.170 | YA-240 | 173 |
| YA-144 | 0.201 | YA-193 | 1.365 | YA-241 | 0.93 |
| YA-145 | 0.034 | YA-194 | 0.544 | YA-242 | 3.75 |
| YA-146 | 544.8 | YA-195 | 0.68 | YA-243 | 0.69 |
| YA-150 | 0.004 | YA-196 | 0.48 | YA-244 | 1.17 |
| YA-151 | 0.045 | YA-197 | 0.57 | YA-246 | 2.86 |
| YA-152 | 1000 | YA-198 | 381.8 | YA-247 | 11 |
| YA-153 | 0.18 | YA-199 | 15.56 | YA-248 | 0.78 |
| YA-156 | 0.045 | YA-200 | 25.43 | YA-251 | 0.65 |
| YA-157 | 0.03 | YA-201 | 0.39 | YA-252 | 1000 |
| YA-158 | 0.0478 | YA-202 | 9.60 | YA-253 | 97.8 |
| YA-159 | 1000 | YA-203 | 1.19 | YA-260 | 0.027 |
| YA-264 | 0.029 | YA-266 | 0.320 | YA-267 | 0.03 |
| YA-268 | 0.02 | YA-271 | 0.025 | YA-273 | 0.05 |
| YA-274 | 0.048 | YA-287 | 0.038 | YA-288 | 0.018 |
| YA-294 | 0.038 | YA-295 | 0.02 | YA-296 | 0.011 |
| YA-297 | 0.014 | YA-298 | 0.016 | YA-324 | 0.007 |
| YA-291 | 0.31 | YA-303 | 0.01 | YA-325 | 0.017 |
| YA-326 | 0.010 | YA-327 | 0.40 | YA-332 | 0.18 |
| YA-333 | 0.066 | YA-334 | 0.084 | YA-336 | 2.48 |
| YA-337 | 2.20 | YA-338 | 0.057 | YA-339 | 0.075 |
| YA-348 | 0.019 | YA-350 | 0.17 | YA-354 | 0.26 |
| YA-355 | 1.2 | YA-357 | 0.30 | YA-358 | 0.032 |
| YA-360 | 0.006 | YA-366 | 0.048 | YA-367 | 0.103 |
| YA-368 | 0.051 | YA-370 | 1.563 | YA-379 | 0.0150 |
| YA-380 | 0.191 | YA-381 | 0.052 | YA-382 | 0.175 |
| YA-383 | 0.074 | YA-384 | 0.338 | YA-387 | 0.041 |
| YA-388 | 0.058 | YA-396 | 1.188 | YA-403 | 0.272 |

The $EC_{50}$ of parts of the compounds listed in Table 3 was superior to TAK448, showing strong activity, indicating that the compounds of the present disclosure can effectively bind kiss 1 receptor (GPR54) at the level of in vitro biochemical experiments, so the compounds of the present disclosure has the potential to become effective therapeutic drugs for tumors.

Effect Embodiment 2 Experimental Data on Plasma Stability of Some Compounds

1. Preparation of 50 mM Phosphate Buffer:

The 5.750 g $Na_2HPO_4$, 1.141 g $NaH_2PO_4$, and 4.095 g NaCl (Shanghai Titan) weighed was dissolved in 1000 mL ultrapure water and the pH was adjusted to 7.4 to give 50 mM phosphate buffer containing 70 mM NaCl. The prepared phosphoric acid buffer solution was stored in the refrigerator at 4° C. and was valid for one week.

2. Preparation of compound stock solution:
1). 5 mg/mL of test compound: 5 mg of compound was weighted and dissolved in 1 mL of DMSO.
2). 20 mM control: 2.728 mg of Fuka was dissolved in 0.5 mL of DMSO. 3.878 mg of benzalkonium bromide was dissolved in 0.5 mL of DMSO (Amresco).

3. Preparation of experimental plasma:
The frozen plasma (human: Shanghai wise chemistry; Rats and mice: Shanghai Sciple-Bikai; Dogs and monkeys: Suzhou Xishan Zhongke) were taken out of the −80° C. refrigerator, immediately placed in a 37° C. water bath, slightly shaken to melt it, then the thawed plasma was poured into a centrifuge tube, centrifuged at 3000 rpm for 8 min, and the supernatant was taken for experiments. The pH value of plasma was detected by a pH Meter & Sensor (METTLER TOLEDO). Only plasma with a pH value between 7.4 and 8 was used in the experiment. The plasma was placed on an ice bath for later use.

4. Preparation of administration solution:
1). 125 g/ml test compound solution: 5 μL of 5 mg/mL test compound (see step 2) was added into 195 μL DMSO; 500 μM control solution: 20 mM control stock solution (see step 2) was added to 195 μL DMSO.
2). 0.5% BSA phosphate buffer solution: 0.05 g BSA was added to 10 mL phosphate buffer solution (see step 1);
3). 5 g/ml of test compound administration solution: 40 μL of 125 μg/mL of test compound solution was added into 960 μL 0.5% BSA phosphate buffer solution, stirred and mixed evenly, and the administration solution was preheated in a 37° C. water bath for 5 minutes.

20 μM reference substance administration solution: 40 μL of 500 μM reference substance administration solution was added into 960 μL 0.5% BSA phosphate buffer solution, stirred and mixed evenly, and the administration solution was preheated in a 37° C. water bath for 5 minutes.

5. 10 μL of 5 μg/mL of the test compound and 20 μM of the control substance administration solution were respectively added to the wells set at different time points (0 minutes, 1 hour, 2 hours and 4 hours) on the 96-well plate, and the number of duplicate samples was 3.

6. 500 μL of ACN (IS) containing 5% FA was added to the well set at 0 minute hour, then 90 μL of plasma was added, after mixing, sealing film was pasted and placed at 4° C. (number of duplicate samples was 3).

7. 90 μL of plasma was added to the wells with set time points of 1 hour, 2 hours and 4 hours respectively, the number of duplicate samples was 3, and timing was started (the final concentration of the test compound was 500 ng/ml; The control was 2 μM).

8. Then, when the timer shows 1 hour, 2 hours and 4 hours, 500 μL of ACN (IS) solution containing 5% FA were added to the holes, respectively, at corresponding time points to terminate the reaction, and after mixing, sealing films were pasted and placed at 4° C.

9. All samples (0 minutes, 1 hour, 2 hours and 4 hours) at different time points on a 96-well plate were shaken for 10 minutes at 600 rpm/min on an oscillator (MTS 2/4, IKA), and then the samples were centrifuged for 15 minutes at 5594×g in a centrifuge (Multifuge×3R, thermo Fisher).

10. 150 μL of supernatant was taken from the centrifuged sample and sent to LC-MS/MS for analysis (conventional polypeptide LC-MS/MS analysis method). The calculated half-life of the corresponding compounds were shown in Table 4.

TABLE 4

Experimental Data on Plasma Stability of Compounds

| Polypeptide number | Rat plasma (T½ (h)) |
|---|---|
| YA-3 | 10.06 |
| YA-150 | 6.67 |
| YA-156 | 44.38 |
| YA-157 | 6.67 |
| YA-162 | 6.96 |
| YA-172 | 9.42 |
| YA-175 | 2.05 |
| YA-180 | 9.63 |
| YA-182 | 5.32 |
| YA-201 | 2.65 |
| YA-220 | 59.02 |
| YA-230 | 3.64 |
| YA-264 | 13.05 |
| YA-271 | 15.63 |
| YA-273 | 166.40 |
| YA-288 | 27.48 |
| YA-296 | 2.73 |
| YA-298 | 12.68 |
| YA-324 | 0.29 |
| YA-325 | 4.26 |
| YA-326 | 4.97 |
| YA-350 | 0.22 |
| YA-360 | 79.86 |

Although specific embodiments of the present disclosure have been described above, those skilled in the art should understand that these were merely embodiments and various changes or modifications can be made to these embodiments without departing from the principles and essence of the present disclosure. Therefore, the scope of protection of the present disclosure was defined by the appended claims.

What is claimed is:

1. A peptide compound, or a pharmaceutically acceptable salt thereof, a tautomer thereof, or a solvate thereof, wherein said peptide compound is:

Palm-PEG8-Gly-Gly-(D-Tyr)-Hyp-Asn-Thr-Phe-azaGly-Leu-Arg(Me)-Trp-NH2

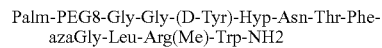

wherein Palm is palmitoyl.

2. A pharmaceutical composition comprising the peptide compound of claim 1, or a pharmaceutically acceptable salt thereof, a tautomer thereof, or a solvate thereof, and one or more pharmaceutical excipients.

* * * * *